US011008627B2

(12) United States Patent
Andeshmand et al.

(10) Patent No.: US 11,008,627 B2
(45) Date of Patent: May 18, 2021

(54) DIAGNOSTIC SYSTEM

(71) Applicant: Talis Biomedical Corporation, Menlo Park, CA (US)

(72) Inventors: Sayeed Andeshmand, Dublin, CA (US); Thomas H. Cauley, III, Redwood City, CA (US); John Dixon, Moss Beach, CA (US); David Glade, San Ramon, CA (US); Hédia Maamar, El Dorado Hills, CA (US); Michael John McAdams, Los Gatos, CA (US); Dzam-Si Jesse Ng, Fremont, CA (US); David Alexander Rolfe, San Francisco, CA (US)

(73) Assignee: Talis Biomedical Corporation, Menlo Park, CA (US)

( * ) Notice: Subject to any disclaimer, the term of this patent is extended or adjusted under 35 U.S.C. 154(b) by 0 days.

(21) Appl. No.: 16/655,028

(22) Filed: Oct. 16, 2019

(65) Prior Publication Data

US 2021/0047678 A1    Feb. 18, 2021

Related U.S. Application Data

(60) Provisional application No. 62/887,469, filed on Aug. 15, 2019.

(51) Int. Cl.
| | | |
|---|---|---|
| *C12Q 1/689* | (2018.01) | |
| *C12Q 1/6844* | (2018.01) | |
| *B01L 3/00* | (2006.01) | |

(52) U.S. Cl.
CPC ........ *C12Q 1/689* (2013.01); *B01L 3/502761* (2013.01); *C12Q 1/6844* (2013.01); *B01L 2200/16* (2013.01); *B01L 2300/047* (2013.01); *B01L 2300/0681* (2013.01); *B01L 2300/0809* (2013.01)

(58) Field of Classification Search
CPC ............ B01L 3/5027; B01L 3/502707; B01L 3/5085; B01L 7/52; B01L 2200/0621; B01L 2200/10; G01N 27/44791
See application file for complete search history.

(56) References Cited

U.S. PATENT DOCUMENTS

| | | |
|---|---|---|
| 2,350,534 A | 6/1944 | Rosinger |
| 2,598,362 A | 11/1945 | Daniels |
| 2,428,410 A | 10/1947 | Daniels |
| 2,982,132 A | 5/1961 | Mendlowitz |
| 2,990,256 A | 6/1961 | Lovins |
| 3,211,433 A | 10/1965 | Chrostowski et al. |
| 3,454,178 A | 7/1969 | Bender et al. |
| 3,495,253 A | 2/1970 | Richards |
| 3,503,410 A | 3/1970 | Richards |
| 3,504,799 A | 4/1970 | Ogle |
| 3,570,819 A | 3/1971 | Rosinger |
| 3,656,495 A | 4/1972 | Noren |
| 4,007,639 A | 2/1977 | Haeckel |
| 4,070,249 A | 1/1978 | Janin et al. |
| 4,119,407 A | 10/1978 | Goldstein et al. |
| 4,608,231 A | 8/1986 | Witty et al. |
| 4,618,476 A | 10/1986 | Columbus |
| 4,964,539 A | 10/1990 | Mueller |
| 5,256,571 A | 10/1993 | Hurley et al. |
| 5,522,155 A | 6/1996 | Jones |
| 5,639,074 A | 6/1997 | Greenhill et al. |
| 5,662,866 A | 9/1997 | Siegel et al. |
| 5,922,591 A | 7/1999 | Anderson et al. |
| 6,015,531 A | 1/2000 | Colin et al. |
| 6,250,618 B1 | 6/2001 | Greenhill |
| 6,254,071 B1 | 7/2001 | Greenhill |
| 6,357,907 B1 | 3/2002 | Cleveland et al. |
| 6,374,684 B1 | 4/2002 | Dority |
| 6,416,215 B1 | 7/2002 | Terentiev |
| 6,511,634 B1 | 1/2003 | Bradshaw et al. |
| 6,517,231 B1 | 2/2003 | Biardeau et al. |
| 6,528,641 B2 | 3/2003 | Lader |
| 6,637,463 B1 | 10/2003 | Lei et al. |
| 6,663,276 B2 | 12/2003 | Yale |
| 6,702,256 B2 | 3/2004 | Killeen et al. |

(Continued)

FOREIGN PATENT DOCUMENTS

| | | |
|---|---|---|
| CN | 107429281 A | 12/2017 |
| EP | 501796 A2 | 9/1992 |

(Continued)

OTHER PUBLICATIONS

Kobayashi et al., "Use of a genetically-engineered *Escherichia coli* strain as a sample process control for quantification of the host-specific bacterial genetic markers," App. Microbiol. Biotechnolo., vol. 97, pp. 9165-9173. (Year: 2013).*

Terranova et al., "How to Process Sputum Samples and Extract Bacterial DNA for Microbiota Analysis," International Journal of Molecular Sciences, October, vol. 19, pp. 1-12. (Year: 2018).*

Cauley et al.; U.S. Appl. No. 16/130,927 entitled "Vented converging capillary biological sample port and reservoir," filed Sep. 13, 2018.

(Continued)

*Primary Examiner* — Young J Kim

(74) *Attorney, Agent, or Firm* — Shay Glenn LLP

(57) ABSTRACT

Methods and systems are provided for point-of-care nucleic acid amplification and detection. One embodiment of the point-of-care molecular diagnostic system includes a cartridge and an instrument. The cartridge can accept a biological sample, such as a urine or blood sample. The cartridge, which can comprise one or more of a loading module, lysis module, purification module and amplification module, is inserted into the instrument which acts upon the cartridge to facilitate various sample processing steps that occur in order to perform a molecular diagnostic test.

27 Claims, 127 Drawing Sheets

(56) References Cited

U.S. PATENT DOCUMENTS

| | | |
|---|---|---|
| 6,758,465 B1 | 7/2004 | Greenhill et al. |
| 6,779,557 B2 | 8/2004 | Weiss |
| 6,813,568 B2 | 11/2004 | Powell et al. |
| 6,843,281 B1 | 1/2005 | Barth et al. |
| 6,889,710 B2 | 5/2005 | Wagner |
| 7,075,040 B2 | 7/2006 | McFadden et al. |
| 7,143,787 B1 | 12/2006 | Bauerle et al. |
| 7,159,848 B2 | 1/2007 | Brennen |
| 7,169,277 B2 | 1/2007 | Ausserer et al. |
| 7,172,896 B2 | 2/2007 | Cheng et al. |
| 7,179,423 B2 | 2/2007 | Böhm et al. |
| 7,204,139 B2 | 4/2007 | Takayama |
| 7,347,617 B2 | 3/2008 | Pugia et al. |
| 7,377,291 B2 | 5/2008 | Moon et al. |
| 7,387,898 B1 | 6/2008 | Gordon |
| RE40,511 E | 9/2008 | Weiss |
| 7,449,326 B2 | 11/2008 | Fritz et al. |
| 7,484,880 B2 | 2/2009 | Cleveland et al. |
| 7,503,203 B2 | 3/2009 | Gamache et al. |
| 7,544,506 B2 | 6/2009 | Breidford et al. |
| 7,681,595 B2 | 3/2010 | Kim et al. |
| 7,754,472 B2 | 7/2010 | Schwind et al. |
| 7,763,453 B2 | 7/2010 | Clemmens et al. |
| 7,855,069 B2 | 12/2010 | Lee et al. |
| 7,871,575 B2 | 1/2011 | Baeuerle et al. |
| 7,914,994 B2 | 3/2011 | Pourahmadi et al. |
| 7,998,437 B2 | 8/2011 | Berndt et al. |
| 8,008,080 B2 | 8/2011 | Tokhtuev et al. |
| 8,012,427 B2 | 9/2011 | Bommarito et al. |
| 8,016,264 B2 | 9/2011 | Takemasa et al. |
| 8,017,409 B2 | 9/2011 | Tokhtuev et al. |
| 8,048,386 B2 | 11/2011 | Dority et al. |
| 8,186,381 B2 | 5/2012 | Wilen |
| 8,186,382 B2 | 5/2012 | Wilen |
| 8,191,578 B2 | 6/2012 | Weiss |
| 8,202,492 B2 | 6/2012 | Linder et al. |
| 8,216,853 B2 | 7/2012 | Miller et al. |
| 8,222,049 B2 | 7/2012 | Linder et al. |
| 8,225,817 B2 | 7/2012 | Wilen |
| 8,272,401 B2 | 9/2012 | McLean |
| 8,286,663 B2 | 10/2012 | Kallback et al. |
| 8,298,763 B2 | 10/2012 | Regan |
| 8,304,245 B2 | 11/2012 | Kuypers et al. |
| 8,309,308 B2 | 11/2012 | Tisi et al. |
| 8,318,439 B2 | 11/2012 | Battrell et al. |
| 8,329,453 B2 | 12/2012 | Battrell et al. |
| 8,349,564 B2 | 1/2013 | Macioszek et al. |
| 8,399,190 B2 | 3/2013 | Belgrader et al. |
| 8,404,440 B2 | 3/2013 | Solli et al. |
| 8,434,930 B2 | 5/2013 | Huhta |
| 8,476,063 B2 | 7/2013 | Jovanovich et al. |
| 8,586,348 B2 | 11/2013 | Wang et al. |
| 8,622,086 B2 | 1/2014 | Servin |
| 8,656,955 B2 | 2/2014 | Price |
| 8,679,423 B2 | 3/2014 | Fouillet |
| 8,709,787 B2 | 4/2014 | Handique |
| 8,728,765 B2 | 5/2014 | Ching et al. |
| 8,741,235 B2 | 6/2014 | Janisch et al. |
| 8,763,640 B2 | 7/2014 | Kojima et al. |
| 8,770,226 B2 | 7/2014 | Wilen et al. |
| 8,772,017 B2 | 7/2014 | Battrell et al. |
| 8,852,863 B2 | 10/2014 | Rothmann et al. |
| 8,857,792 B2 | 10/2014 | Parrie et al. |
| 8,865,089 B2 | 10/2014 | Blatt et al. |
| 8,876,081 B2 | 11/2014 | Tower |
| 8,883,487 B2 | 11/2014 | Collier et al. |
| 8,887,754 B2 | 11/2014 | Dahlke et al. |
| 8,900,828 B2 | 12/2014 | Smith et al. |
| 8,911,688 B2 | 12/2014 | Gransee et al. |
| 8,911,941 B2 | 12/2014 | Michlitsch |
| 8,938,103 B2 | 1/2015 | Durand et al. |
| 8,940,526 B2 | 1/2015 | Ririe et al. |
| 8,960,230 B2 | 2/2015 | Weber |
| 8,962,308 B2 | 2/2015 | Wilson et al. |
| 9,040,288 B2 | 5/2015 | Handique et al. |
| 9,056,291 B2 | 6/2015 | Battrell et al. |
| 9,080,207 B2 | 7/2015 | Handique et al. |
| 9,089,883 B2 | 7/2015 | Stoeters et al. |
| 9,108,192 B2 | 8/2015 | Weber et al. |
| 9,126,161 B2 | 9/2015 | Lee et al. |
| 9,132,398 B2 | 9/2015 | Zhou et al. |
| 9,132,423 B2 | 9/2015 | Battrell et al. |
| 9,169,934 B2 | 10/2015 | Bunner et al. |
| 9,174,210 B2 | 11/2015 | Selden et al. |
| 9,186,638 B2 | 11/2015 | Claussen et al. |
| 9,194,504 B2 | 11/2015 | Cormier et al. |
| 9,199,238 B2 | 12/2015 | Koltzscher et al. |
| 9,200,315 B2 | 12/2015 | Jung et al. |
| 9,259,734 B2 | 2/2016 | Williams et al. |
| 9,274,132 B2 | 3/2016 | Wilson et al. |
| 9,283,560 B2 | 3/2016 | Dothie |
| 9,289,787 B2 | 3/2016 | Doak et al. |
| 9,304,334 B2 | 4/2016 | Progler |
| 9,308,530 B2 | 4/2016 | Hanafusa |
| 9,309,879 B2 | 4/2016 | Schmidt et al. |
| 9,315,768 B2 | 4/2016 | Vrouwe et al. |
| 9,316,321 B2 | 4/2016 | McCarty |
| 9,316,324 B2 | 4/2016 | Berndt |
| 9,329,112 B2 | 5/2016 | Smith et al. |
| 9,333,471 B2 | 5/2016 | Carrera Fabra et al. |
| 9,339,602 B2 | 5/2016 | Carlisle et al. |
| 9,383,020 B2 | 7/2016 | Jackson |
| 9,421,545 B2 | 8/2016 | Servin |
| 9,463,461 B2 | 10/2016 | Wang et al. |
| 9,469,871 B2 | 10/2016 | Bearinger et al. |
| 9,533,879 B2 | 1/2017 | Cao et al. |
| 9,550,600 B2 | 1/2017 | Whitaker et al. |
| 9,556,478 B2 | 1/2017 | Zhou et al. |
| 9,561,504 B2 | 2/2017 | Palmieri et al. |
| 9,573,128 B1 | 2/2017 | McClelland |
| 9,574,225 B2 | 2/2017 | Himmelreich et al. |
| 9,579,651 B2 | 2/2017 | Phan et al. |
| 9,580,679 B2 | 2/2017 | Njoroge et al. |
| 9,623,415 B2 | 4/2017 | Andreyev et al. |
| 9,669,409 B2 | 6/2017 | Dority et al. |
| 9,678,065 B2 | 6/2017 | Sugarman et al. |
| 9,726,588 B2 | 8/2017 | Hofmann et al. |
| 9,732,374 B2 | 8/2017 | Buse et al. |
| 9,771,553 B2 | 9/2017 | Vulto et al. |
| 9,777,317 B2 | 10/2017 | Spoto et al. |
| 9,804,091 B2 | 10/2017 | Nicholls et al. |
| 9,808,802 B2 | 11/2017 | Dothie et al. |
| 9,822,356 B2 | 11/2017 | Ismagilov et al. |
| 9,822,890 B2 | 11/2017 | Juncker et al. |
| 9,901,923 B2 | 2/2018 | Lee et al. |
| 9,956,534 B2 | 5/2018 | Hammerschmidt et al. |
| 9,976,176 B2 | 5/2018 | Bau et al. |
| 10,000,788 B2 | 6/2018 | Straus |
| 10,046,322 B1 | 8/2018 | Cauley |
| 10,125,393 B2 | 11/2018 | Esfandyarpour et al. |
| 10,173,215 B2 | 1/2019 | Weber |
| 10,183,293 B2 | 1/2019 | Weber |
| 10,190,165 B2 | 1/2019 | Chiang et al. |
| 10,450,616 B1 | 10/2019 | Dedent et al. |
| 10,525,468 B2 | 1/2020 | Dority et al. |
| 2001/0012612 A1* | 8/2001 | Petersen ............... B01L 3/502 435/5 |
| 2001/0039369 A1 | 11/2001 | Terentiev |
| 2002/0124879 A1 | 9/2002 | Kaplan et al. |
| 2003/0116203 A1 | 6/2003 | Fleischer |
| 2003/0116206 A1 | 6/2003 | Hartshorne et al. |
| 2004/0163958 A1 | 8/2004 | Kao et al. |
| 2004/0184964 A1 | 9/2004 | Watanabe et al. |
| 2004/0208751 A1 | 10/2004 | Lazar et al. |
| 2004/0265172 A1 | 12/2004 | Pugia et al. |
| 2005/0086830 A1 | 4/2005 | Zukor et al. |
| 2005/0214947 A1 | 9/2005 | Cox |
| 2005/0244308 A1 | 11/2005 | Tanaami et al. |
| 2005/0244837 A1 | 11/2005 | McMillan |
| 2005/0276728 A1 | 12/2005 | Muller-Cohn et al. |
| 2006/0039831 A1 | 2/2006 | Natarajan et al. |
| 2006/0073075 A1 | 4/2006 | Nagaoka et al. |
| 2006/0090800 A1 | 5/2006 | Banerjee et al. |
| 2006/0099567 A1 | 5/2006 | Muller-Cohn et al. |

(56) References Cited

U.S. PATENT DOCUMENTS

| | | |
|---|---|---|
| 2007/0014695 A1 | 1/2007 | Yue et al. |
| 2007/0105206 A1 | 5/2007 | Lu et al. |
| 2007/0128083 A1 | 6/2007 | Yantz et al. |
| 2007/0280856 A1 | 12/2007 | Ulmanella et al. |
| 2007/0280857 A1 | 12/2007 | Song et al. |
| 2008/0176209 A1 | 7/2008 | Muller et al. |
| 2008/0182301 A1 | 7/2008 | Handique et al. |
| 2008/0257754 A1 | 10/2008 | Pugia et al. |
| 2008/0268514 A1 | 10/2008 | Muller et al. |
| 2009/0047191 A1 | 2/2009 | Zainiev et al. |
| 2009/0061450 A1 | 3/2009 | Hunter |
| 2009/0071828 A1 | 3/2009 | Squires et al. |
| 2009/0081768 A1 | 3/2009 | Yang et al. |
| 2009/0098555 A1 | 4/2009 | Roth et al. |
| 2009/0136385 A1 | 5/2009 | Handique et al. |
| 2009/0170064 A1 | 7/2009 | Salinas |
| 2010/0276445 A1 | 11/2010 | Jacobs et al. |
| 2011/0036862 A1 | 2/2011 | Kanai et al. |
| 2011/0081363 A1 | 4/2011 | Whitney et al. |
| 2011/0207621 A1 | 8/2011 | Montagu et al. |
| 2011/0287948 A1 | 11/2011 | Suresh et al. |
| 2011/0289043 A1 | 11/2011 | Suresh et al. |
| 2011/0293558 A1 | 12/2011 | Suresh et al. |
| 2012/0034707 A1 | 2/2012 | Datta et al. |
| 2012/0052572 A1 | 3/2012 | Whitney et al. |
| 2012/0064505 A1 | 3/2012 | Suresh et al. |
| 2012/0082599 A1 | 4/2012 | Weber |
| 2012/0122108 A1 | 5/2012 | Handique et al. |
| 2012/0190589 A1 | 7/2012 | Anderson et al. |
| 2012/0270225 A1 | 10/2012 | Wakeley et al. |
| 2013/0109106 A1 | 5/2013 | Klunder et al. |
| 2013/0302787 A1 | 11/2013 | Agarwal et al. |
| 2013/0331298 A1 | 12/2013 | Rea |
| 2014/0192613 A1 | 7/2014 | Terentiev |
| 2014/0194313 A1 | 7/2014 | Craighead et al. |
| 2014/0197101 A1 | 7/2014 | Harjes et al. |
| 2014/0197105 A1 | 7/2014 | DiBiasio et al. |
| 2014/0234952 A1 | 8/2014 | Moore |
| 2015/0020904 A1 | 1/2015 | Gärtner et al. |
| 2015/0167065 A1 | 6/2015 | Nelson et al. |
| 2015/0184760 A1 | 7/2015 | Moeller et al. |
| 2015/0322493 A1 | 11/2015 | Tulp et al. |
| 2016/0038940 A1 | 2/2016 | Babcock |
| 2016/0045655 A1 | 2/2016 | Charest et al. |
| 2016/0158428 A1 | 6/2016 | Charest et al. |
| 2016/0167047 A1 | 6/2016 | Weber et al. |
| 2016/0184824 A1 | 6/2016 | Hansen et al. |
| 2016/0209331 A1 | 7/2016 | Babic et al. |
| 2016/0243550 A1 | 8/2016 | Ying et al. |
| 2016/0258880 A1 | 9/2016 | Smorgon et al. |
| 2016/0289669 A1 | 10/2016 | Fan et al. |
| 2016/0310948 A1 | 10/2016 | Nowakowski et al. |
| 2016/0326476 A1 | 11/2016 | Maisch et al. |
| 2016/0367981 A1 | 12/2016 | Wunderle et al. |
| 2016/0367993 A1 | 12/2016 | Huang et al. |
| 2017/0014821 A1 | 1/2017 | Fabra et al. |
| 2017/0218436 A1 | 8/2017 | Azimi et al. |
| 2017/0274381 A1 | 9/2017 | Selden et al. |
| 2017/0276599 A1 | 9/2017 | Li |
| 2017/0327867 A1 | 11/2017 | Dohale et al. |
| 2018/0015467 A1 | 1/2018 | Liang et al. |
| 2018/0080067 A1 | 3/2018 | Li et al. |
| 2018/0243739 A1 | 8/2018 | Schenk zu Schweinsberg et al. |
| 2019/0040451 A1* | 2/2019 | Mahony ............... A61B 10/02 |
| 2019/0160443 A1 | 5/2019 | Cauley et al. |
| 2019/0201898 A1 | 7/2019 | Cucchi et al. |
| 2019/0249799 A1 | 8/2019 | Cauley et al. |
| 2019/0291111 A1 | 9/2019 | Cauley |
| 2020/0182379 A1 | 6/2020 | Cauley et al. |

FOREIGN PATENT DOCUMENTS

| | | |
|---|---|---|
| EP | 1982768 A2 | 7/2009 |
| EP | 3406340 A1 | 11/2018 |
| GB | 2516667 A | 2/2016 |
| WO | WO96/022630 A1 | 7/1996 |
| WO | WO96/041080 A1 | 12/1996 |
| WO | WO02/010732 A1 | 2/2002 |
| WO | WO02/012734 A1 | 2/2002 |
| WO | WO02/031372 A1 | 4/2002 |
| WO | WO02/036253 A2 | 5/2002 |
| WO | WO02/090771 A2 | 11/2002 |
| WO | WO2008/024319 A2 | 2/2008 |
| WO | WO2009/035847 A1 | 3/2009 |
| WO | WO2009/112030 A1 | 9/2009 |
| WO | WO2013/106458 A2 | 7/2013 |
| WO | WO2013/156199 A1 | 10/2013 |
| WO | WO2016/005741 A1 | 1/2016 |
| WO | WO2016/090264 A1 | 6/2016 |
| WO | WO2017/210334 A1 | 12/2017 |
| WO | WO2018/001647 A1 | 1/2018 |
| WO | WO2018/001648 A1 | 1/2018 |
| WO | WO2018/111728 A1 | 6/2018 |
| WO | WO2018/121961 A1 | 7/2018 |
| WO | WO2019/183608 A1 | 9/2019 |

OTHER PUBLICATIONS

Andeshmand et al.; U.S. Appl. No. 16/655,007 entitled "Diagnostic system," filed Oct. 16, 2019.

Yan et al.; Multiplex detection of bacteria on an integrated centrifugal disk using bead-beating lysis and loop-mediated amplification; Scientific Reports; 7(1460); pp. 1-11; May 3, 2017.

Cauley et al.; U.S. Appl. No. 16/468,588, entitled "Capsule containment of dried reagents," filed Jun. 11, 2019.

* cited by examiner

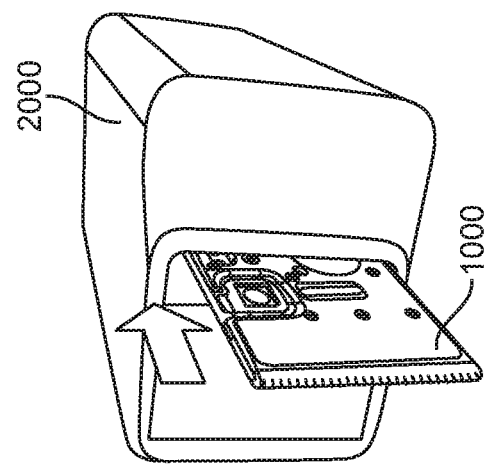
FIG. 3
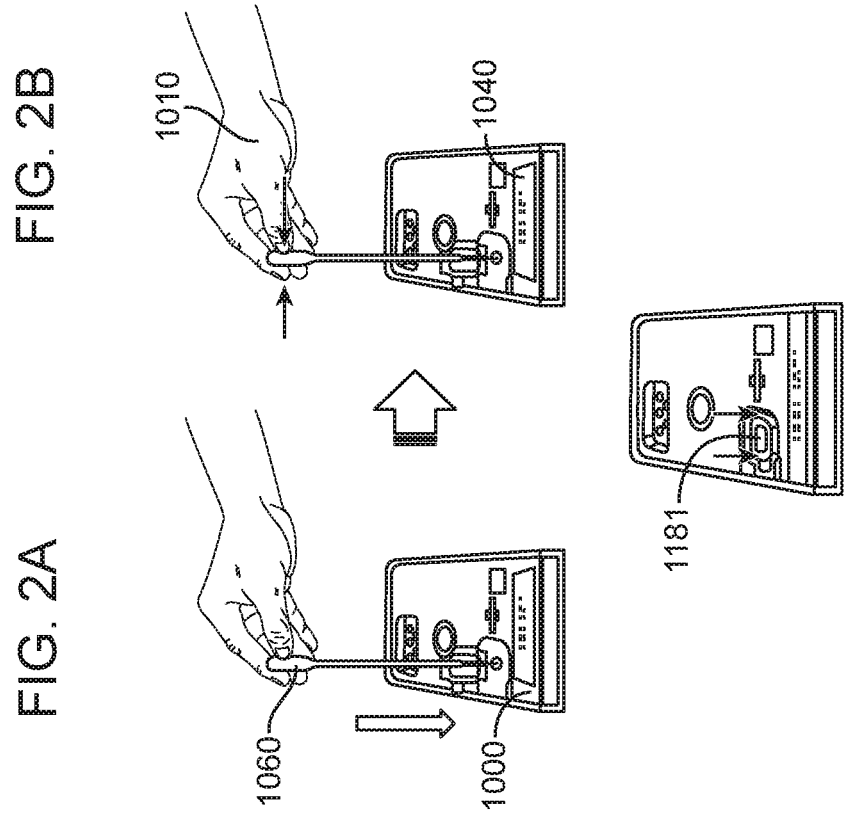
FIG. 2A
FIG. 2B
FIG. 2C

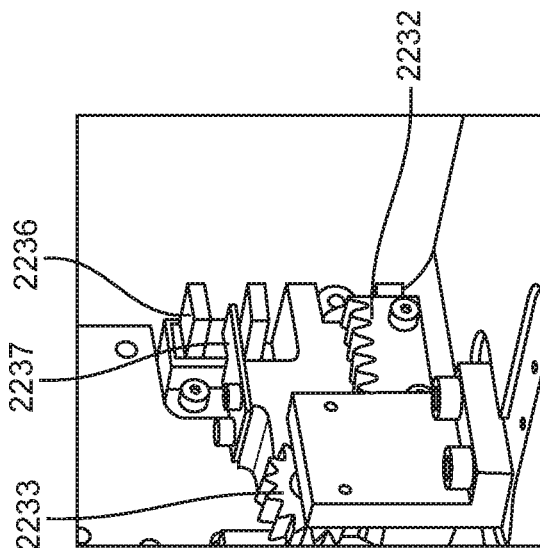
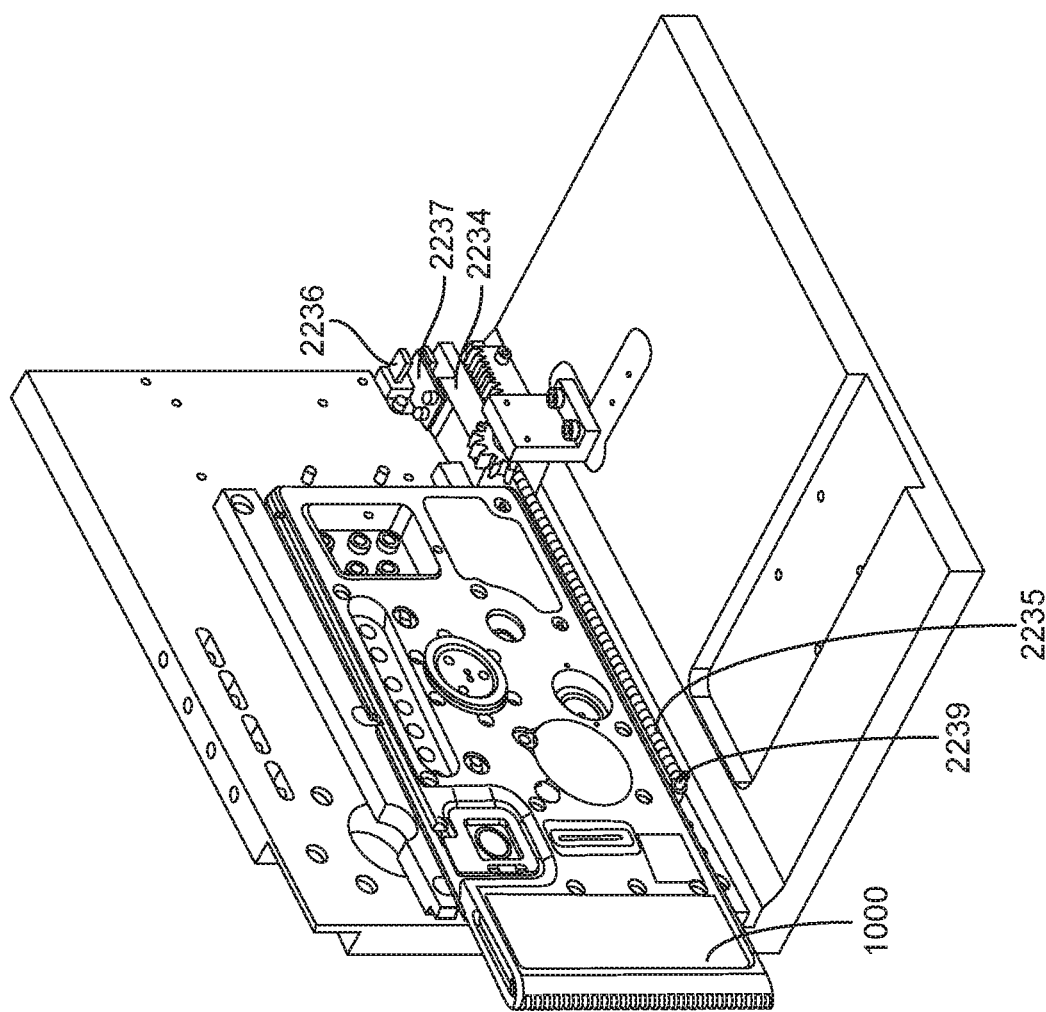
FIG. 19B
FIG. 19A

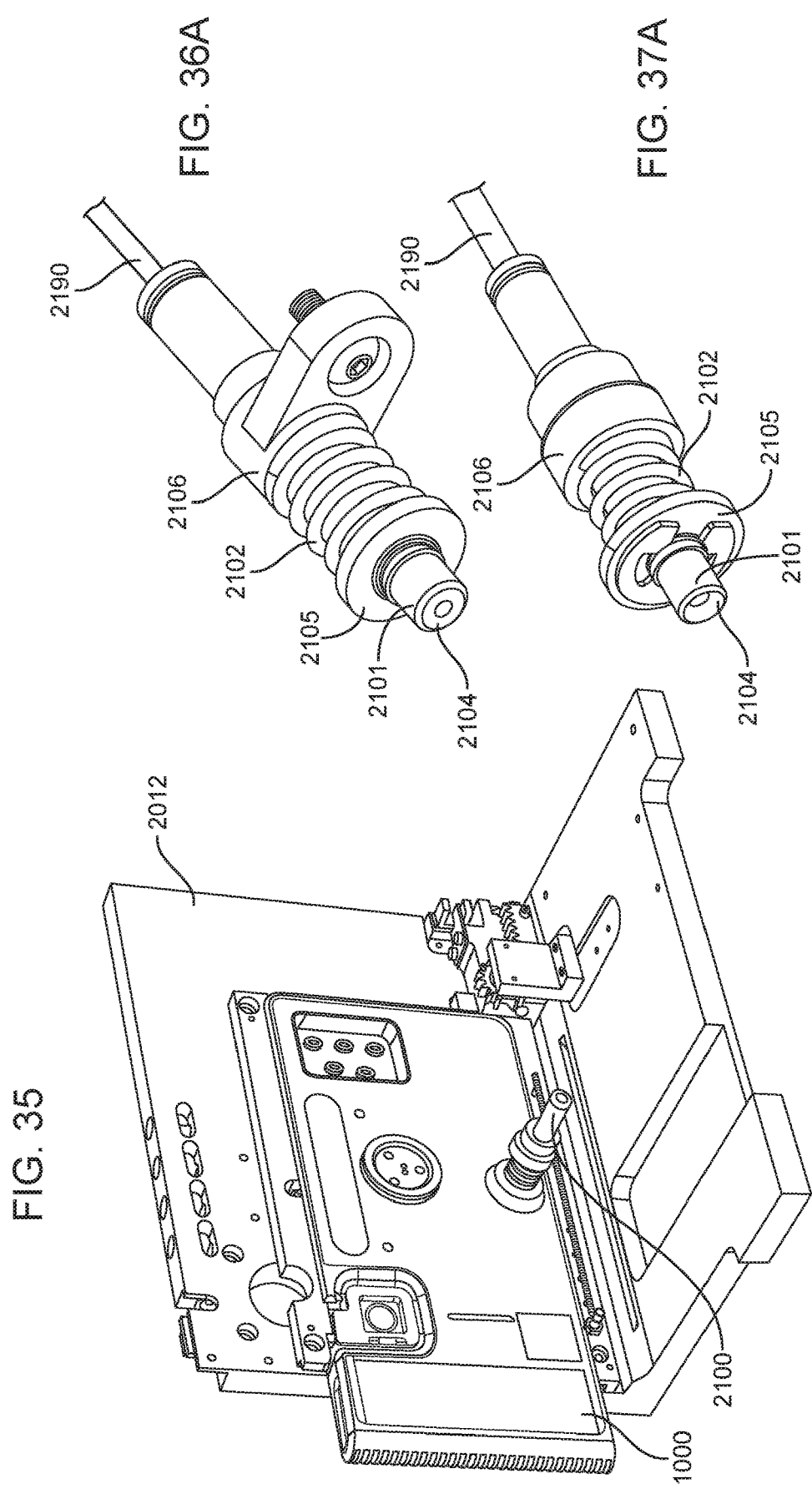

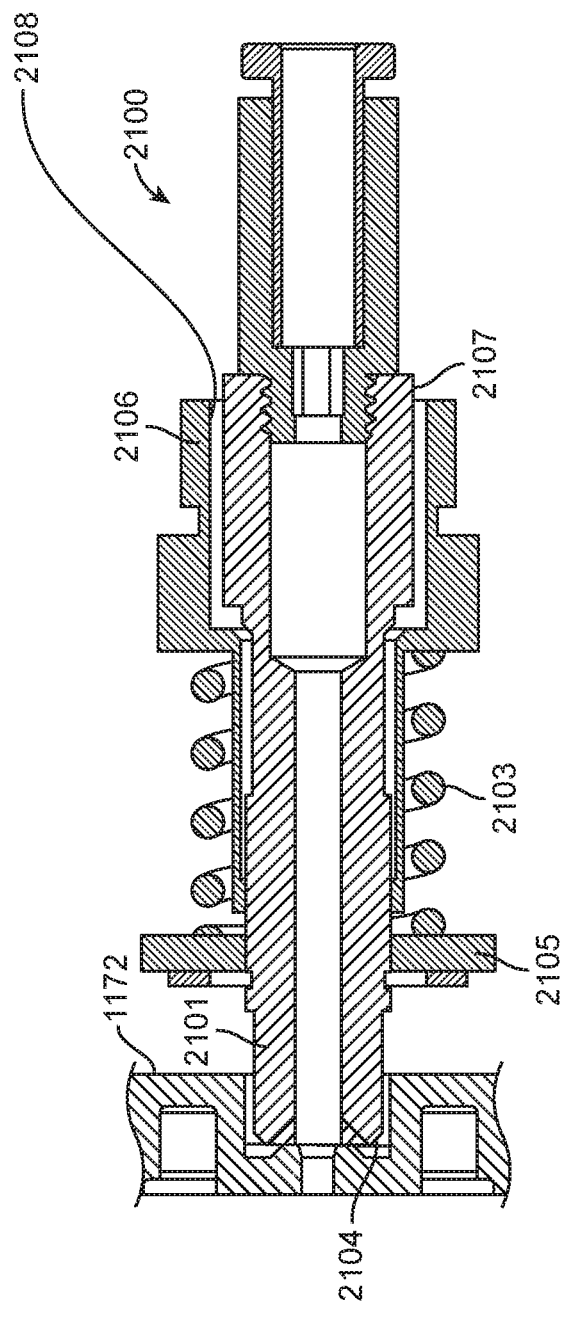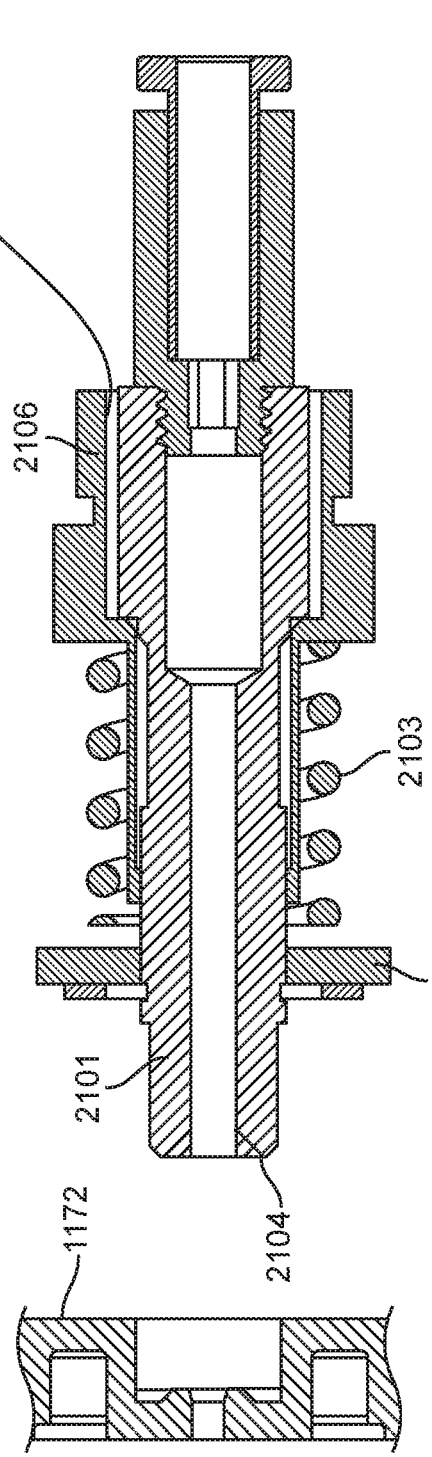
FIG. 36B
FIG. 36C

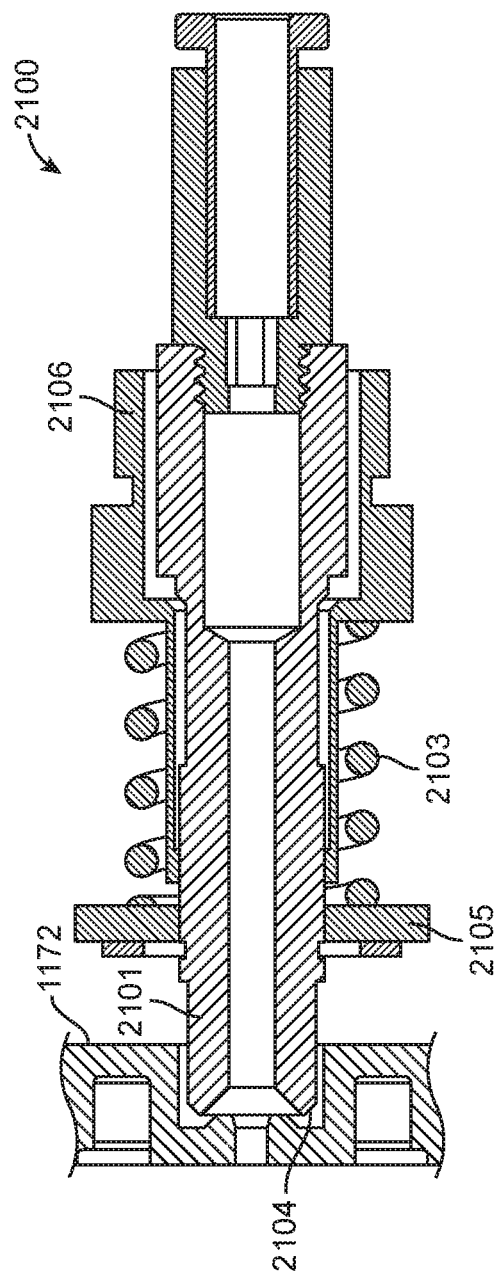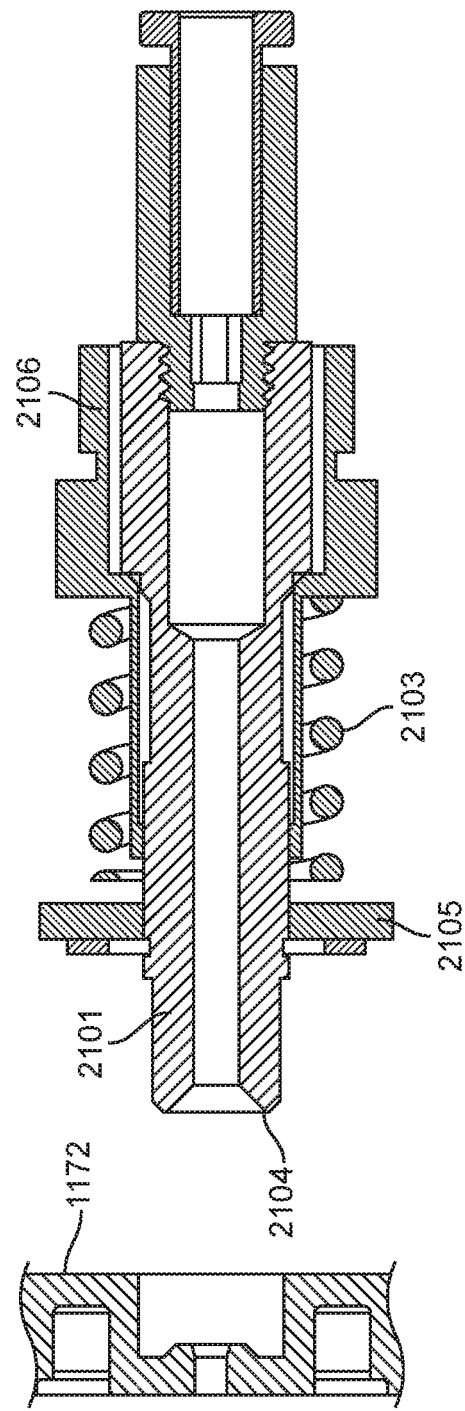
FIG. 37B
FIG. 37C

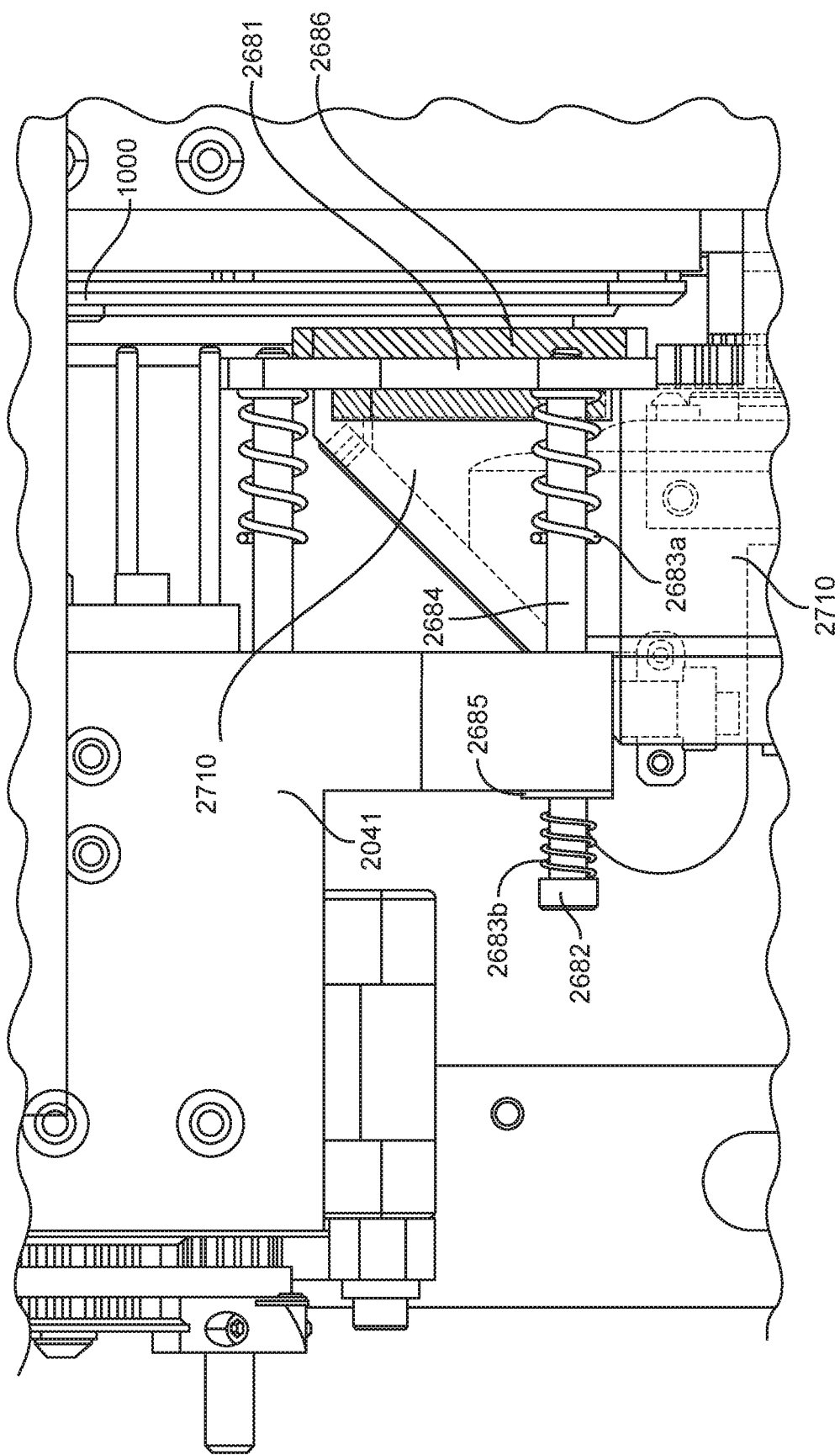

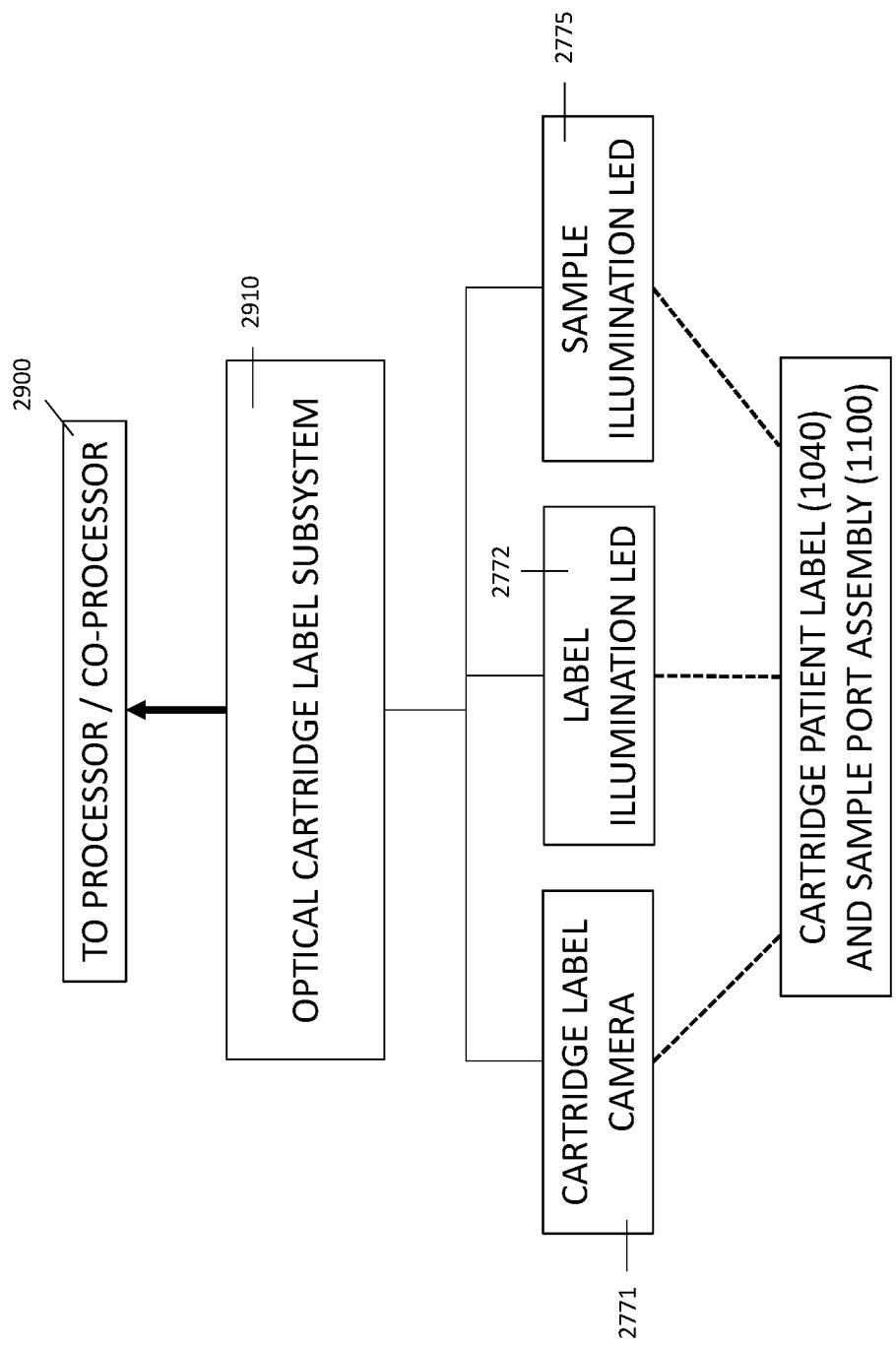

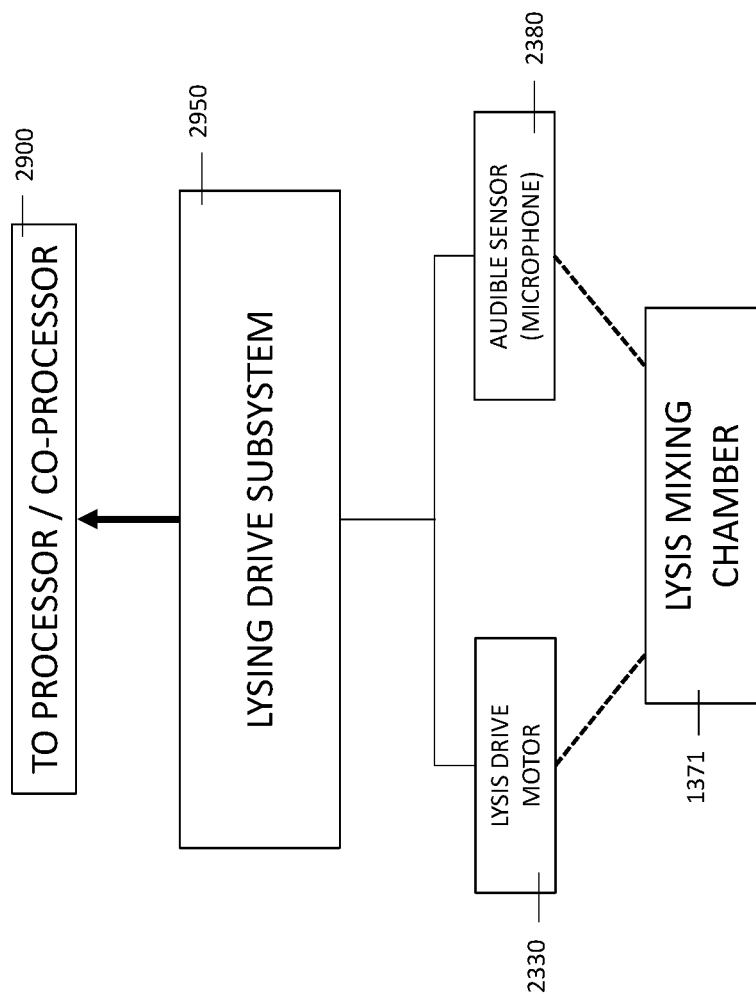

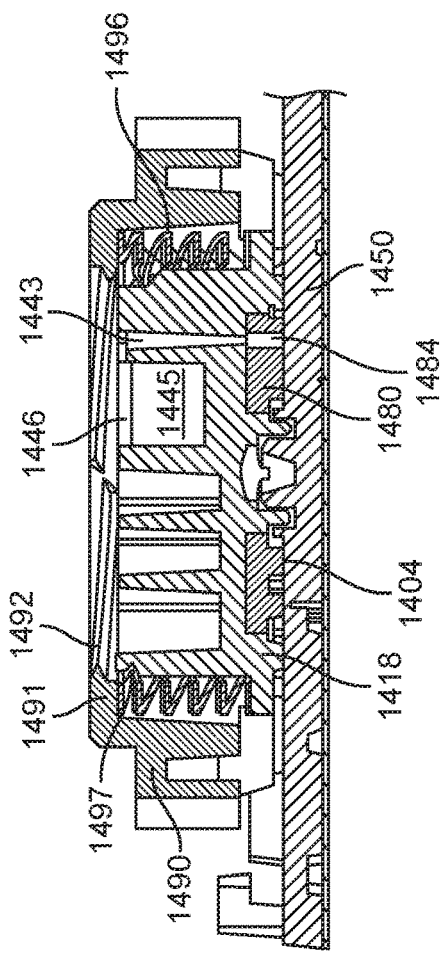
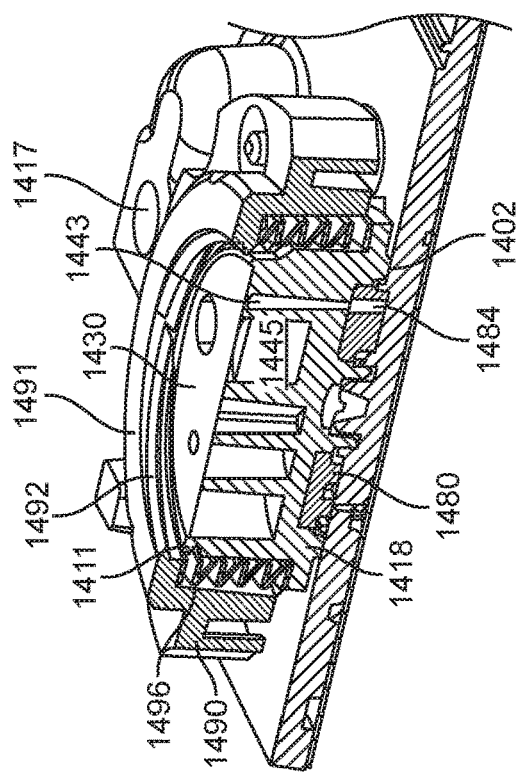
FIG. 81
FIG. 80

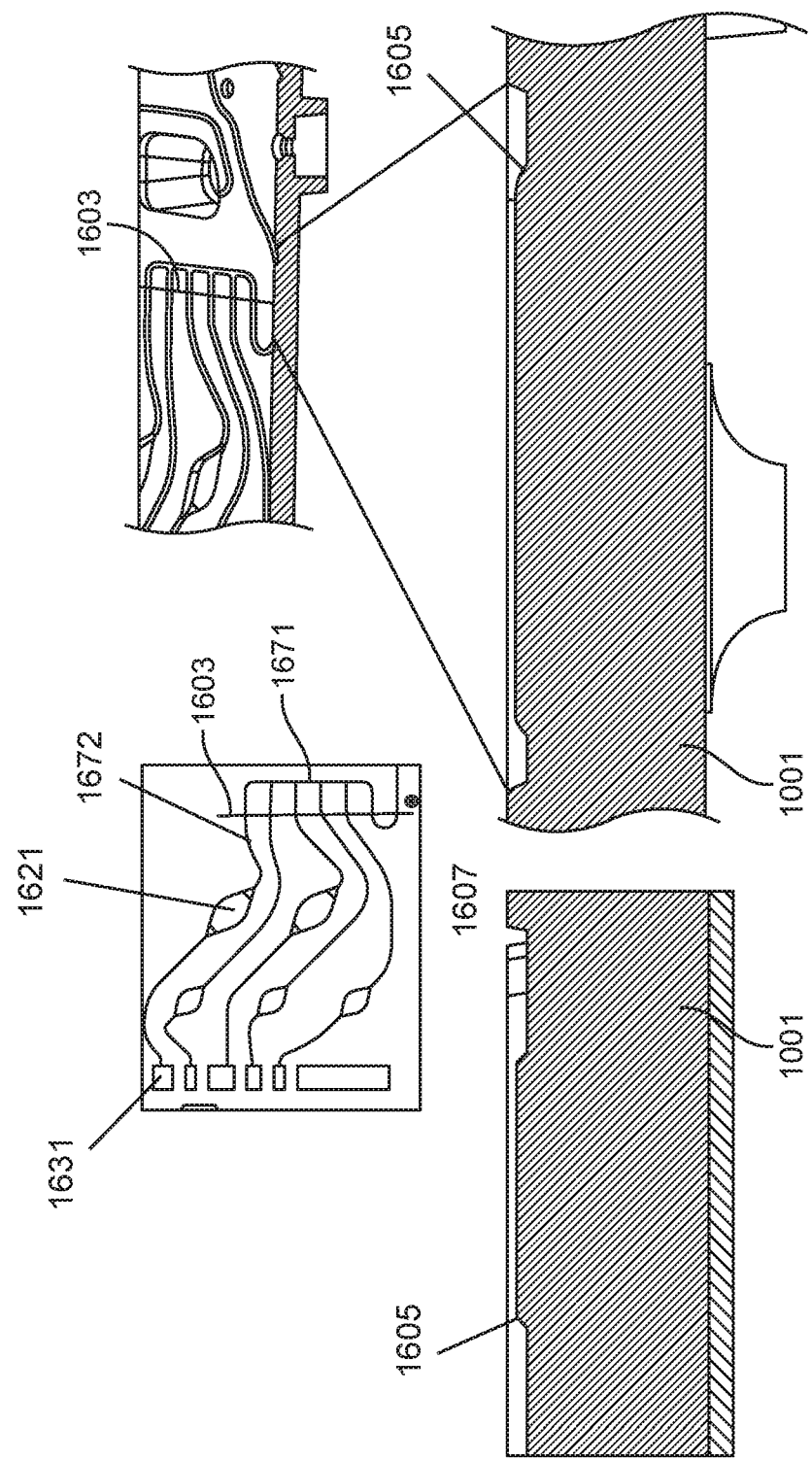

| Number | Label | Number | Label | Number | Label |
|---|---|---|---|---|---|
| 1000 | cartridge | 1130 | process control chamber | 1193 | main pneumatic via |
| 1001 | fluidics card | 1131 | process control chamber inlet | 1194 | pneumatic via |
| 1002 | first film | 1132 | process control chamber outlet | 1195 | input via |
| 1003 | second film | 1133 | process control plug | 1200 | frangible seal area |
| 1004 | cartridge cover | 1140 | entry port | 1201 | first frangible seal |
| 1005 | cartridge label | 1145 | liquid trap | 1202 | second frangible seal |
| 1006 | fluidic side | 1150 | gas conduit | 1203 | third frangible seal |
| 1007 | feature side | 1160 | channel | 1204 | fourth frangible seal |
| 1010 | user | 1161 | channel | 1205 | fifth frangible seal |
| 1020 | handle | 1165 | vent | 1206 | sixth frangible seal |
| 1021 | notch | 1170 | cartridge pneumatic interface | 1207 | seventh frangible seal |
| 1022 | interference feature | 1171 | main pneumatic line | 1330 | filter assembly |
| 1040 | patient label area | 1172 | pneumatic interface cover adaptor | 1331 | filter |
| 1050 | sample window | 1173 | inlet filter plug | 1332 | inlet via |
| 1051 | seal area label | 1174 | pneumatic inlets | 1333 | outlet via |
| 1052 | pneumatic interface label perforations | 1175 | pneumatic line | 1334 | flow directors |
| 1053 | computer readable visual code | 1176 | sample chamber pneumatic inlet | 1335 | deformation space |
| 1060 | pipette | 1177 | pneumatic line | 1336 | filter plug |
| 1100 | sample port assembly | 1178 | mixing chamber inlet | 1360 | channel |
| 1101 | fill chamber | 1180 | sample transfer channel | 1361 | channel |
| 1102 | fill chamber outlet | 1181 | bead filter channels | 1362 | channel |
| 1110 | metering chamber | 1182 | sample exit channel | 1370 | via |
| 1111 | metering chamber inlet | 1190 | cap | 1371 | lysis chamber |
| 1113 | metering channel | 1191 | top of the cap | 1372 | via |
| 1114 | ball | 1192 | air inlet via | 1373 | mixing chamber inlet |
| 1120 | overflow chamber | 1193 | air outlet via | 1386 | sample transfer channel |
| 1121 | overflow chamber inlet | | via | 1387 | bead filter channels |
| 1122 | overflow channel | | | 1388 | sample exit channel |
| 1123 | overflow channel inlet | | | 1390 | stir bar |
| | | | | 1400 | rotary valve |
| | | | | 1402 | rotor stator interface |
| | | | | 1404 | gasket stator interface |

| Number | Label |
|---|---|
| 1410 | rotor |
| 1411 | rotor threaded portion |
| 1413 | outer face |
| 1415 | rotor central opening |
| 1417 | propulsion engagement openings |
| 1418 | compression limiter |
| 1422 | peripheral lip |
| 1430 | rotor cap |
| 1441 | inlet |
| 1442 | outlet |
| 1443 | 1st conduit |
| 1444 | 2nd conduit |
| 1445 | solid support |
| 1446 | solid support chamber |
| 1448 | exit from solid support chamber |
| 1449 | flow channel spacer |
| 1450 | stator |
| 1452 | stator valving face |
| 1453 | stator port |
| 1454 | passages |
| 1460 | wash inlet via |
| 1461 | wash outlet via |
| 1462 | inlet via |
| 1463 | outlet via |
| 1470 | waste collection element |
| 1471 | waste inlet |
| 1472 | vent channel |
| 1473 | vent |
| 1474 | waste outlet |
| 1475 | wash buffer reservoir |

FIG. 103

| | | | | | | |
|---|---|---|---|---|---|---|
| wash inlet | 1476 | metering channel | 1557 | instrument | 2000 | housing | 2106 |
| wash outlet | 1477 | metering vent | 1560 | fixed bracket assembly | 2010 | outer surface of plunger | 2107 |
| outlet filter plug | 1478 | via | 1580 | fixed support bracket | 2011 | inner surface of housing | 2108 |
| gasket | 1480 | via | 1581 | first surface of fixed support bracket | 2012 | step-up feature | 2109 |
| gasket inlet | 1484 | metering via | 1582 | | | clearance | 2110 |
| gasket outlet | 1485 | vent | 1583 | second surface of fixed support bracket | 2013 | pneumatic subsystem | 2130 |
| retention element | 1490 | reaction area | 1600 | linear actuator | 2014 | pump | 2131 |
| retention ring | 1491 | heat stake | 1603 | notch | 2015 | pressure regulator | 2132 |
| threaded portion of retention ring | 1492 | raised platform | 1605 | lead screw | 2016 | proportional valve | 2133 |
| | | u-bend | 1607 | sensor | 2017 | pressure sensor | 2134 |
| retention ring lip | 1493 | independent fluidic pathway | 1610 | pins | 2018 | accumulator | 2135 |
| biasing element | 1496 | | | hard stop sensor | 2019 | output selector valve | 2136 |
| sloping feature | 1497 | assay chamber | 1621 | moving bracket assembly | 2040 | manifold block | 2137 |
| elution buffer reservoir | 1500 | entry conduit | 1622 | clamp block | 2041 | control board | 2138 |
| elution reservoir inlet | 1501 | air chamber | 1631 | first surface of clamp block | 2042 | pump filter | 2160 |
| elution reservoir outlet | 1502 | pneumatic conduit | 1632 | | | regulator inlet | 2161 |
| eluent inlet via | 1503 | tapered inlet | 1641 | linear slide | 2043 | pump outlet filter | 2162 |
| eluate outlet via | 1504 | tapered outlet | 1642 | lead nut | 2044 | tubing | 2190 |
| rehydration chamber | 1520 | channel | 1670 | extension springs | 2045 | bleed orifice | 2191 |
| rehydration chamber inlet | 1521 | main channel | 1671 | ledge | 2046 | grommets | 2194 |
| | | loading channels | 1672 | flag | 2047 | latch and pin assembly | 2210 |
| rehydration chamber outlet | 1522 | assay inlet via | 1680 | enclosure | 2070 | clamp hard stop | 2211 |
| | | assay outlet via | 1681 | metal sheet | 2071 | latch | 2212 |
| reagent plug | 1523 | thermal clamping area | 1690 | slot | 2072 | spring | 2213 |
| magnetic ball | 1524 | recess | 1752 | front | 2073 | latch release arm | 2214 |
| channel | 1550 | plug | 1770 | foot | 2074 | latch release arm slot | 2215 |
| channel | 1551 | plug cap flange | 1773 | pneumatic interface | 2100 | pin | 2216 |
| channel | 1552 | plug cap internal cavity | 1774 | steel plunger | 2101 | tab | 2217 |
| channel | 1553 | plug bottom surface | 1776 | compression spring | 2102 | loading assembly | 2230 |
| channel | 1554 | central opening | 1777 | extension stop | 2103 | rails | 2231 |
| channel | 1555 | central opening side wall | 1778 | plunger surface | 2104 | rack | 2232 |
| channel | 1556 | raised annulus | 1797 | shim | 2105 | pinion | 2233 |

FIG. 104

| | | | | | | |
|---|---|---|---|---|---|---|
| pusher carriage | 2234 | first driven magnet field focuser | 2352 | flow vane | 2605 | fold mirror | 2704 |
| ejection spring | 2235 | | | flow guide frame | 2606 | camera mount adaptor | 2705 |
| load position sensor | 2236 | second driven magnet | 2356 | heater plenum | 2607 | objective lens | 2706 |
| flag | 2237 | second driven magnet field focuser | 2357 | reaction well zone | 2620 | beam splitter block | 2707 |
| damper | 2238 | | | first surface of chemistry heater plate | 2621 | optical block | 2710 |
| post | 2239 | driven magnet spindle | 2361 | | | pocket | 2711 |
| guide | 2240s | driven magnet holder / spacer | 2365 | second surface of chemistry heater plate | 2622 | excitation lens cell | 2730 |
| frangible seal block | 2260 | | | | | excitation LED | 2731 |
| frangible seal pins | 2261 | perforations | 2377 | machined pocket geometry | 2623 | aperture | 2732 |
| frangible seal pocket | 2262 | microphone | 2380 | | | plano-convex lens | 2733 |
| hard stop | 2263 | valve drive assembly | 2400 | grooves | 2624 | aspheric lens | 2734 |
| linear slide | 2264 | valve drive | 2401 | heat staker assembly | 2640 | bandpass filter | 2735 |
| gap | 2265 | valve drive pins | 2402 | staker bar assembly | 2641 | heat sink | 2736 |
| sensor | 2266 | motor | 2403 | linear actuation motor | 2642 | thermal isolation spacer | 2737 |
| door support assembly | 2280 | interference sensor | 2404 | spring | 2643 | temperature sensor | 2738 |
| door support | 2281 | end of valve drive shaft | 2405 | heat staker fan | 2644 | photodiode | 2739 |
| spring | 2282 | pulley | 2406 | inductive linear sensor | 2645 | emission lens cell | 2750 |
| | | belt | 2407 | staker blade | 2660 | image lens | 2751 |
| magnetic mixing assembly | 2300 | valve drive shaft | 2408 | wire heater | 2661 | longpass filter | 2752 |
| | | homing sensor | 2409 | depth stop | 2662 | image plane | 2760 |
| driving magnet system | 2310 | rehydration motor | 2510 | thermal clamp assembly | 2680 | label imaging assembly | 2770 |
| first driving magnet | 2311 | cartridge heater assembly | 2550 | clamp plate | 2681 | camera | 2771 |
| first magnet field focuser | 2312 | | | thermal clamp posts | 2682 | tri color LED | 2772 |
| second driving magnet | 2316 | cartridge heater | 2551 | springs | 2683 | aperture | 2773 |
| second driving magnet field focuser | 2317 | cartridge heater zone | 2552 | shoulder screw | 2684 | diffuser | 2774 |
| | | insulator | 2553 | bushing | 2685 | cellular antenna | 2800 |
| driving magnet spindle | 2321 | cutouts | 2554 | light frame | 2686 | antenna ground plate | 2810 |
| driving magnet holder / spacer | 2325 | chemistry heater assembly | 2600 | reaction imaging assembly | 2700 | display | 2820 |
| drive motor | 2330 | chemistry heater | 2601 | reaction camera | 2701 | | |
| drive belt | 2332 | chemistry heater plate | 2602 | dichroic beam splitter | 2702 | | |
| driven magnet system | 2350 | chemistry heater fan | 2603 | light trap | 2703 | | |
| first driven magnet | 2351 | fan plenum | 2604 | | | | |

DIAGNOSTIC SYSTEM

II. CROSS REFERENCE TO RELATED APPLICATIONS

This application claims the benefit of U.S. Provisional Patent Application No. 62/887,469, filed Aug. 15, 2019, titled "DIAGNOSTIC SYSTEM," which is herein incorporated by reference in its entirety.

I. STATEMENT REGARDING FEDERALLY SPONSORED RESEARCH OR DEVELOPMENT

This invention was made with government support under contract number HR0011-11-2-0006 awarded by the Department of Defense (DARPA). The government has certain rights in the invention.

This invention was made with government support under contract number IDSEP160030-02 awarded by the Department of Health and Human Services (ASPR). The government has certain rights in the invention.

III. FIELD OF THE INVENTION

A molecular diagnostic instrument for performing tests on a sample contained in an integrated diagnostic cartridge.

IV. BACKGROUND OF THE INVENTION

In the U.S. alone, over one billion infections occur each year. To combat this, advancements in molecular diagnostic testing have enabled medical professionals to diagnose infectious diseases accurately. Nearly all molecular diagnostics testing currently is performed in centralized laboratories. While such tests performed in central laboratories are very accurate, results can be delayed several days or longer and they require expensive, high throughput instrumentation, regulated infrastructure, and trained personnel. For example, high throughput instrumentation generally processes many (e.g. 96 or 384 or more) samples at a time. Samples are collected during a time period, e.g., a day, and are then processed in one large batch. Additionally, requiring trained technician, responsible for operating laboratory equipment, adding reagents, and overseeing sample processing, e.g., moving samples from step to step, are too expensive or unavailable to practices in sparsely populated or economically challenged locations.

As an alternative to centralized laboratory testing, some testing can be performed at the point of care (POC) providing near patient rapid diagnosis outside of a laboratory environment. However, there are limited POC testing options available and many known POC tests have poor sensitivity (30-70%), as compared to highly sensitive central-lab molecular diagnostic tests. Current POC testing options tend to be single analyte tests with low analytical quality. These tests are used alongside clinical algorithms to assist in diagnosis, but are frequently verified by higher quality, laboratory tests for the definitive diagnosis. Thus, neither consumers nor physicians achieve a rapid, accurate test result in the time frame required to "test and treat" a patient in one visit. As a result, doctors and patients often determine an empiric course of treatment before they know the diagnosis. This lack of knowledge has tremendous ramifications: either antibiotics are not prescribed when needed, leading to disease progress and/or transmission to another host; or antibiotics are prescribed when not needed, leading to new antibiotic-resistant strains in the community.

In one specific example, Gram-negative *Neisseria gonorrhoeae* has progressively developed resistance to the antibiotic drugs prescribed to treat it and is one of only three organisms on the CDC's list of urgent threats. Preventing the spread of gonorrhea relies on prompt diagnosis and treatment of infected persons and their partners. The turn-around time for centralized lab testing is 1-5 days. Therefore, physicians are faced with one of two choices: (1) wait days for test results before treating a patient and risk that a positive patient may continue to spread the infection through their partners, and their partners' partners or (2) treat empirically while the patient is in front of them. In a study of 1103 emergency room patients at Johns Hopkins, 440 patients who had a suspected CT or NG infection were treated with antibiotics though the vast majority, 323 patients, ultimately turned out to be negative. As a direct result of the overuse and misuse of antibiotics through empiric therapy, antibiotic resistance in gonorrhea is on the verge of becoming a public health crisis. To prevent the development of future antibiotic resistant strains, molecular diagnostic testing at the point of care can prevent unnecessary antibiotics from being prescribed and provide rapid diagnosis and treatment.

Highly trained personnel are required to perform molecular diagnostic tests because these sophisticated assays are powered by nucleic acid amplification methods, such as PCR, and carried out on biologic samples, which typically contain a variety of substances inhibitory to amplification. However, such trained personnel typically are not available at the locations where patients are being seen, i.e. at the point of care. Additional challenges associated with the point of care environment include fulfilling physician or clinical workflow compatibility coupled with an unknown skill level for system users. Accordingly, point of care molecular diagnostic systems must be designed for the ease of use by system users and be robust in performing sample preparation and amplification, with minimal user interaction, to generate reliable diagnostic results Thus, despite the existence of some point of care diagnostic systems, a need exists for improved devices and methods for molecular diagnostic testing. In particular, an unmet need continues for an easy-to-use system enabling rapid molecular diagnostic capabilities in the point of care environment.

V. SUMMARY

In general, in one embodiment, an instrument includes an enclosure, a fixed support bracket within the enclosure, a first imaging system mounted on the fixed support bracket within the enclosure adjacent to the slot, a second imaging system mounted on the fixed support bracket within the enclosure configured to collect images from a second imaging area within the enclosure, and a clamp block within the enclosure and moveable relative to the fixed support bracket. The first imaging system is configured to collect images from a first imaging area within the enclosure. The second imaging area is in non-overlapping relation to the first imaging area. The first imaging system and the second imaging system; a drive system on the fixed support bracket is configured to position the clamp block relative to the fixed support bracket; and a slot is positioned in the enclosure to provide access to an interior portion of the enclosure between the fixed support bracket and the clamp block.

This and other embodiments can include one or more of the following features. The clamp block can be positioned between the first imaging system and the second imaging system. A valve drive assembly, a pneumatic interface and a frangible seal block can be connected to and move with the clamp block. The frangible seal block can be directly connected to the valve drive assembly. The frangible seal block can be configured to move together with the valve drive assembly and the pneumatic interface and independent of the valve drive assembly and the pneumatic interface. The instrument can further include an upper rail within the enclosure aligned to an upper portion of the slot and a lower rail within the enclosure aligned to a lower portion of the slot. The instrument can further include a loading assembly within the enclosure in sliding relation to the lower rail. The loading assembly can move between a loading position and a loaded position. When in the loading position, the loading assembly can be positioned in a forward most position towards the slot and when in the loaded position the loading assembly is engaged with a load position sensor. The load position sensor can provide an electronic indication when the loading assembly has translated into the loaded position. The instrument can further include a first heater and a second heater mounted on the fixed support bracket. The first heater can be positioned to heat a portion of the enclosure between the first imaging area and the second imaging area. The second heater can be positioned to heat a portion of the enclosure only within the second imaging area. The instrument can further include an opening within the fixed support bracket and a heat stake assembly positioned to move a heating element through the opening. The opening can be positioned on the fixed support bracket to allow the heating element to interact within the enclosure between the first imaging area and the second imaging area. Opening can be positioned within the fixed support bracket such that the heating element may perform a heat staking operation directly adjacent to but outside of the second imaging area. The clamp block can partially block the slot when the clamp block is positioned at a closest position to the fixed support bracket.

In general, in one embodiment, an instrument includes an enclosure, a fixed support bracket within the enclosure, a moving bracket assembly within the enclosure and moveable relative to the fixed support bracket, a drive system configured to position the moving bracket assembly relative to the fixed support bracket, a slot positioned in the enclosure to provide access to an interior portion of the enclosure between the fixed support bracket and the moving bracket assembly; and an upper rail and a lower rail in the enclosure positioned adjacent to the slot wherein a cartridge positioned between the upper rail and the lower rail remains in a vertical position between the fixed support bracket and the moving bracket assembly.

This and other embodiments can include one or more of the following features. The instrument can further include a feature within the upper rail or the lower rail positioned to interfere with the movement of a cartridge improperly aligned with respect to the upper rail and the lower rail. The instrument can further include a loading assembly within the enclosure positioned to engage with a cartridge moving along the upper rail and the lower rail. The instrument can further include a latch and pin assembly positioned adjacent to the upper rail adapted to engage a pin with a cartridge moving along the upper rail. The instrument can further include a touch screen display on an exterior of the enclosure. The instrument can further include a cellular communications module within the enclosure. The cellular communication module can be adjacent to the slot. The instrument can further include a first heater, a driving magnet assembly, a second heater, a magnetic rehydration chamber motor, a reaction camera and a heat staker assembly are coupled to fixed support bracket and positioned to interact with a corresponding portion of a cartridge positioned between the upper rail and the lower rail. The instrument can further include a first imaging system mounted on the fixed support bracket within the enclosure adjacent to the slot. The first imaging system can be configured to collect images from a first imaging area within the enclosure and a second imaging system mounted on the fixed support bracket within the enclosure configured to collect images from a second imaging area within the enclosure wherein the second imaging area is in non-overlapping relation to the first imaging area. The first imaging area can include a label of a cartridge positioned within the enclosure between the upper rail and the lower rail. The second imaging area can include one or more assay chambers of a cartridge positioned within the enclosure between the upper rail and the lower rail. The instrument can further include a clamp block, a frangible seal block, a valve drive assembly, a pneumatic interface, a thermal clamp assembly, a portion of a magnetic mixing assembly coupled to move along with the clamp block during operation of the drive system. The instrument can further include a plenum adjacent to the chemistry heater and a fan in fluid communication with the plenum. The heat stake assembly can further include a staker blade positioned to move relative to a depth stop. The staker blade can be coupled to a linear actuation motor and a spring with pivot washer.

In general, in one embodiment, an integrated diagnostic cartridge includes a loading module, a lysis module, a purification module, and a reaction module. The loading module, the lysis module, the purification module and the reaction module are arranged for use while the cartridge is in a vertical orientation.

This and other embodiments can include one or more of the following features. The integrated diagnostic cartridge can further include one or more fluid filling conduits arranged to flow into an upper portion of a chamber within a fluidic card of the integrated diagnostics cartridge and one or more fluid outlet conduits arranged to flow out of a lower portion of the chamber within the fluidic card of the integrated diagnostics cartridge. The chamber can be one or more of a lysis chamber, a waste chamber, a metering chamber, or a rehydration chamber. The chamber can be a lysis chamber further including a filter assembly in fluid communication with a fluid outlet conduit of the lysis chamber.

In general, in one embodiment, an integrated diagnostic cartridge includes a loading module including a sample port assembly having a fill chamber, a metering chamber, and an overflow chamber arranged in fluid communication, a lysis module, a purification module, and a reaction module.

This and other embodiments can include one or more of the following features. The metering chamber can include a sample window for observing the height of a sample within the metering chamber. The integrated diagnostic cartridge can further include a buoyant ball in the metering chamber adapted for use with the sample window. The fill chamber can include a cap operable to provide access to the fill chamber. The cap can be positioned for interaction with a door support assembly of a diagnostic instrument. The cartridge can be in a vertical orientation when in use within a diagnostic instrument and a fluid channel connects an outlet at a lower portion of the fill chamber with an inlet to the metering chamber located in an upper portion of the metering chamber. The metering chamber can include a transparent sample window. The integrated diagnostic cartridge can further include a buoyant ball within the metering chamber. Said buoyant ball can be adapted to appear adjacent to the transparent sample window permitting an assessment of the height of the sample liquid in the metering chamber. The metering chamber can include a buoyant ball for assessing a height of a sample liquid in the metering chamber.

In general, in one embodiment, an integrated diagnostic cartridge includes a loading module, a lysis module including a mixing assembly having a lysis chamber containing a lysis agent and a non-magnetized stir bar, a purification module, and a reaction module.

This and other embodiments can include one or more of the following features. The non-magnetized stir bar can be made from a metal having a magnetic permeability to be responsive to a rotating magnetic field induced between a drive magnetic element and a driven magnetic element of a magnetic drive system. The metal can include a ferritic stainless steel or a duplex stainless steel. The non-magnetized stir bar can be made from a metal selected from the group consisting of a carbon steel, a mild carbon steel, a low alloy steel, a tool steel, a metal alloy contain nickel, a metal alloy containing cobalt, a non-austenitic stainless steel, a ferritic grade of stainless steel including 430 steel, Altlas CR12 steel, 444 steel, F20S steel, a duplex grade of steel including 2205 steel, 2304 steel, 2101 steel, 2507 steel and a martensitic grade of steel such as 431 steel, 416 steel, 420 steel and 440C steel wherein the metal has a magnetic permeability to be responsive to a rotating magnetic field produced within the lysis chamber. The metal can have a magnetic permeability between 500-1,000,000. The non-magnetized stir bar can be coated with an impermeable material to prevent corrosion by a chemical lysis buffer in lysis chamber. The impermeable material can be PTFE, parylene C, parylene D, a functionalized perfluoropolyether (PFPE), Xylan Fluoropolymer, epoxy, or urethane. When in use within a diagnostic instrument, the non-magnetized stir bar can be disposed between a driving magnet system and a driven magnet system of a magnetic mixing assembly in the diagnostic instrument, wherein the driving magnet system is configured to rotate the non-magnetized stir bar within the lysis chamber at at least 1000 rpm. The lysis agent can be a mechanical agent. The mechanical agent can be ceramic beads, glass beads or steel beads. The lysis agent can be a chemical agent. The chemical agent can be an anionic detergent, a cationic detergent, a non-ionic detergent or a chaotropic agent. The cartridge can be configured for testing of one or more target pathogens that is a virus or a gram-negative bacterium. The integrated diagnostic cartridge can further include a fluid inlet in fluid communication with the lysis chamber and a fluid outlet in fluid communication with the lysis chamber and a filter in fluid communication with the fluid outlet of the lysis chamber. The integrated diagnostic cartridge can further include a fluid inlet to the lysis chamber and a fluid outlet to lysis chamber wherein the lysis chamber is isolated from the other modules on the cartridge by a first frangible seal in fluid communication with the fluid inlet to the lysis chamber and a second frangible seal in fluid communication with the fluid outlet to the lysis chamber. The integrated diagnostic cartridge can further include a process control chamber having an inlet, an outlet and a plug including a process control wherein the process control chamber is in fluid communication with the lysis chamber inlet.

In general, in one embodiment, an integrated diagnostic cartridge includes a loading module, a lysis module, a purification module including a rotary valve and a reaction module. The rotary valve includes a stator including a stator face and a plurality of passages, each passage including a port at the stator face. A rotor operably connected to the stator and including a rotational axis, a rotor valving face, and a flow channel having an inlet and an outlet at the rotor valving face, and a retention element biasing the stator and the rotor together at a rotor-stator interface to form a fluid tight seal. The flow channel includes a porous solid support.

This and other embodiments can include one or more of the following features. The rotary valve can further include a gasket between the stator face and the rotor valving face. The stator can include a displaceable spacer for preventing the gasket from sealing against at least one of the rotor and stator. When the spacer is displaced, the gasket can seal the rotor and stator together in a fluid-tight manner. Then the cartridge is positioned within a diagnostic instrument, engagement with a valve drive assembly of the diagnostic instrument can displace the spacer and seals the rotor and stator together in a fluid-tight manner. A rotation movement can be performed by the valve drive assembly of the diagnostic instrument, displaces the spacer and seals the rotor and stator together in a fluid-tight manner.

In general, in one embodiment, an integrated diagnostic cartridge includes a loading module, a lysis module, a purification module including a rotary valve and a reaction module. A rotary valve include a rotor including a rotor valving face, an outer face opposite the rotor valving face, and a rotational axis, a stator, a gasket interposed between the stator and the rotor valving face, and a displaceable spacer for preventing the gasket from sealing against at least one of the rotor and stator, wherein, when the spacer is displaced the gasket seals the rotor and stator together in a fluid-tight manner.

This and other embodiments can include one or more of the following features. The porous solid support can be a polymeric. The porous solid support can be selected from the group consisting of alumina, silica, celite, ceramics, metal oxides, porous glass, controlled pore glass, carbohydrate polymers, polysaccharides, agarose, Sepharose™, Sephadex™, dextran, cellulose, starch, chitin, zeolites, synthetic polymers, polyvinyl ether, polyethylene, polypropylene, polystyrene, nylons, polyacrylates, polymethacrylates, polyacrylamides, polymaleic anhydride, membranes, hollow fibers and fibers, and any combination thereof. The rotor valving face can include a gasket interposed at the rotor-stator interface. The rotor can include a plurality of flow channels, each flow channel comprising an inlet, an outlet, and a porous solid support. The purification module can further include a waste collection element, a wash buffer reservoir and an elution buffer reservoir.

In general, in one embodiment, an integrated diagnostic cartridge includes a loading module, a lysis module, a purification module; and a reaction module including a plurality of individual assay chambers. At least one surface in each one of the plurality of individual assay chambers is provided by a plug including a body with a bottom surface, a central opening in the body, and a dried reagent on the bottom surface. The body is formed from a material transmissive to excitation wavelengths and emission wavelengths in at least one of a red spectrum, a blue spectrum and a green spectrum.

This and other embodiments can include one or more of the following features. The bottom surface of the plug body can include a cavity in the bottom surface with the dried reagent within the cavity. The plug can have a plug thickness between a central opening bottom and the plug body bottom, and further a depth of the cavity is less than 90% of the plug thickness, is less than 70% of the plug thickness or is less than 50% of the plug thickness. The plug can have a polished or smooth finish facilitating the transmissivity of the excitation wavelengths and the emission wavelengths. The dried reagent can be selected from the group consisting of nucleic acid synthesis reagents, nucleic acids, nucleotides, nucleobases, nucleosides, monomers, detection reagents, catalysts or combinations thereof. The dried reagent can be a continuous film adhered to the plug bottom surface. The dried reagent can be a lyophilized reagent.

In general, in one embodiment, an integrated diagnostic cartridge includes a loading module, a lysis module, a purification module, and a reaction module including one or more assay chambers. Each assay chamber includes a tapered inlet, a tapered outlet, and a plug including a bottom surface and a central opening in the body. The body is formed from a material transmissive to excitation wavelengths and emission wavelengths in at least one of an ultraviolet spectrum, a blue spectrum, a green spectrum and a red spectrum. Two curved boundaries, wherein each curved boundary extends from the tapered inlet to the tapered outlet such that together, the two curved boundaries and the plug enclose a volume of the assay chamber; and a shoulder extending from each curved boundary. The plug contacts each shoulder such that a boundary of the assay chamber is provided by the two curved boundaries, the shoulders extending from each of the curved boundaries and the plug.

In general, in one embodiment, an integrated diagnostic cartridge includes a loading module, a lysis module, a purification module, and a reaction module. The reaction module includes a common fluid pathway, and a plurality of independent, continuous fluidic pathways connected to the common fluid pathway. Each independent, continuous fluidic pathway includes an assay chamber, and a pneumatic compartment. The assay chamber is connected to the common fluid pathway, the assay chamber having a fluid volume defined in part by a plug having a dried reagent thereon. The pneumatic compartment, having a pneumatic volume, is connected to the common fluid pathway via the assay chamber. Each fluidic pathway of the plurality of independent, continuous fluidic pathways is a closed system excluding the connection between the assay chamber and common fluid source. Each assay chamber further includes a double tapered chamber. The double tapered chamber includes a tapered inlet in fluidic communication with a terminus of the entry conduit of the fluidic pathway, a tapered outlet in fluidic communication with a terminus of the pneumatic compartment, and two curved boundaries. Each curved boundary extends from the tapered inlet to the tapered outlet such that together, the two curved boundaries enclose the volume of the assay chamber. A shoulder extending from each curved boundary wherein the plug contacts each shoulder such that a boundary of the assay chamber is provided by the two curved boundaries, the shoulders extending from each of the curved boundaries and the plug.

This and other embodiments can include one or more of the following features. The two curved boundaries can be formed in a monolithic substrate or a fluidic card of the cartridge. The body of the plug can protrude into the monolithic substrate of the assay chamber at a depth such that the assay chamber volume can be readily changed by altering the depth at which the body of the plug protrudes into the monolithic substrate of the assay chamber.

In general, in one embodiment, an integrated diagnostic cartridge includes a loading module, a lysis module, a purification module, and a reaction module. The reaction module includes a reagent storage component including a capsule capable of holding a liquid or solid sample. Said capsule includes an opening, a closed end and a wall extending from the closed end to the opening. The capsule is oval-shaped and the wall is rounded, and the closed end and wall define an interior volume having a substantially smooth surface.

In general, in one embodiment, an integrated diagnostic cartridge includes a loading module, a lysis module, a purification module, and a reaction module including a capsule capable of holding a liquid or a solid sample. Said capsule includes an inner surface extending from the bottom of said capsule to an oval-shaped opening at the top of the capsule, wherein said inner surface is substantially smooth and includes a concave shape extending from the bottom of the capsule, and a planar layer affixed around the oval-shaped opening of said capsule and oriented in the same plane as the oval-shaped opening of said capsule. Said planar layer includes a top surface and a bottom surface. Said top surface is aligned with the inner surface of said capsule at said oval-shaped opening to provide a continuous surface.

This and other embodiments can include one or more of the following features. Said capsule can be capable of holding a volume from approximately 50 µL to approximately 200 µL or wherein said oval-shaped opening is contained within an area of 9 mm×9 mm. Said capsule can include a dried reagent. The integrated diagnostic cartridge can include a fluidic card and a cover. At least two of the loading module, the lysis module, the purification module and the reaction module can be formed in or supported by the fluidic card. At least two of the loading module, the lysis module, the purification module and the reaction module can be formed in or supported by the cover. The fluidic card can further include a notch positioned to engage with a latch and pin assembly of a diagnostic instrument to secure the integrated diagnostic cartridge in a testing position within the diagnostic instrument. The integrated diagnostic cartridge can further include an interference feature on the cover. The interference feature can be sized and positioned to interact with one of an upper rail or a lower rail of a loading instrument of a diagnostic instrument. A thickness of the fluidic card can be selected for sliding arrangement within an upper rail and a lower rail of a loading instrument of the diagnostic instrument. A total sample process volume of the integrated diagnostic cartridge can be provided by increasing the thickness of the cartridge. A diagnostic instrument can be adapted and configured to accommodate the increased thickness of the cartridge by increasing a width of a loading slot of the diagnostic instrument to accommodate the increased thickness of the cartridge or a displacement range of a cartridge clamping system of the diagnostic instrument is adapted to accommodate the increased thickness of the cartridge. The integrated diagnostic cartridge can further include a cartridge front face and a cartridge rear face forming an upper spacing and a lower spacing wherein each of the upper spacing and the lower spacing is sized and positioned to engage with an upper rail and a lower rail of an instrument configured to read the integrated diagnostic cartridge. The integrated diagnostic cartridge of can further include an interference feature within the upper spacing or the lower spacing positioned to ensure the cartridge engages with the upper rail and the lower rail in a desired orientation. The integrated diagnostic cartridge can further include a plurality of frangible seal chambers in fluid communication with at least one or more of the loading module, the lysis module, the purification module or the reaction module. The integrated diagnostic cartridge can further include a label section. The integrated diagnostic cartridge can further include one or more machine readable marking indicating the sample type to be used in the cartridge or target pathogen to be detected. The integrated diagnostic cartridge can further include a pneumatic interface. Prior to loading the cartridge into a diagnostic instrument, a lysis chamber in the cartridge can contains lysis buffer. The integrated diagnostic cartridge can further include machine readable code adapted and configured to identify the cartridge to a diagnostic instrument or an image of a patient identification marking. The integrated diagnostic cartridge can further include a film adhered to a surface of the monolithic substrate. The film can form one surface of the assay chamber. The integrated diagnostic cartridge can further include a first film adhered to a surface of at least a portion of the cartridge. The first film can form one surface of one or more chambers, compartments, or fluid conduits of the loading module, the lysis module, the purification module and the reaction module. The integrated diagnostic cartridge can further include a second film adhered to the first film. The second film can have a higher melting temperature than the first film. The integrated diagnostic cartridge can further include a heat staked region formed in each of the fluidic pathways using the first film or the second film. The heat staked region can seal off the common fluid pathway from the assay chamber and the pneumatic chamber. The integrated diagnostic cartridge can further include a raised platform within each of the plurality of independent, continuous fluidic pathways the raised platform positioned between an inlet to the assay chamber and the common fluid pathway. The heat staked region can be formed using a portion of the raised platform.

In general, in one embodiment, a method of testing a sample suspected of containing one or more target pathogens includes: (1) accepting a cartridge having a sample port assembly containing the sample suspected of containing the one or more target pathogens; (2) advancing the sample suspected of containing the one or more target pathogens to a lysis chamber having at least one lysis reagent therein; (3) mixing the sample with the at least one lysis agent to generate a lysed sample; (4) passing the lysed sample through a first porous solid support to capture a nucleic acid on the porous solid support; (5) releasing the captured nucleic acid from the first porous solid support to generate an enriched nucleic acid; (6) distributing the enriched nucleic acid to two or more assay chambers; (7) combining the enriched nucleic acid with one or more amplification reagents; (8) isolating each one of the two or more assay chambers from each one of all the other two or more assay chambers; and (9) performing an isothermal amplification reaction within each one of the two or more assay chambers while simultaneously detecting amplification product, wherein presence of an amplification product is an indication of a presence, an absence or a quantity of the target pathogen in the sample suspected of containing the target pathogen.

This and other embodiments can include one or more of the following features. The sample can be a biological sample obtained from a mammal. The mammal can be a person providing a biological sample. The sample can be obtained from a food product, a natural non-growth hormone crop sample, a crop sample, a water sample, a non-biological fluid sample or a soil sample. The step of accepting a cartridge step can further include reading a ID code on the cartridge and determining to proceed with the method of testing. The accepting a cartridge step can further include obtaining and analyzing an image of a sample window of the sample port assembly and determining to proceed with the method of testing. The sample in the sample port assembly can be in fluid communication with a fill chamber, a metering chamber, and an overflow chamber. The sample window can be transparent and formed in at least a portion of a wall of the metering chamber. Obtaining an image can further include obtaining an image via the transparent sample window. Analyzing an image can further include assessing a height of a sample liquid in the metering chamber via the transparent sample window. The step of obtaining and analyzing an image can further include obtaining an image of the metering chamber including a buoyant ball and analyzing the image includes identifying a location of the ball within the metering chamber and determining to proceed with the method based on the location of the ball. The accepting a cartridge step can further include obtaining and analyzing an image of a patient label area and determining to proceed with the method of testing. The accepting a cartridge step can further include confirming a rotary valve on the cartridge is in a shipping configuration before proceeding to the advancing the sample step. The accepting a cartridge step can further include obtaining a reading from an interference sensor on a valve drive assembly and confirming based on the reading that a rotary valve on the cartridge is not in an operational configuration prematurely. The accepting a cartridge step can further include engaging a rotary valve on the cartridge with a valve drive assembly and rotating the rotary valve into an operational configuration. Rotating the rotary valve in an operational configuration can place a rotary valve gasket into contact with a stator on the cartridge. The step of accepting a cartridge can further include moving a moving bracket assembly for engaging the cartridge with a door support assembly, a pneumatic interface, and a thermal clamp assembly. The moving step can be a single continuous movement. The step of accepting a cartridge can further include moving a frangible seal block having a plurality of frangible seal pins into position to engage one or more frangible seals on the cartridge. Moving the frangible seal block can simultaneously engage the plurality of frangible seal pins with the one or more frangible seals on the cartridge. Moving the frangible seal block sequentially can engage the plurality of frangible seal pins with the one or more frangible seals on the cartridge. The step of moving a frangible seal block can be performed after performing the step of moving a moving bracket assembly. The step of moving a frangible seal block can be performed initially with the moving bracket assembly and ends in a position separate from the clamp block. The step of accepting a cartridge can further include moving a clamp block and a frangible seal block together for engaging the cartridge. The method of testing a sample can further include moving the clamp block together with the frangible seal block until the cartridge is engaged with a door support assembly, a pneumatic interface, and a thermal clamp assembly. The method of testing a sample can further include only driving the frangible seal block assembly to engage one of more frangible seals on the cartridge simultaneously or sequentially.

In mixing the sample with the at least one lysis agent, the lysis agent can be a mechanical agent. The mechanical agent can be ceramic beads, glass beads or steel beads, and the mixing the sample step can include rotating the stir bar at at least 1000 rpm. The method of testing a sample can further include mixing the sample including rotating the stir bar or the ceramic, glass or steel beads along with a chemical lysis agent. The suspected pathogen can be a gram-positive bacteria, a fungus or a plant cell. In the mixing the sample with the at least one lysis agent step, the at least one lysis agent can be a chemical lysis agent. The one or more target pathogens can be a virus or a gram-negative bacterium and the chemical lysis reagent is a chaotropic agent. Prior to passing the lysed sample through the porous solid support, the method can further include passing the lysed sample through a size-exclusion filter, wherein nucleic acid passes through the filter. The enriched nucleic acid can be combined with one or more amplification reagents before the distributing step. The one or more amplification reagents can be selected from the group consisting of a DNA polymerase, a reverse transcriptase, a helicase, nucleotide triphosphates (NTPs), a magnesium salt, a potassium salt, an ammonium salt, and a buffer. The one or more amplification reagents can further include a primer. Isothermal amplification can be initiated prior to distributing the enriched nucleic acid to the two or more assay chambers. After the distributing step, but prior to performing the isothermal amplification reaction, the method can further include combining the enriched nucleic acid with a primer set specific to one of the one or more target pathogens. A first assay chamber can contain a primer set specific to a first nucleic acid sequence. The first nucleic acid sequence can be present in one of the one or more target pathogens. Prior to mixing the sample with at least one lysis agent, a process control can be added to the sample and the first nucleic acid sequence is present in the process control. Prior to passing lysed sample through the porous solid support, a process control can be added to the lysed sample and the first nucleic acid sequence is present in the process control. A second assay chamber can contain a primer set specific to a second nucleic acid sequent, wherein the second nucleic acid sequence is present in one of the one or more target pathogens. The performing an isothermal amplification reaction step can be completed in less than 20 minutes. The performing an isothermal amplification reaction step can be completed in less than 15 minutes. The performing an isothermal amplification reaction step can be completed in less than 10 minutes.

The method of testing a sample can further include providing a result containing a determination made during the performing step relating to the presence, the absence or the quantity of the target pathogen in the sample suspected of containing the target pathogen. The method can further include, prior to advancing the sample to a lysis chamber, pretreating the sample with a chemical reaction. The sample can be sputum and the chemical reaction is incubation with a mucolytic agent. The mucolytic agent can be dithiothreitol or n-acetylcysteine. The method can further include, prior to advancing the sample to a lysis chamber, pretreating the sample with an enzymatic reaction. The enzymatic reaction can be incubation of the sample with a nuclease, a protease, an amylase, a glycosylase, or a lipase. Pretreating can include incubating the sample with a DNase. Pretreating can include incubating the sample with a protease. The protease can be selected from pronase, chymotrypsin, trypsin and pepsin. The method can further include, prior to advancing the sample to a lysis chamber, pretreating the sample with a physical treatment. The physical treatment can include passing the sample through a size-exclusion filter in a first direction. The target pathogen can pass through the filter. The target pathogen may or may not pass through the filter and is thereby captured on a fill port side of the size-exclusion filter. The method of testing can further include passing a volume of suspension buffer through the size-exclusion filter in a second direction. The second direction can be opposite the first direction, thereby releasing the target pathogen from the fill port side of the filter. The volume of suspension buffer can be less than the volume of the sample, and the target pathogen can be more concentrated than in the loaded sample. The physical treatment can include exposing the sample to a capture agent immobilized on a solid substrate. The method of testing a sample can further include, after exposure, separating the solid substrate from the sample. The capture agent can be a capture antibody. The capture agent can be an antibody with affinity for red blood cells. The solid substrate can be a magnetic bead. The capture agents can have affinity for a class of cells including the one or more target pathogens and the method can further include (1) incubating the magnetic beads with the sample, (2) engaging a magnet to draw the magnetic beads to a location within the sample loading structure, (3) washing away unbound sample, (4) releasing the magnet, and (5) re-suspending the magnetic beads and passing the suspension, including target pathogen bound to the magnetic beads, to the lysis chamber.

The sample can be sputum and the method can further include, prior to mixing the sample with the at least one lysis reagent, bead beating the sputum to liquefy the sample. The bead beating can include mixing the sputum with ceramic, glass, or steel beads. The bead beating can include mixing the sputum with ceramic, glass, or steel beads and dithiothreitol. Prior to distributing the enriched nucleic acid to the assay chambers, the method can further include passing the enriched nucleic acid through a second porous solid support. The second porous solid support can be the same as the first porous solid support. The enriched nucleic acid can be mixed with a matrix binding agent prior to passing through the second solid support. Matrix binding agent can be an alcohol or a salt solution. The second porous solid support can be different than the first porous solid support, and the second solid support can have an affinity for nucleic acid and the method can further releasing the captured nucleic acid from the second solid support to generate a twice-enriched nucleic acid. The second porous solid support can be different than the first porous solid support. Prior to passing the lysed sample through a first porous solid support, the method can further include passing the lysed sample through a second porous solid support. The second solid support does not bind nucleic acid and can have affinity for one or more contaminants, thereby removing contaminant from the lysed sample.

The method of testing a sample can further include releasing the cartridge from engagement with a clamp block and a frangible seal block after completing the performing an isothermal amplification reaction step. The method of testing a sample can further include displaying a result produced after the step of performing an isothermal amplification reaction step. The method of testing a sample can further include storing in a computer memory a result produced after the step of performing an isothermal amplification reaction step. The method of testing a sample can further include maintaining the cartridge in a vertical orientation while performing the steps of testing a sample. The cartridge can be inclined no more than 30 degrees while in the vertical orientation. The cartridge can be inclined no more than 15 degrees while in the vertical orientation.

The method of testing a sample can further include moving a heat staker assembly into contact with the cartridge after performing the step of isolating each one of the two or more assay chambers from each one of all the other two or more assay chambers. The method of testing a sample can further include providing a pneumatic pressure in the cartridge while moving the heat staker assembly into contact with the cartridge. The method of testing a sample can further include forming a heat stake region in the cartridge after performing the step of isolating each one of the two or more assay chambers from each one of all the other two or more assay chambers. The method of testing can further include obtaining a first image of a level of fluid in each of the one or more assay chambers after the step of isolating each one of the two or more assay chambers from each one of all the other two or more assay chambers and before a step of forming a heat stake region on the cartridge and obtaining a second image of a level of fluid in each of the one or more assay chambers after a step of forming a heat stake region is formed. The method of testing a sample can further include determining the quality of the heat stake by comparing the level of fluid in the first image to the level of fluid in the second image. The method of testing a sample can further include rotating a rotary valve on the cartridge prior to performing the advancing the sample step. The method of testing a sample can further include advancing the sample to the lysis chamber using a pneumatic signal introduced into the rotary valve. The method of testing a sample can further include rotating a rotary valve on the cartridge prior to performing the step of passing the lysed sample through a first porous solid support to capture a nucleic acid on the porous solid support. The method of testing a sample can further include passing the lysed sample through the first porous solid support using a pneumatic signal introduced into the rotary valve. The method of testing a sample can further include distributing the enriched nucleic acid to two or more assay chambers using a rotary valve on the cartridge and a pneumatic signal introduced into the rotary valve.

In general, in one embodiment, an integrated diagnostic cartridge includes a loading module, a lysis module, a purification module, and a reaction module. The loading module is in fluidic communication with the lysis module and the purification module is in fluidic communication with the reaction module. Further, the loading module, the lysis module, the purification module and the reaction module are arranged for use while the cartridge is in a vertical orientation.

This and other embodiments can include one or more of the following features. The integrated diagnostic cartridge can further include one or more fluid filling conduits arranged to flow into an upper portion of a vertically oriented chamber within a fluidic card of the integrated diagnostics cartridge and one or more fluid outlet conduits arranged to flow out of a lower portion of the vertically oriented chamber within the fluidic card of the integrated diagnostics cartridge. The vertically oriented chamber can further include a filter assembly in fluid communication with a fluid outlet conduit of the vertically oriented chamber. The lysis module can include a mixing assembly having a vertically oriented lysis chamber containing a lysis agent and a non-magnetized stir bar. The non-magnetized stir bar can be made from a metal having a magnetic permeability to be responsive to a rotating magnetic field induced between a drive magnetic element and a driven magnetic element of a magnetic drive system. The non-magnetized stir bar can be coated with an impermeable material to prevent corrosion by a chemical lysis buffer in the vertically oriented lysis chamber. When in use within a diagnostic instrument, the non-magnetized stir bar can be disposed between a driving magnet system and a driven magnet system of a magnetic mixing assembly in the diagnostic instrument. The driving magnet system can be configured to rotate the non-magnetized stir bar within the vertically oriented lysis chamber at least 1000 rpm. The integrated diagnostic cartridge can further include a fluid inlet to the vertically oriented lysis chamber and a fluid outlet to lysis chamber wherein the vertically oriented lysis chamber can be isolated from the other modules on the cartridge by a first frangible seal in fluid communication with the fluid inlet to the vertically oriented lysis chamber and a second frangible seal in fluid communication with the fluid outlet to the vertically oriented lysis chamber. The integrated diagnostic cartridge can further include a fluidic card and a cover. The fluidic card can further include a first film adhered to a surface of at least a portion of the fluidic card, wherein the first film forms one surface of one or more chambers, compartments, or fluid conduits of the loading module, the lysis module, the purification module and the reaction module. The integrated diagnostic cartridge can further include an interference feature on the cover, wherein the interference feature can be sized and positioned to interact with one of an upper rail or a lower rail of a loading apparatus of a diagnostic instrument. A thickness of the fluidic card can be selected for sliding arrangement within an upper rail and a lower rail of a loading apparatus of the diagnostic instrument. A total sample process volume of the integrated diagnostic cartridge can be related to a thickness of the cartridge corresponding to a spacing between the one or more chambers, compartments, or fluid conduits of the loading module, the lysis module, the purification module and the reaction module formed in the fluidic card and the first film. A diagnostic instrument can be adapted and configured to accommodate a variation of the thickness of the cartridge by increasing a width of a loading slot of the diagnostic instrument to accommodate the increased thickness of the cartridge or a displacement range of a cartridge clamping system of the diagnostic instrument is adapted to accommodate the increased thickness of the cartridge. The integrated diagnostic cartridge can further include a cartridge front face and a cartridge rear face forming an upper spacing and a lower spacing wherein each of the upper spacing and the lower spacing can be sized and positioned to engage with the upper rail and lower rail of the diagnostic instrument. The integrated diagnostic cartridge can further include an interference feature within the upper spacing or the lower spacing positioned to ensure the cartridge engages with the upper rail and the lower rail in a desired orientation. The integrated diagnostic cartridge can further include a plurality of frangible seal chambers in fluid communication with at least one or more of the loading module, the lysis module, the purification module or the reaction module. The integrated diagnostic cartridge can further include a machine-readable code adapted and configured to identify the cartridge to a diagnostic instrument or an image of a patient identification marking.

In general, in one embodiment, an integrated diagnostic cartridge includes a loading module, a lysis module, a purification module including a rotary valve and a reaction module. The loading module, the lysis module, the purification module and the reaction module are arranged for use while the cartridge is in a vertical orientation. The purification module including a rotary valve includes (a) a stator including a stator face and a plurality of passages, each passage including a port at the stator face; (b) a rotor operably connected to the stator and including a rotational axis, a rotor valving face, and a flow channel having an inlet and an outlet at the rotor valving face, wherein the flow channel includes a porous solid support; and (c) a retention element biasing the stator and the rotor together at a rotor-stator interface to form a fluid tight seal.

This and other embodiments can include one or more of the following features. The rotary valve can further include a gasket between the stator face and the rotor valving face.

The stator can include a displaceable spacer for preventing the gasket from sealing against at least one of the rotor and stator. When the spacer is displaced, the gasket can seal the rotor and stator together in a fluid-tight manner. When the cartridge is positioned within a diagnostic instrument, engagement with a valve drive assembly of the diagnostic instrument can displace the spacer and seal the rotor and stator together in a fluid-tight manner. The purification module can further include a waste collection element, a wash buffer reservoir and an elution buffer reservoir. The integrated diagnostic cartridge can further include a pneumatic interface in fluidic communication with at least the purification module.

In general, in one embodiment, an integrated diagnostic cartridge includes a loading module, a lysis module, a purification module, and a reaction module. The reaction includes a plurality of individual assay chambers, wherein at least one surface in each one of the plurality of individual assay chambers assay chambers is provided by a plug including a body with a bottom surface, a central opening in the body; and a dried reagent on the bottom surface. The body is formed from a material transmissive to excitation wavelengths and emission wavelengths in at least one of a red spectrum, a blue spectrum and a green spectrum. The loading module, the lysis module, the purification module and the reaction module are arranged for use while the cartridge is in a vertical orientation.

This and other embodiments can include one or more of the following features. The integrated diagnostic cartridge of claim 24, wherein the bottom surface of the plug body comprises a cavity in the bottom surface with the dried reagent within the cavity, and wherein the plug has a plug thickness between a central opening bottom and the plug body bottom, and further wherein a depth of the cavity is less than 90% of the plug thickness, is less than 70% of the plug thickness or is less than 50% of the plug thickness. The plug can have a polished or smooth finish facilitating the transmissivity of the excitation wavelengths and the emission wavelengths. The dried reagent can be selected from the group consisting of nucleic acid synthesis reagents, nucleic acids, nucleotides, nucleobases, nucleosides, monomers, detection reagents, catalysts or combinations thereof. The body of the plug can protrude into the monolithic substrate of the assay chamber at a depth such that the assay chamber volume can be readily changed by altering the depth at which the body of the plug protrudes into the monolithic substrate of the assay chamber. The integrated diagnostic cartridge can further include at least one fluid inlet conduit to each one of the plurality of individual assay chambers of the reaction module wherein each one of the at least one fluid inlet conduits further includes a heat staked region. A heat stake in the heat staked region can fluidically isolate the reaction module from the loading module, the lysis module, and the purification module.

In general, in one embodiment, a method of testing a sample suspected of containing one or more target pathogens includes accepting a cartridge having a sample port assembly containing the sample suspected of containing the one or more target pathogens, advancing the sample suspected of containing the one or more target pathogens to a lysis chamber having at least one lysis reagent therein, mixing the sample with the at least one lysis agent to generate a lysed sample, passing the lysed sample through a first porous solid support to capture a nucleic acid on the porous solid support, releasing the captured nucleic acid from the first porous solid support to generate an enriched nucleic acid, distributing the enriched nucleic acid to two or more assay chambers, combining the enriched nucleic acid with one or more amplification reagents, isolating each one of the two or more assay chambers from each one of all the other two or more assay chambers, and performing an isothermal amplification reaction within each one of the two or more assay chambers while simultaneously detecting amplification product, wherein presence of an amplification product is an indication of a presence, an absence or a quantity of the target pathogen in the sample suspected of containing the target pathogen.

This and other embodiments can include one or more of the following features. In mixing the sample with the at least one lysis agent, the lysis agent can be a mechanical agent. The mechanical agent can be ceramic beads, glass beads or steel beads, and the mixing the sample step can include rotating a stir bar within the lysis chamber at at least 1000 rpm. Mixing the sample can include rotating the stir bar or the ceramic, glass or steel beads along with a chemical lysis agent. The at least one lysis agent can be a chemical lysis agent. The one or more target pathogens can be a virus or a gram-negative bacterium and the lysis reagent is a chaotropic agent. Prior to passing the lysed sample through the porous solid support, the method can further include passing the lysed sample through a size-exclusion filter, wherein nucleic acid passes through the filter. The enriched nucleic acid can be combined with one or more amplification reagents before the distributing step. The one or more amplification reagents can include a primer. The performing of the isothermal amplification reaction step can be initiated prior to the distributing the enriched nucleic acid to the two or more assay chambers step. After the distributing step, but prior to performing the isothermal amplification reaction step, the method can further include combining the enriched nucleic acid with a primer set specific to one of the one or more target pathogens. A first assay chamber can contain a primer set specific to a first nucleic acid sequence. The first nucleic acid sequence can be present in one of the one or more target pathogens. Prior to mixing the sample with at least one lysis agent, a process control can be added to the sample and the first nucleic acid sequence is present in the process control. Prior to passing lysed sample through the porous solid support, a process control can be added to the lysed sample and the first nucleic acid sequence is present in the process control. A second assay chamber can contain a primer set specific to a second nucleic acid sequence. The second nucleic acid sequence can be present in one of the one or more target pathogens. The performing an isothermal amplification reaction step can be completed in less than 15 minutes. The method of testing a sample can further include providing a result containing a determination made during the performing step relating to the presence, the absence or the quantity of the target pathogen in the sample suspected of containing the target pathogen. The method can further include, prior to advancing the sample to a lysis chamber, pretreating the sample with a chemical reaction. The sample can be sputum and the chemical reaction is incubation with a mucolytic agent. The method can further include, prior to advancing the sample to a lysis chamber, pretreating the sample with an enzymatic reaction. The enzymatic reaction can be incubation of the sample with a nuclease, a protease, an amylase, a glycosylase, or a lipase. The method can further include, prior to advancing the sample to a lysis chamber, pretreating the sample with a physical treatment. The physical treatment can include passing the sample through a size-exclusion filter in a first direction. The physical treatment can include exposing the sample to a capture agent immobilized on a solid substrate. The method of testing a sample can further include, after exposure, separating the solid substrate from the sample. The capture agent can be an antibody with affinity for red blood cells. The sample can be sputum and the method can further include, prior to mixing the sample with the at least one lysis reagent, bead beating the sputum to liquify the sample. The bead beating can include mixing the sputum with ceramic, glass, or steel beads. Prior to distributing the enriched nucleic acid to the assay chambers, the method can further include passing the enriched nucleic acid through a second porous solid support.

VI. DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 2A and FIG. 2B depict an integrated diagnostic cartridge, configured to be used in conjunction with a diagnostic instrument, during filling by a user, in accordance with an embodiment.

FIG. 2C depicts an integrated diagnostic cartridge with a loading module sealed after filling is completed and prior to being inserted into a diagnostic instrument, in accordance with an embodiment.

FIG. 3 depicts an integrated diagnostic cartridge being inserted into a diagnostic instrument to perform a diagnostic test, in accordance with an embodiment.

Figure 4B:
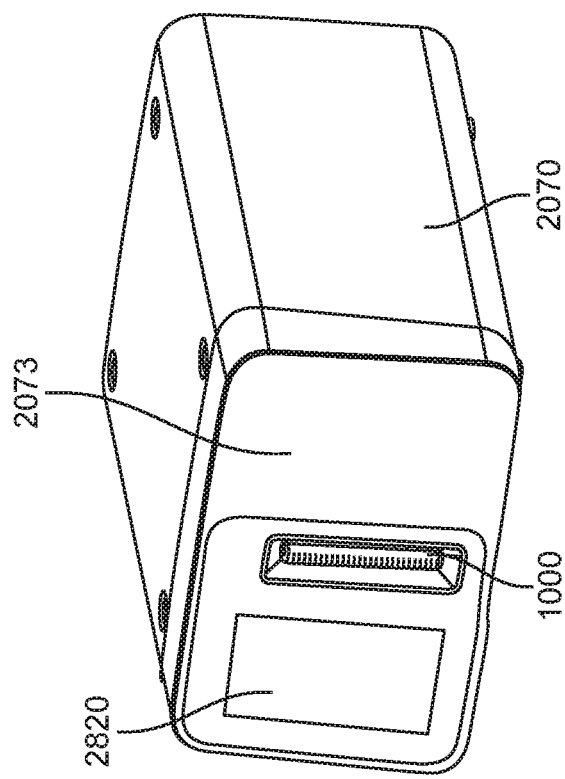
FIG. 4B depicts a diagnostic instrument when running a diagnostic test on an integrated diagnostic cartridge, in accordance with an embodiment.
Figure 4A:
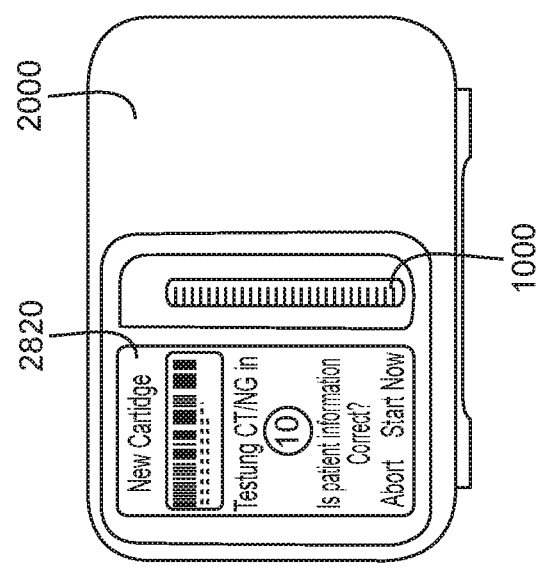
FIG. 4A depicts a diagnostic instrument after an integrated diagnostic cartridge is inserted during initialization of a diagnostic test. The integrated diagnostic instrument is shown having a display configured to show information associated with a diagnostic test run, in accordance with an embodiment.
Figure 16A:
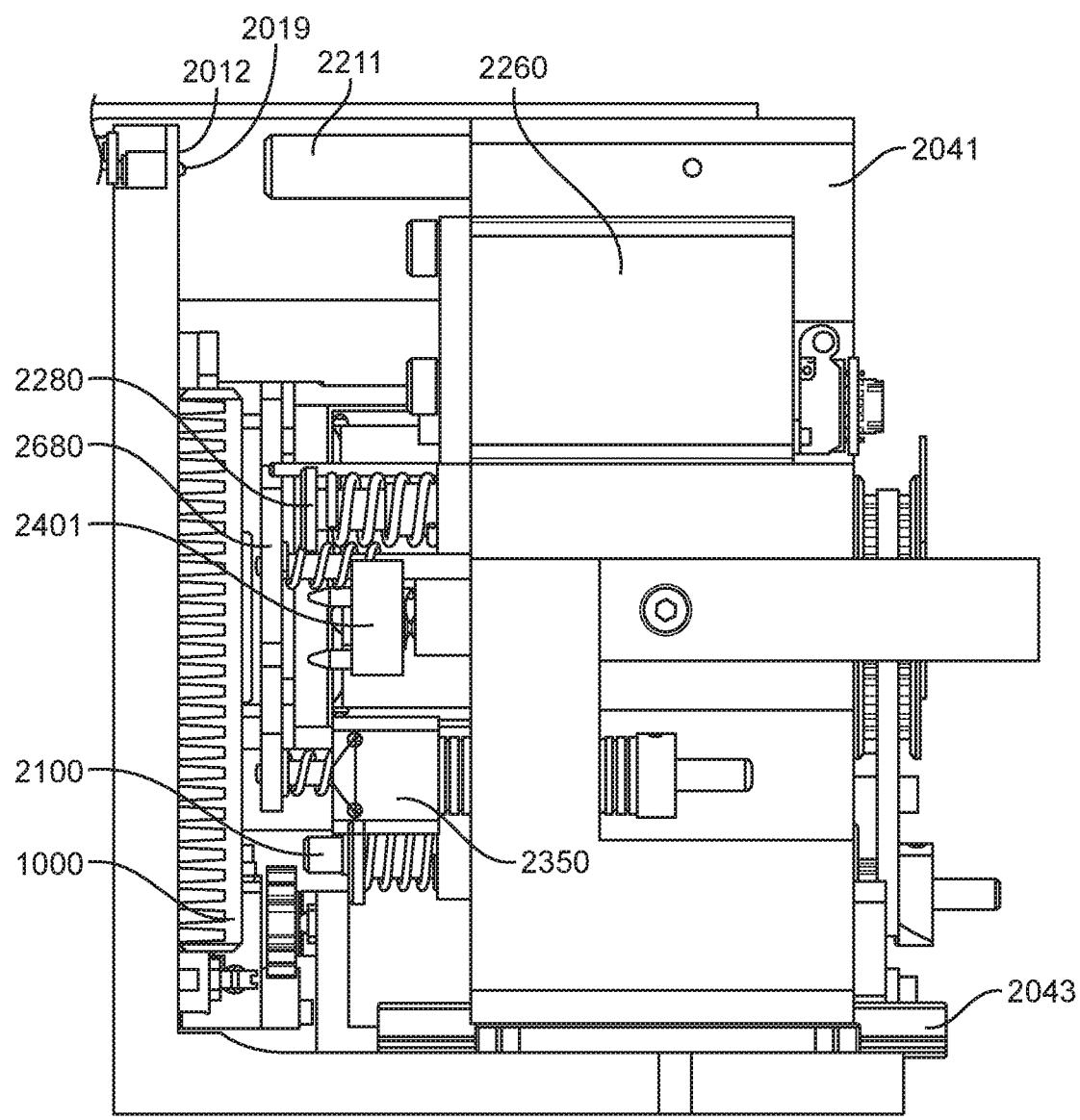
FIG. 16A is a view of a clamping subsystem with an integrated diagnostic cartridge inserted between a fixed bracket assembly and moving bracket assembly taken from the front of a diagnostic instrument, as seen in FIG. 4A. The clamping subsystem is in a zero clamping position.
Figure 16B:
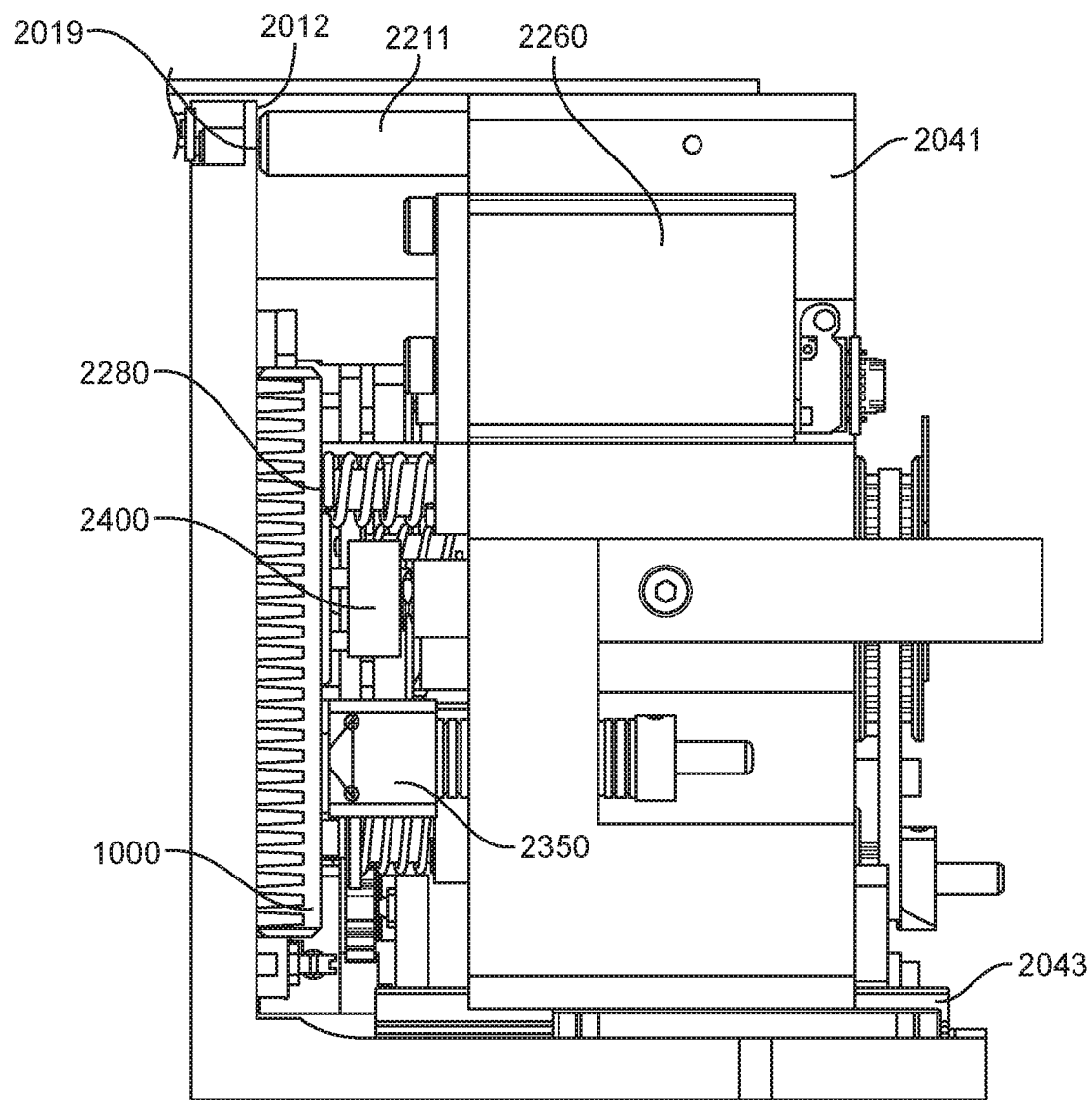

FIG. 16B is a view of a clamping subsystem with an integrated diagnostic cartridge inserted between a fixed bracket assembly and a moving bracket assembly taken from the front of a diagnostic instrument, as seen in FIG. 4A. The clamping subsystem is in a first clamping position with a valve drive assembly and a thermal clamp assembly of the moving bracket assembly contacting the integrated diagnostic cartridge.

Figure 16C:
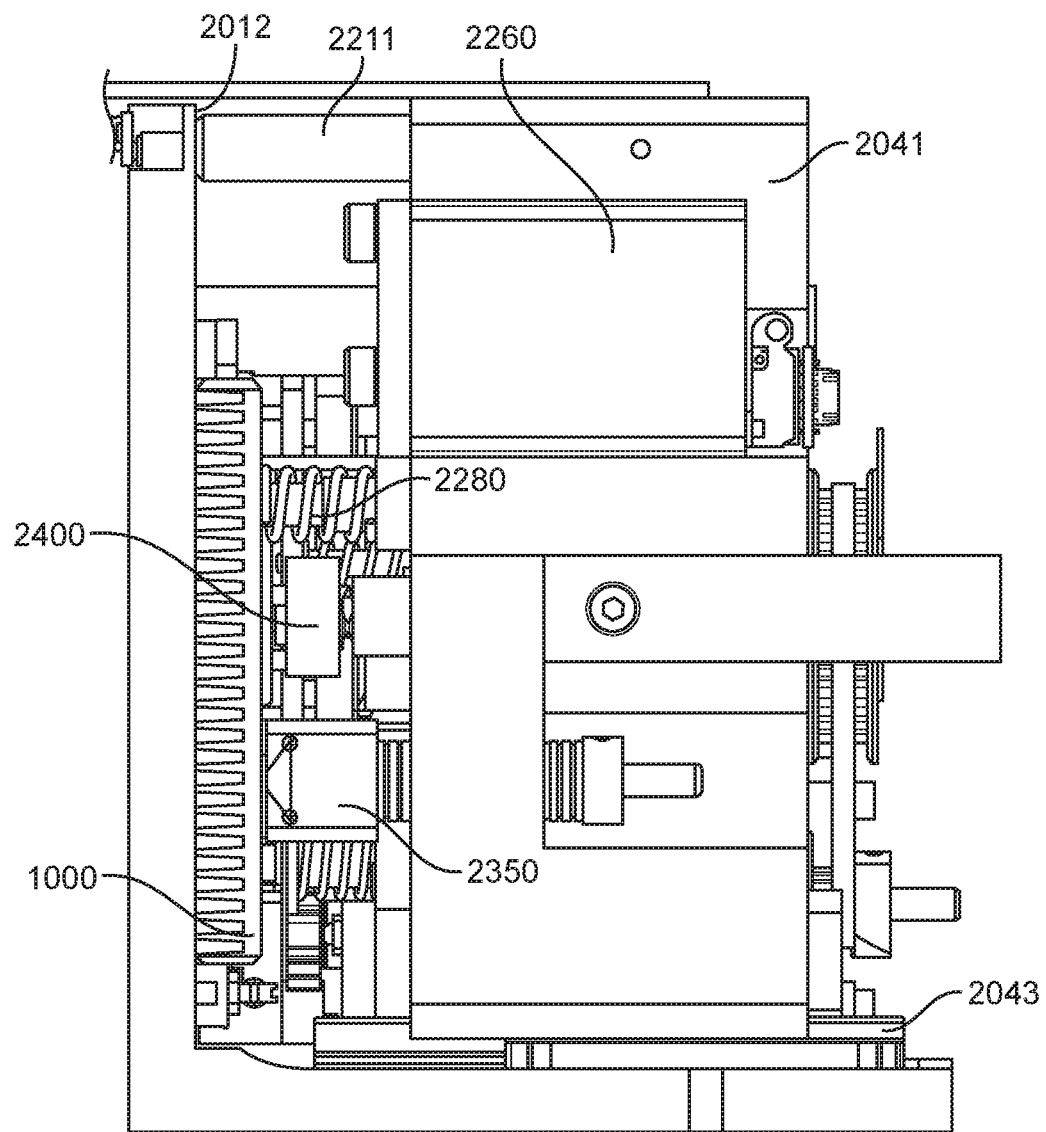

FIG. 16C is a view of a clamping subsystem with an integrated diagnostic cartridge inserted between a fixed bracket assembly and a moving bracket assembly taken from the front of a diagnostic instrument, as seen in FIG. 4A. The clamping subsystem is in a second clamping position to clamp the integrated diagnostic cartridge. A valve drive assembly, a thermal clamp assembly, a door support assembly, and a pneumatic interface of the moving bracket assembly contact the integrated diagnostic cartridge.

Figure 16D:
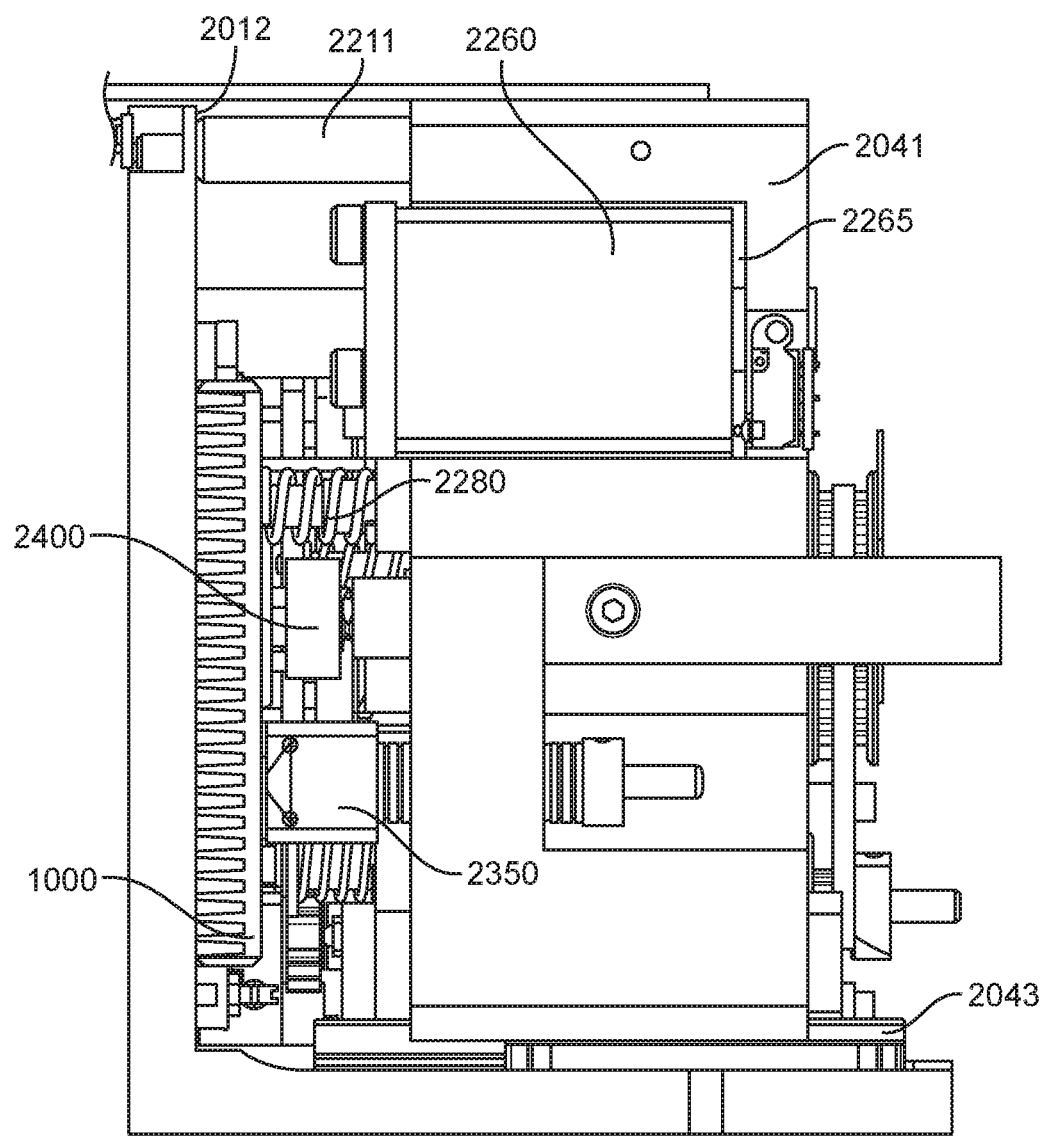

FIG. 16D is a view of a clamping subsystem with an integrated diagnostic cartridge inserted between a fixed bracket assembly and a moving bracket assembly taken from the front of a diagnostic instrument, as seen in FIG. 4A. The clamping subsystem is in a third clamping position to render the integrated diagnostic cartridge fluidically active with a frangible seal block.

Figure 16E:
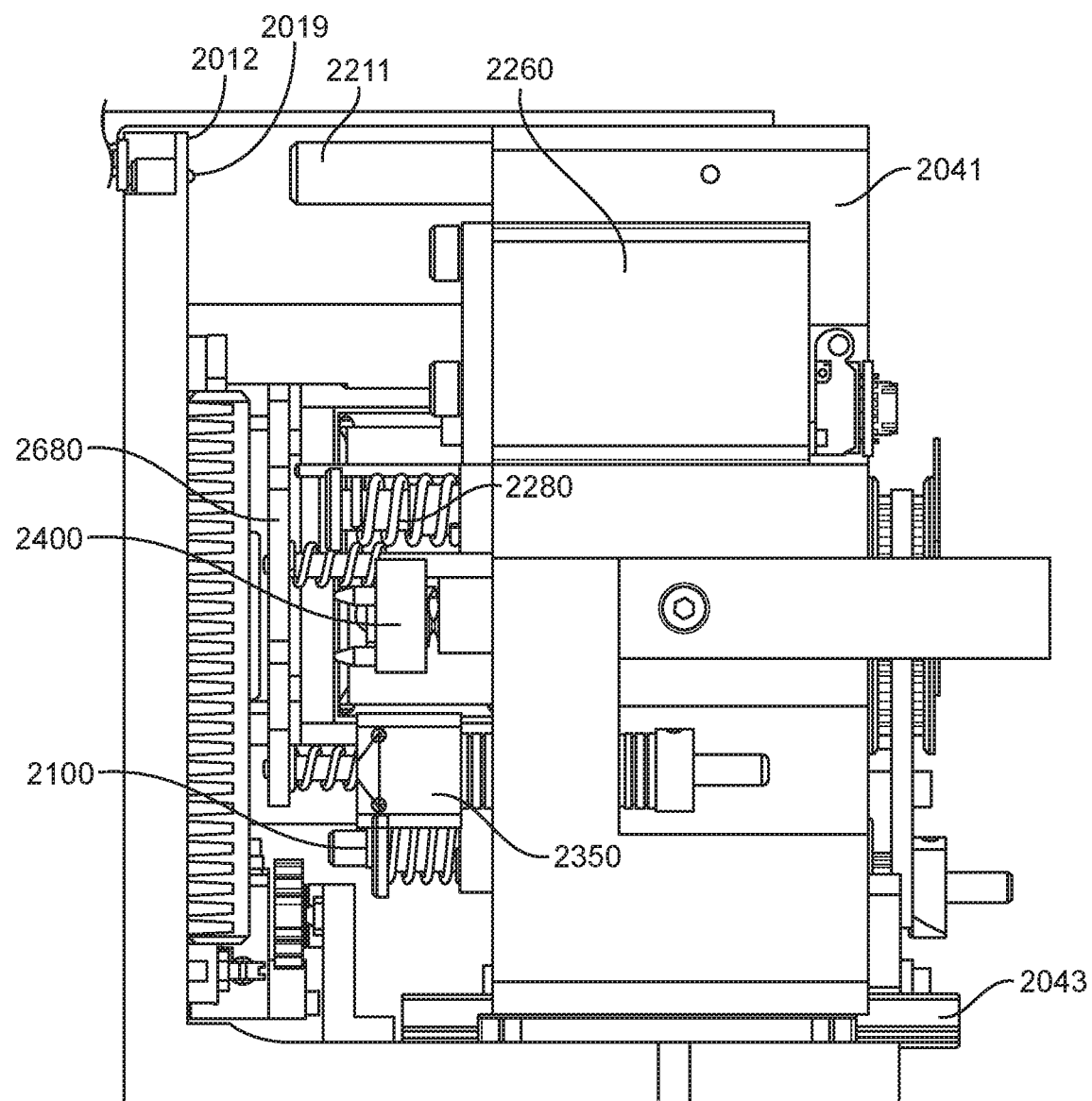

FIG. 16E is a view of a clamping subsystem with an integrated diagnostic cartridge inserted between a fixed bracket assembly and a moving bracket assembly taken from the front of a diagnostic instrument, as seen in FIG. 4A. The clamping subsystem is in a fourth clamping position to unclamp the integrated diagnostic cartridge and eject the integrated diagnostic cartridge from the clamping subsystem.

Figure 17C:
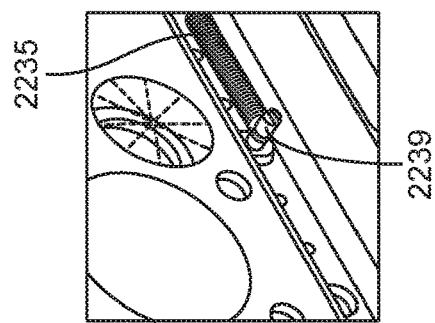
Figure 17B:
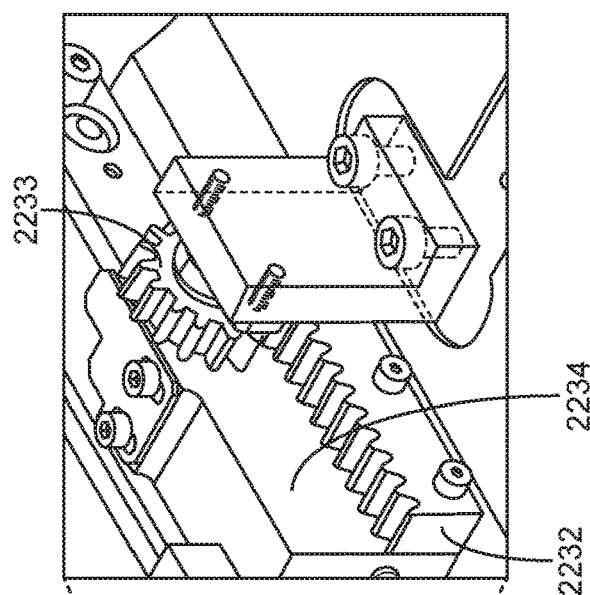
Figure 17A:
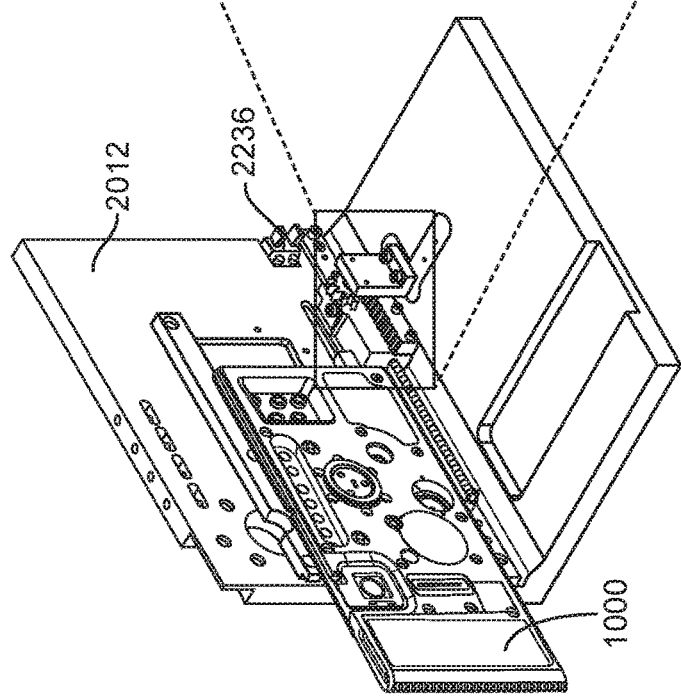

FIG. 17A is a frontal perspective view of a fixed support bracket of a clamping subsystem. The fixed support bracket is shown with a loading assembly for accepting and ejecting an integrated diagnostic cartridge. An integrated diagnostic cartridge is seen in a loading position.

FIG. 17B is an enlarged view of a loading assembly, as shown in FIG. 17A, in a loading position.

FIG. 17C. is an enlarged partial view of a loading assembly, as shown in FIGS. 17A and 17B, depicting a spring which provides a motive force for ejecting an integrated diagnostic cartridge.

Figure 18A:
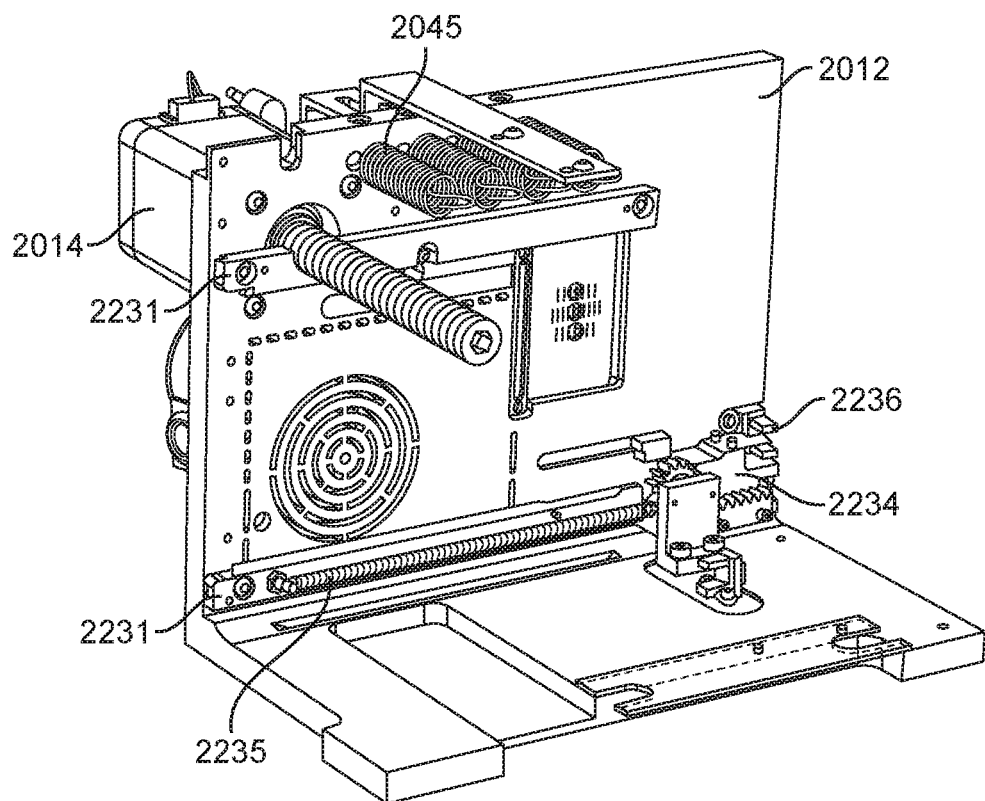

FIG. 18A is another frontal perspective view of a fixed support bracket of a clamping subsystem. The fixed support bracket is shown with a loading assembly from FIG. 17A for accepting and ejecting an integrated diagnostic cartridge. The loading assembly is now shown in a loaded position.

Figure 18B:
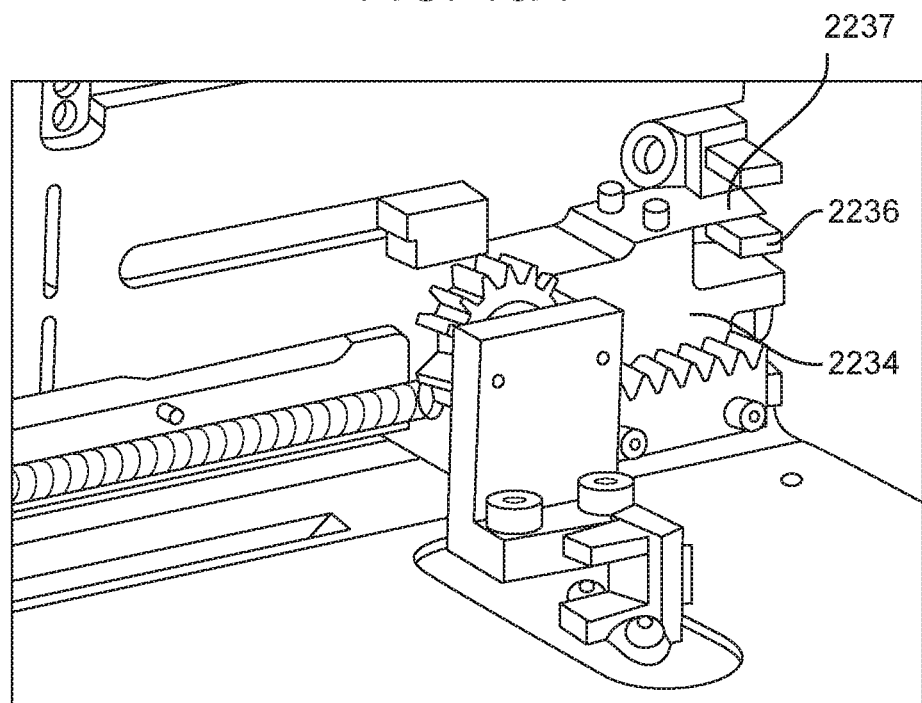

FIG. 18B is an enlarged view of a loading assembly in a loaded position. A load position sensor on the loading assembly is triggered by a flag.

FIG. 19A is a perspective frontal view of a fixed support bracket of a clamping subsystem with an integrated diagnostic cartridge inserted into a loading assembly from FIGS. 17A and 18A. The integrated diagnostic cartridge is in a loaded position.

FIG. 19B is an additional enlarged view of a loading assembly in a loaded position similar to FIG. 18B. A load position sensor on the loading assembly is triggered by a flag.

Figure 19C:
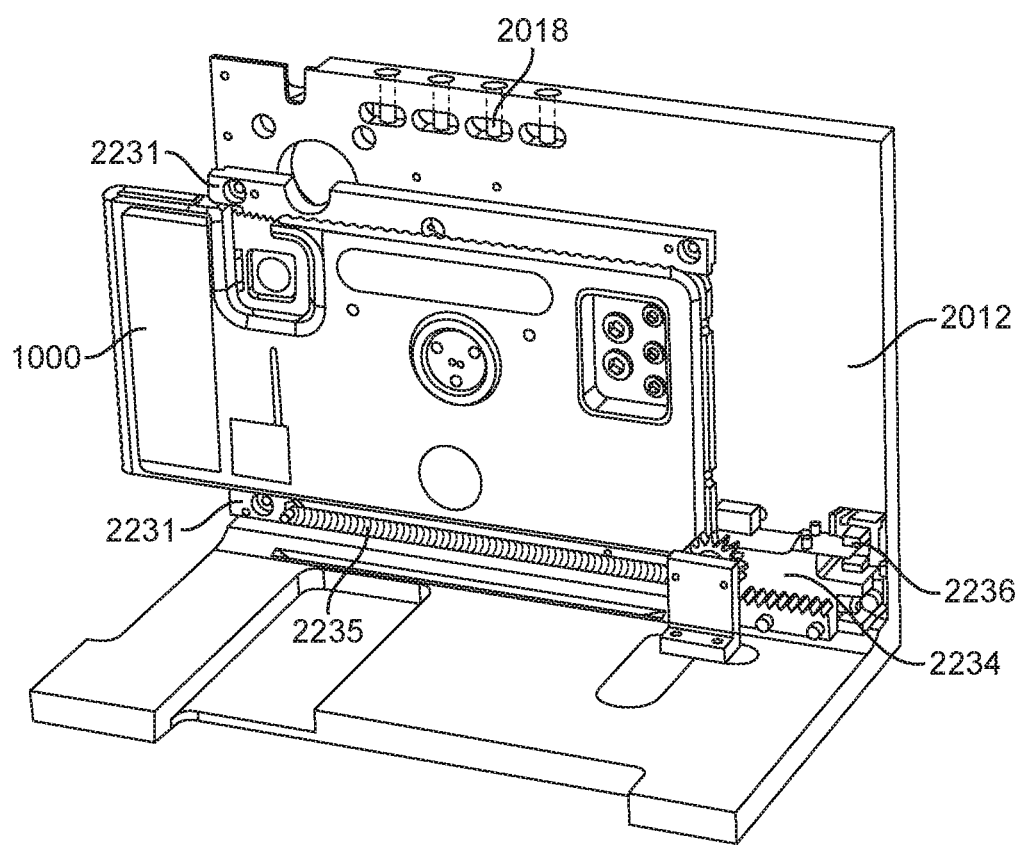

FIG. 19C is an additional frontal view of FIG. 19A with a fixed bracket assembly of a clamping subsystem and an integrated diagnostic cartridge inserted into a loading assembly. The integrated diagnostic cartridge and loaded assembly is shown in a loaded position.

Figure 20:
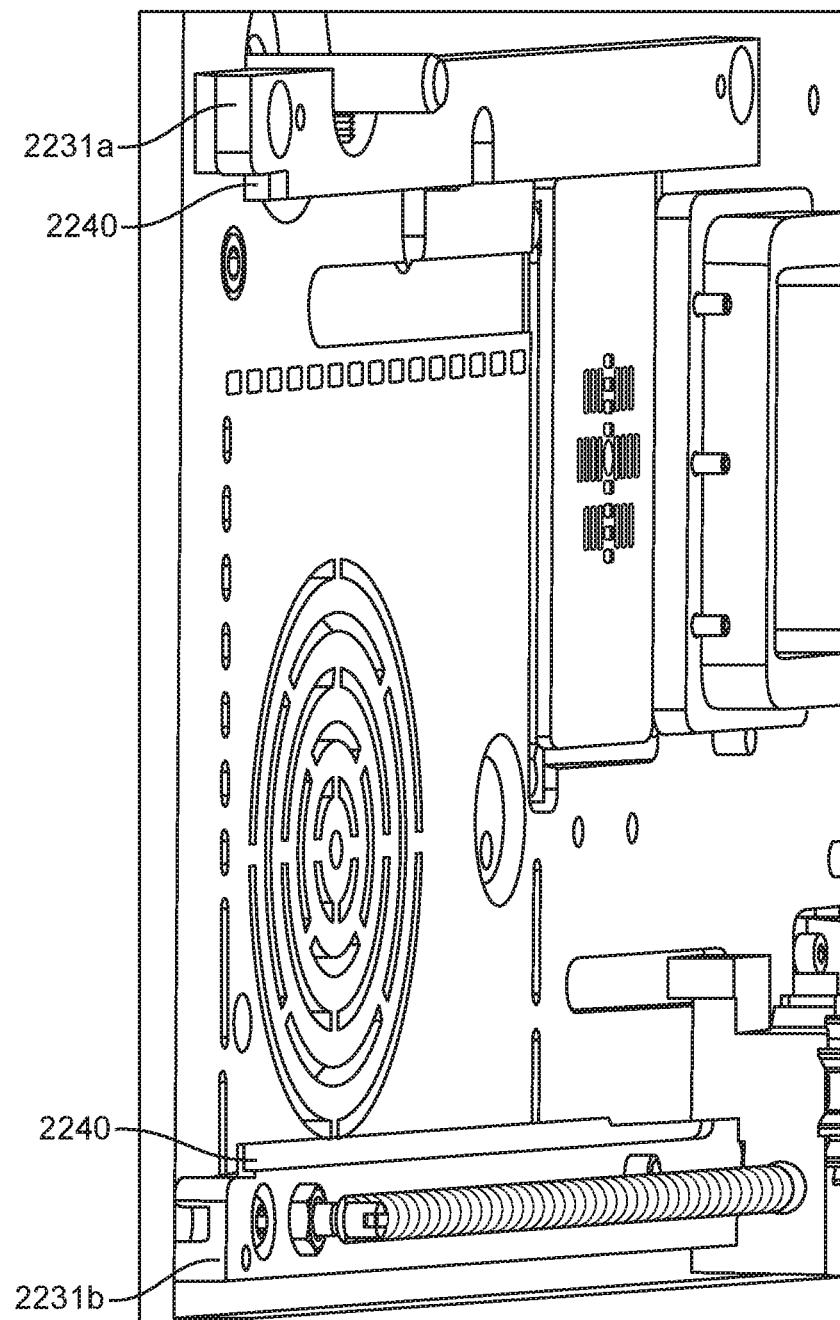

FIG. 20 is a perspective view of loading assembly rails showing guide features extending along the rails.

Figure 21:
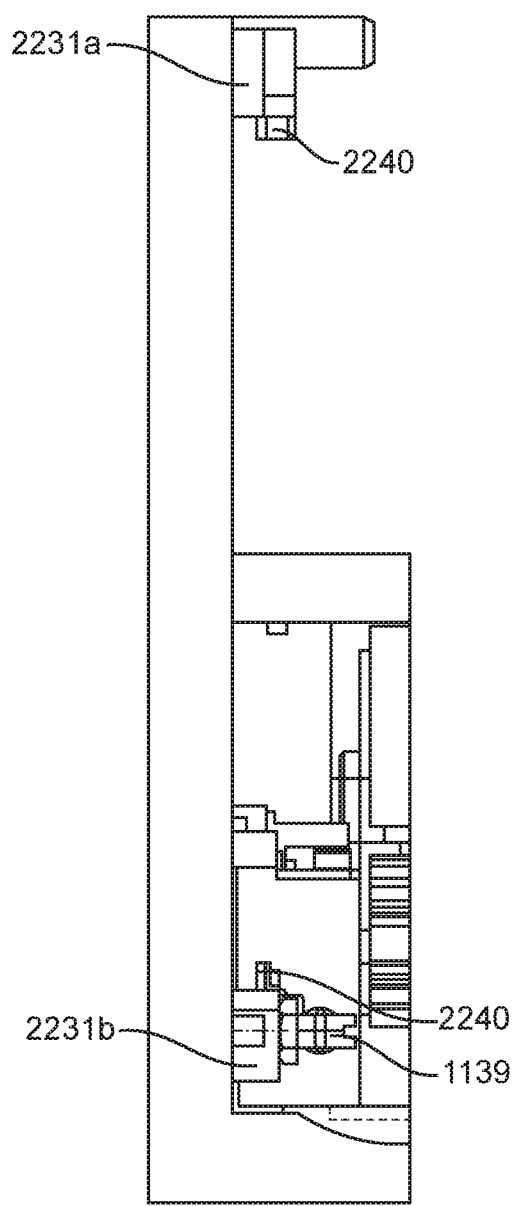

FIG. 21 is an illustration of a loading assembly with rails viewed from the front of a diagnostic instrument, as seen in FIGS. 4A and 16A-16E.

Figure 22B:
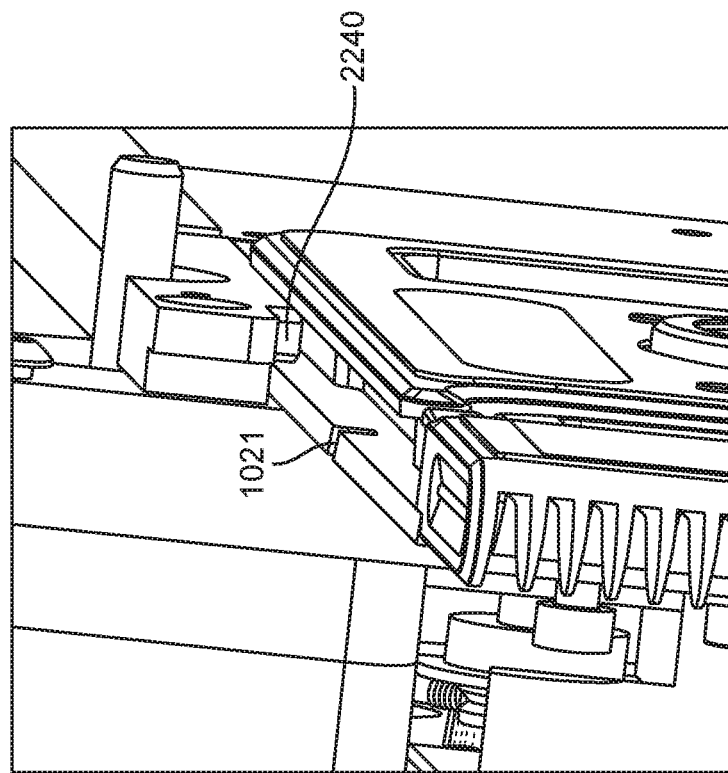
Figure 22A:
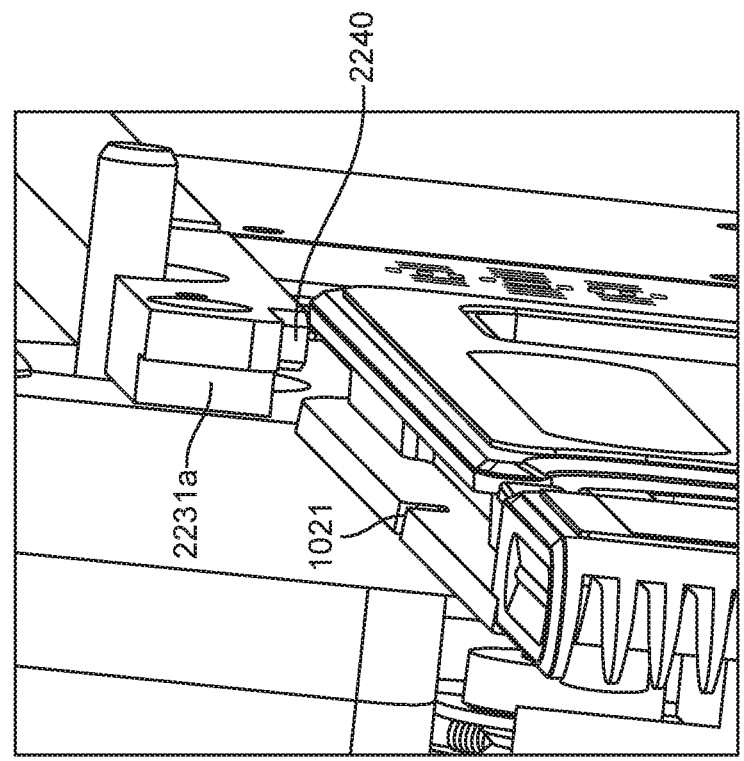

FIG. 22A is a top view of an integrated diagnostic cartridge prior to being loaded into a loading assembly. The integrated diagnostic cartridge is shown with a gap formed between a fluidics card and a cover configured to align with a guide feature on a top rail, as shown in FIGS. 20 and 21.

FIG. 22B is a top view of an integrated diagnostic cartridge during loading into a loading assembly. A guide feature on a top rail is shown inserted between a gap formed between a fluidics card and a cover.

Figure 23B:
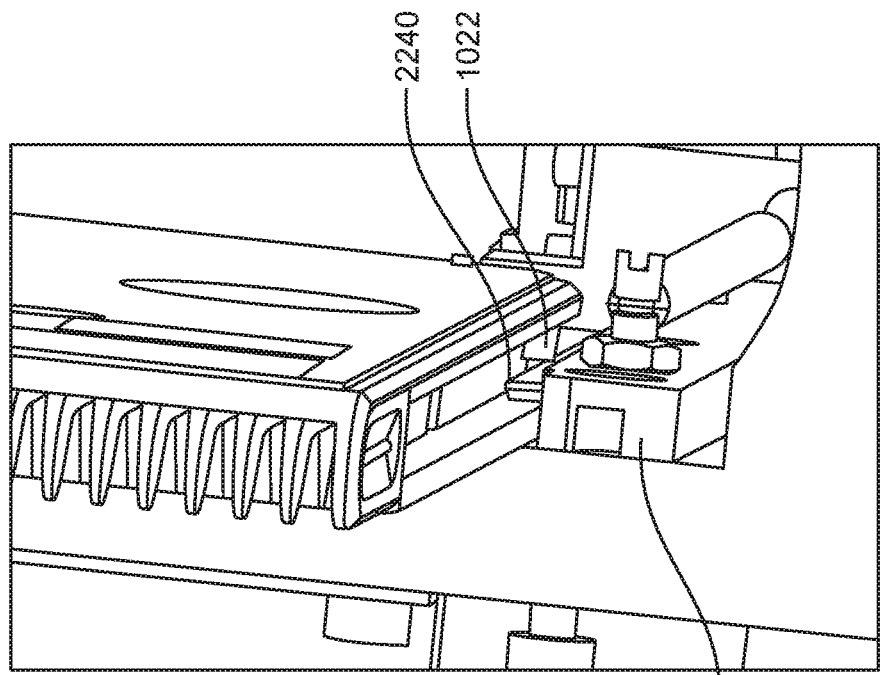
Figure 23A:
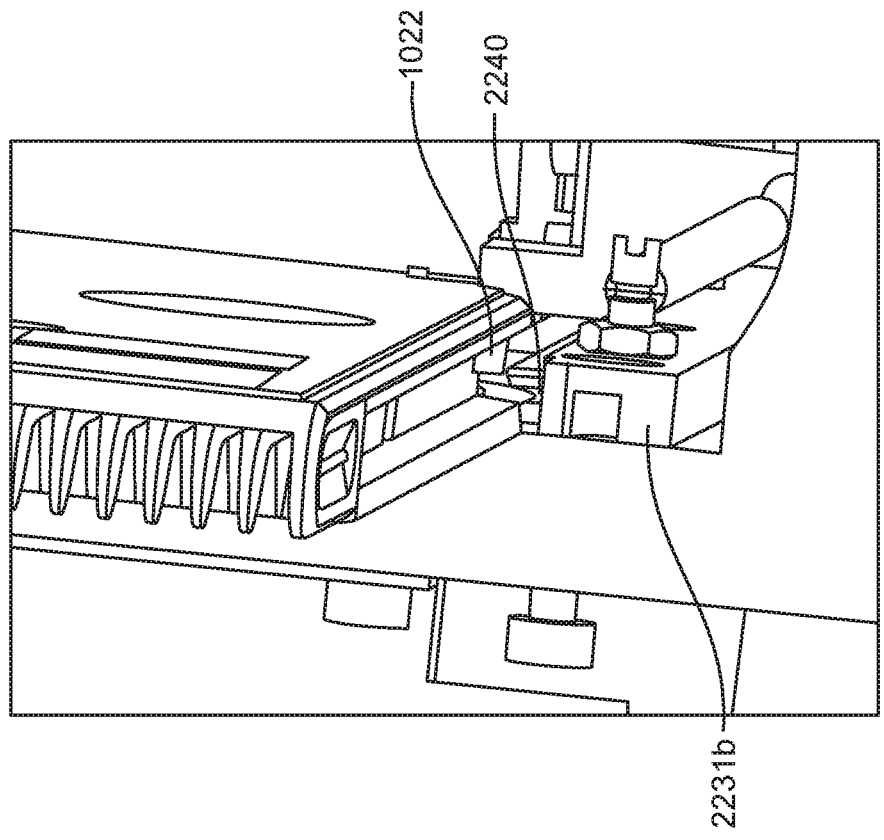

FIG. 23A is a bottom view of an integrated diagnostic cartridge prior to being loaded into a loading assembly. The integrated diagnostic cartridge is shown with a gap formed between a fluidics card and a cover configured to align with a guide feature on a bottom rail, as shown in FIGS. 20 and 21.

FIG. 23B is a bottom view of an integrated diagnostic cartridge during loading into a loading assembly. A guide feature on a bottom rail is shown inserted between a gap formed between a fluidics card and a cover.

Figure 10:
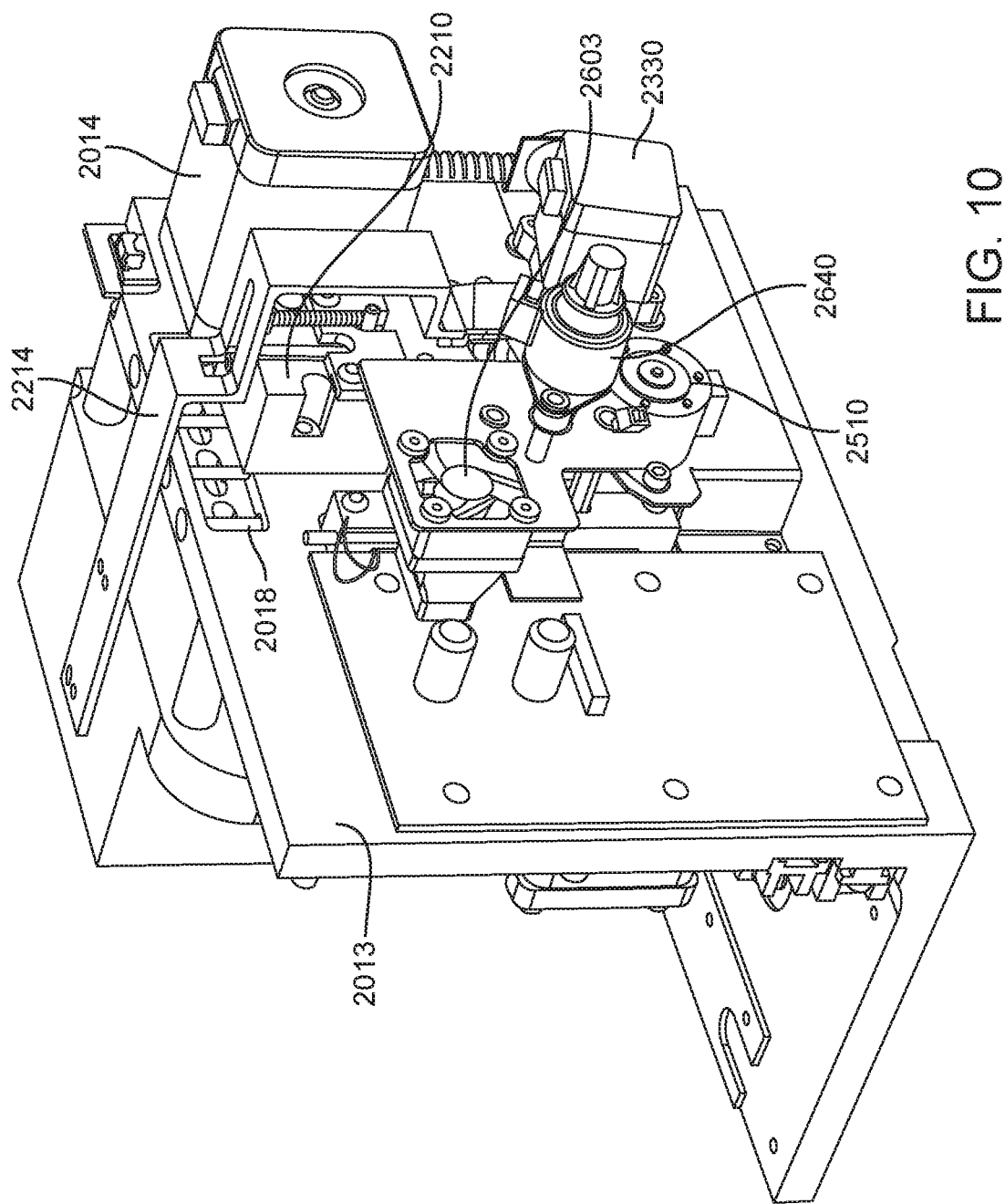
FIG. 10 and FIG. 11 are rear perspective views of a diagnostic instrument clamping subsystem during clamping of an integrated diagnostic cartridge.
Figure 11:
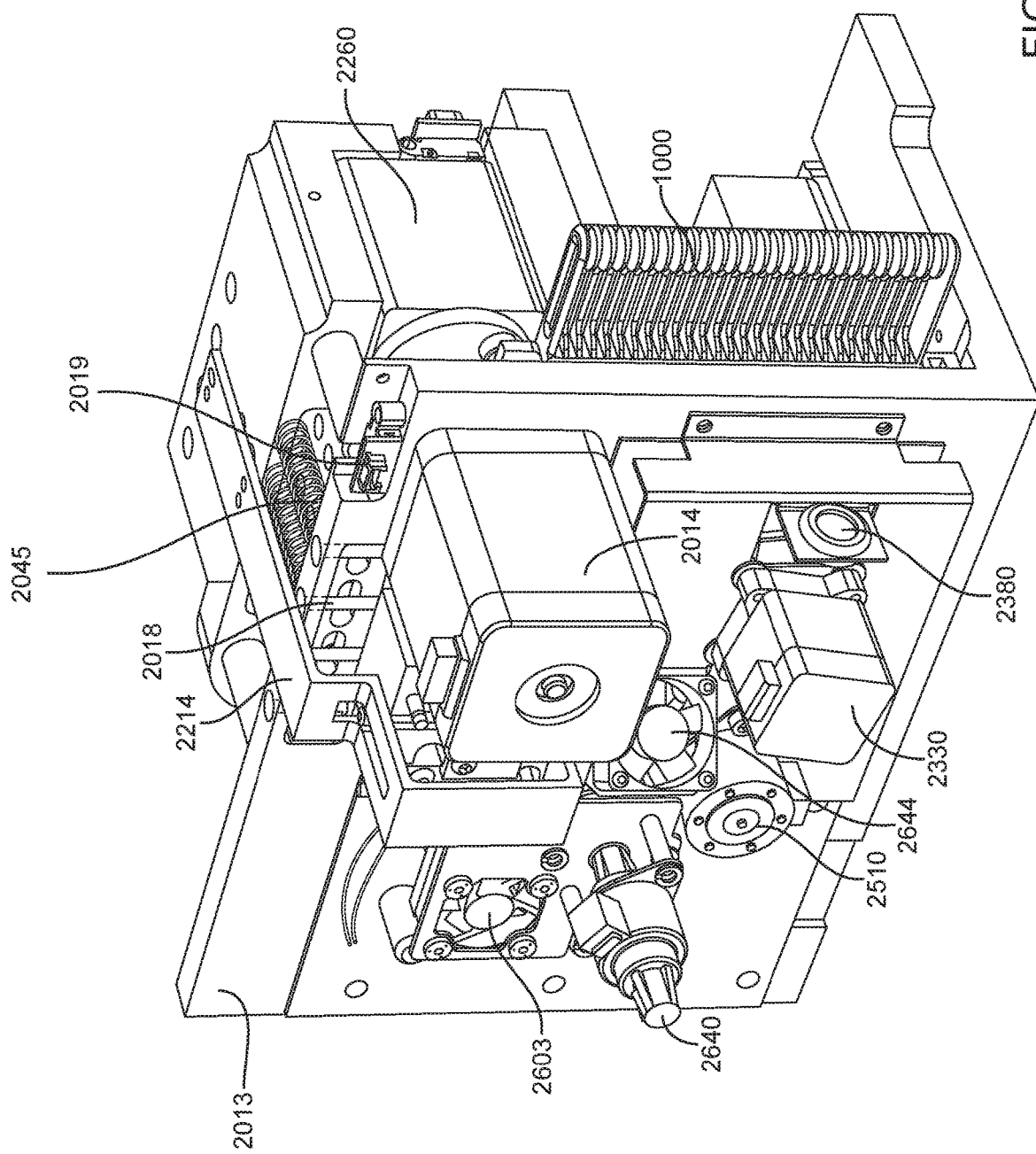
Figure 24:
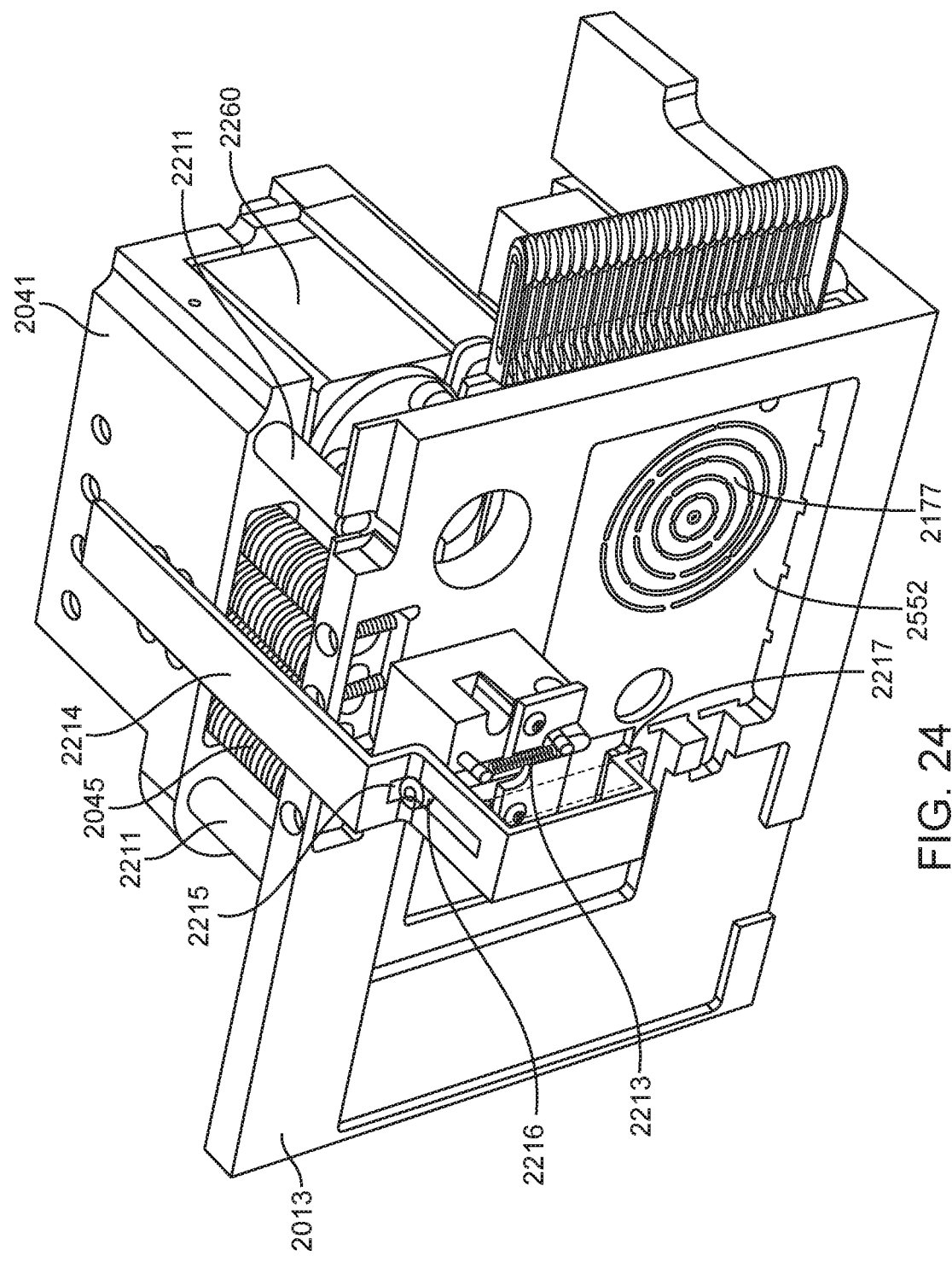

FIG. 24 is a rear perspective view of a latch and pin assembly of a clamping subsystem. An integrated diagnostic cartridge is inserted between a fixed bracket assembly and a moving bracket assembly of the clamping subsystem as shown in FIGS. 10 and 11.

Figure 25B:
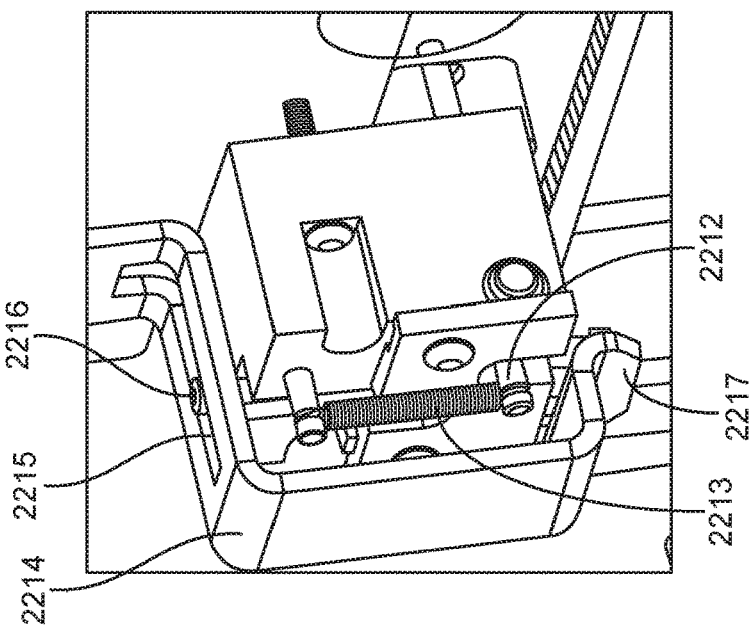
Figure 25A:
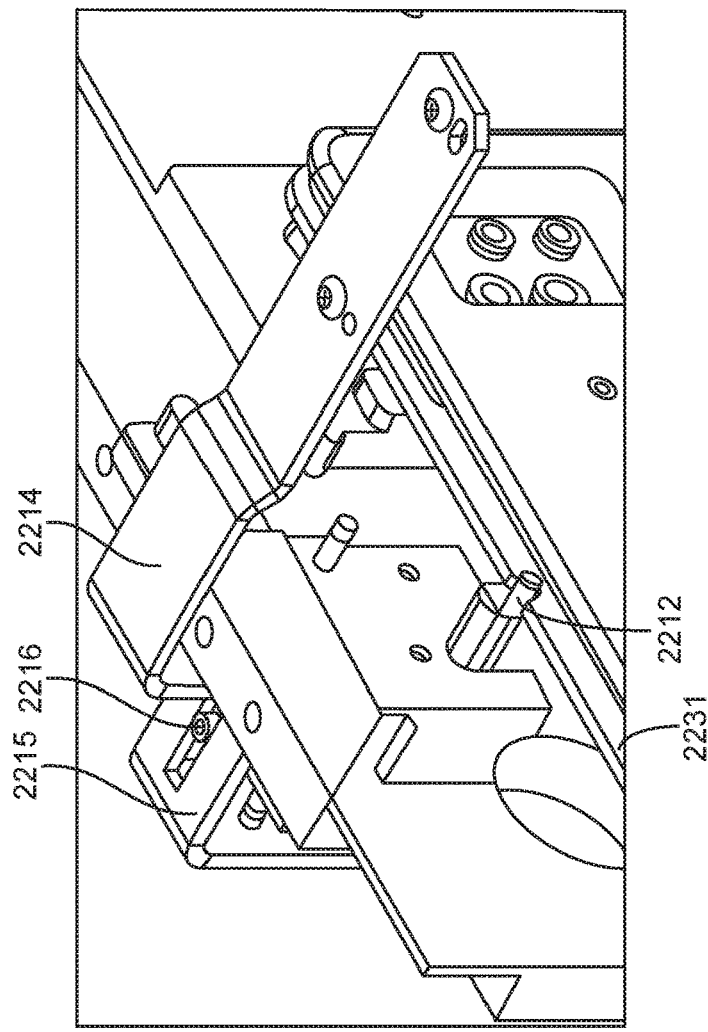

FIG. 25A is a frontal perspective view of a latch and pin assembly of FIG. 24. An integrated diagnostic cartridge is seen inserted and latched. A latch from the latch and pin assembly is shown disposed within a notch of the integrated diagnostic cartridge to prevent the integrated diagnostic cartridge from being ejected.

FIG. 25B is an enlarged view of the latch and pin assembly of FIG. 24.

Figure 25C:
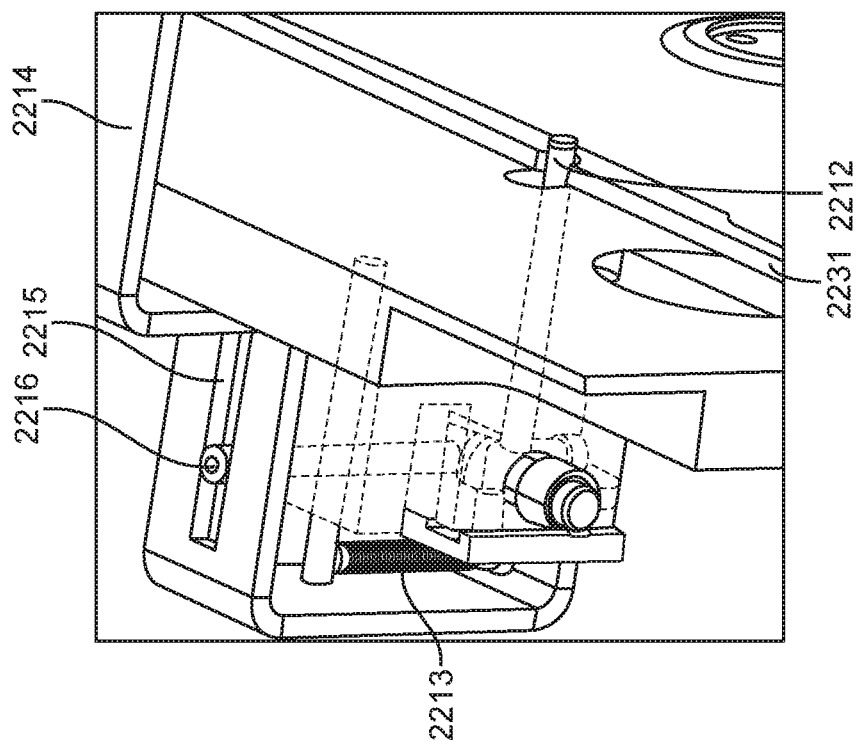

FIG. 25C is an additional view of a latch and pin assembly with a pin positioned within a narrow portion of a latch release arm. A latch from the latch and pin assembly is shown dropped into a notch of an integrated diagnostic cartridge to prevent the integrated diagnostic cartridge from being ejected.

Figure 25D:
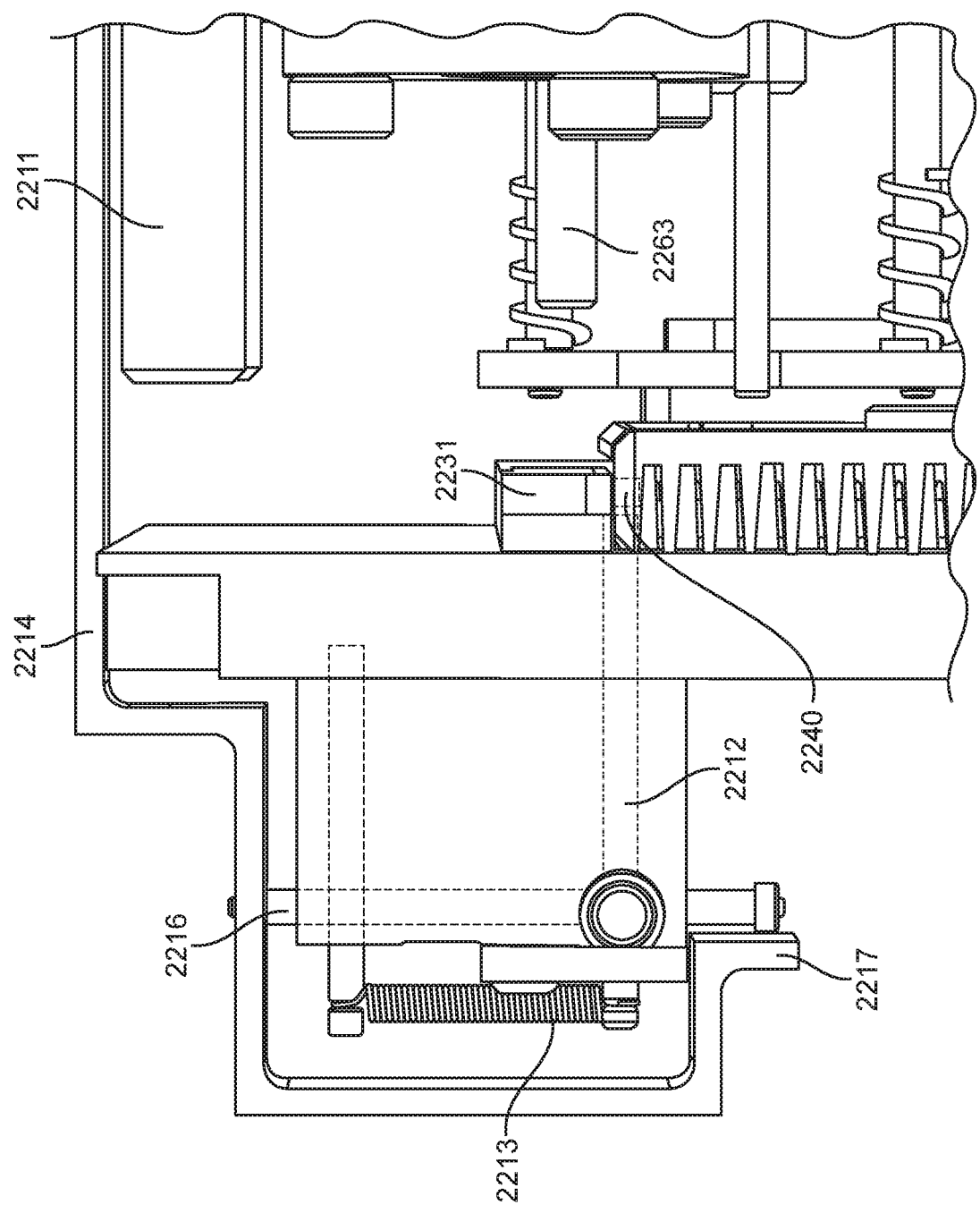

FIG. 25D is an illustration of a latch and pin assembly after an integrated diagnostic cartridge is latched to prevent the integrated diagnostic cartridge from ejection. The integrated diagnostic cartridge is seen in an unclamped position and is viewed from a front of a diagnostic instrument shown in FIG. 4A.

Figure 26A:
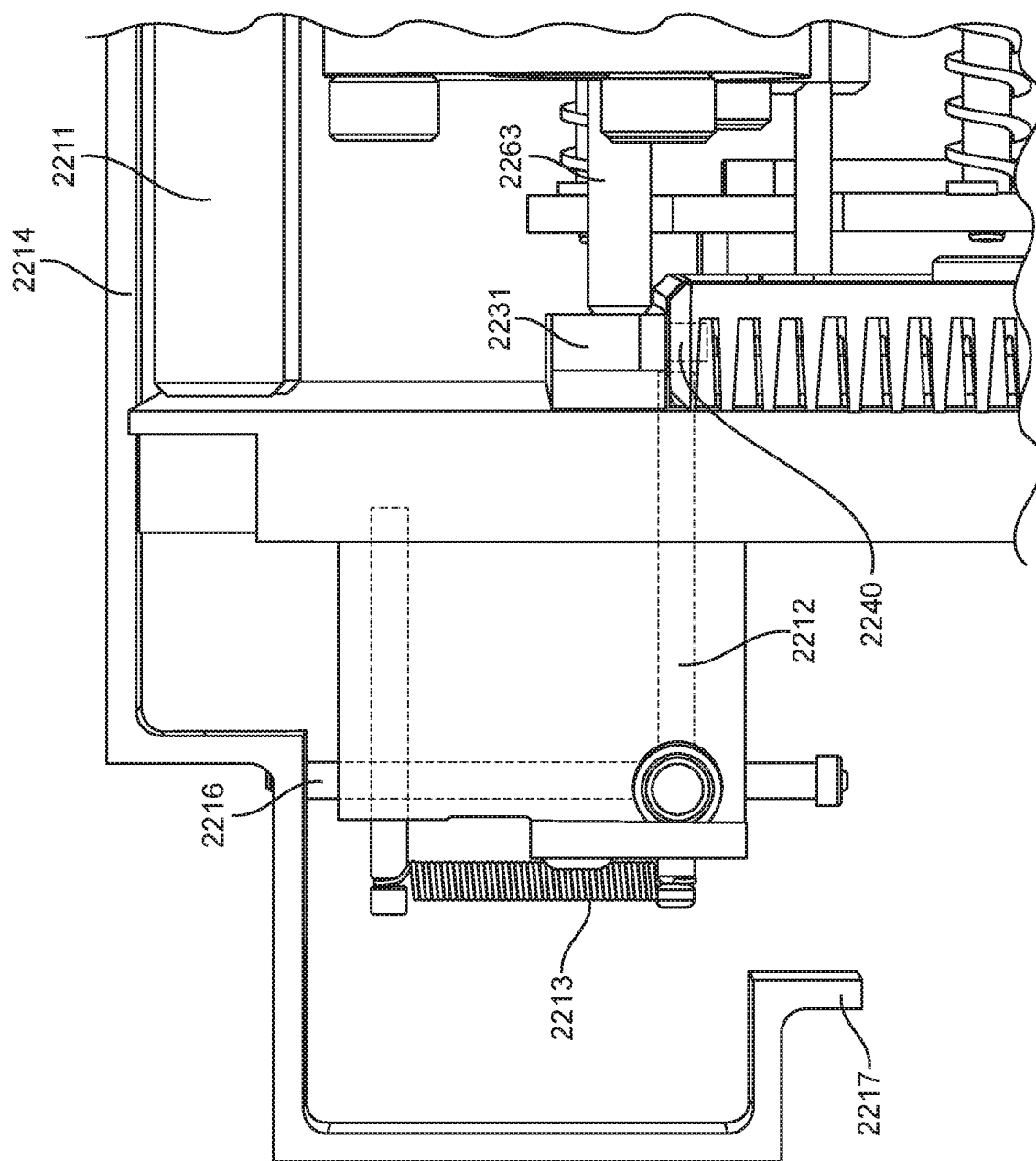

FIG. 26A is an illustration of a latch and pin assembly after an integrated diagnostic cartridge is latched and clamped. The integrated diagnostic cartridge is seen in a clamped position and is viewed from a front of a diagnostic instrument shown in FIG. 4A.

Figure 26B:
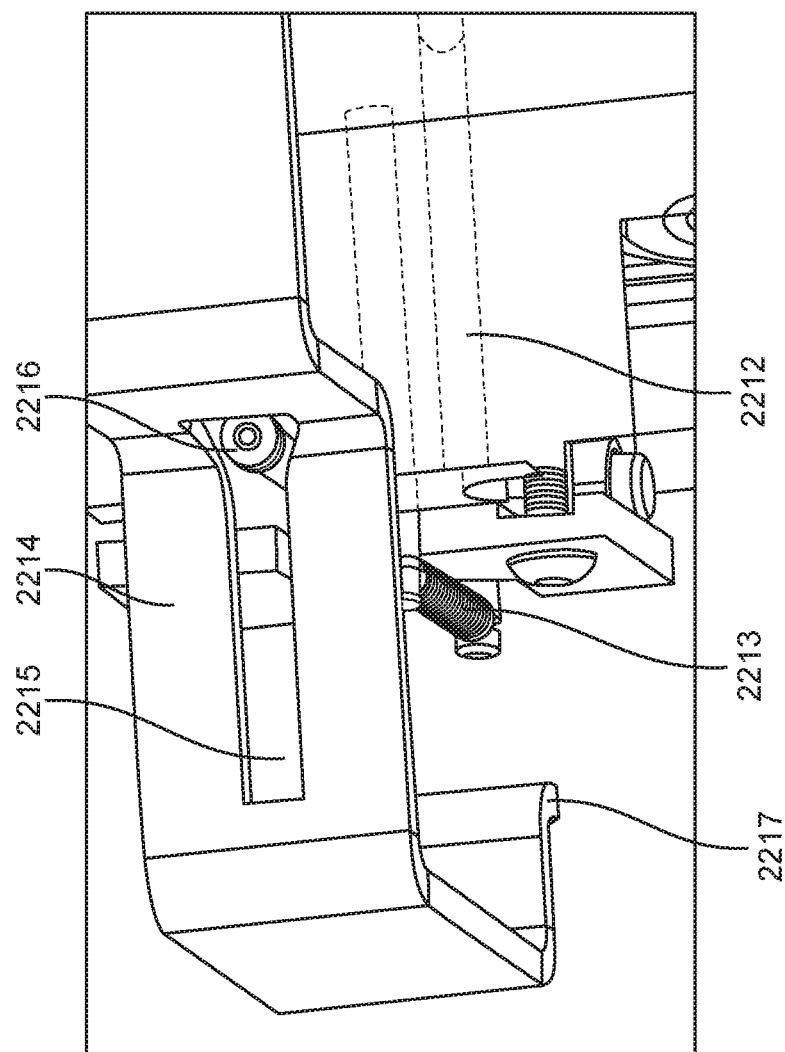

FIG. 26B is a top view of a latch and pin assembly from FIG. 26A. A pin is shown in a wide portion of a latch arm slot when an integrated diagnostic cartridge is in a clamped position.

Figure 27:
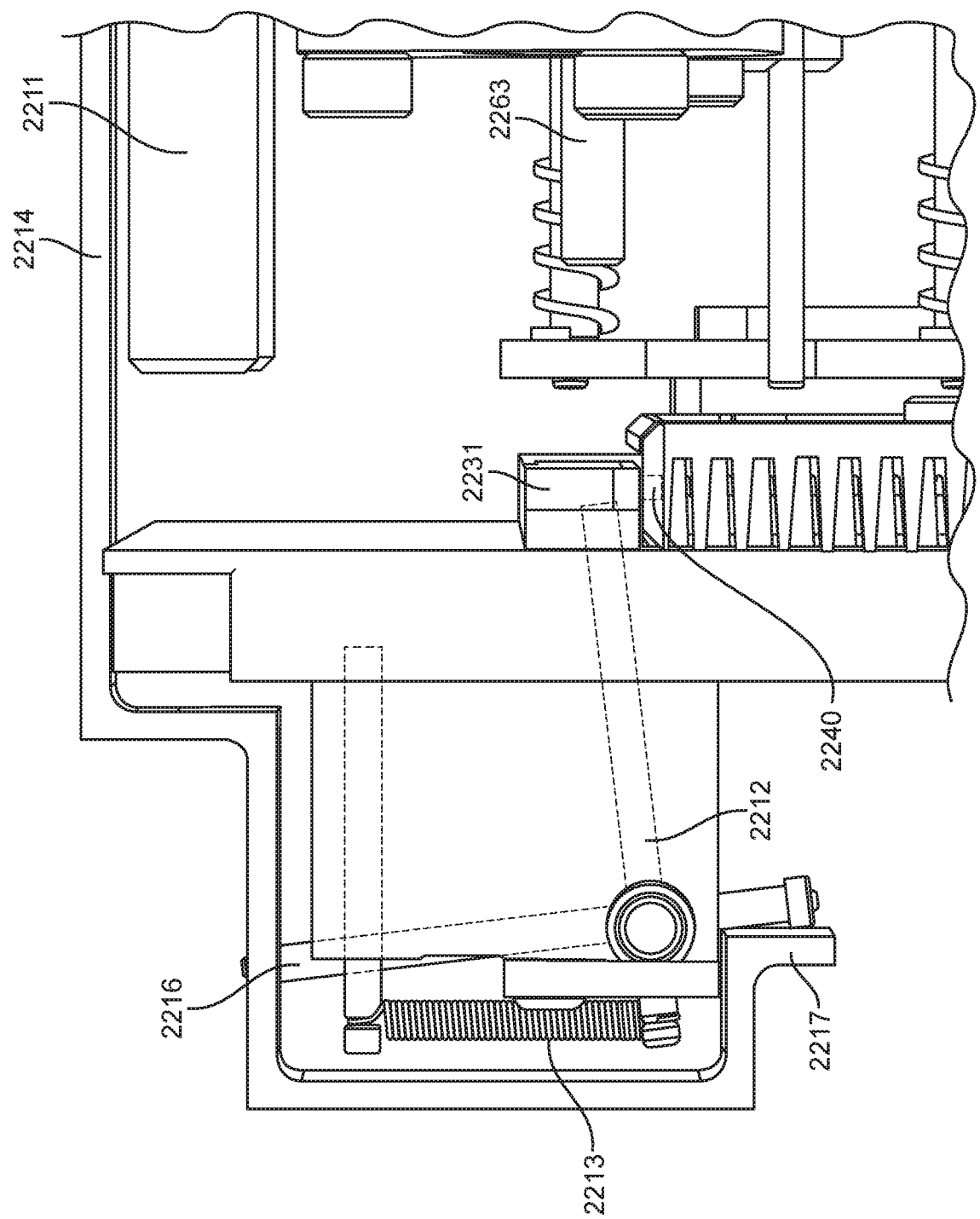

FIG. 27 is an illustration of a latch and pin assembly when an integrated diagnostic cartridge is ejected. The end of a latch release arm is shown contacting the end of a pin to lift the latch and is viewed from a front of a diagnostic instrument shown in FIG. 4A.

Figure 28:
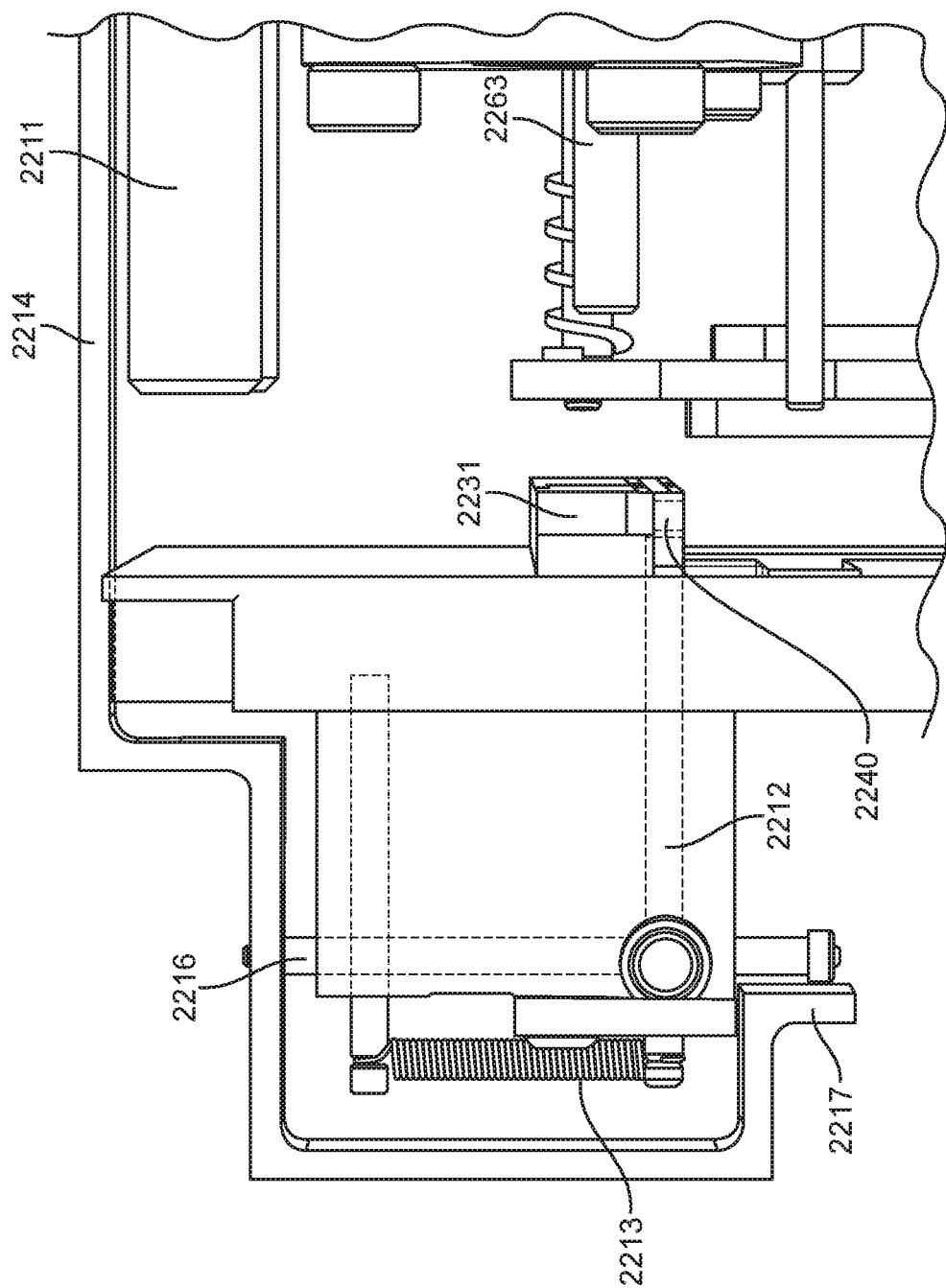

FIG. 28 is an illustration of a latch and pin assembly after an integrated diagnostic cartridge is ejected. The end of a latch release arm is shown not in contact with an end of a pin and is viewed from a front of a diagnostic instrument shown in FIG. 4A.

Figure 29:
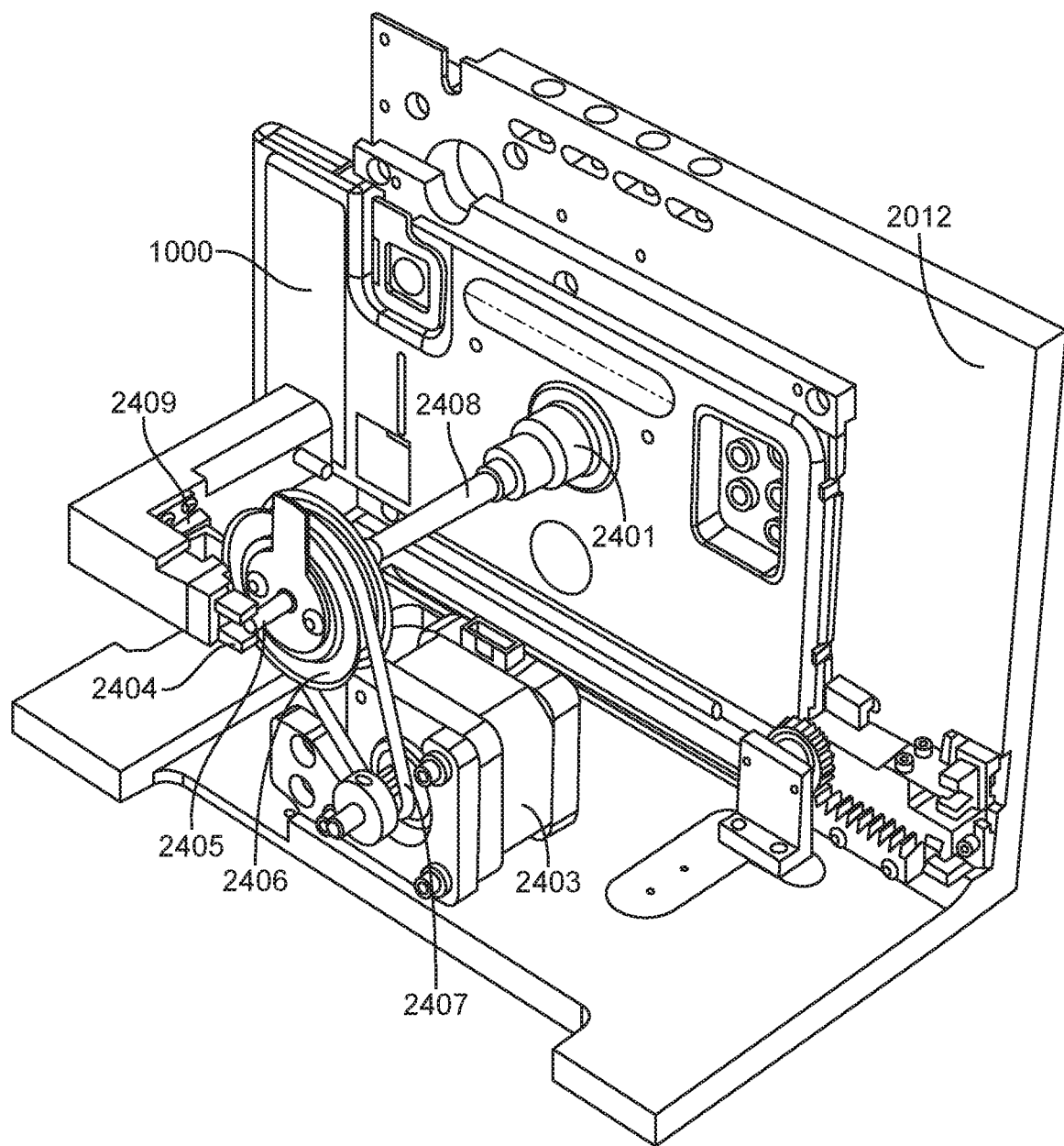

FIG. 29 is a perspective view of a valve drive assembly engaging with a rotary valve on an integrated diagnostic cartridge. The integrated diagnostic cartridge is shown inserted into a loading assembly and is in a loaded position, as demonstrated by FIGS. 18A and 19A.

Figure 30:
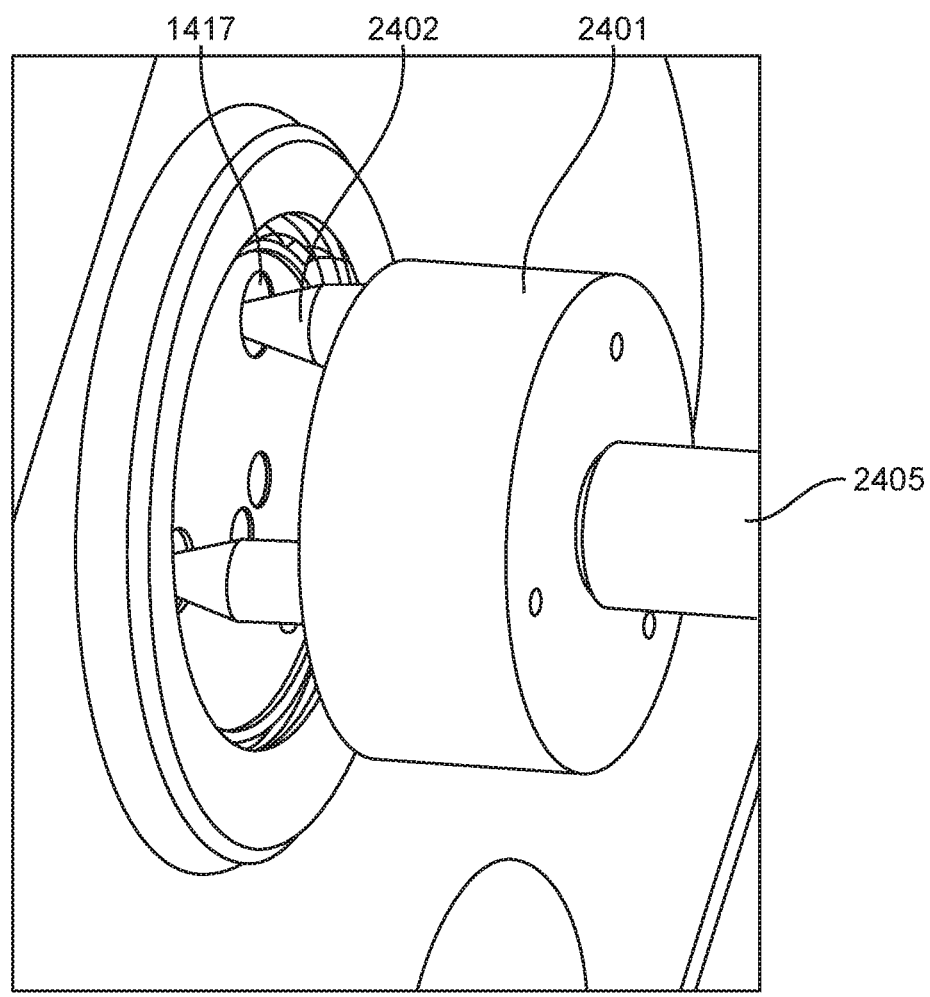

FIG. 30 is an enlarged view of a valve drive assembly from FIG. 29. A valve drive and valve drive pins engage with a rotary valve on an integrated diagnostic cartridge.

Figure 14:
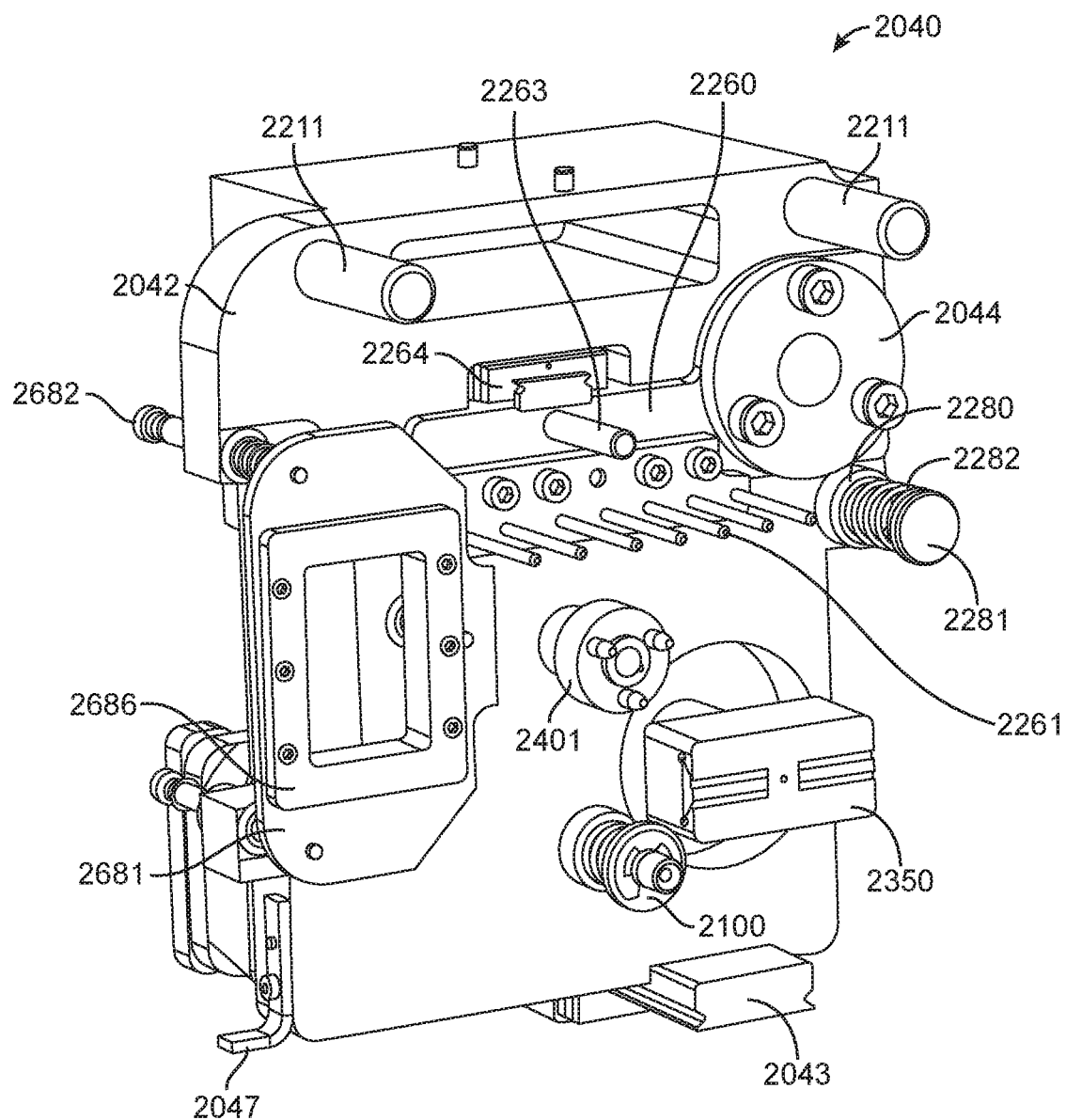
FIG. 14 is a perspective view of a moving bracket assembly of a clamping subsystem. The view of the moving bracket assembly is shown from a first surface of a clamp block.
Figure 15A:
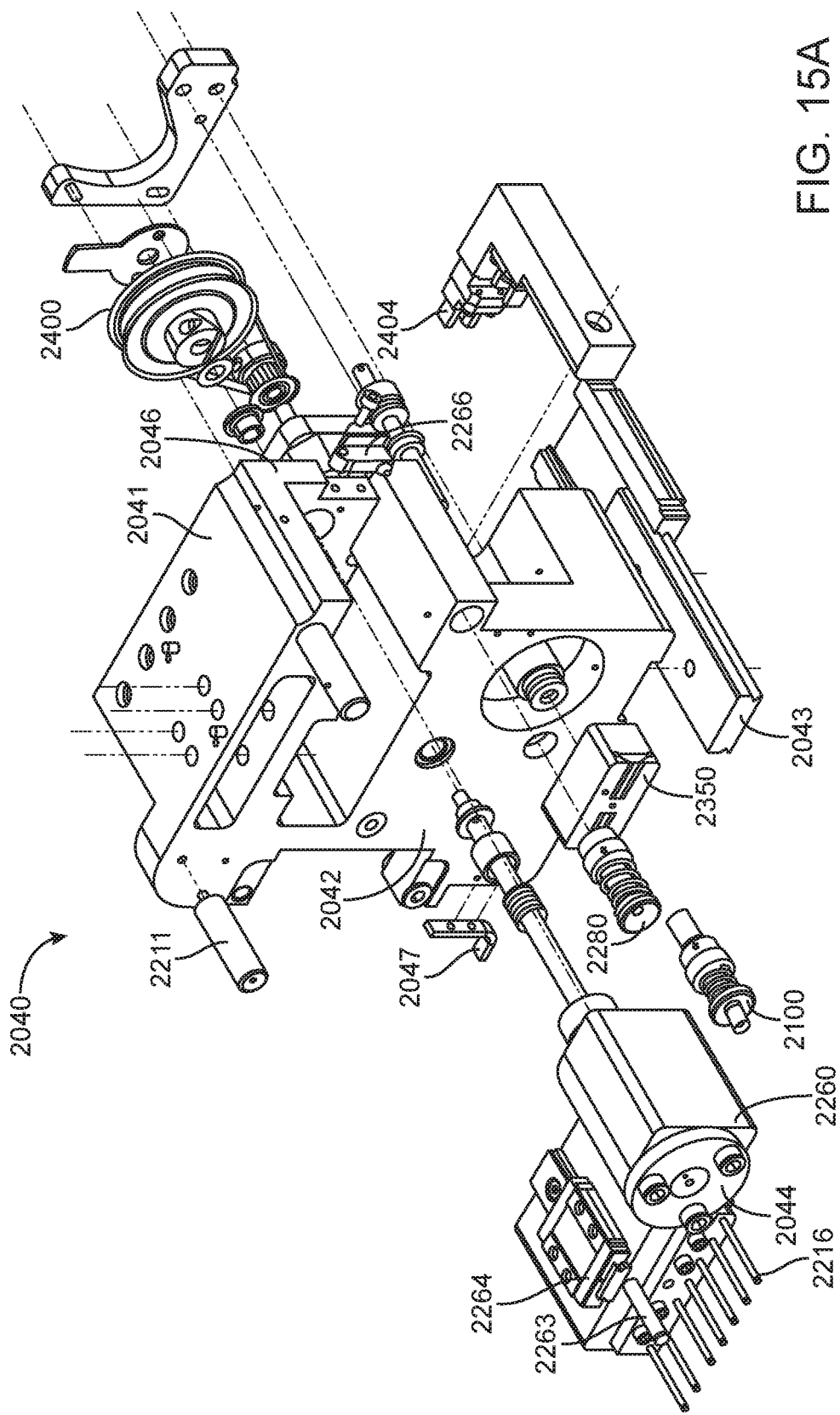
FIG. 15A is a frontal exploded view of a moving bracket assembly of a clamping subsystem.
Figure 15B:
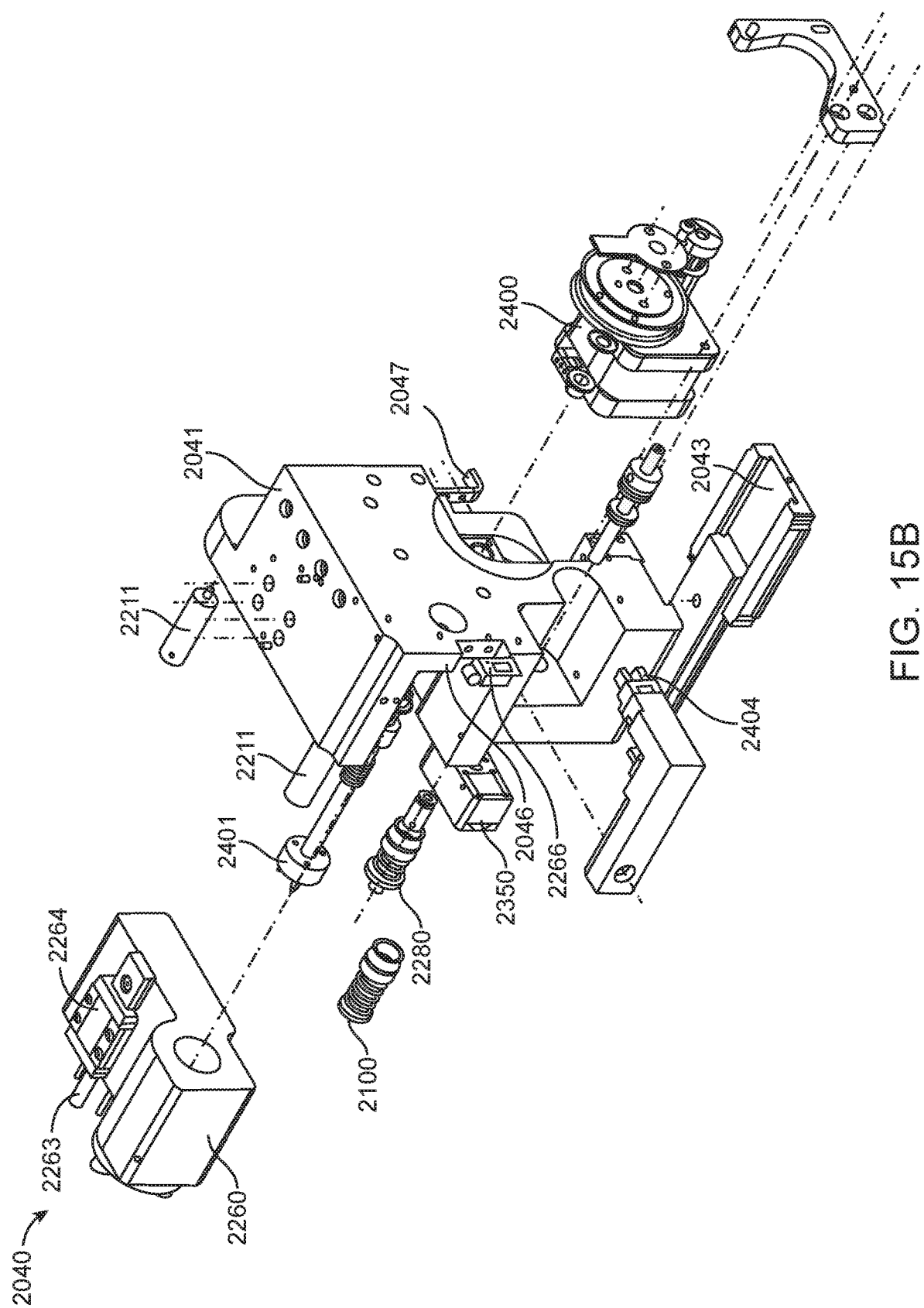
FIG. 15B is a rear exploded view of a moving bracket assembly of a clamping subsystem.
Figure 31:
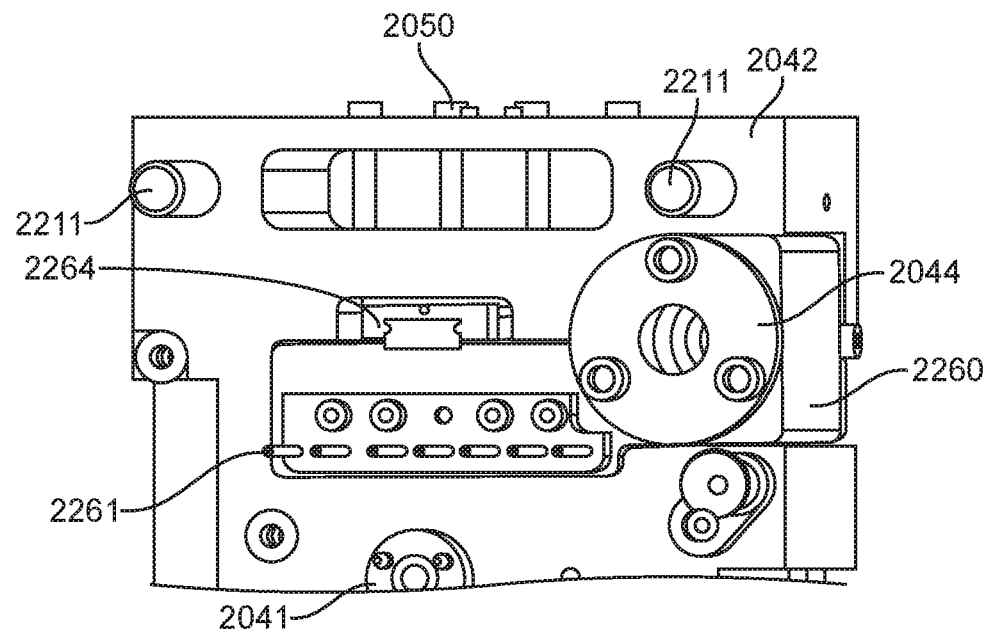

FIG. 31 is an isometric view of a frangible seal block from a moving bracket assembly shown in FIGS. 14, 15A, and 15B, in accordance with an embodiment.

Figure 32:
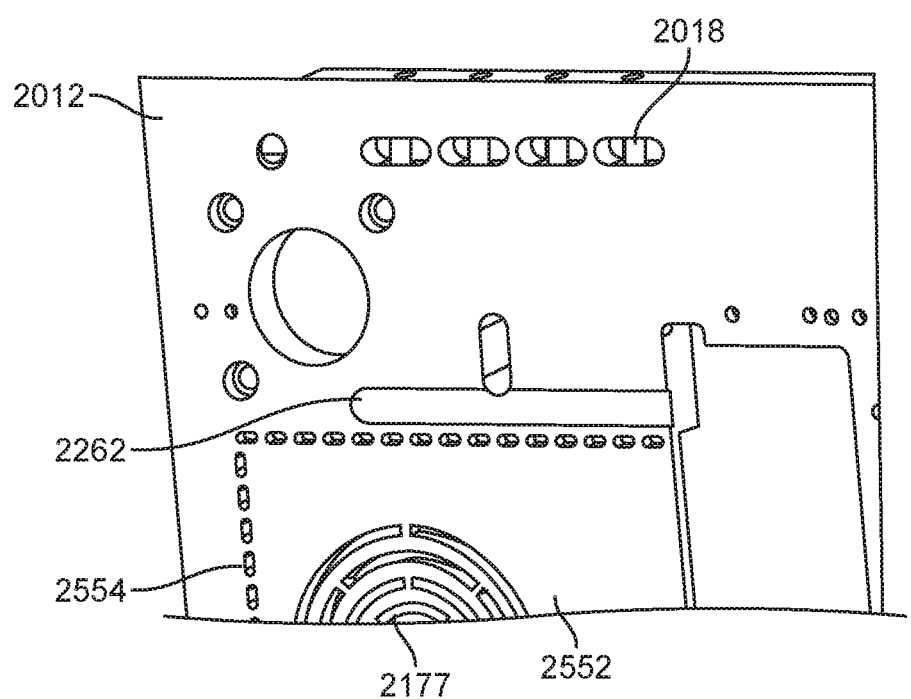

FIG. 32 is an isometric view of a pocket formed within a fixed support bracket of a fixed bracket assembly. The pocket configured to receive portions of a frangible seal block.

Figure 33:
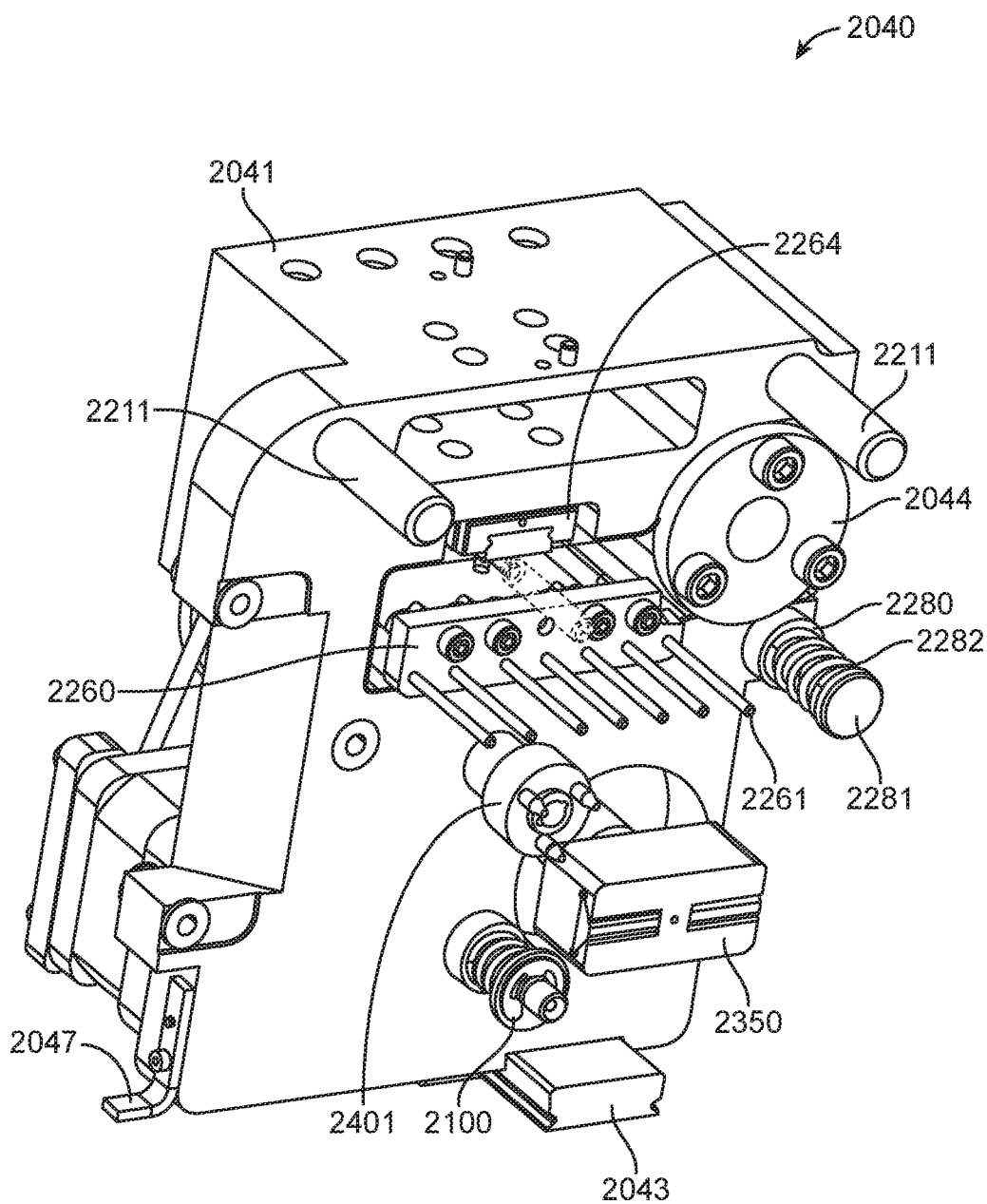

FIG. 33 is a frontal view moving bracket assembly, in accordance with an alternative embodiment. A first frangible seal pin on a frangible seal block is shown to be longer than the remainder of a plurality of frangible seal pins.

Figure 34:
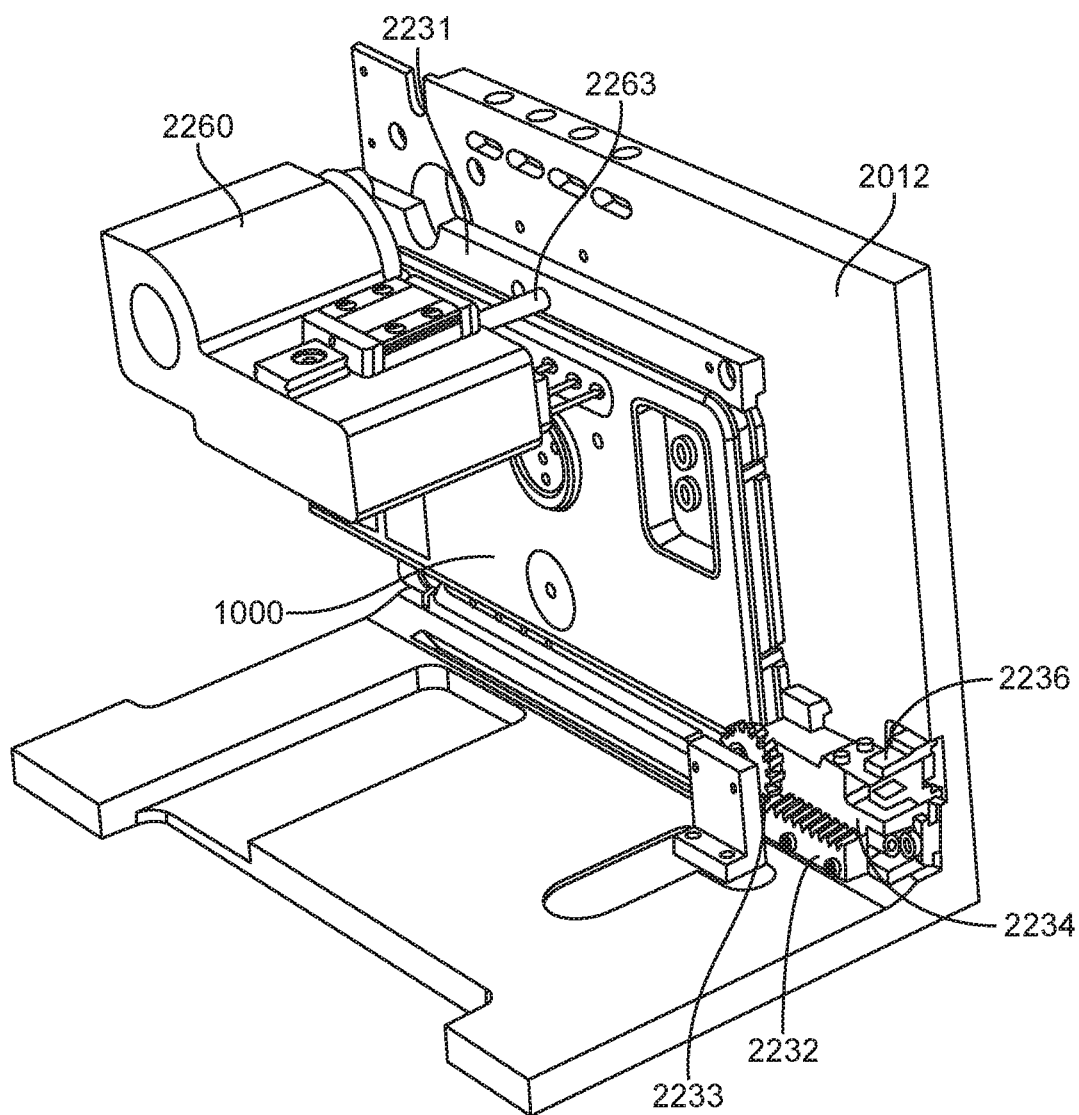

FIG. 34 is an isolated perspective view of a frangible seal block, shown in FIG. 31, engaging with frangible seals on an integrated diagnostic cartridge. The integrated diagnostic cartridge is shown inserted into a loading assembly and is in a loaded position, similarly shown in FIGS. 18A-18B, 19A-19C, and 29.

FIG. 35 is a perspective view of a diagnostic instrument pneumatic interface engaging with an integrated diagnostic cartridge pneumatic interface. The integrated diagnostic cartridge is shown inserted into a loading assembly and is in a loaded position, similarly shown in FIGS. 18A-18B, 19A-19C, 29, and FIG. 34.

FIG. 36A is a frontal perspective view of a diagnostic instrument pneumatic interface, according to one embodiment. The pneumatic interface is shown having a flat plunger surface.

FIG. 36B is a cross-sectional view of FIG. 35. A diagnostic instrument pneumatic interface with a flat plunger surface is engaged with an integrated diagnostic cartridge pneumatic interface cover adaptor. The pneumatic interface is shown with a gimbaling mechanism active.

FIG. 36C is a cross-sectional view of a diagnostic instrument pneumatic interface of with a flat plunger surface retracted from an integrated diagnostic cartridge pneumatic interface cover adaptor during unclamping. The pneumatic interface is shown with a gimbaling mechanism locked.

FIG. 37A is a frontal perspective view of a diagnostic instrument pneumatic interface, according to another embodiment. The pneumatic interface is shown having an angled plunger surface.

FIG. 37B is an additional cross-sectional view of FIG. 35. A diagnostic instrument pneumatic interface with an angled plunger surface is engaged with an integrated diagnostic cartridge pneumatic interface cover adaptor. The pneumatic interface is shown with a gimbaling mechanism active.

FIG. 37C is a cross-sectional view of a diagnostic instrument pneumatic interface with an angled plunger surface retracted from an integrated diagnostic cartridge pneumatic interface cover adaptor during unclamping. The pneumatic interface is shown with a gimbaling mechanism locked.

FIG. 38 is a top down view of a thermal clamp assembly in a zero clamping position.

Figure 39:
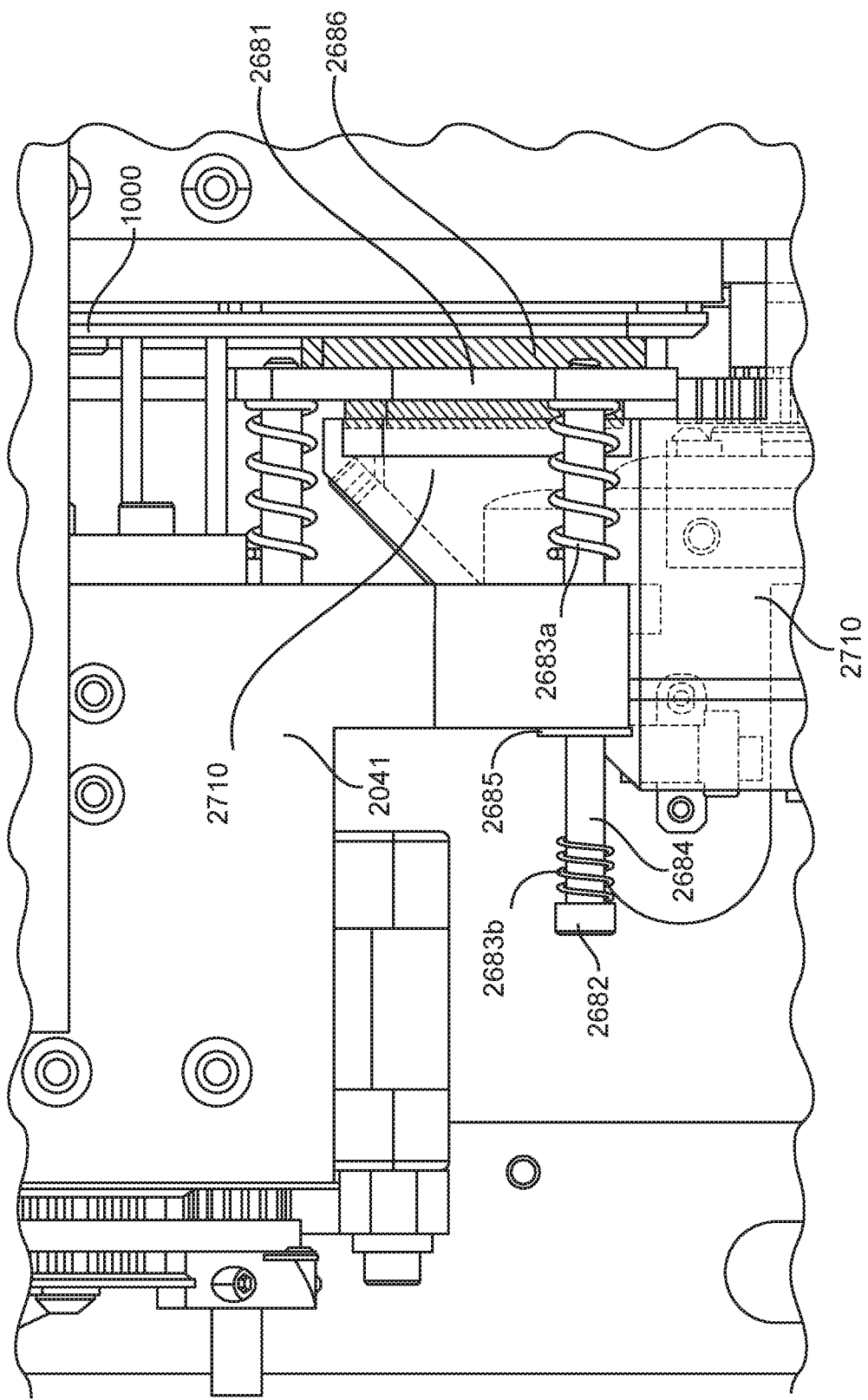

FIG. 39 is a top down view of a thermal clamp assembly in a first clamping position.

Figure 40:
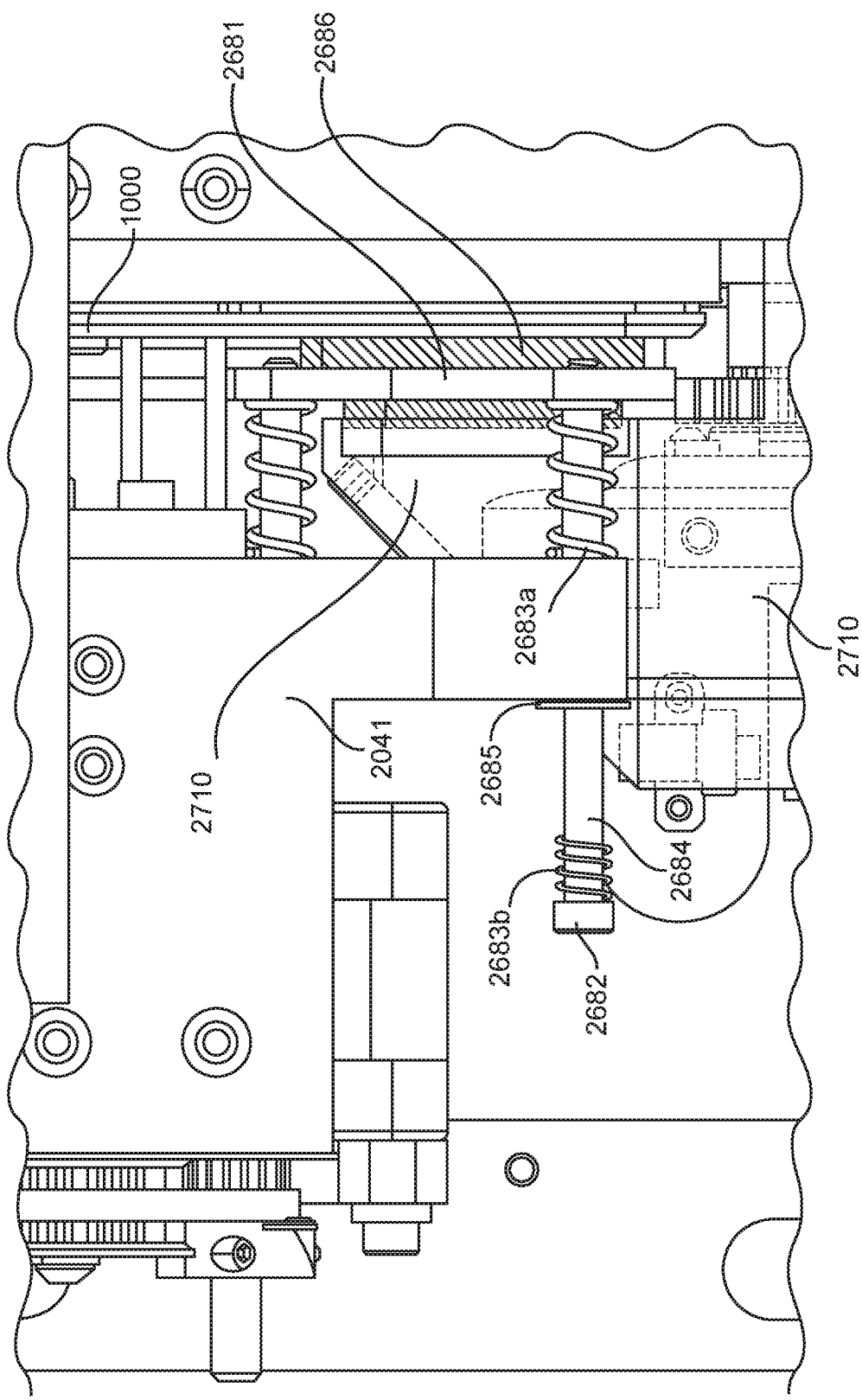

FIG. 40 is a top down view of a thermal clamp assembly in a second clamping position.

Figure 41:
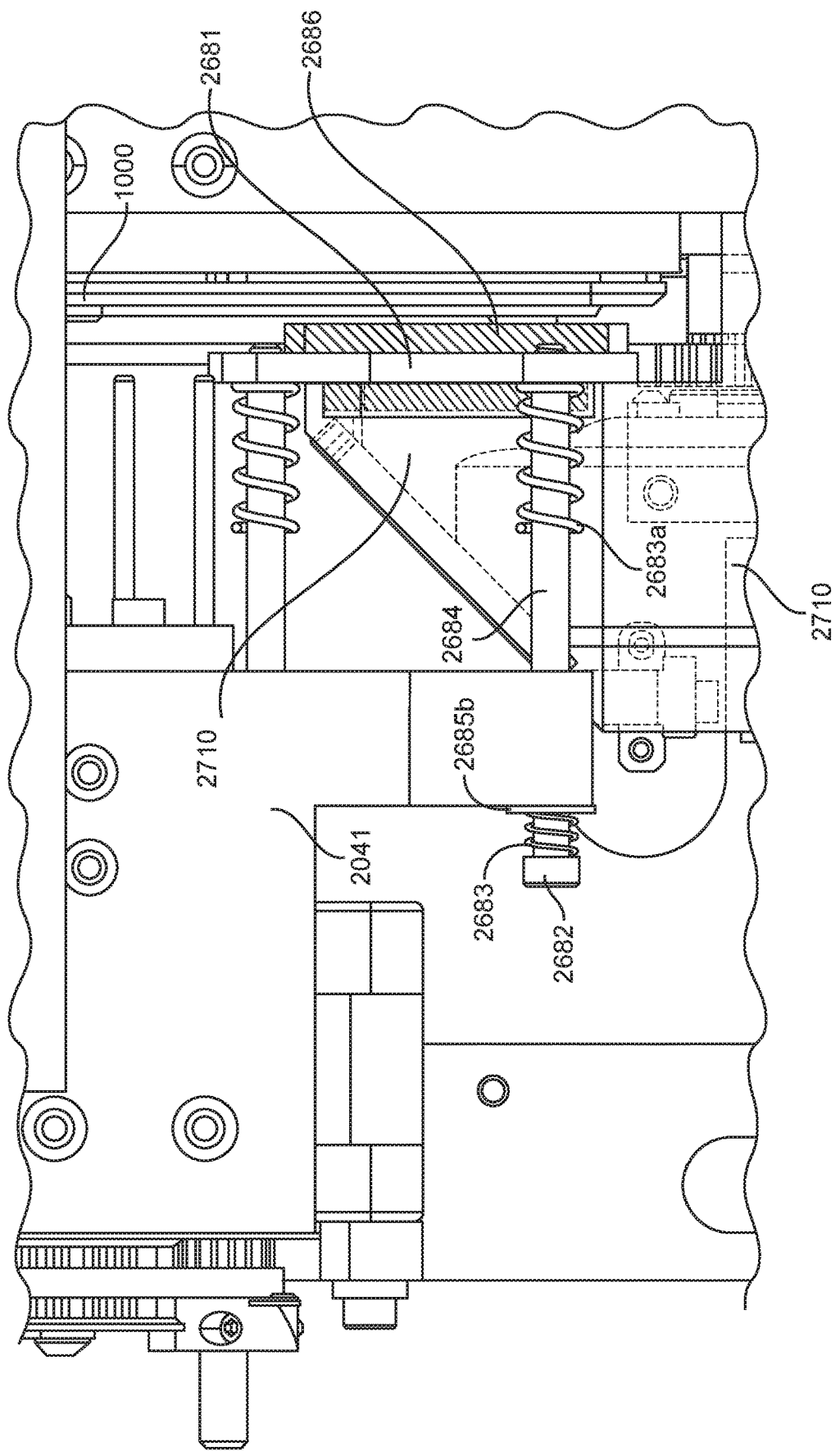

FIG. 41 is a top down view of a thermal clamp assembly in a fourth clamping position.

Figure 42:
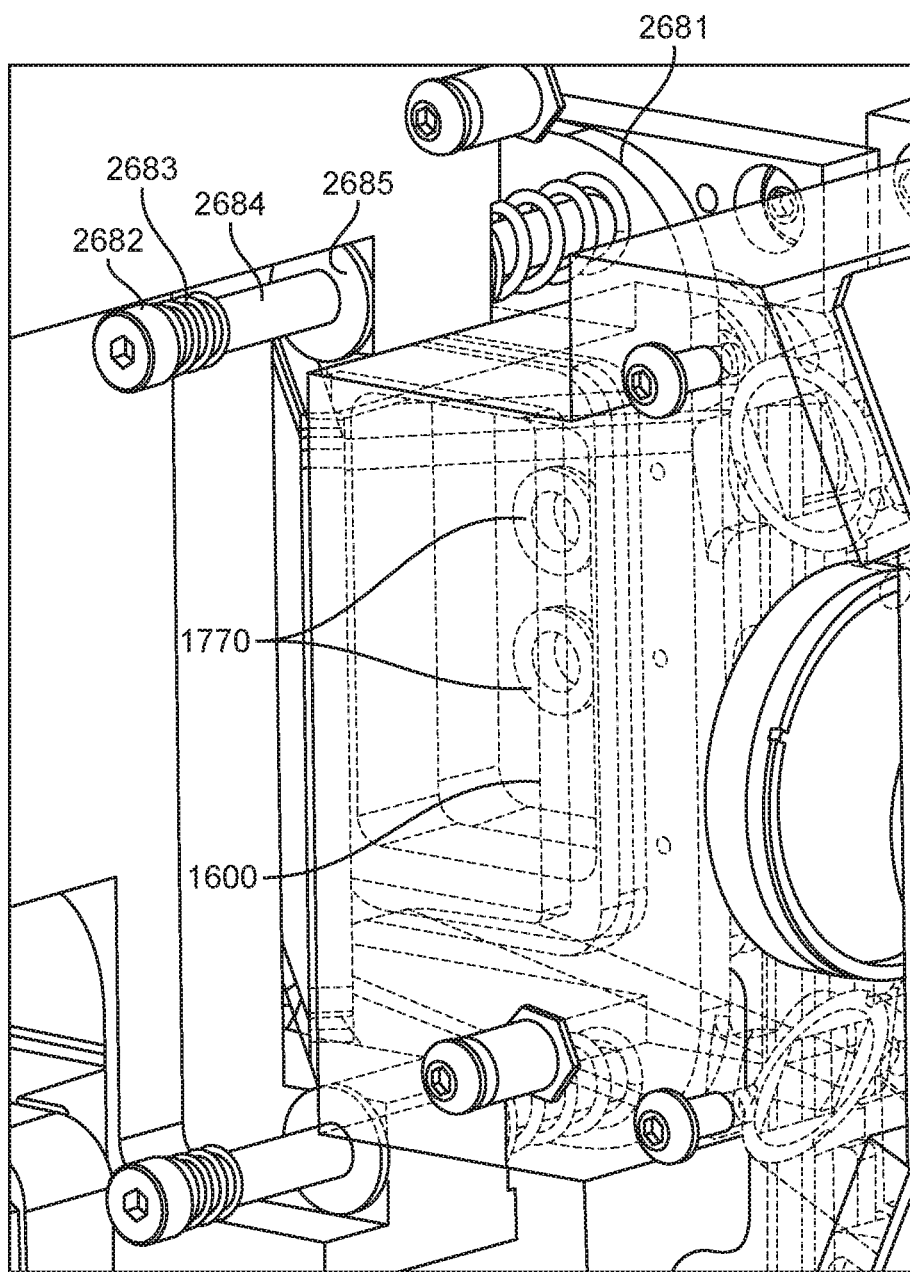

FIG. 42 is a perspective view of a thermal clamp assembly from FIGS. 38-41, engaged with a reaction area of an integrated diagnostic cartridge. An optical block of a reaction imaging assembly is shown enclosing the thermal clamp assembly and reaction area.

Figure 43:
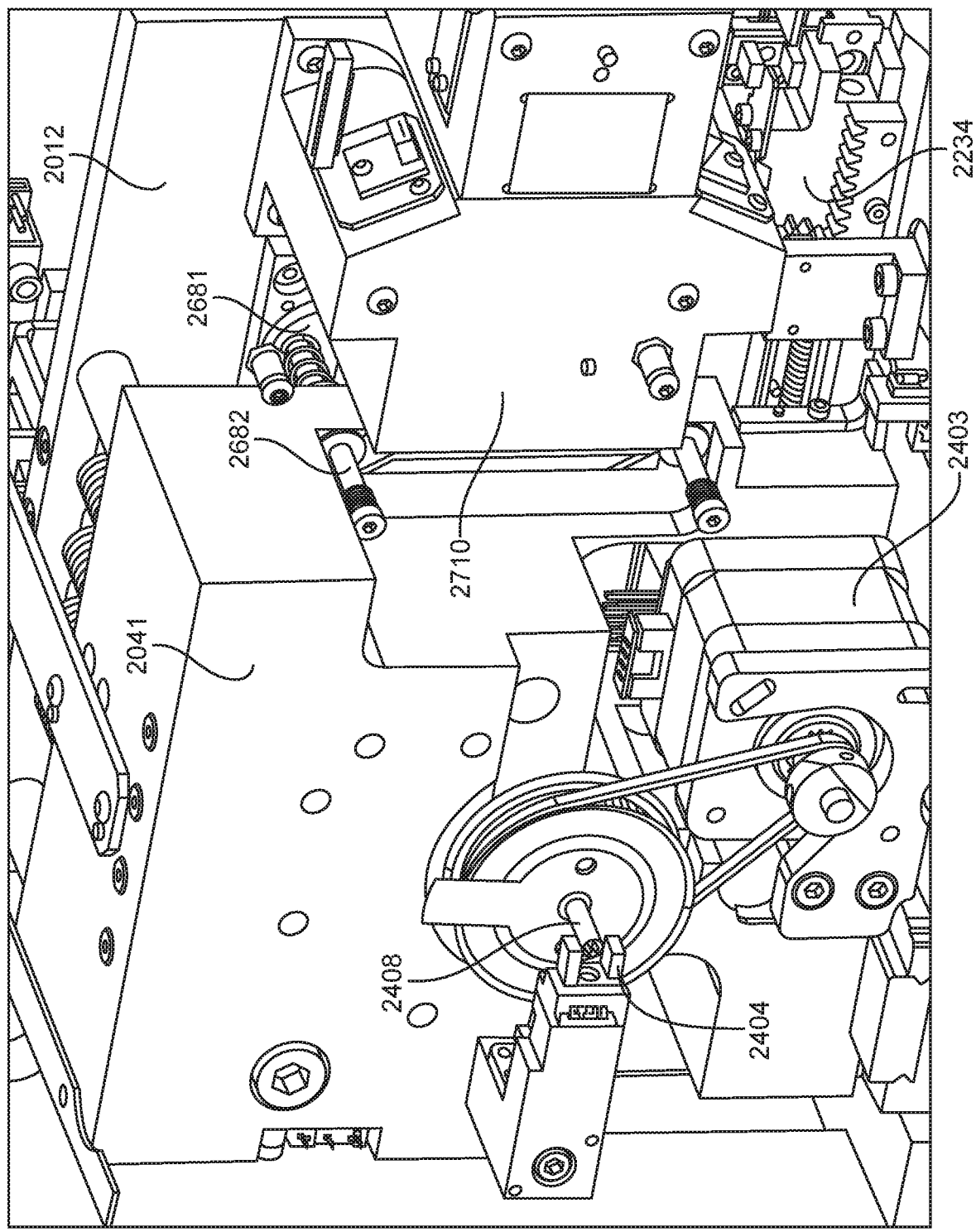

FIG. 43 is an enlarged perspective view of a clamping subsystem from and a reaction imaging assembly of a diagnostic instrument optical subsystem. A thermal clamp assembly from FIGS. 38-42 is shown disposed within the reaction imaging assembly. The clamping subsystem is viewed in a similar perspective in FIGS. 8 and 9.

Figure 44:
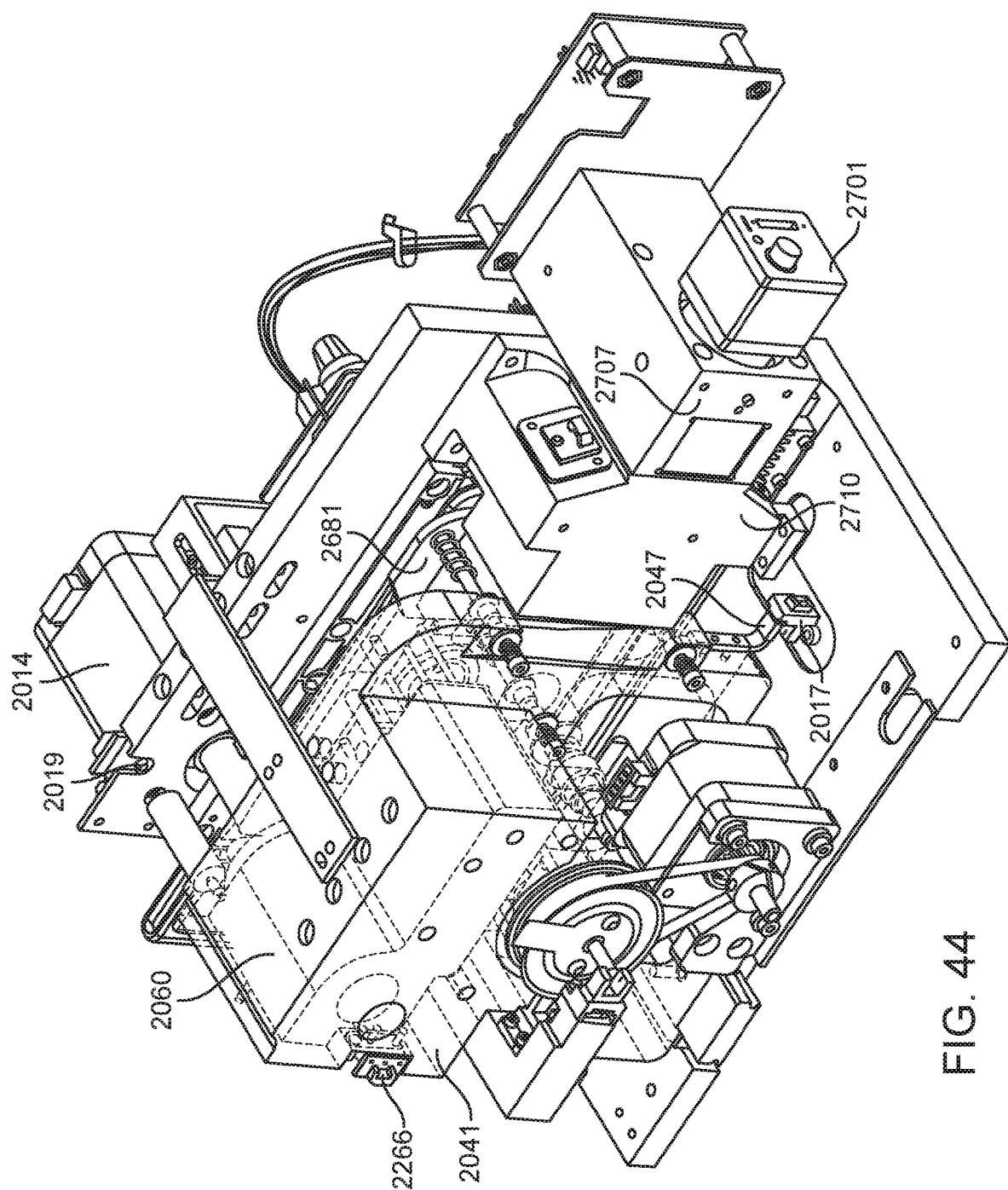

FIG. 44 is a broadened perspective view of FIG. 43. A reaction imaging assembly of a diagnostic instrument optical assembly is shown attached to a fixed support bracket of the clamping subsystem. A clamping subsystem clamps an integrated diagnostic cartridge, as shown in FIGS. 8-13, 16A-16E, 26A, and 38-41. Furthermore, A frangible seal block is shown contained within a clamp block of a moving bracket assembly.

Figure 45:
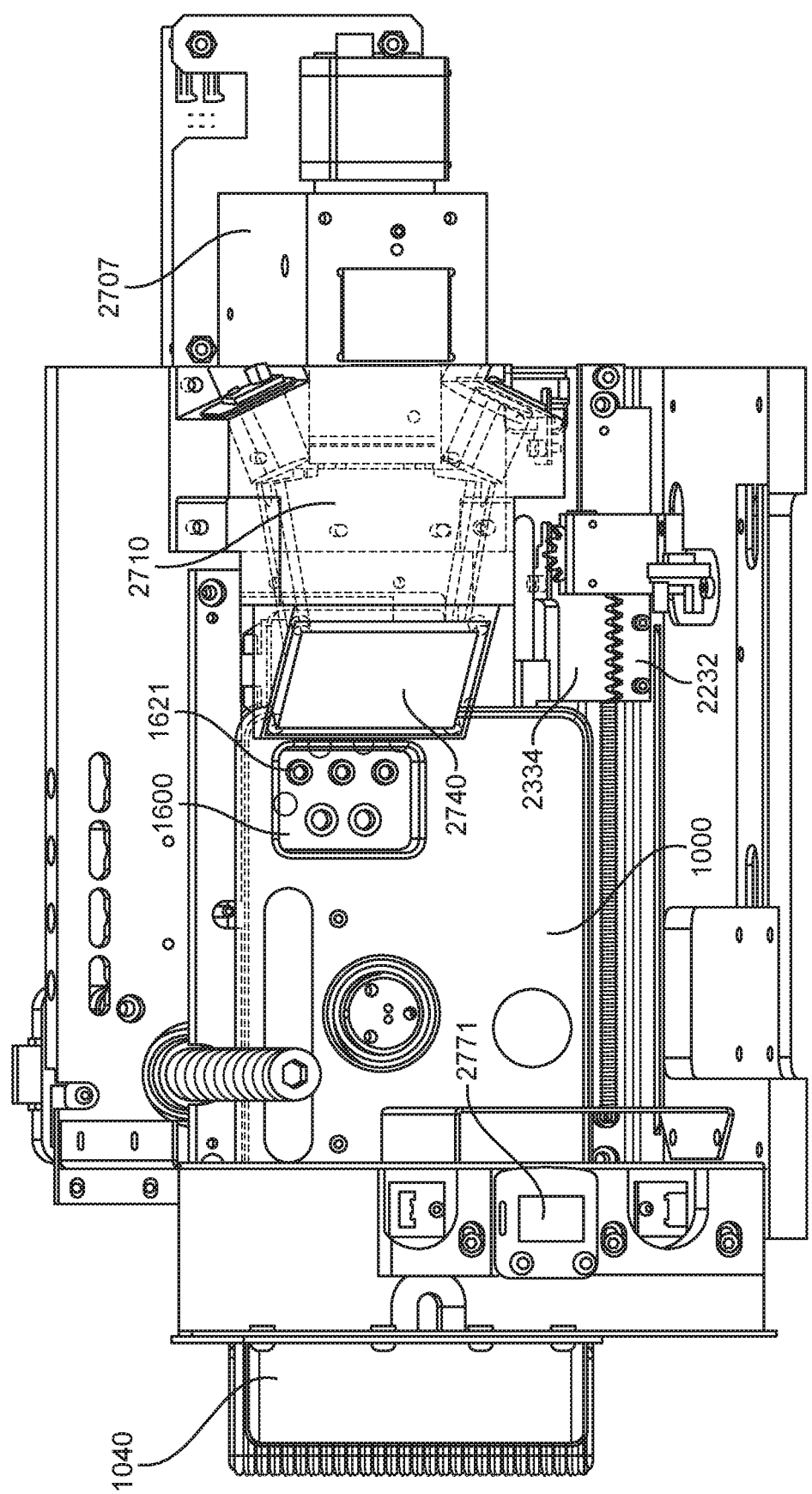

FIG. 45 is an isometric view of a diagnostic instrument optical subsystem comprising a label imaging assembly and a reaction imaging assembly. An integrated diagnostic cartridge is in a loading position, as shown in FIGS. 17A and 17B. A reaction area of the integrated diagnostic cartridge is outside of an optical block from a reaction imaging assembly in a loading position.

Figure 46:
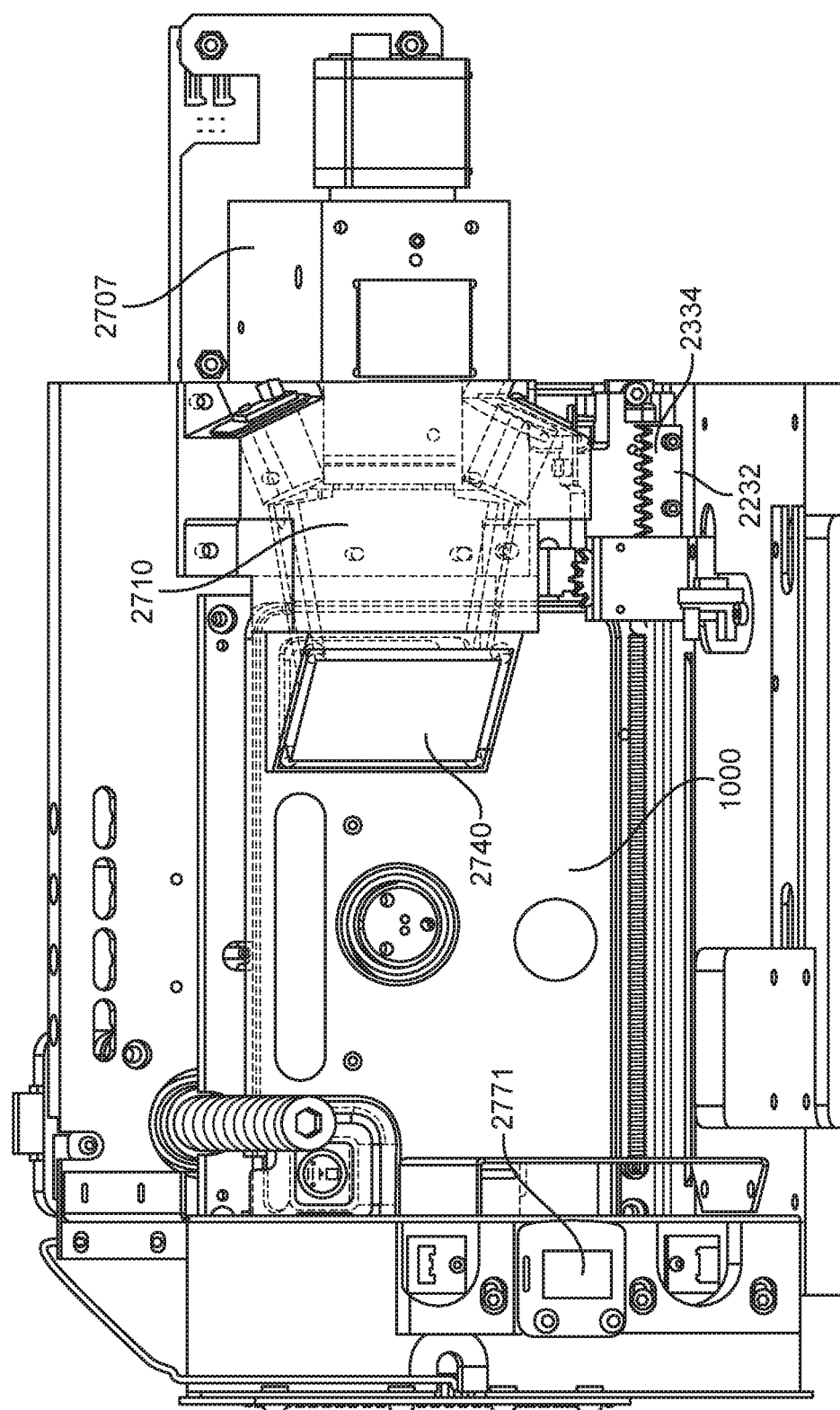

FIG. 46 is an additional isometric view of a diagnostic instrument optical subsystem of FIG. 45. An integrated diagnostic cartridge is in a loaded position, as shown by FIGS. 18A-18B, 19A-19C, 29, 34, and 35. A reaction area of the integrated diagnostic cartridge is disposed below an optical block from a reaction imaging assembly in a loaded position.

Figure 47A:
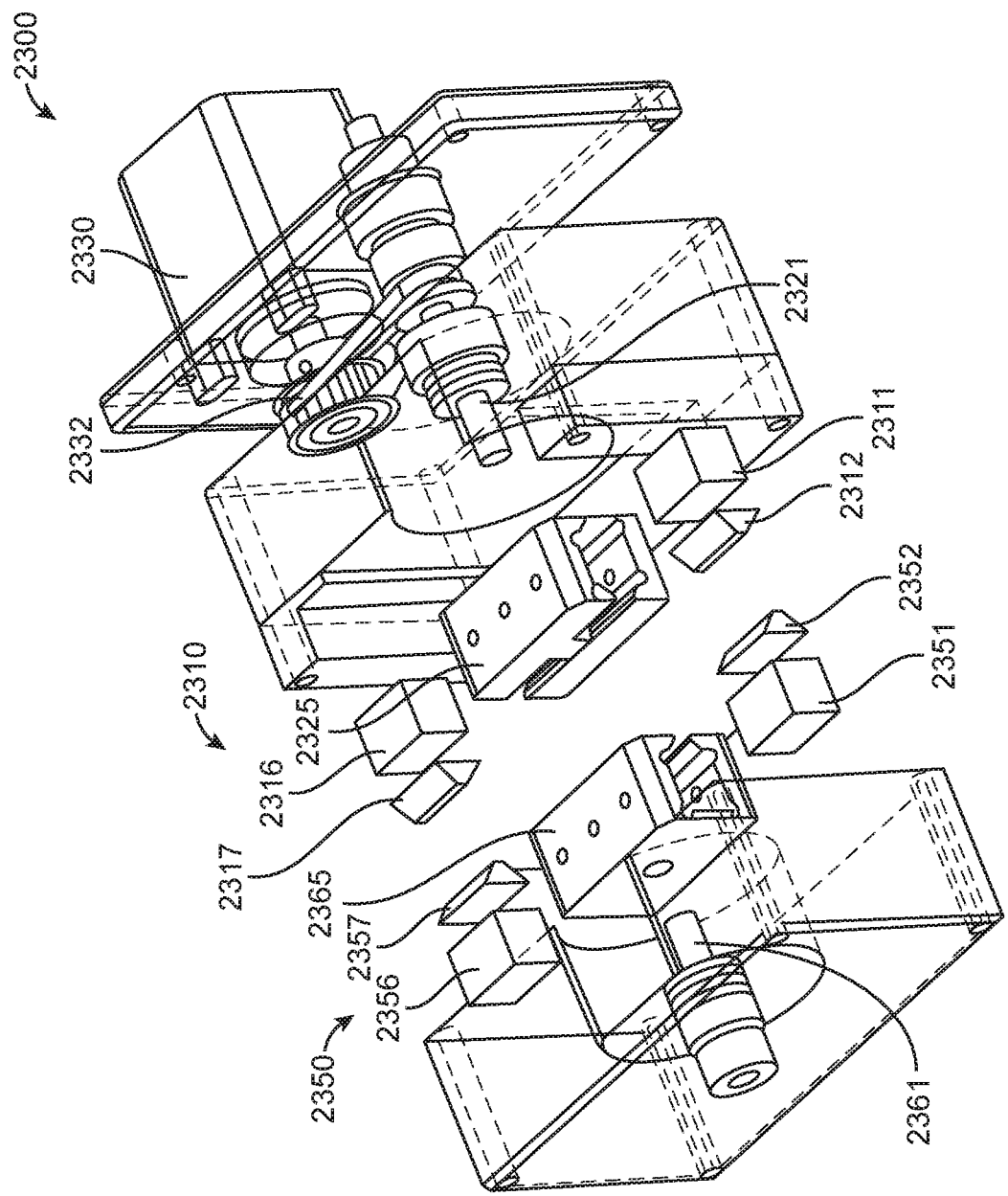

FIG. 47A is an exploded view of a magnetic mixing assembly of a clamping subsystem.

Figure 47B:
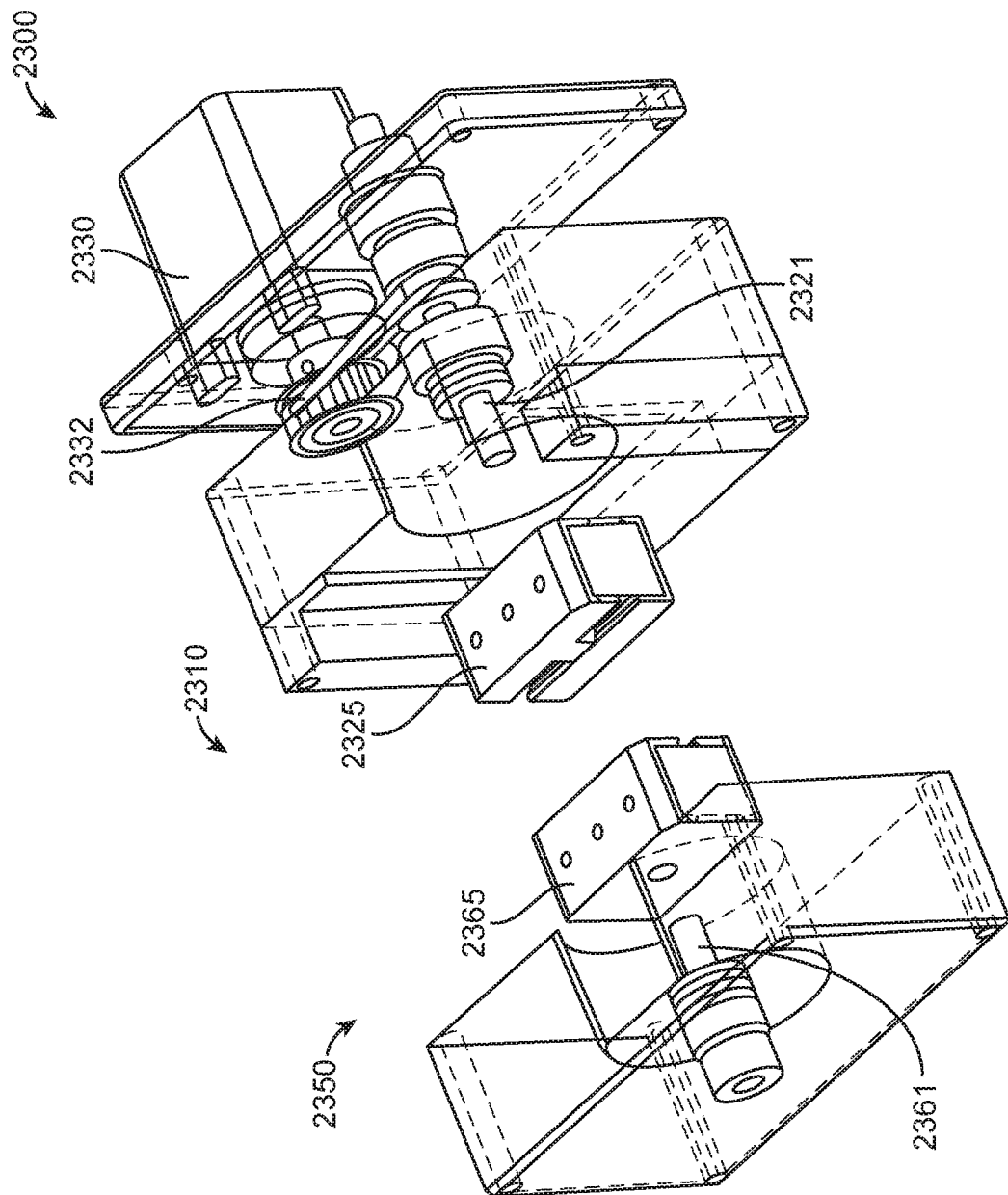

FIG. 47B is a perspective view of a driving magnet system and a driven magnet system of a magnetic mixing assembly.

Figure 6:
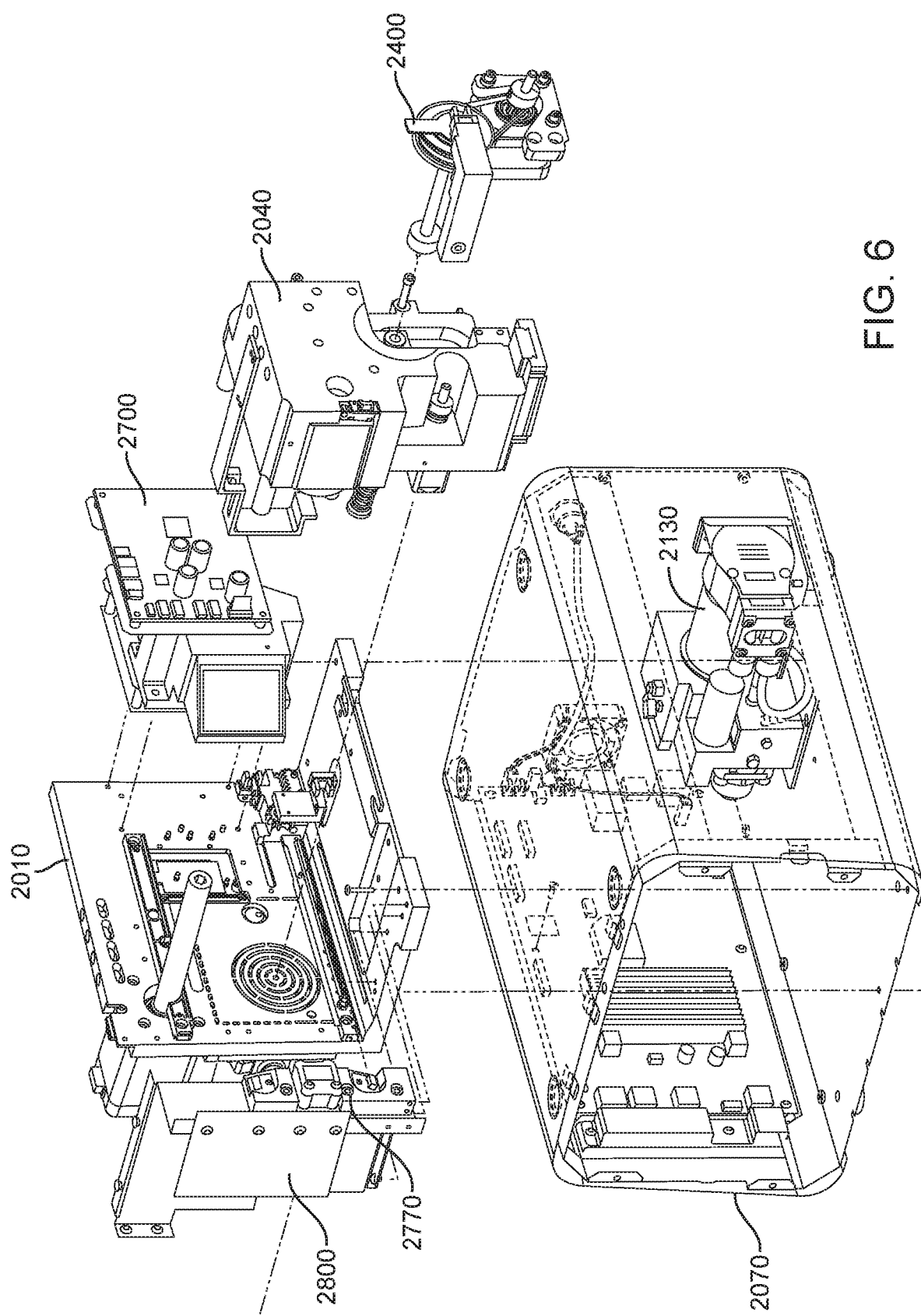
FIG. 6 depicts a frontal exploded illustration of a diagnostic instrument, in accordance with an embodiment.
Figure 7:
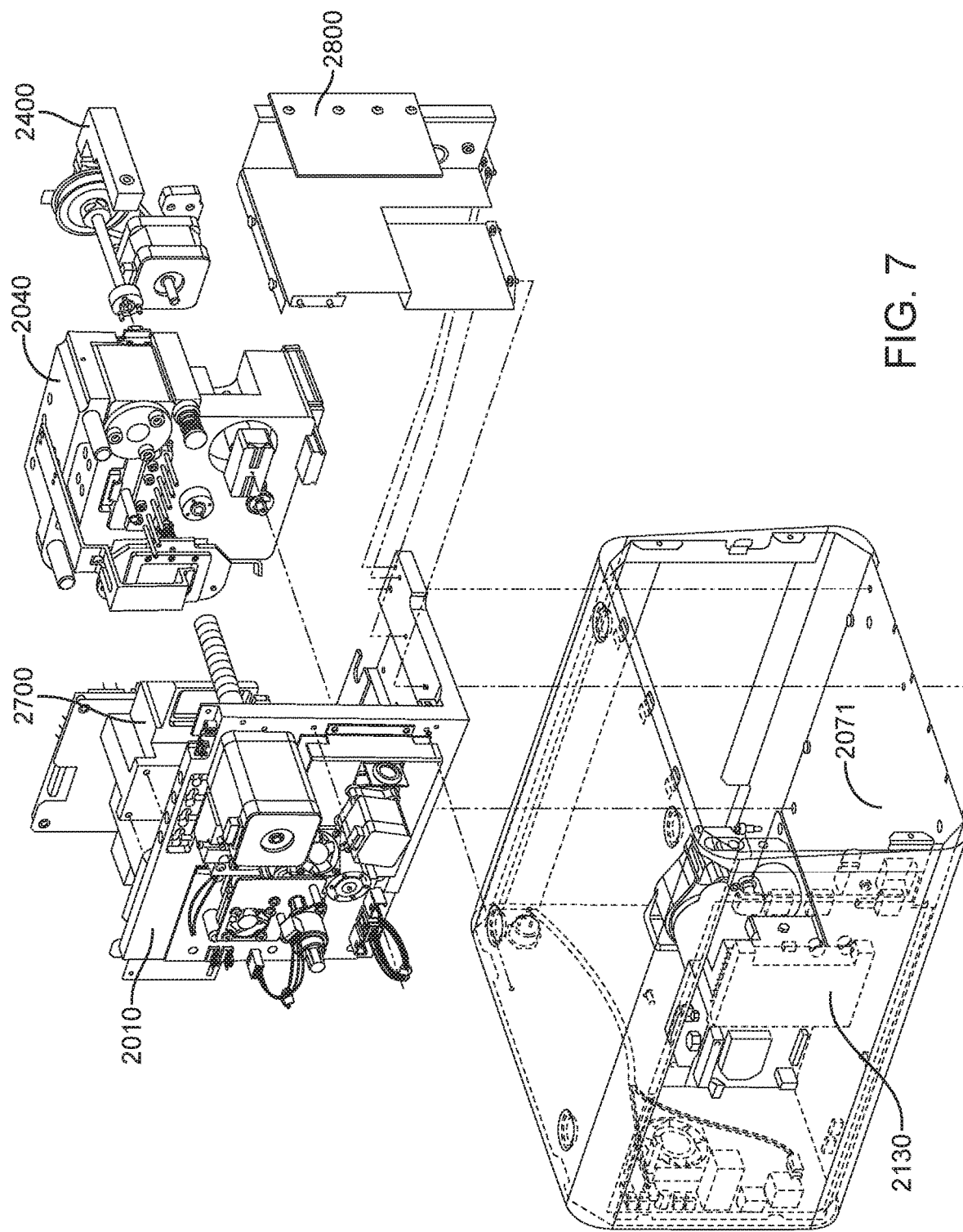
FIG. 7 depicts a rear exploded illustration of a diagnostic instrument, in accordance with an embodiment.
Figure 48:
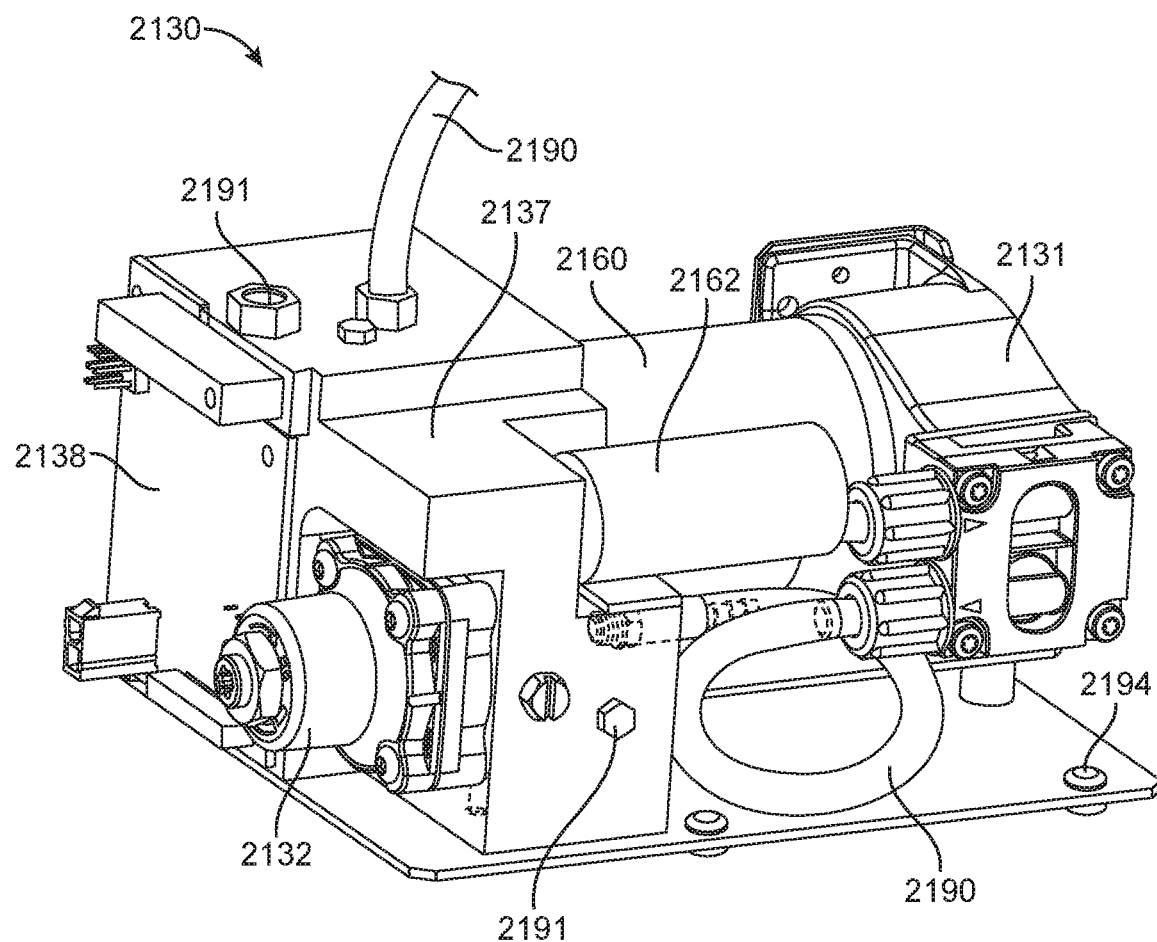

FIG. 48 is a perspective view of a diagnostic instrument pneumatic subsystem shown in FIGS. 6 and 7.

Figure 49:
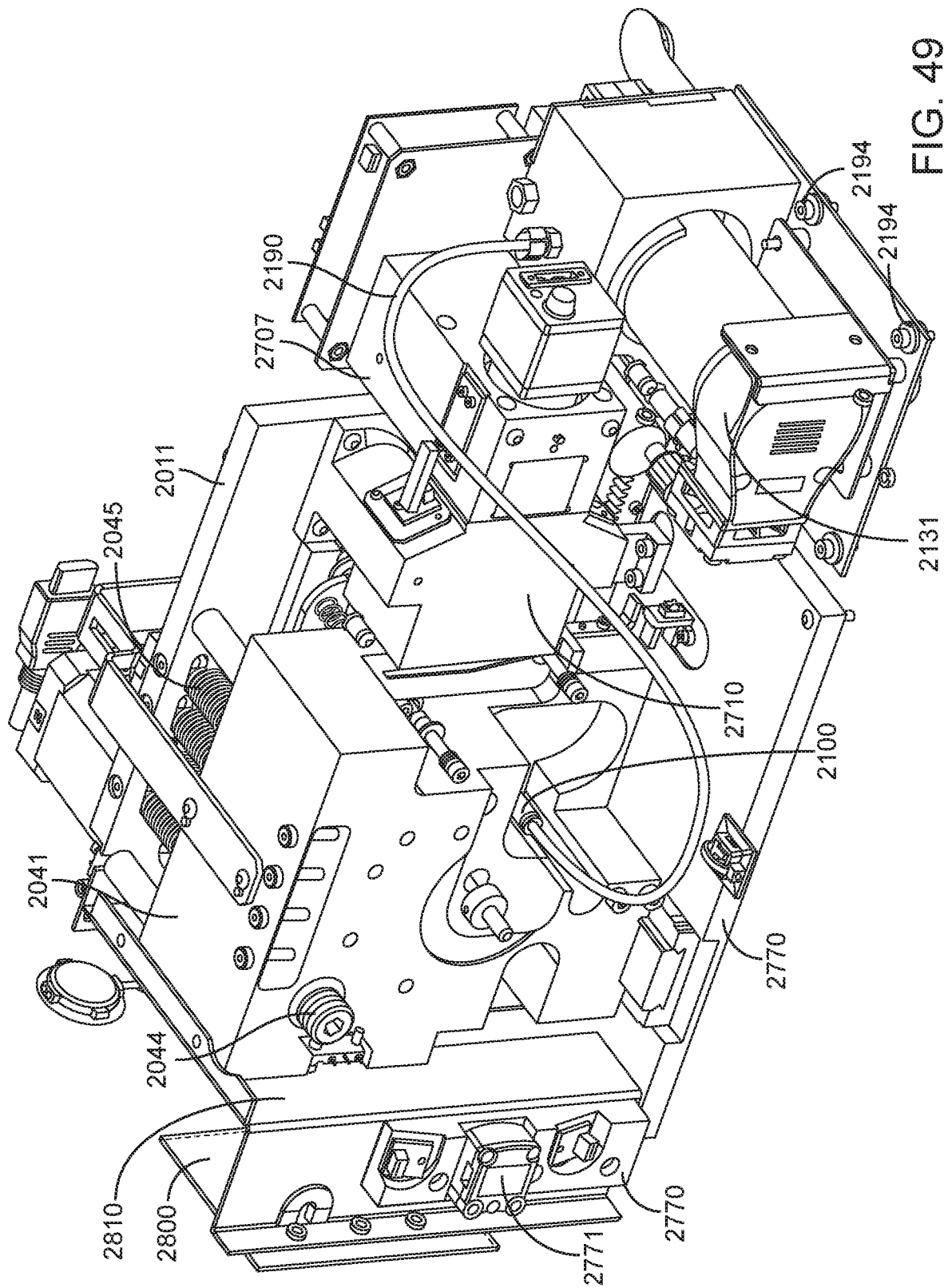

FIG. 49 is an enlarged perspective internal view of FIGS. 6 and 7. An arrangement of a clamping subsystem, an optical subsystem, and a pneumatic subsystem is readily apparent in this view. A valve drive assembly is removed from a moving bracket assembly to show a pneumatic interface, shown in FIGS. 35-37C, is connected to the pneumatic subsystem, shown in FIG. 48, via tubing.

Figure 50:
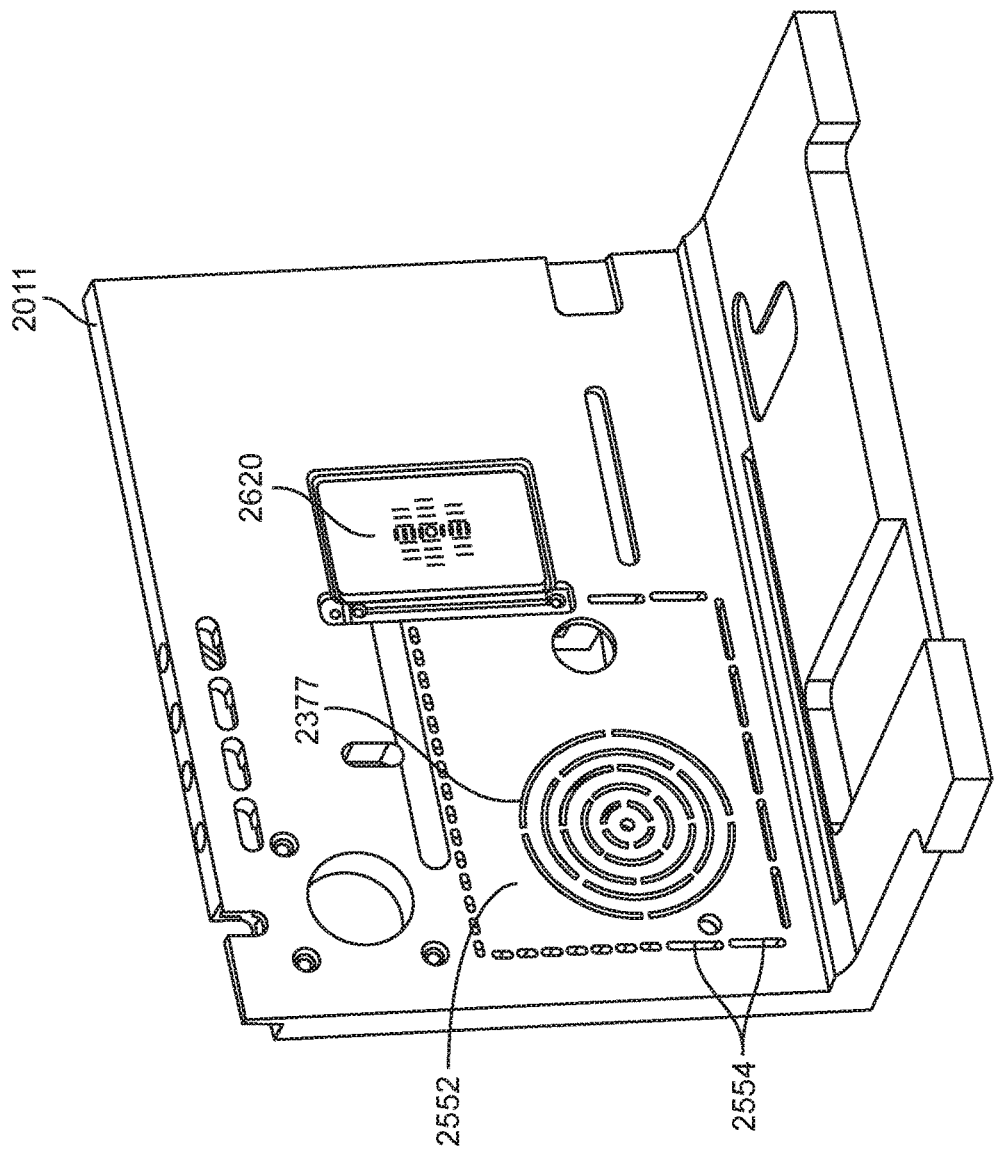

FIG. 50 is a perspective frontal view of a cartridge heating area of a cartridge heater zone and a reaction well zone of a diagnostic instrument thermal subsystem.

Figure 51:
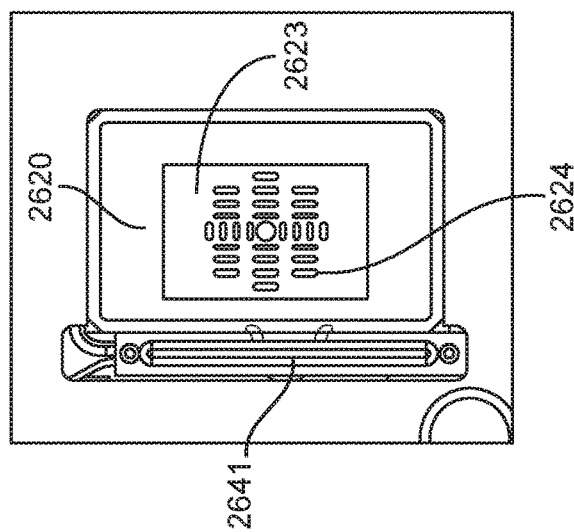

FIG. 51 is an isometric enlarged view of FIG. 50 showing a reaction well zone comprising grooves to form a machined pocket geometry.

Figure 52:
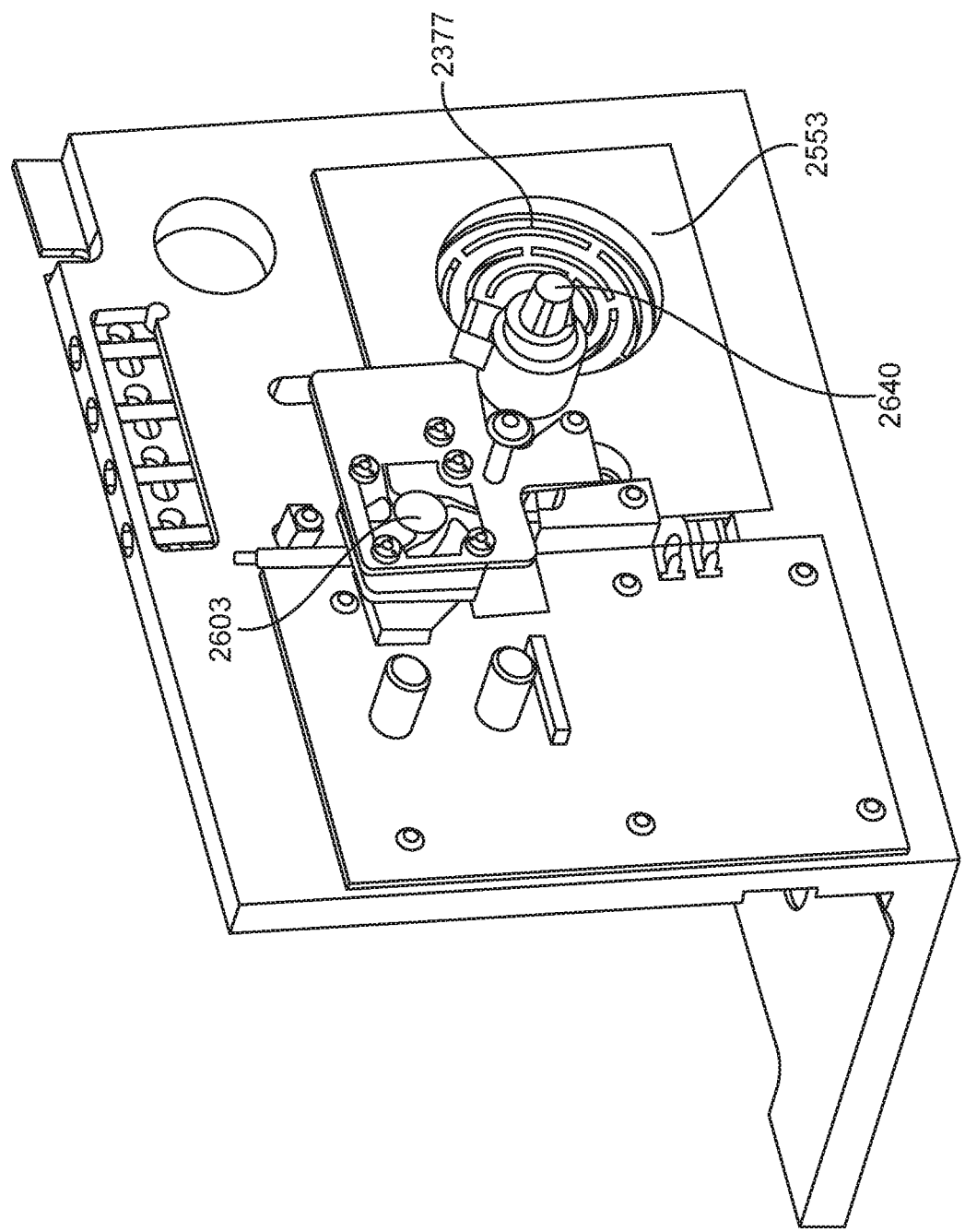

FIG. 52 is a perspective rear view of a cartridge heater assembly of a diagnostic instrument thermal subsystem.

Figure 53:
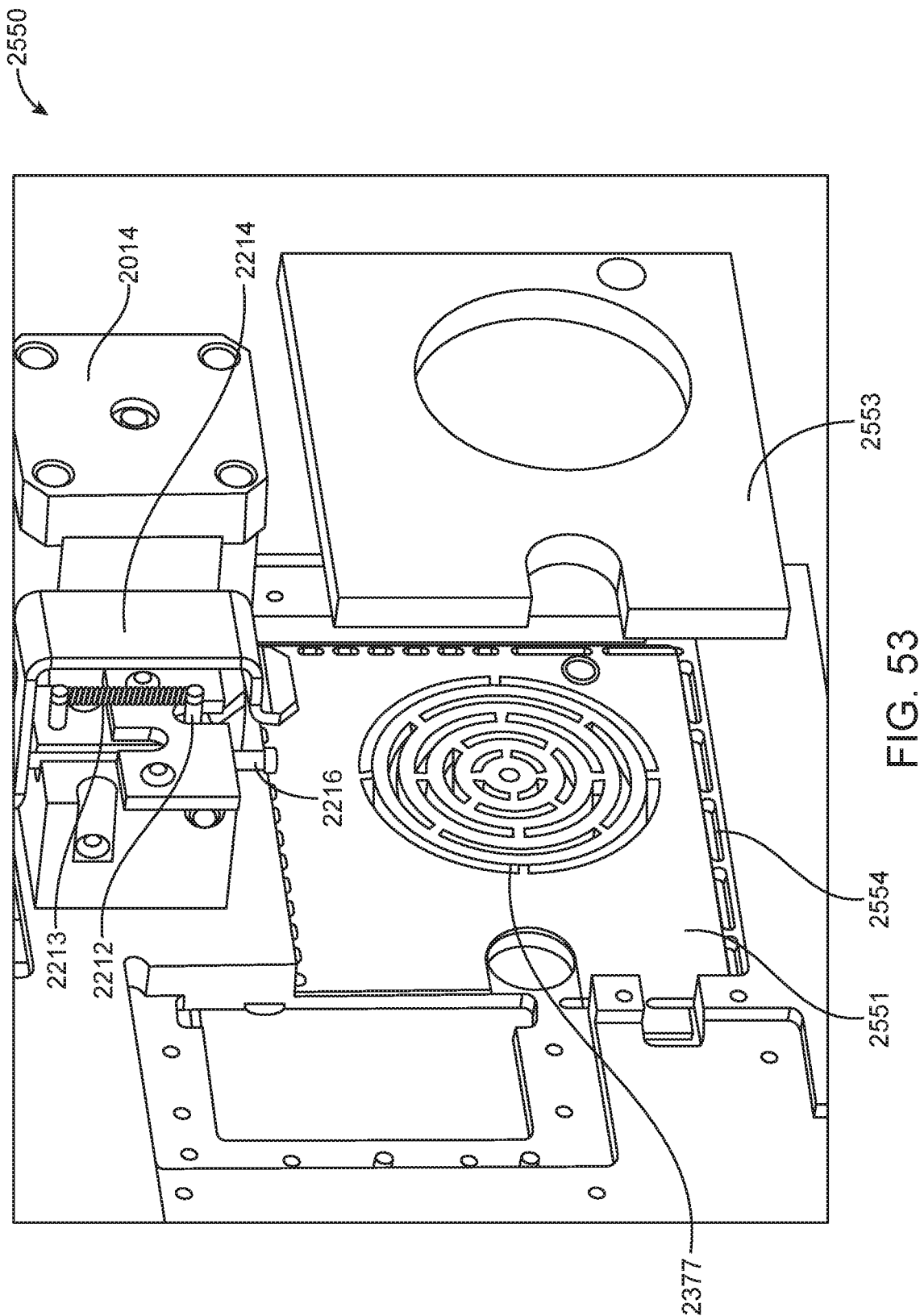

FIG. 53 is an exploded view of FIG. 52. A cartridge heater assembly is shown comprising a chemistry heater, an insulator, a plurality of perforations and a plurality of cutouts.

Figure 54:
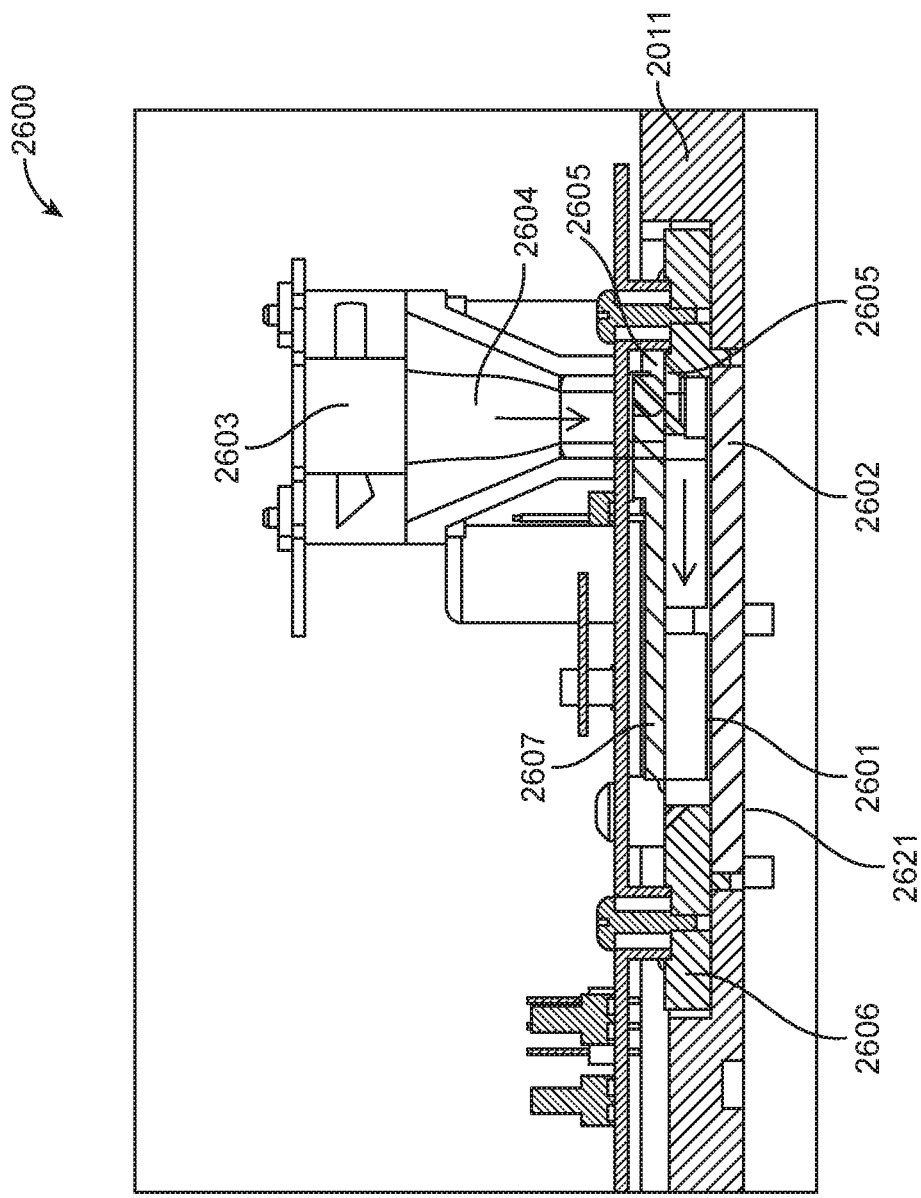

FIG. 54 is a cross-sectional view of a chemistry heater assembly of a diagnostic instrument thermal subsystem.

Figure 55:
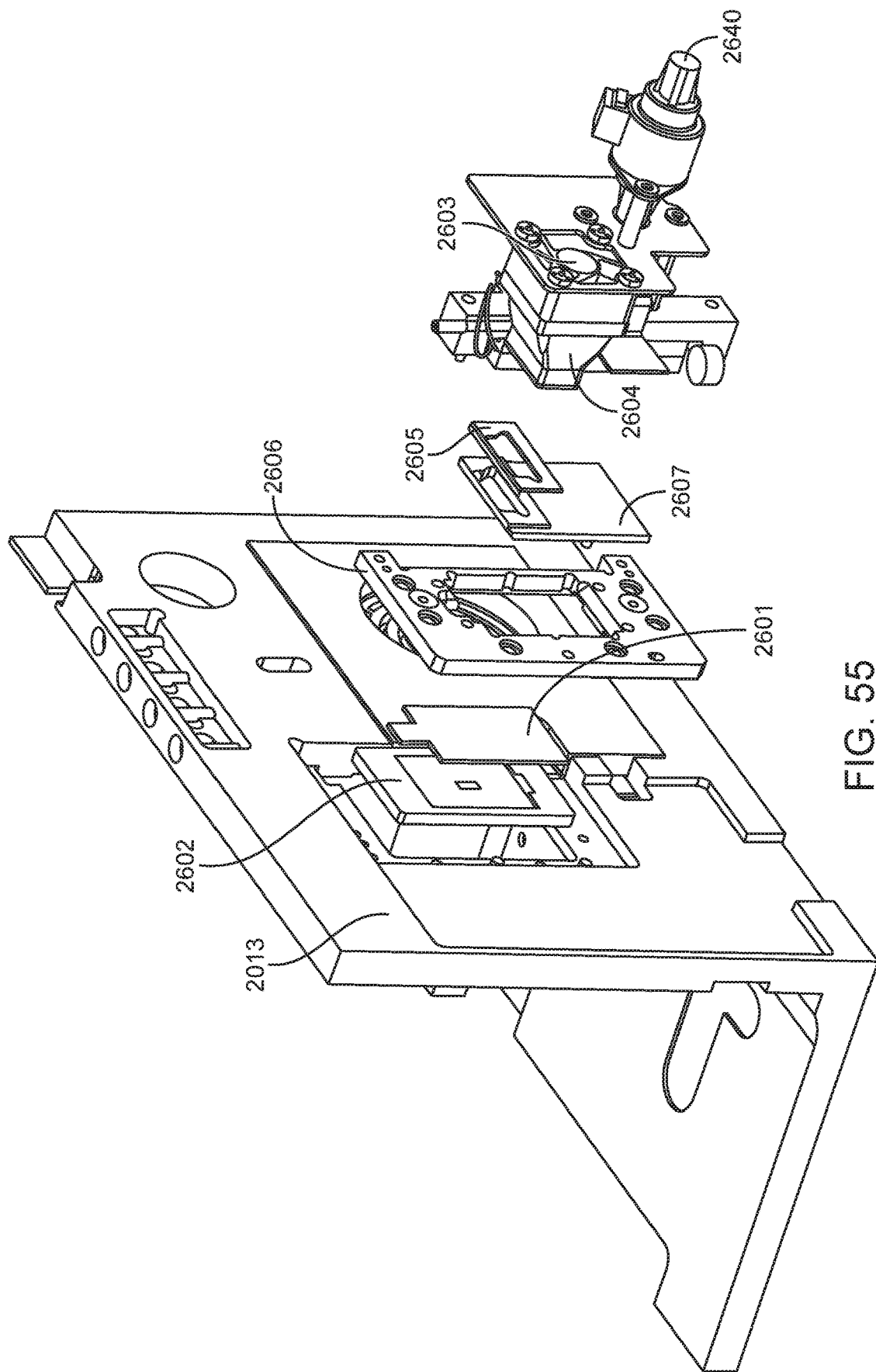

FIG. 55 is an exploded rear view of FIG. 54. A chemistry heater assembly of a diagnostic instrument thermal subsystem is shown comprising a chemistry heater, a chemistry heater plate, a chemistry heater fan, a fan plenum, a flow vane, a flow guide frame, and a heater plenum.

Figure 56:
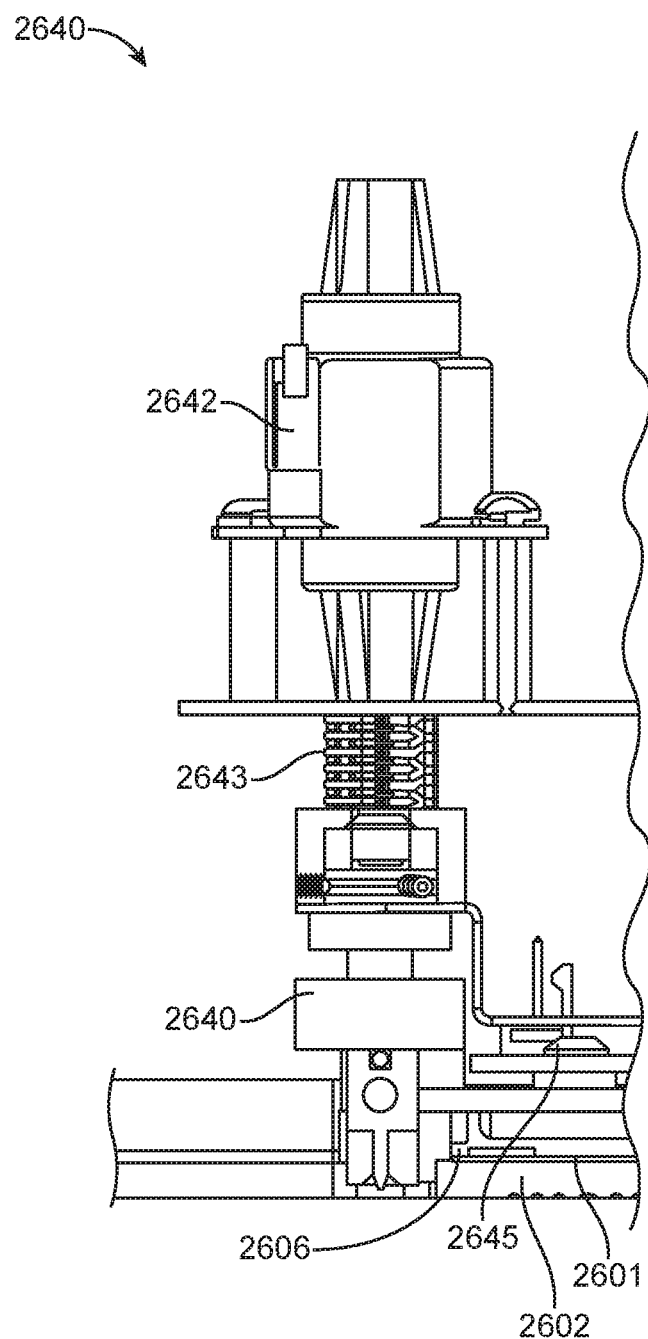

FIG. 56 is a perspective view of a heat staking assembly of a diagnostic instrument thermal subsystem.

Figure 57A:
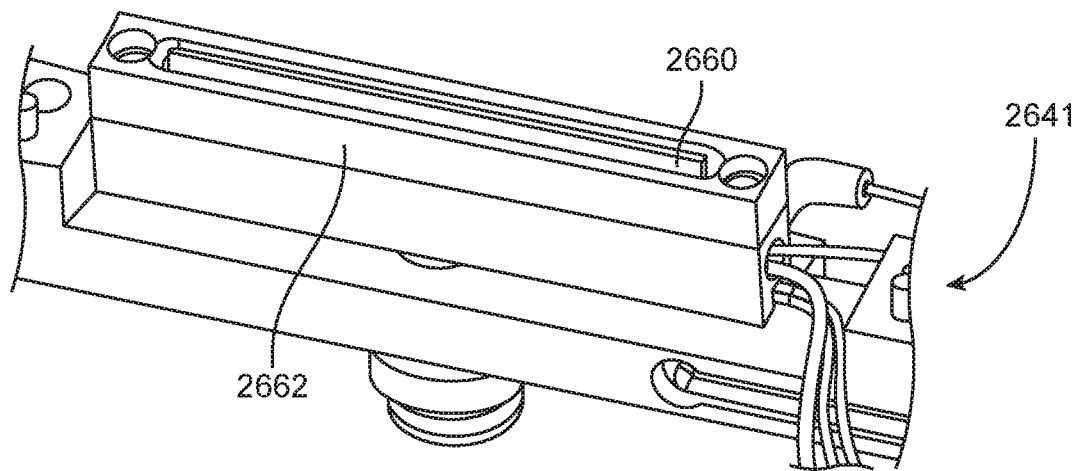

FIG. 57A is an isometric view of a heat staker bar assembly within a heat staking assembly of FIG. 56.

Figure 57B:
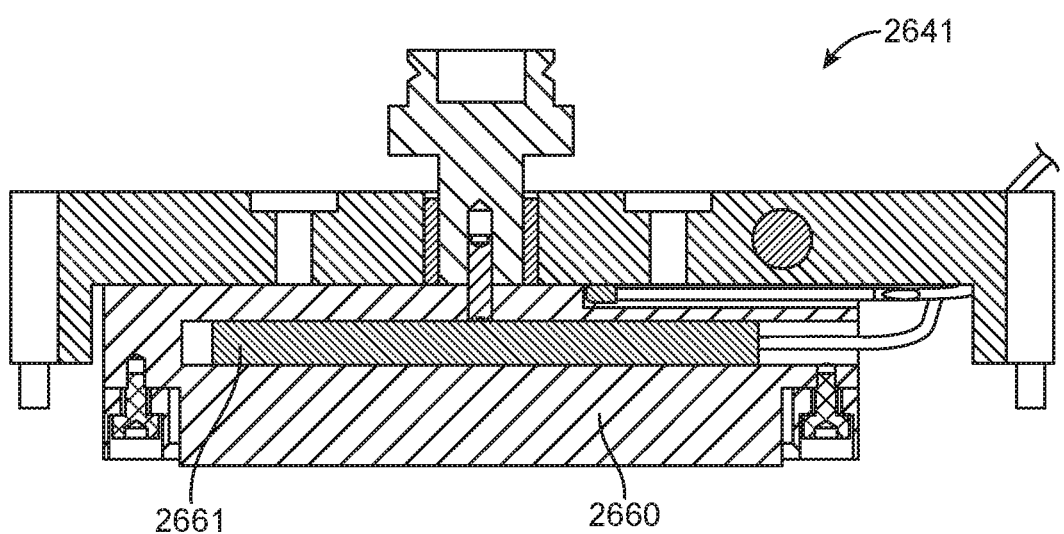

FIG. 57B is a cross-sectional view of FIG. 57A showing a heat staker bar assembly within a heat staking assembly.

Figure 58:
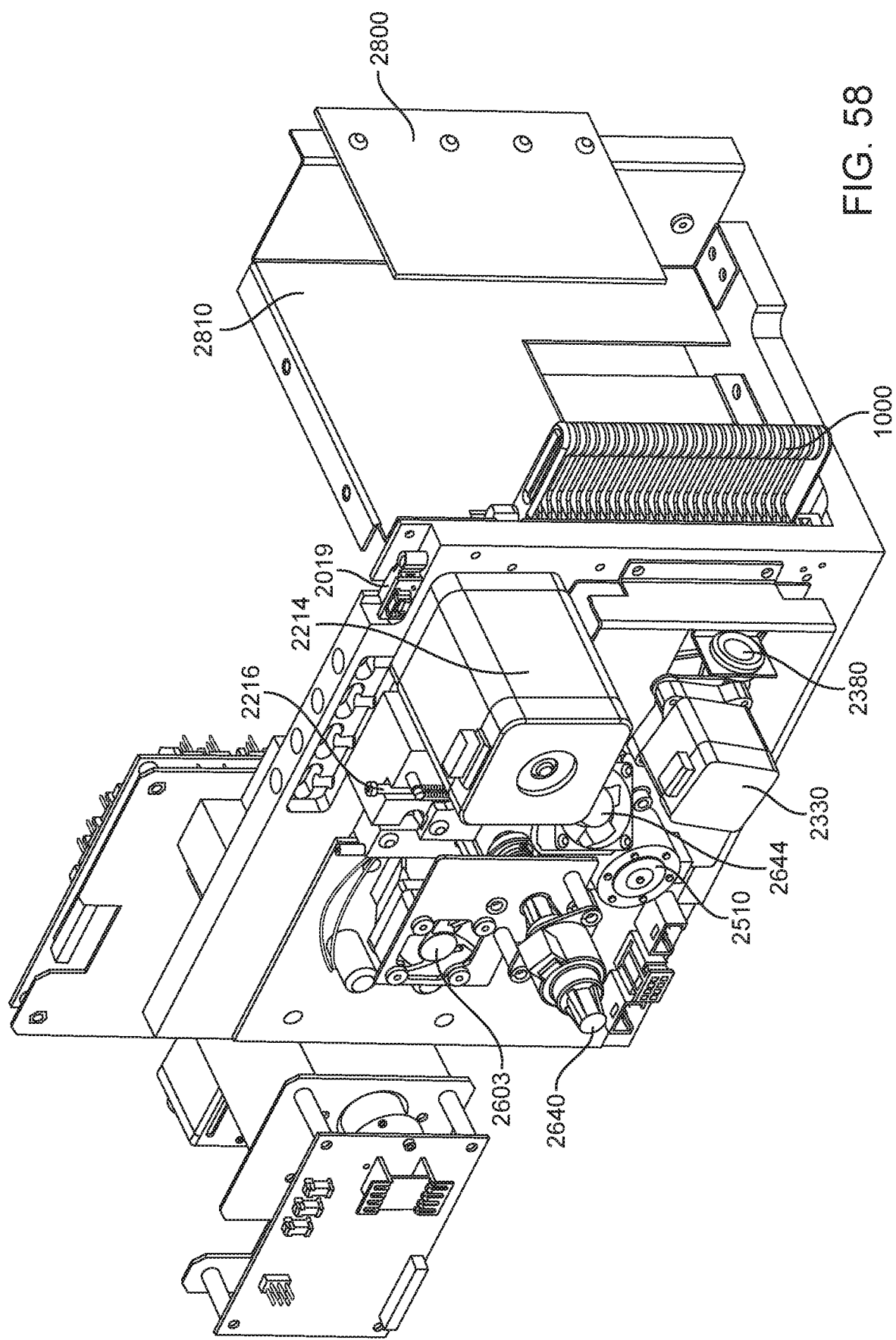

FIG. 58 is a rear perspective view of FIG. 49. An integrated diagnostic cartridge is clamped, as shown in FIGS. 8-11, and is in a loaded position, as described regarding FIGS. 18A-B and 19A-C. A cellular antenna is shown mounted to an antenna ground plate, wherein the ground plate is attached to a fixed support bracket of the fixed bracket assembly.

Figure 59:
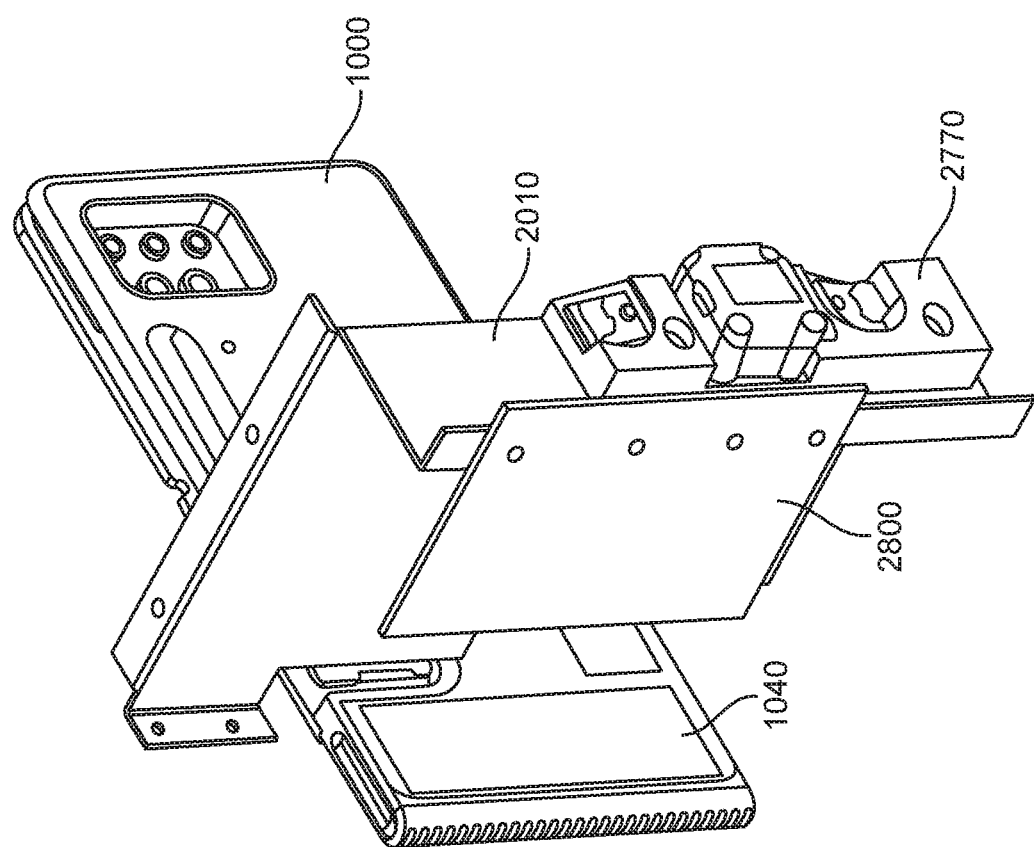

FIG. 59 is an enlarged view of a cellular antenna and label imaging assembly of FIG. 58. The label imaging assembly of a diagnostic instrument is shown fixed to an antenna ground plate. A patient label area of the cartridge label and a loading module are disposed within the field of view of a label imaging assembly camera.

Figure 60:
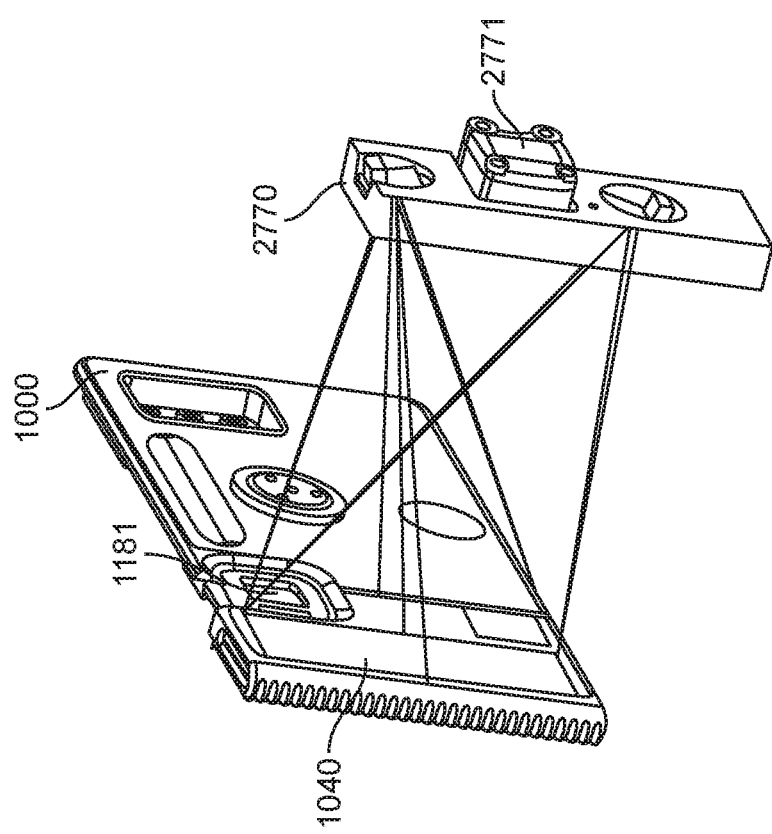

FIG. 60 is a perspective view of a label imaging assembly from FIG. 59. The field of view of the label imaging assembly includes a patient label area of a cartridge label and a loading module of an integrated diagnostic cartridge.

Figure 61:
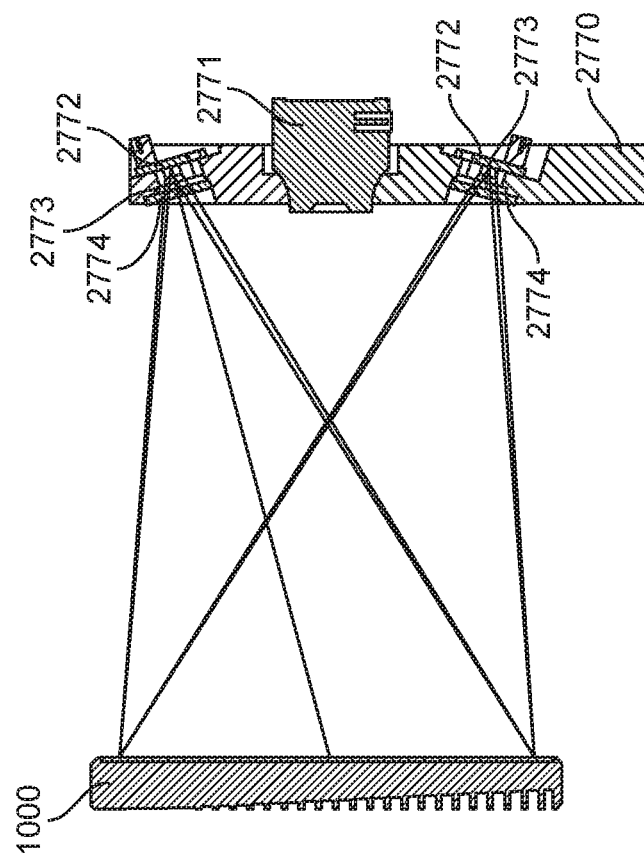

FIG. 61 is a cross-sectional view of a label imaging assembly from FIGS. 59 and 60.

Figure 62:
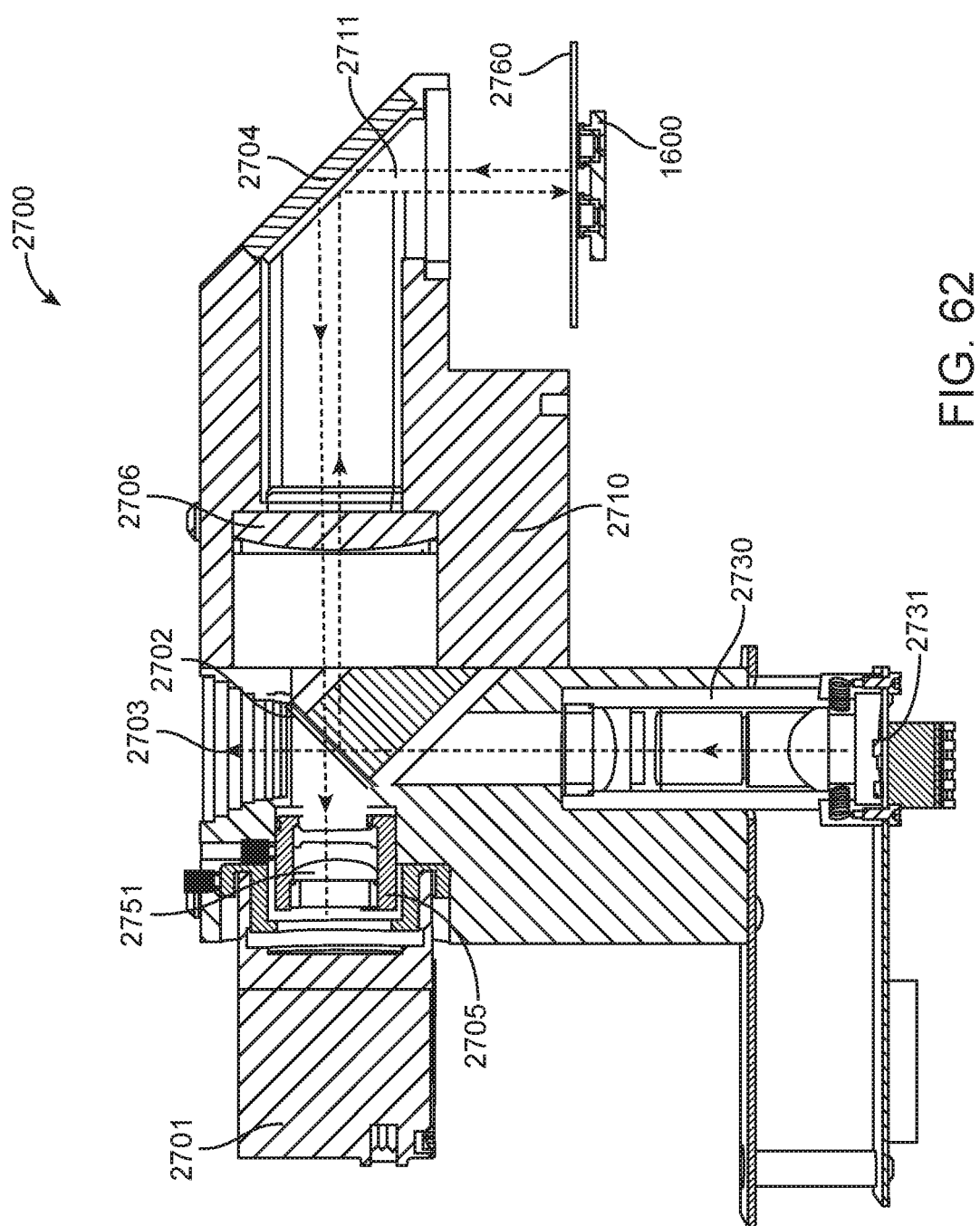

FIG. 62 is a top down cross-sectional view of a reaction imaging assembly of a diagnostic instrument optical subsystem. Excitation wavelengths are shown contacting an image plane of an integrated diagnostic cartridge reaction area. Emission paths are shown emanating from an image plane of an integrated diagnostic cartridge reaction area to a reaction camera.

Figure 63:
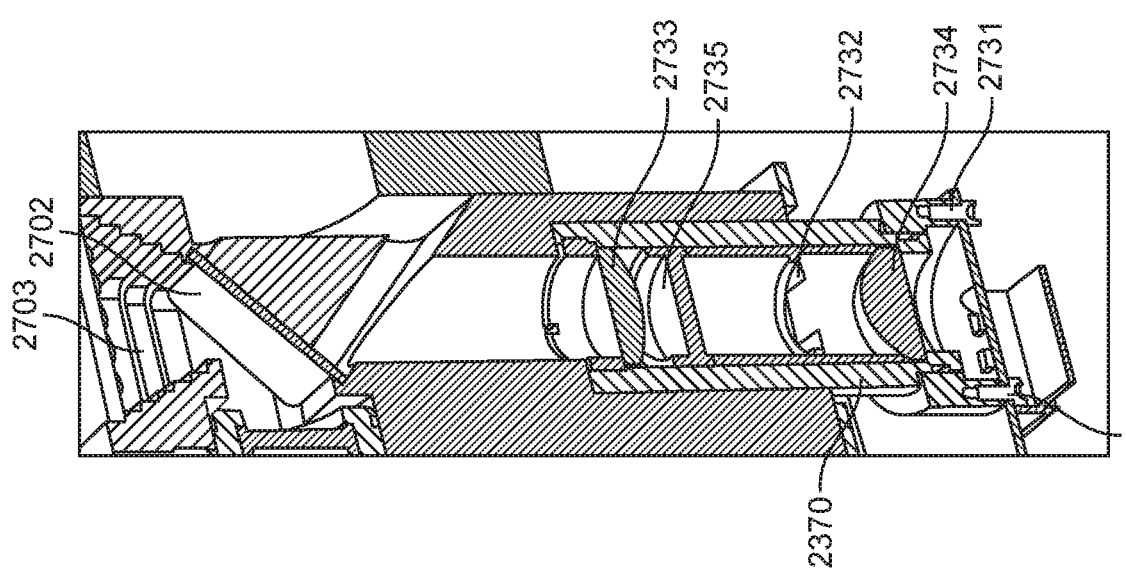

FIG. 63 is a cross-sectional view of an excitation lens cell of a reaction imaging assembly from FIG. 62.

Figure 64:
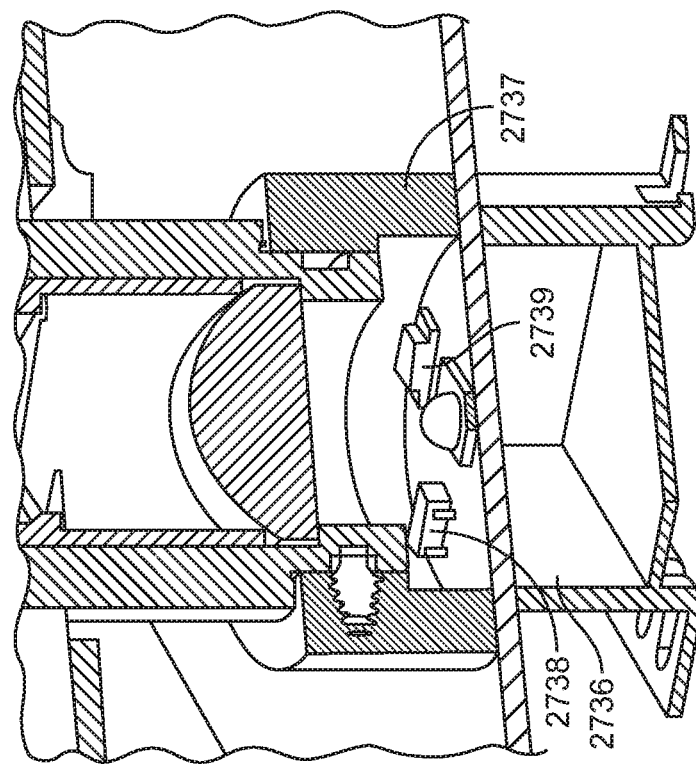

FIG. 64 is an additional enlarged cross-sectional view of a bottom of an excitation lens cell.

Figure 65:
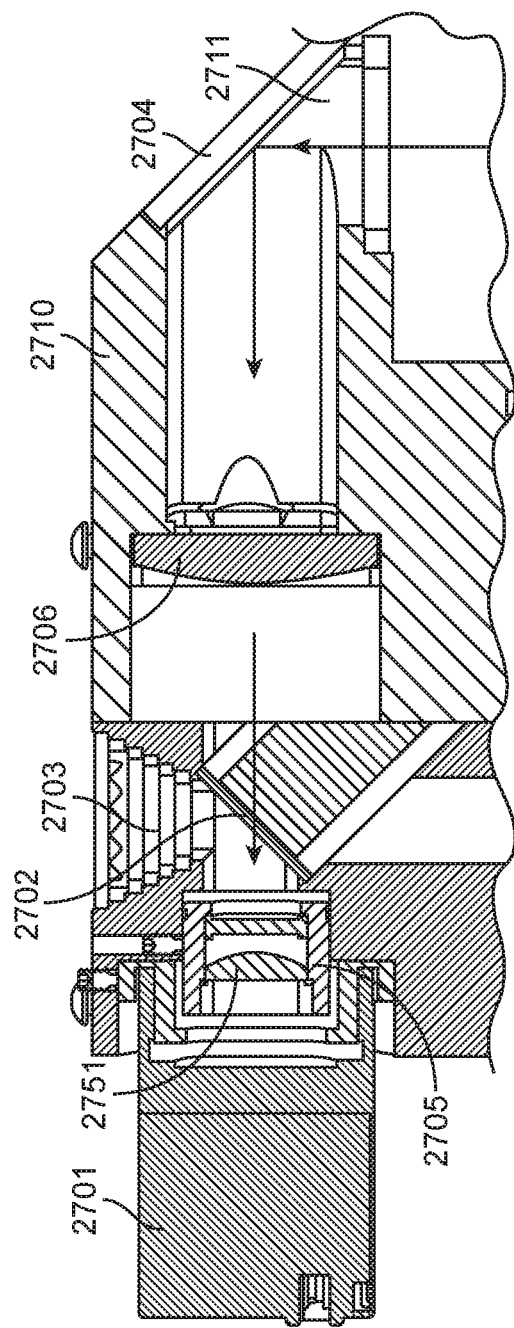

FIG. 65 is an enlarged top down cross-sectional view FIG. 62. A reaction imaging assembly of a diagnostic instrument optical subsystem is shown with emission wavelengths reflected off a fold mirror, through a dichroic beam splitter and into a reaction camera.

Figure 66:
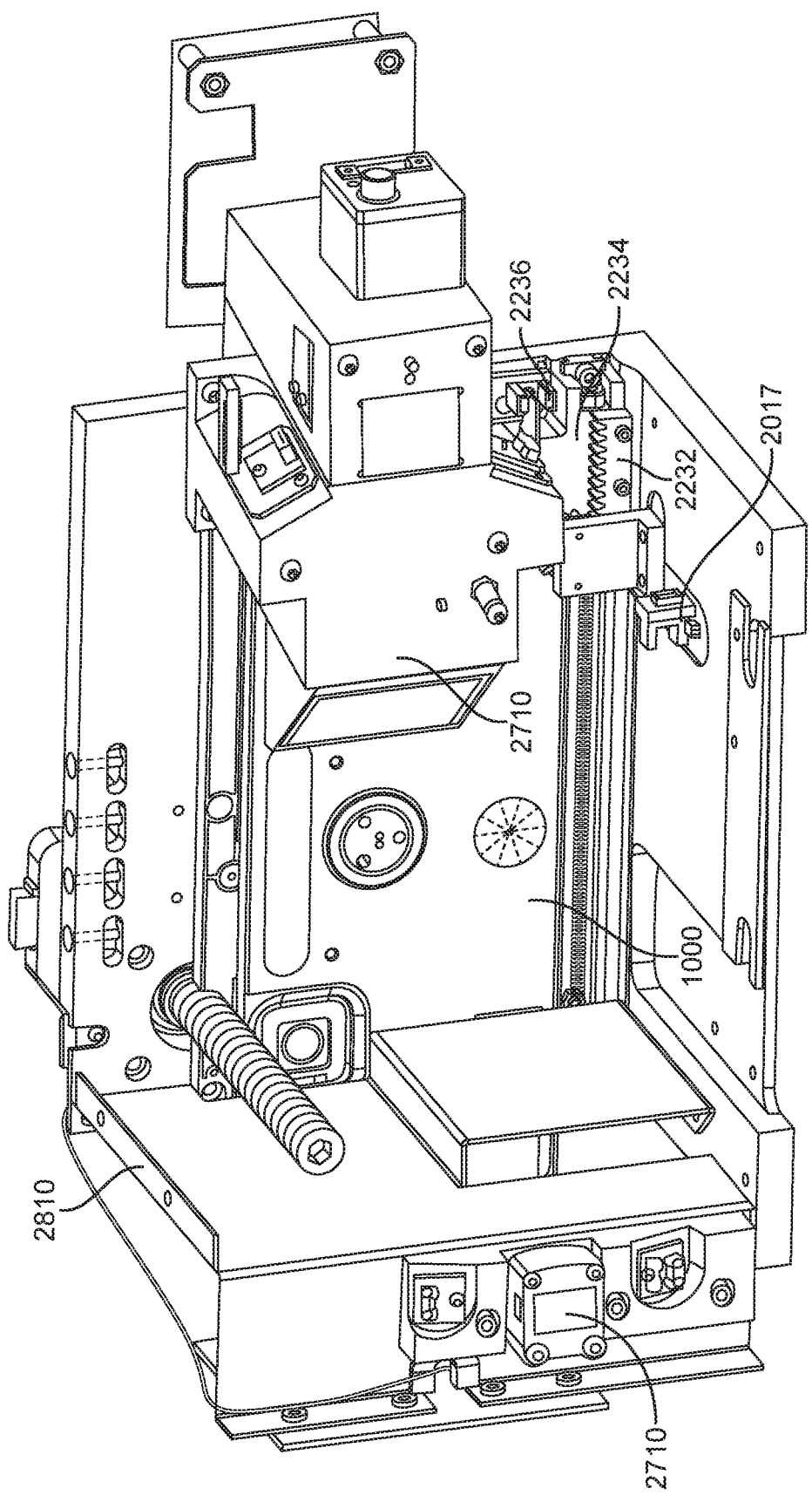

FIG. 66 is an isometric view of a diagnostic instrument optical subsystem, as shown by FIGS. 45 and 46. A label imaging assembly and a reaction imaging assembly of the optical subsystem are attached to a fixed support bracket. An integrated diagnostic cartridge is inserted into a loading assembly and is in a loaded position, as described with regard to FIGS. 18A-18B and 19A-19C.

Figure 67A:
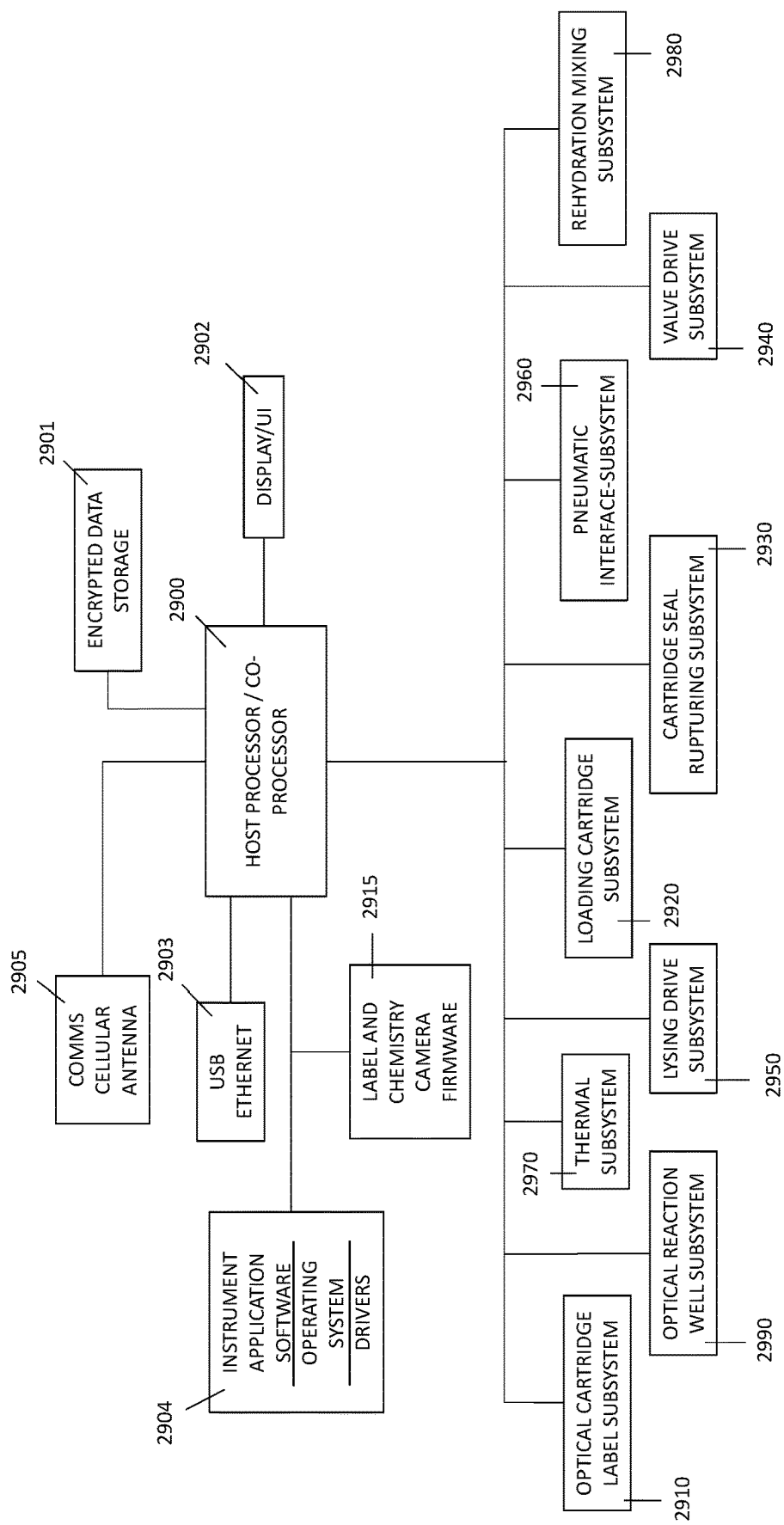

FIG. 67A is a schematic diagram of an exemplary instrument computer control system FIG. 67B is a schematic diagram of the optical cartridge label subsystem of the exemplary computer control system of FIG. 67A.

Figure 67C:
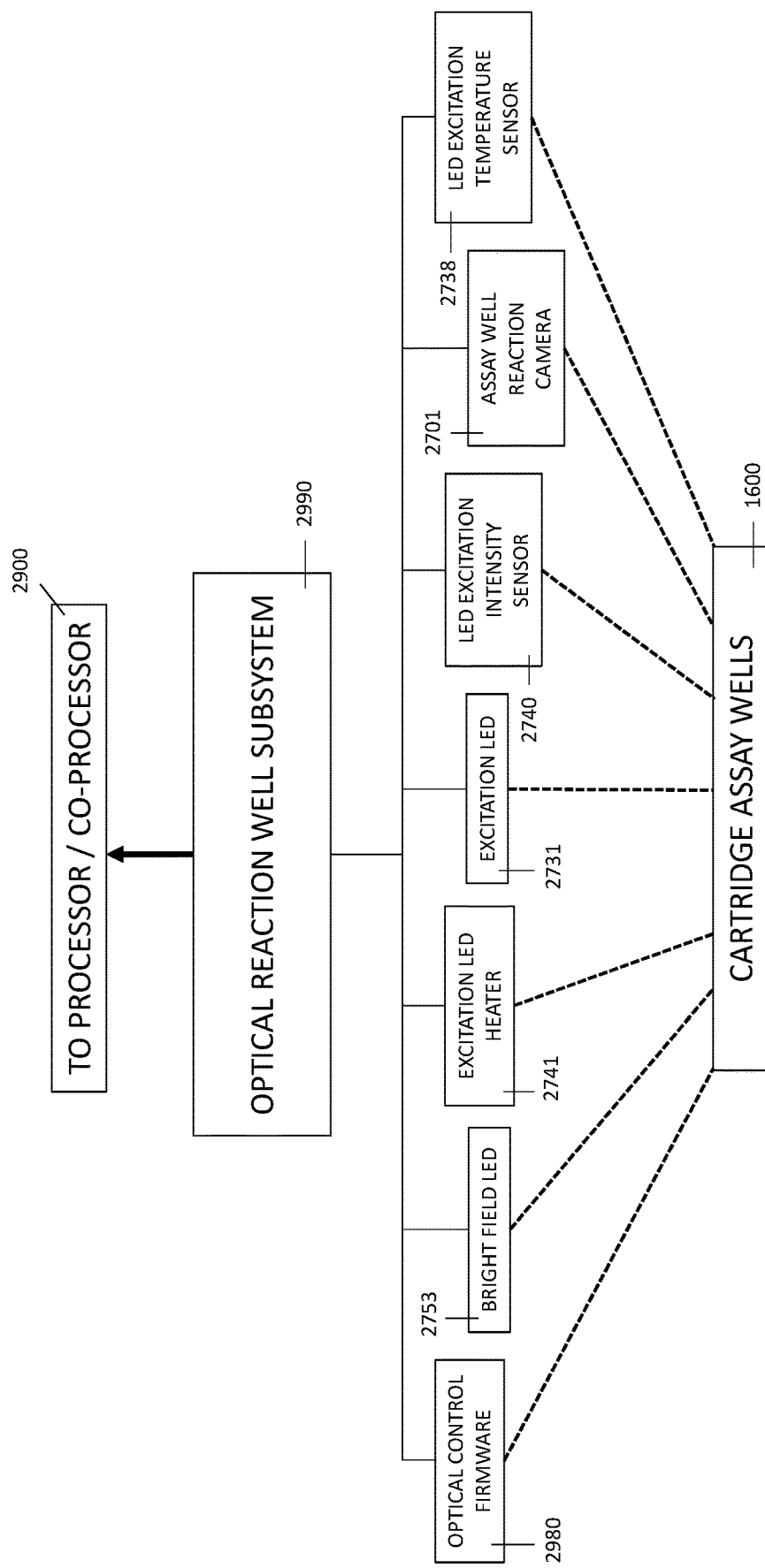

FIG. 67C is a schematic diagram of the optical reaction or assay well subsystem of the exemplary computer control system of FIG. 67A.

Figure 67D:
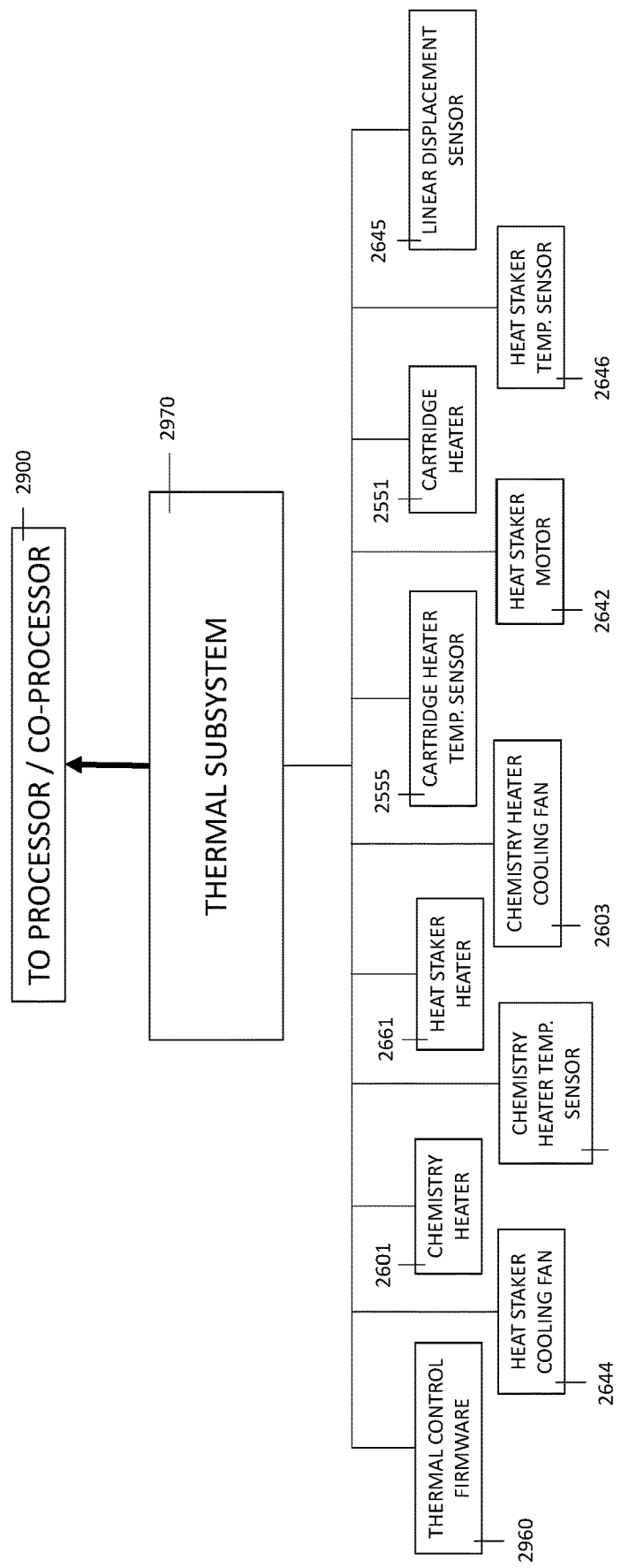

FIG. 67D is a schematic diagram of the thermal subsystem of the exemplary computer control system of FIG. 67A.

FIG. 67E is a schematic diagram of the lysing drive subsystem of the exemplary computer control system of FIG. 67A.

Figure 67F:
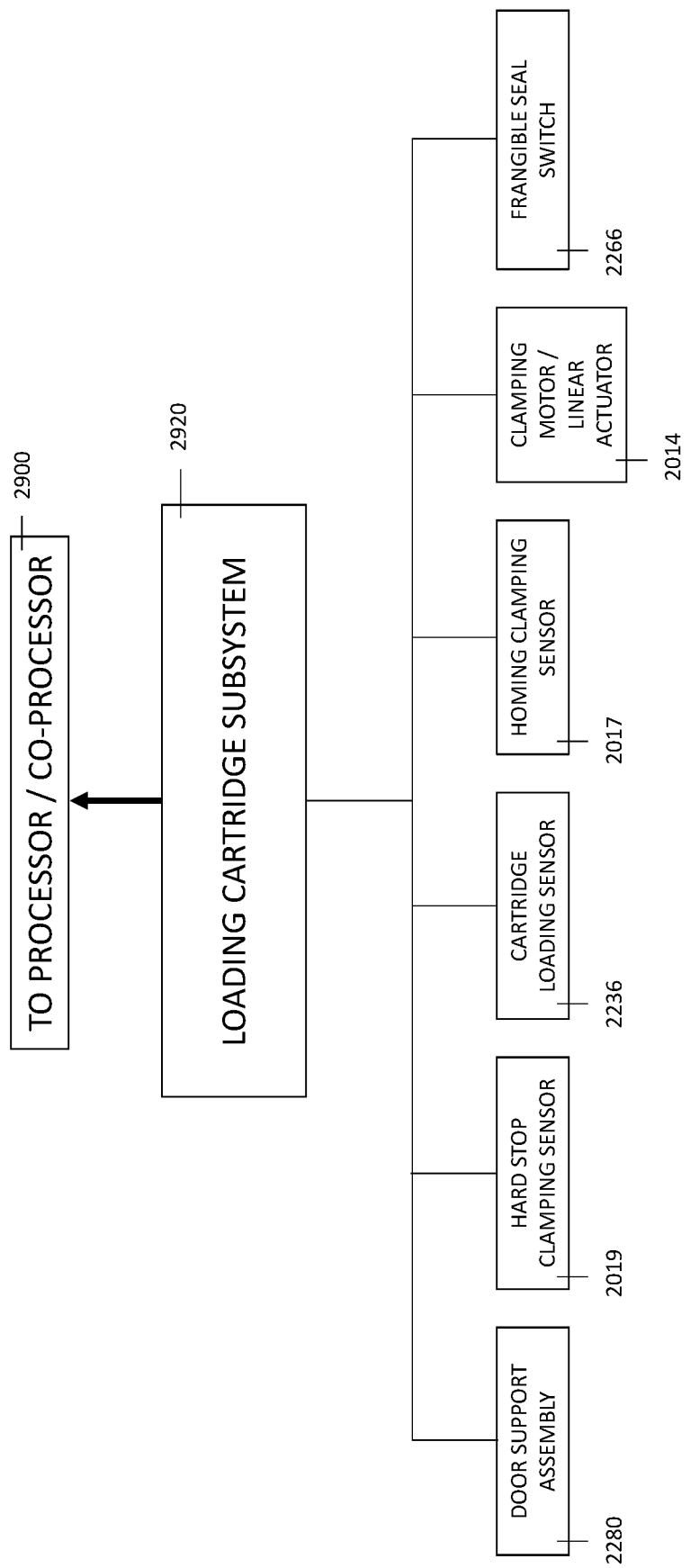

FIG. 67F is a schematic diagram of the loading cartridge subsystem of the exemplary computer control system of FIG. 67A.

Figure 67G:
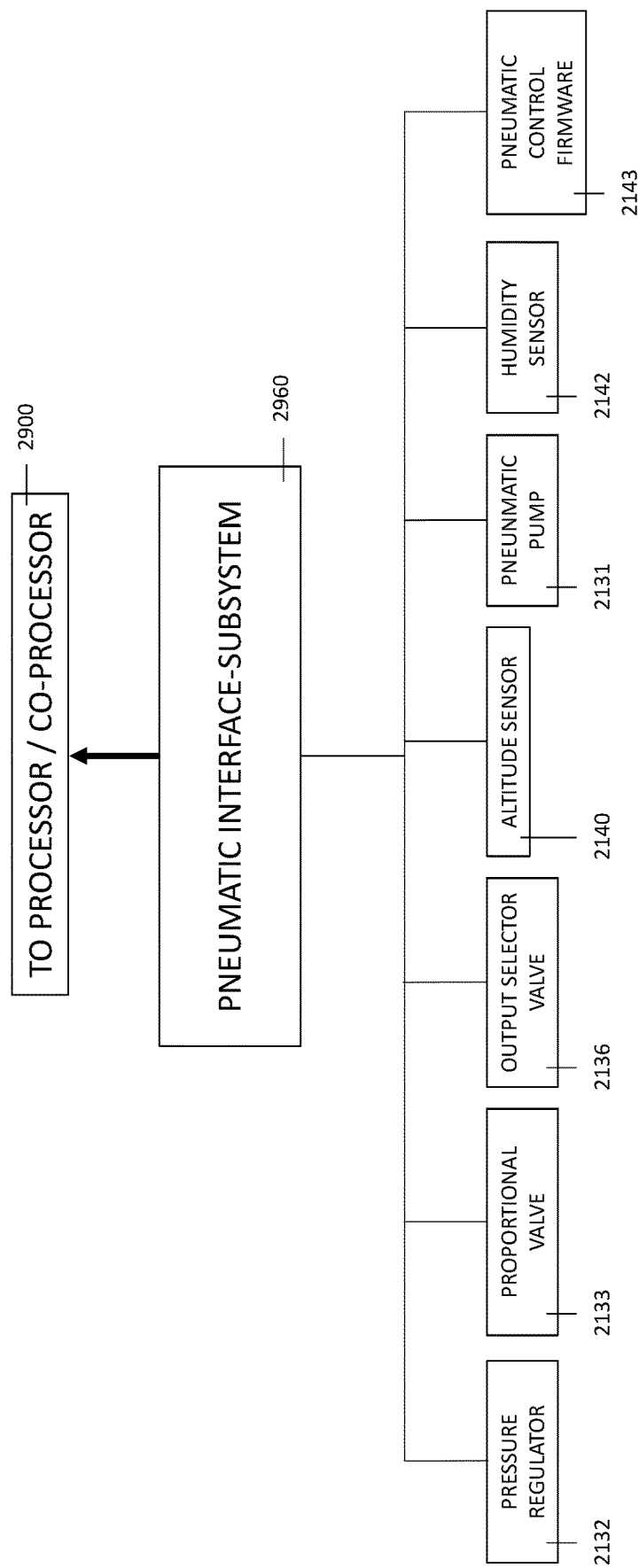

FIG. 67G is a schematic diagram of the pneumatic subsystem of the exemplary computer control system of FIG. 67A.

Figure 67H:
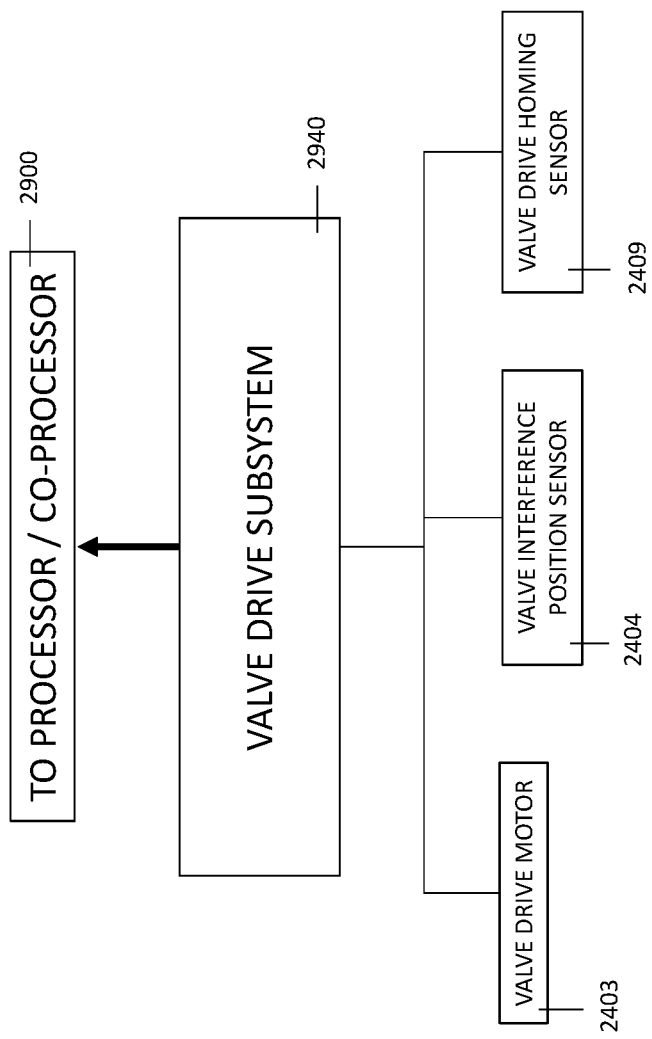

FIG. 67H is a schematic diagram of the valve drive subsystem of the exemplary computer control system of FIG. 67A.

Figure 67I:
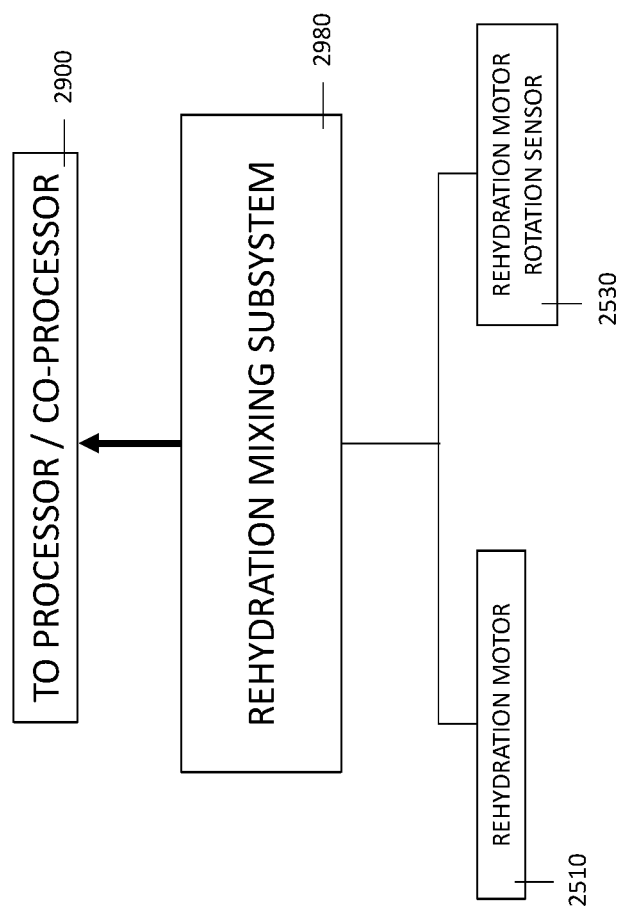

FIG. 67I is a schematic diagram of the rehydration mixing subsystem of the exemplary computer control system of FIG. 67A.

Figure 68:
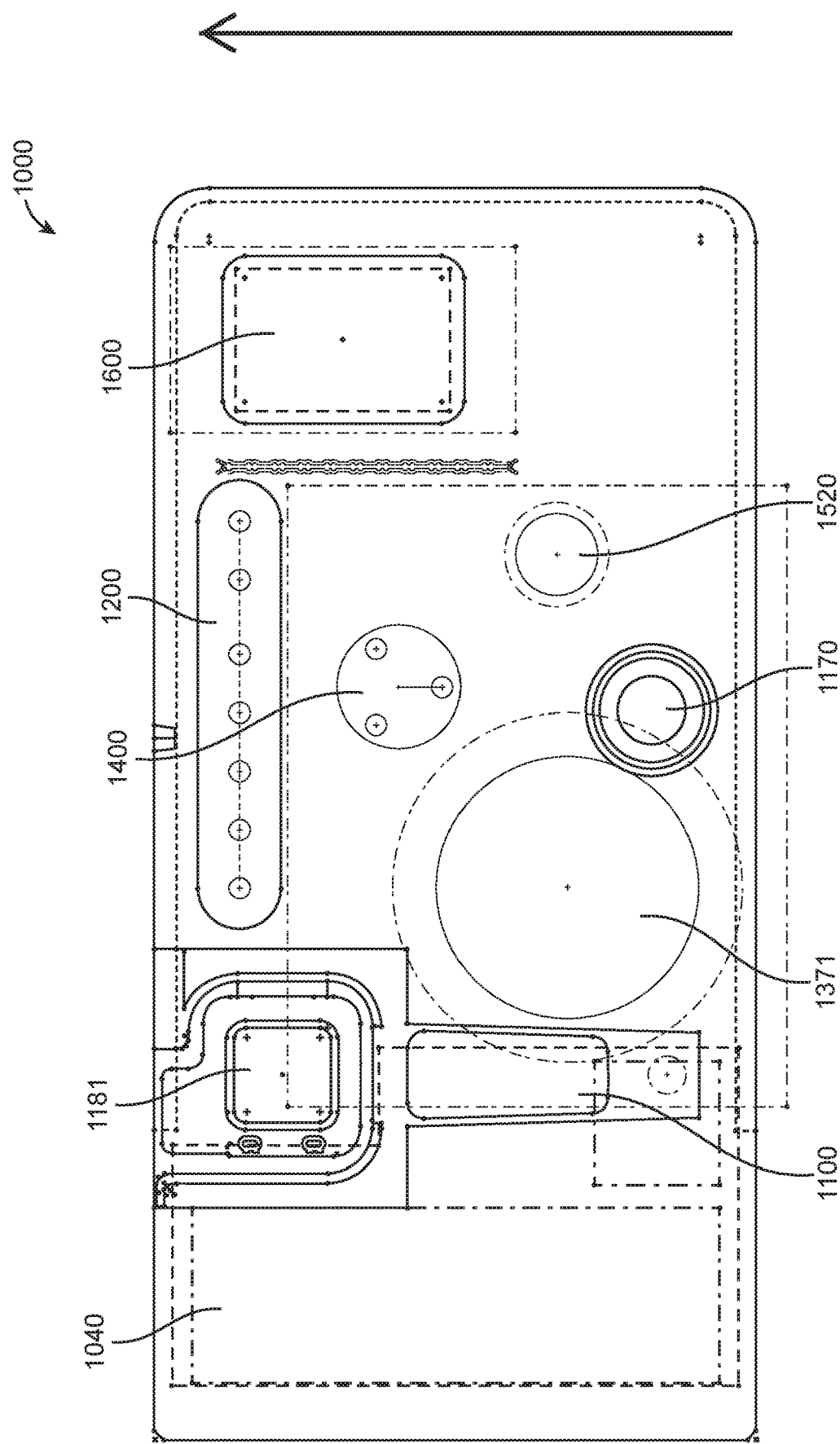

FIG. 68 is a schematic layout of an integrated diagnostic cartridge according to an embodiment described herein.

Figure 69:
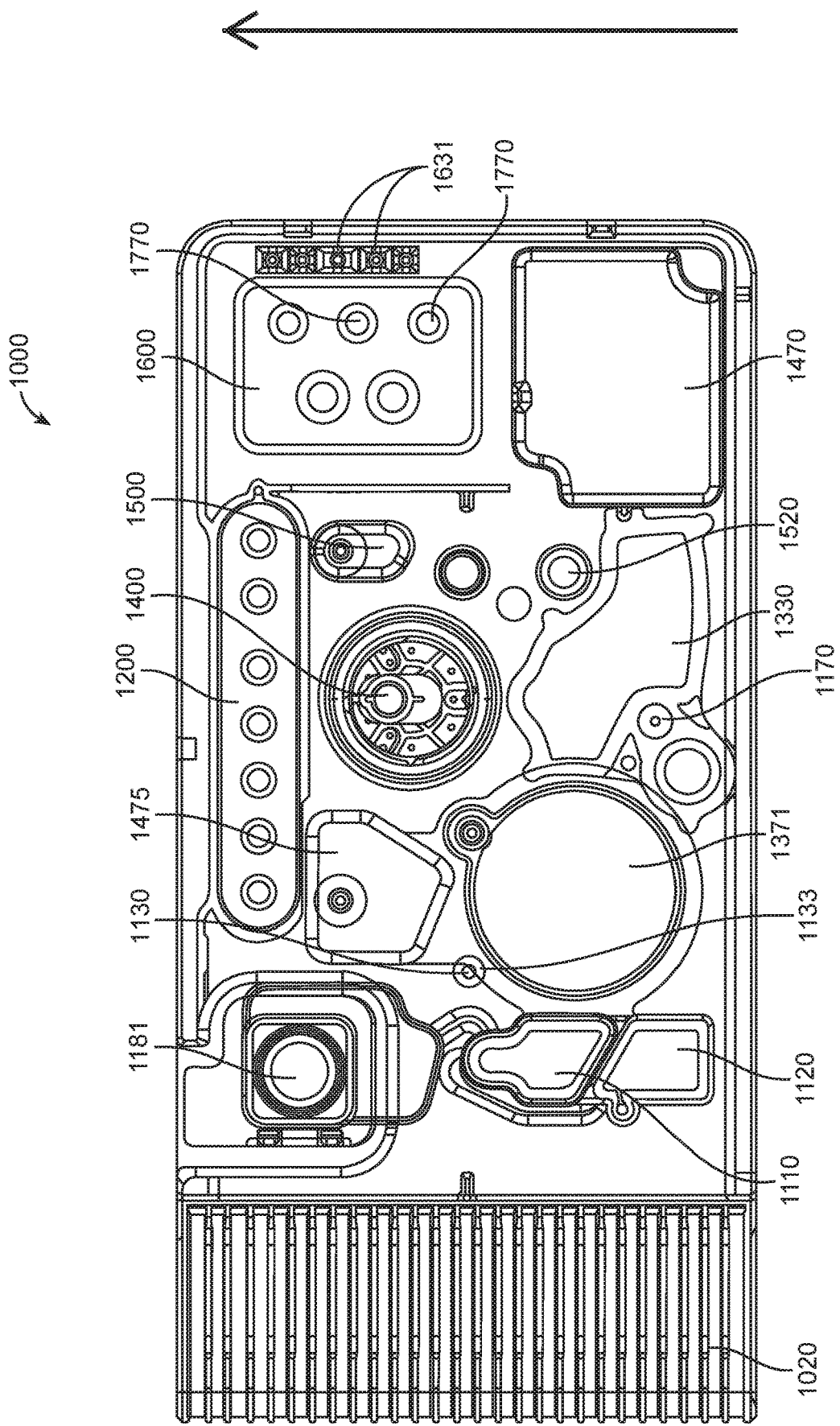

FIG. 69 is an illustration of an integrated diagnostic cartridge, according to an embodiment described herein, viewed from a feature side.

Figure 70:
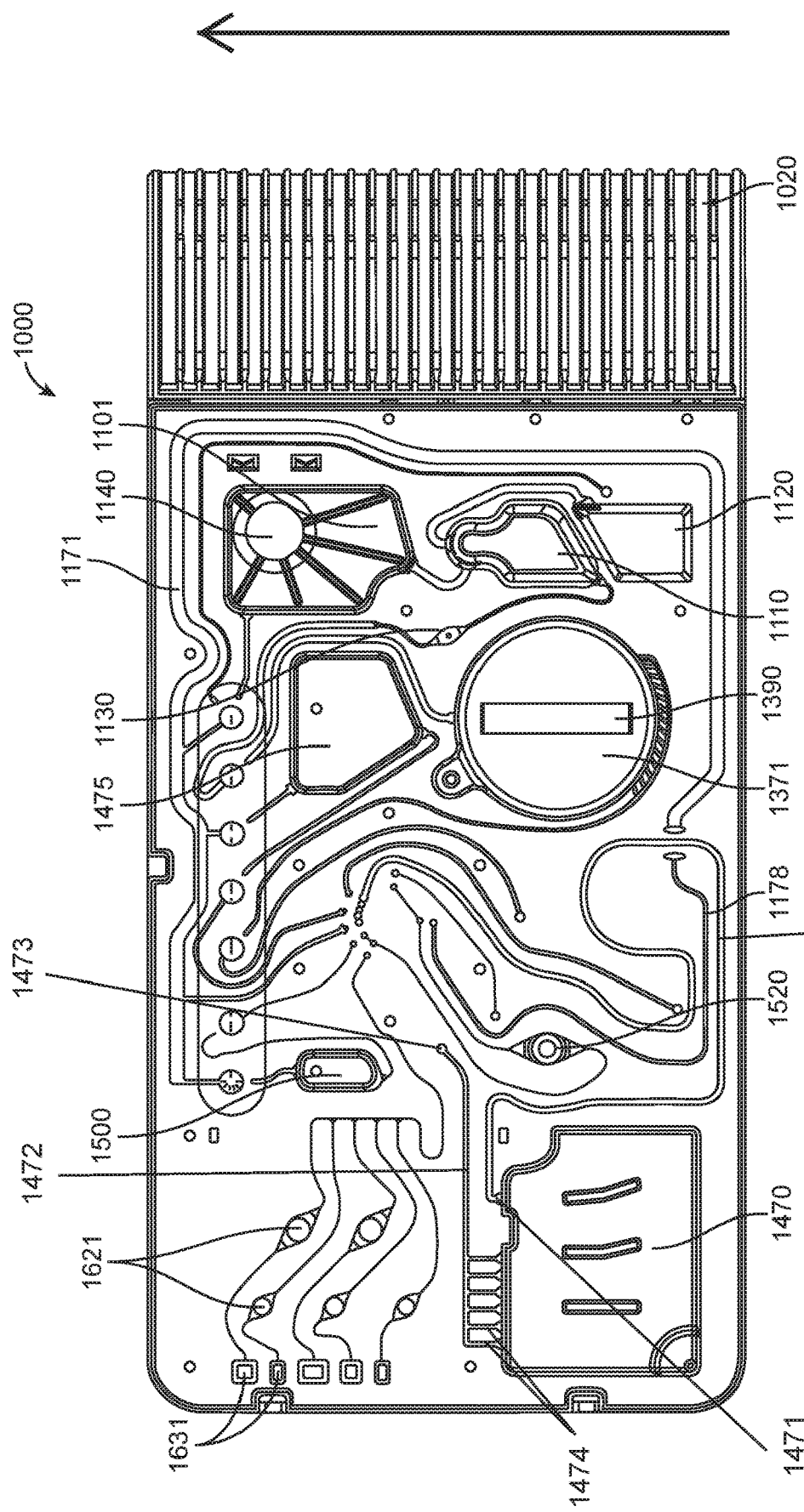

FIG. 70 is an illustration of an integrated diagnostic cartridge, according to an embodiment described herein, viewed from a fluidics side.

Figure 71:
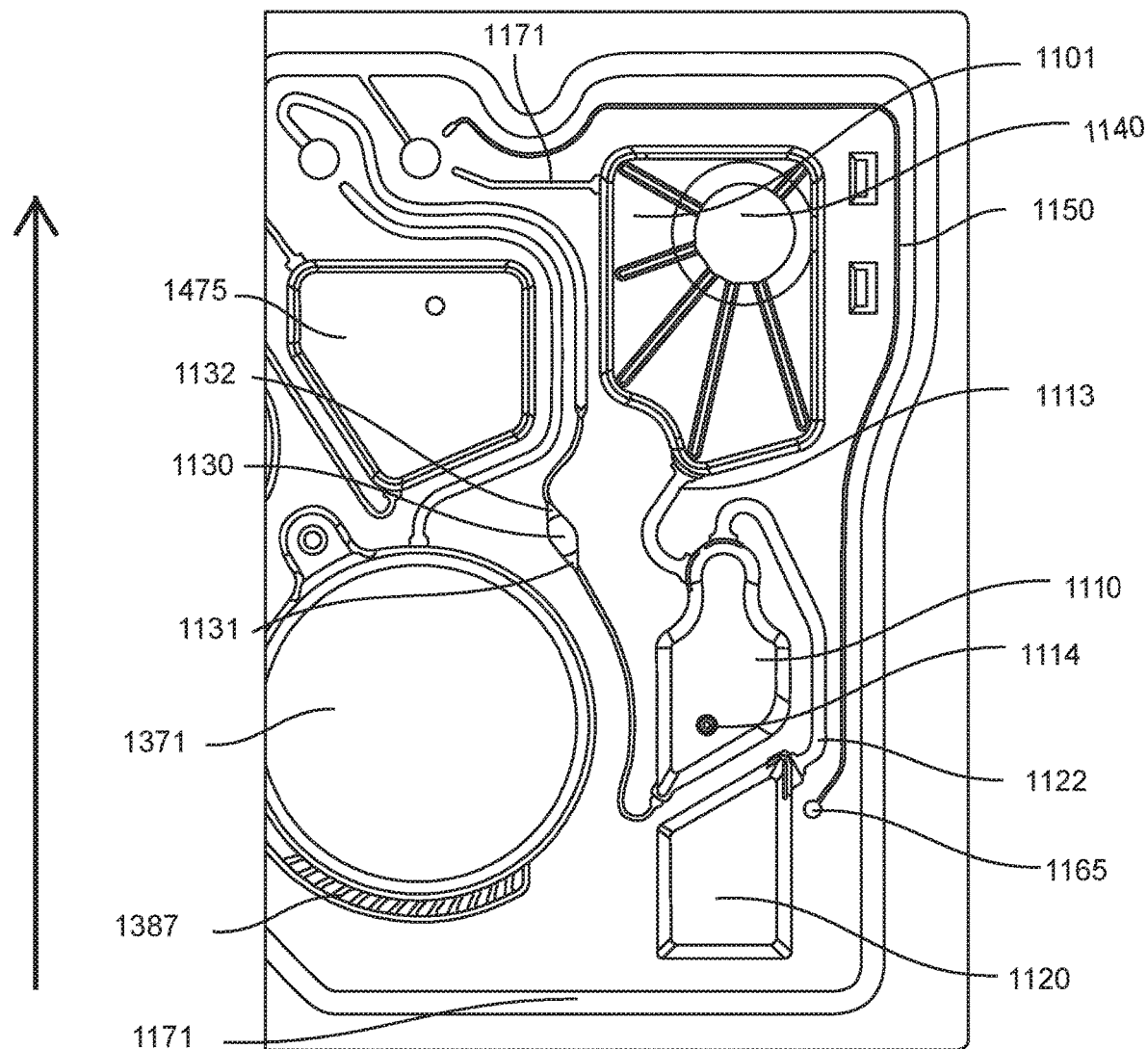

FIG. 71 is an isometric view of a loading module in accordance with an embodiment shown in FIGS. 69 and 70. A fill chamber, a metering chamber, and an overflow chamber are shown in fluidic communication.

Figure 72:
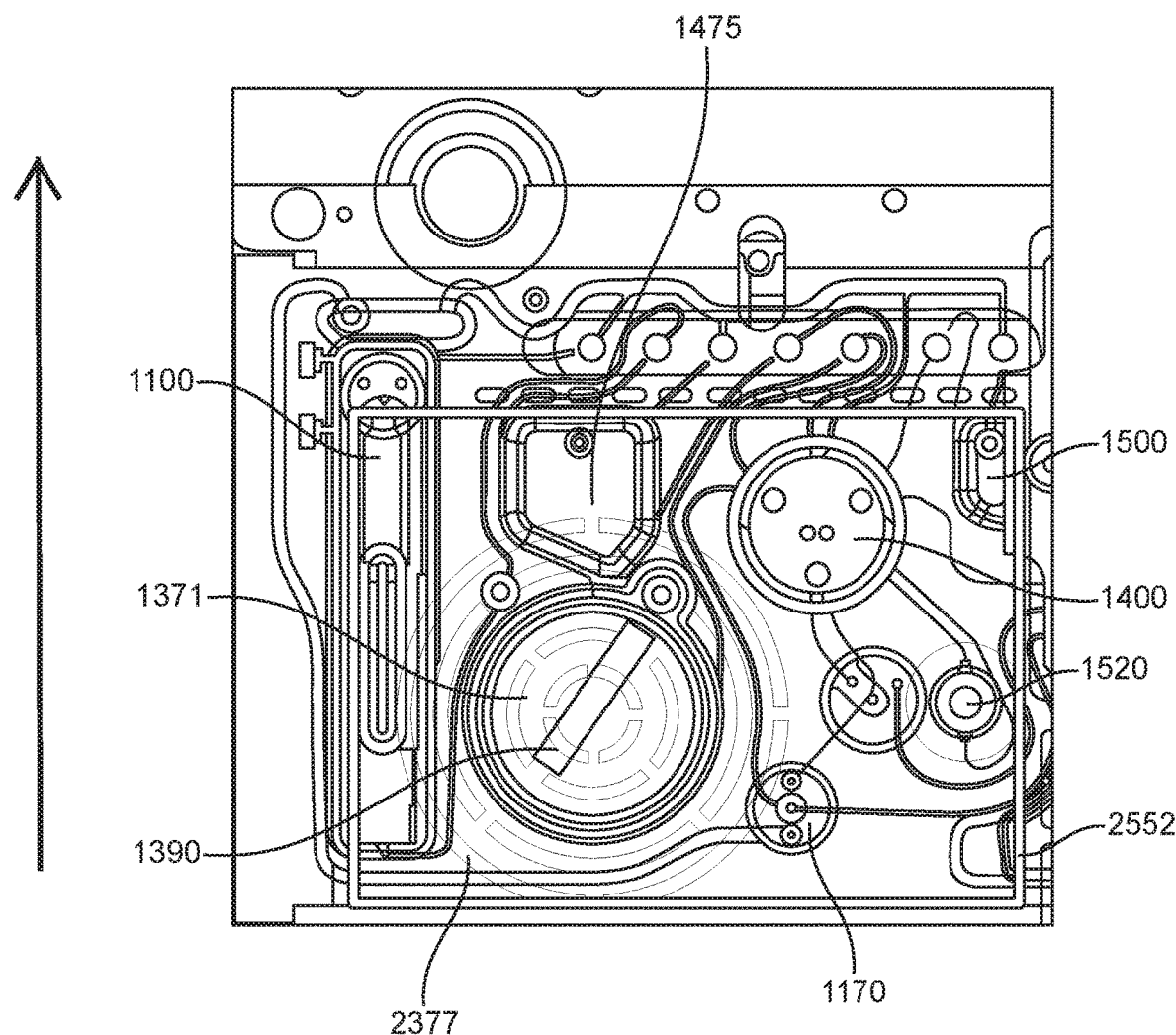

FIG. 72 is a view of an integrated diagnostic cartridge and a cartridge heating zone provided by a diagnostic instrument thermal subsystem.

Figure 73:
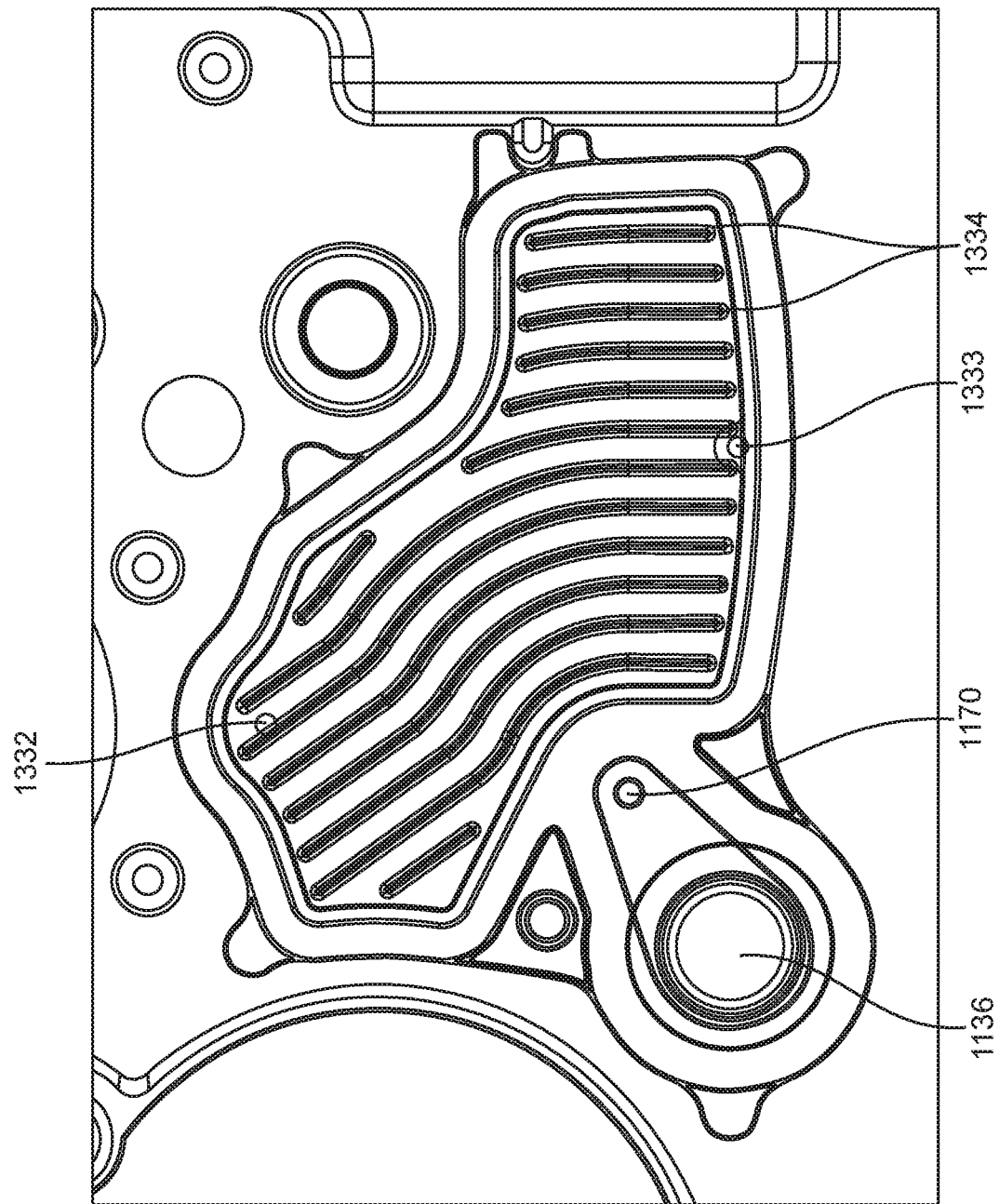

FIG. 73 is a top view of a filter assembly on an integrated diagnostic cartridge, as described herein.

Figure 74:
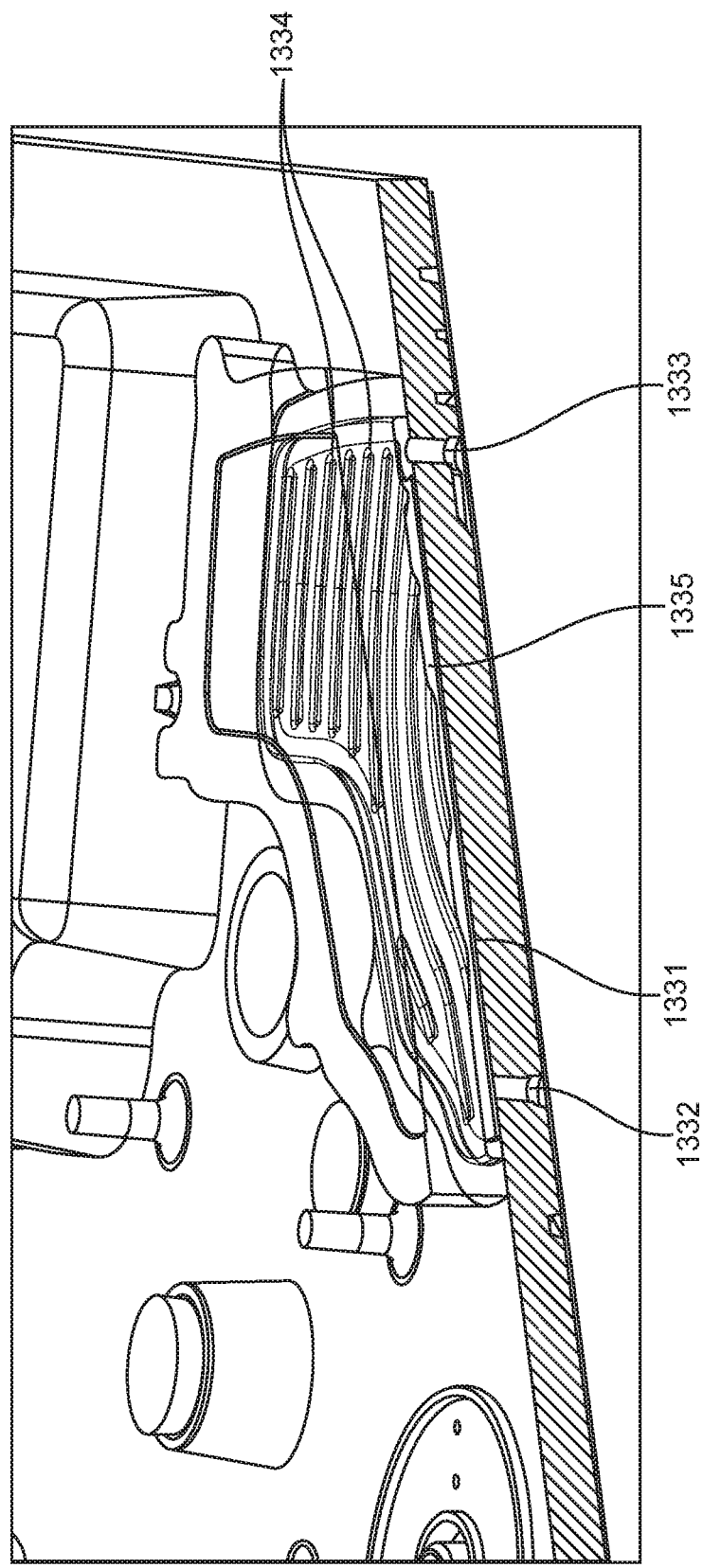

FIG. 74 is a cross-sectional view of a filter assembly shown in FIG. 73.

Figure 75:
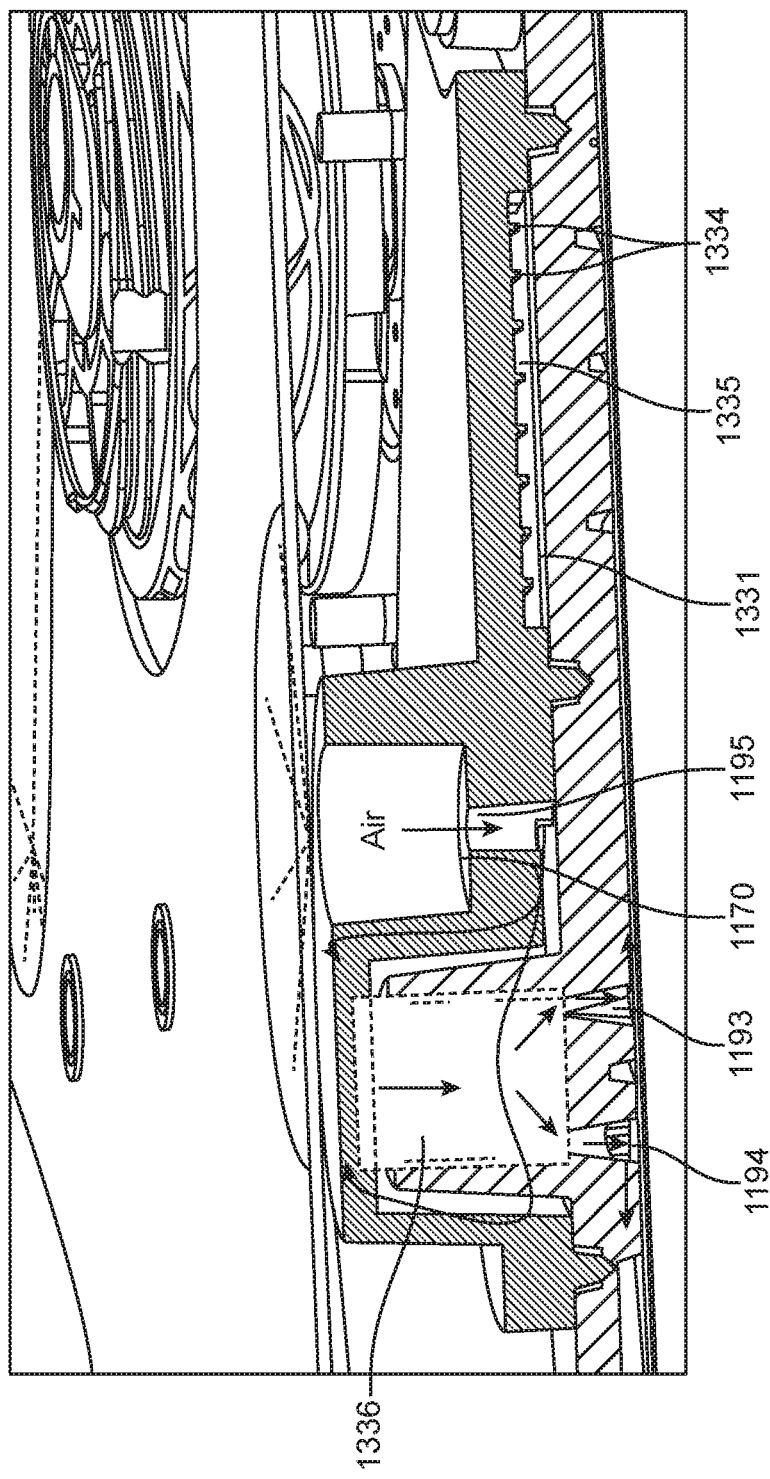

FIG. 75 is a cross-sectional view of an integrated diagnostic cartridge pneumatic interface and a filter assembly illustrated in FIGS. 73 and 74.

Figure 76:
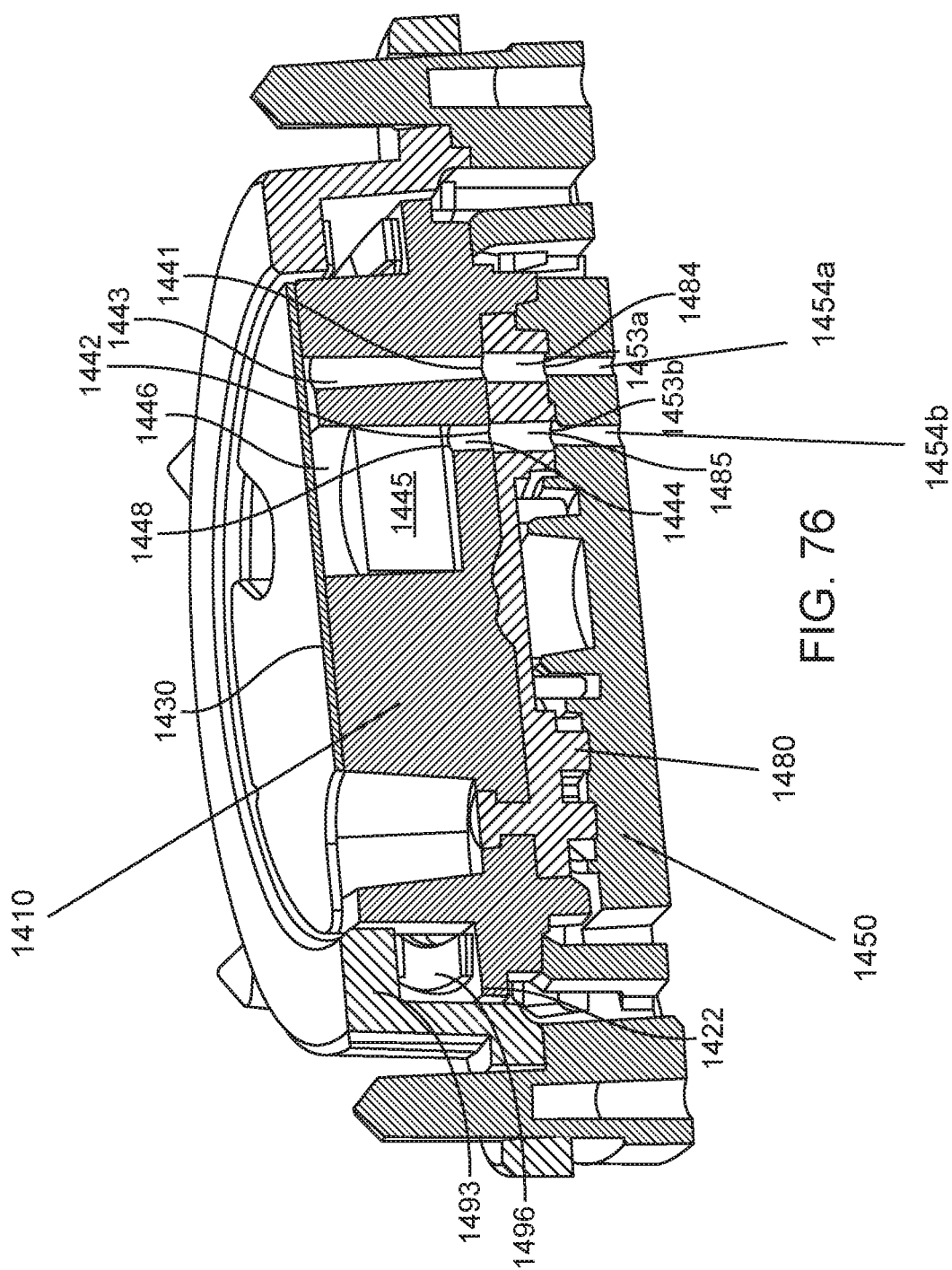

FIG. 76 is a cross-sectional perspective view of a rotary valve illustrating an interface between a rotor and a stator, according to an embodiment of the invention.

Figure 77:
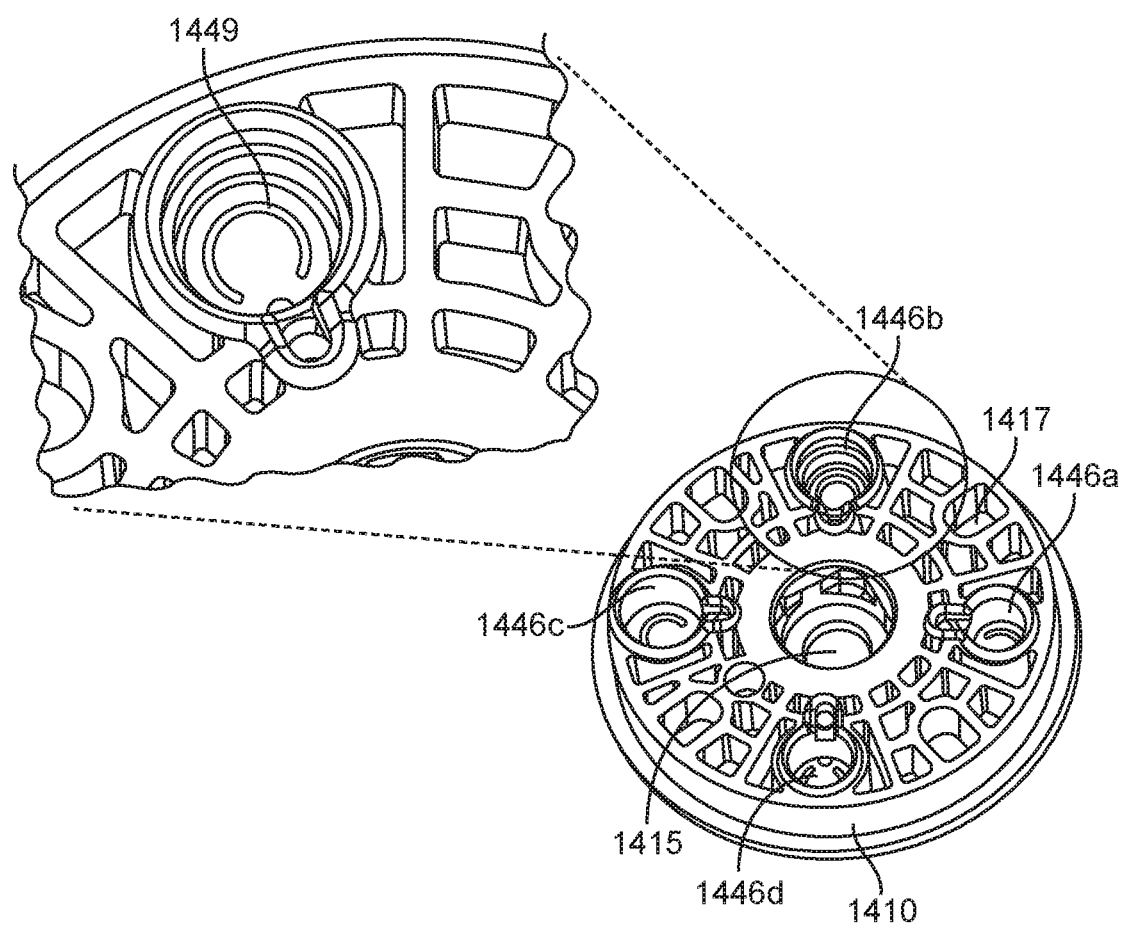

FIG. 77 is a perspective drawing of a rotor comprising a plurality of flow channels. A magnified view of a single solid support chamber within one of the flow channels is shown.

Figure 79:
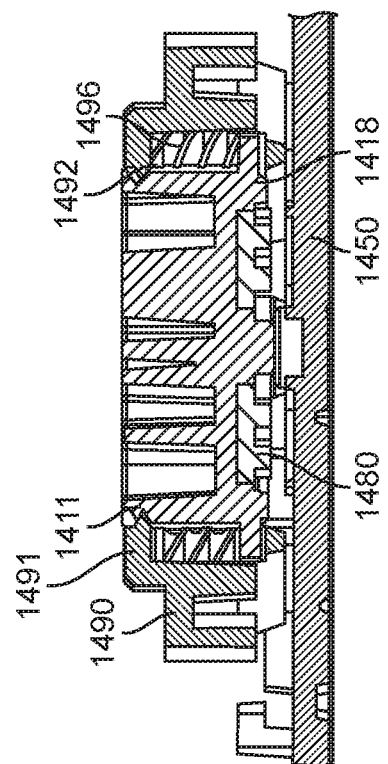
Figure 78:
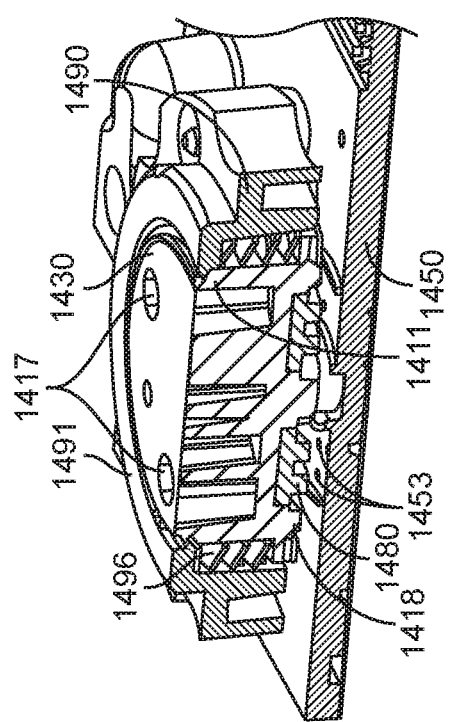

FIGS. 78 and 79 are perspective cross-sectional views of a rotary valve with a threaded rotor in a shipping configuration.

FIGS. 80 and 81 are perspective cross-sectional views of the rotary valve of FIGS. 78 and 79 with a threaded rotor in an operational configuration with a gasket forming a fluid tight seal with the stator.

Figure 82:
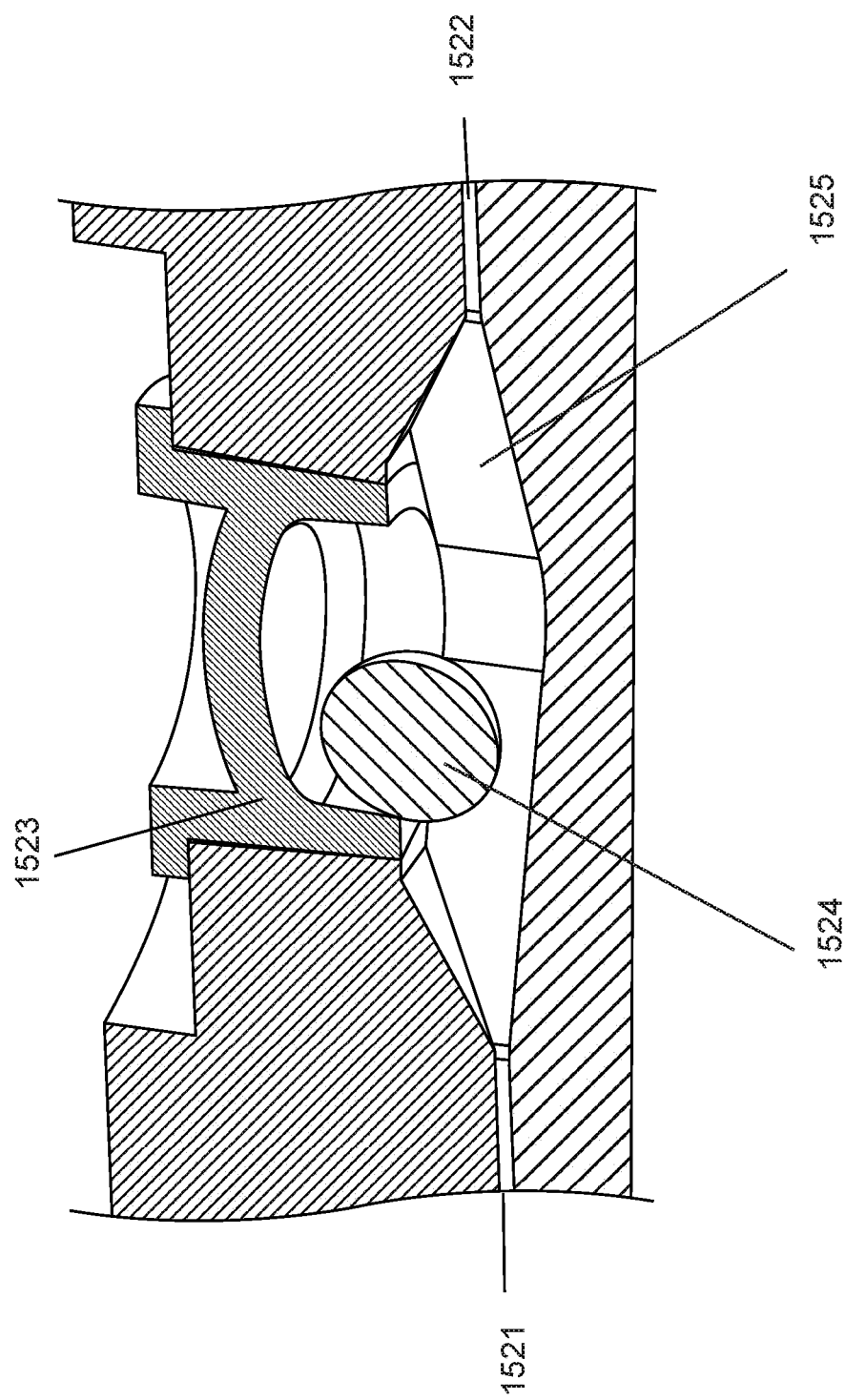

FIG. 82 is a three-dimensional, cross-sectional illustration of a rehydration chamber, in accordance with an embodiment.

Figure 83B:
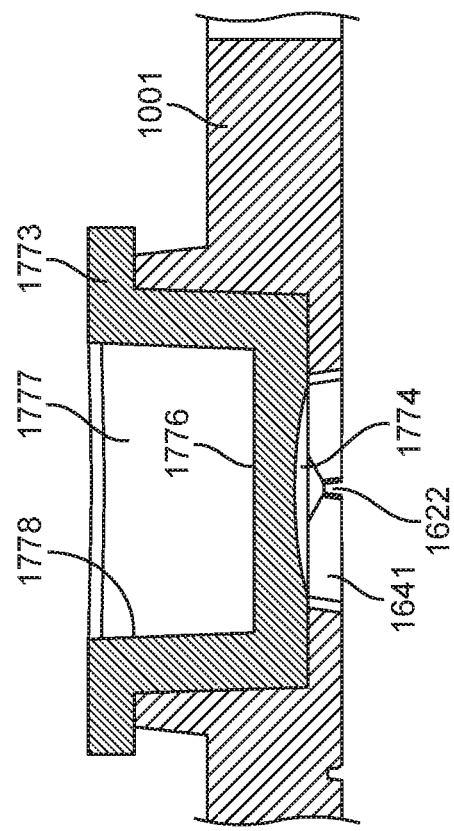
Figure 83A:
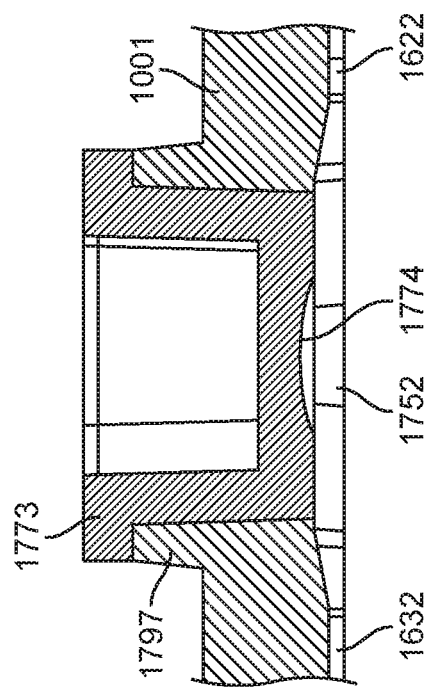

FIG. 83A is a cross-sectional view of an assay chamber taken through an inlet and an outlet.

FIG. 83B is a cross-sectional view of an assay chamber taken through the midpoint of an assay chamber.

Figure 84:
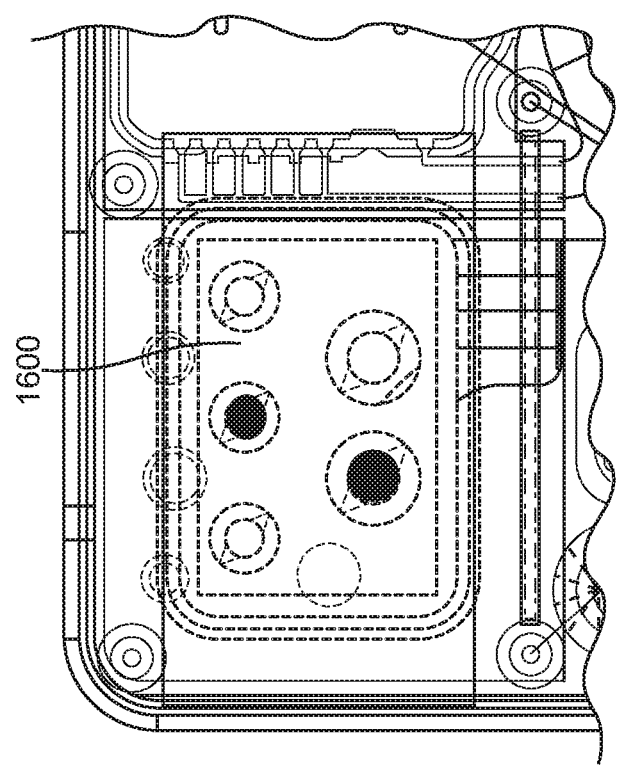

FIG. 84 is a top down illustration of a reaction area with a plurality of assay chambers of FIGS. 83A and 83B showing a signal indicative of the presence of target nucleic acids from a target pathogen viewed through a transparent plug.

FIG. 85 is a cross-sectional illustration of a raised platform within each of the loading channels used to form a portion of a heat staked region. FIG. 85 additionally shows an illustration of a reaction area with a main loading channel configured with a u-bend.

FIG. 86 is a cross-sectional illustration of a raised platform within a main loading channel used to form a portion of a heat staked region.

Figure 87:
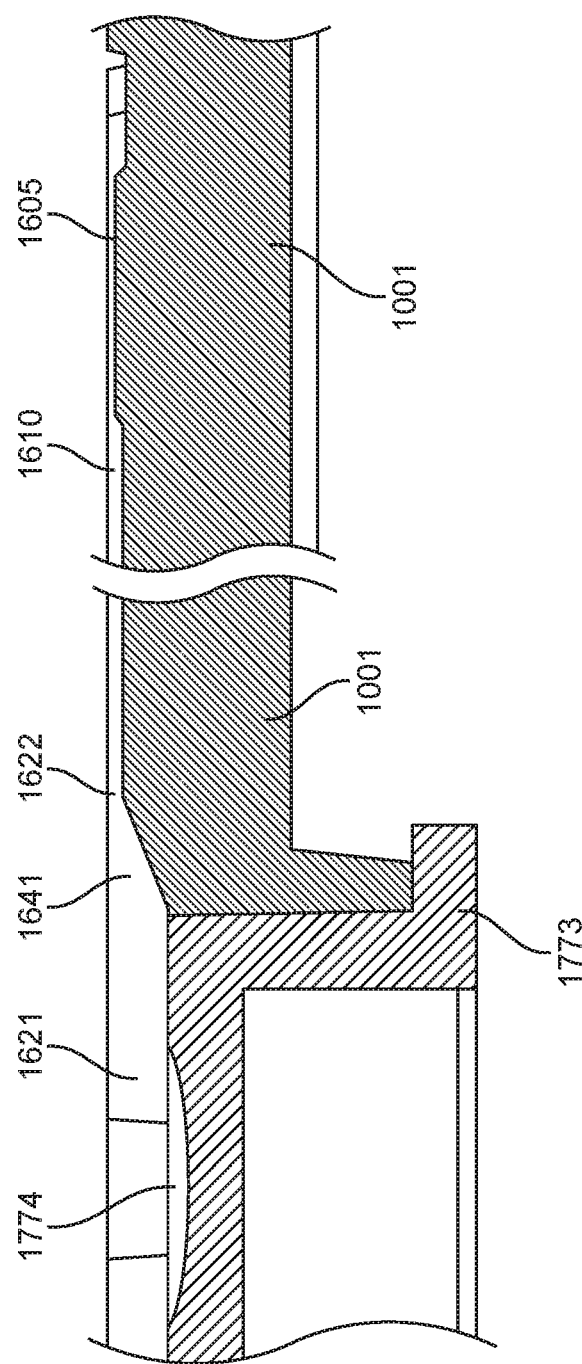

FIG. 87 is a cross-sectional illustration of an assay chamber taken through an inlet and a loading channel with a raised platform of FIGS. 85 and 86 within.

Figure 88:
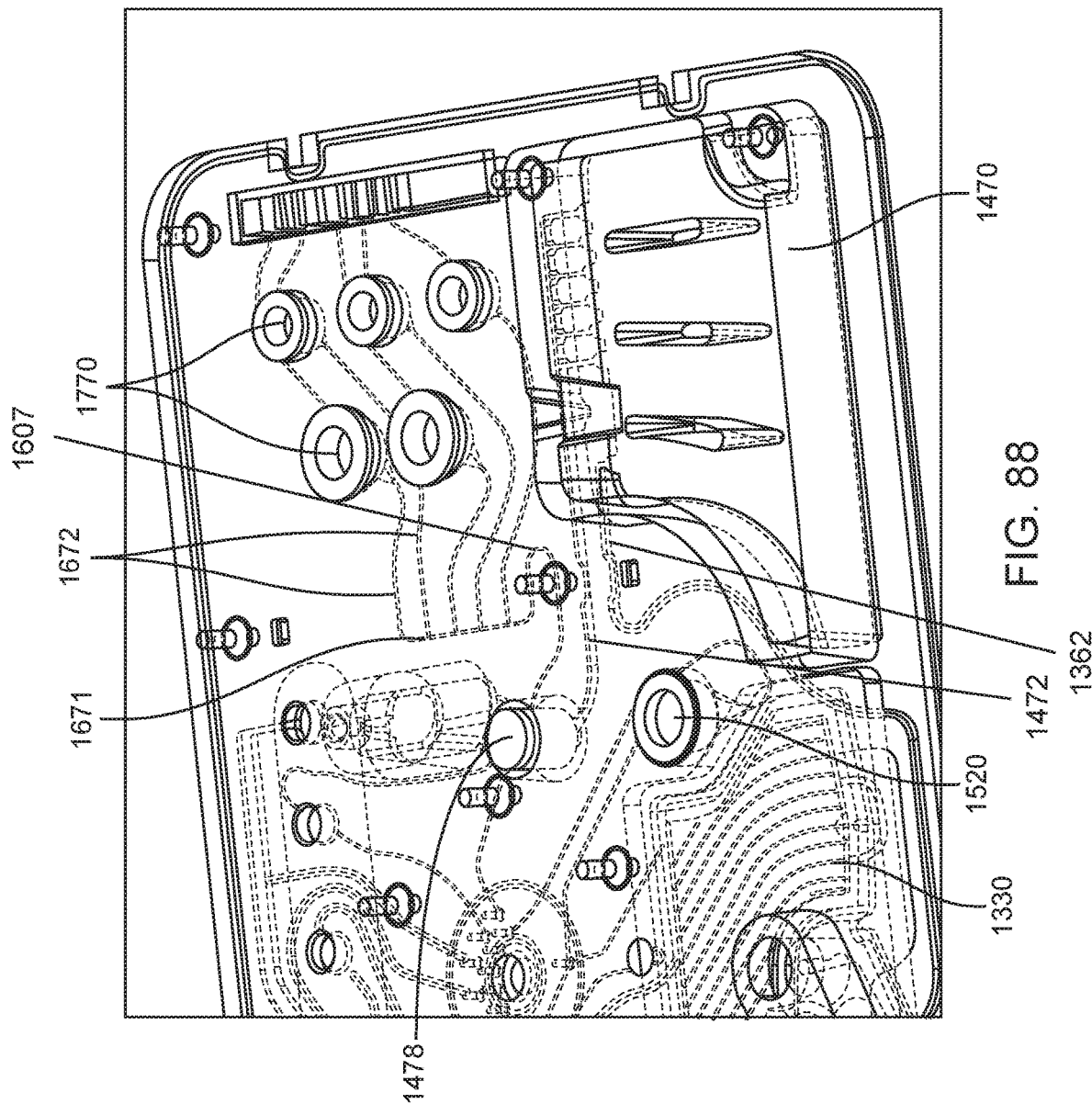

FIG. 88 is an illustration of a waste collection element of an integrated diagnostic cartridge. A channel for filling the waste chamber and a vent channel are shown in proximity to loading channels forming a shared heat staking portion of the integrated diagnostic cartridge.

Figure 89:
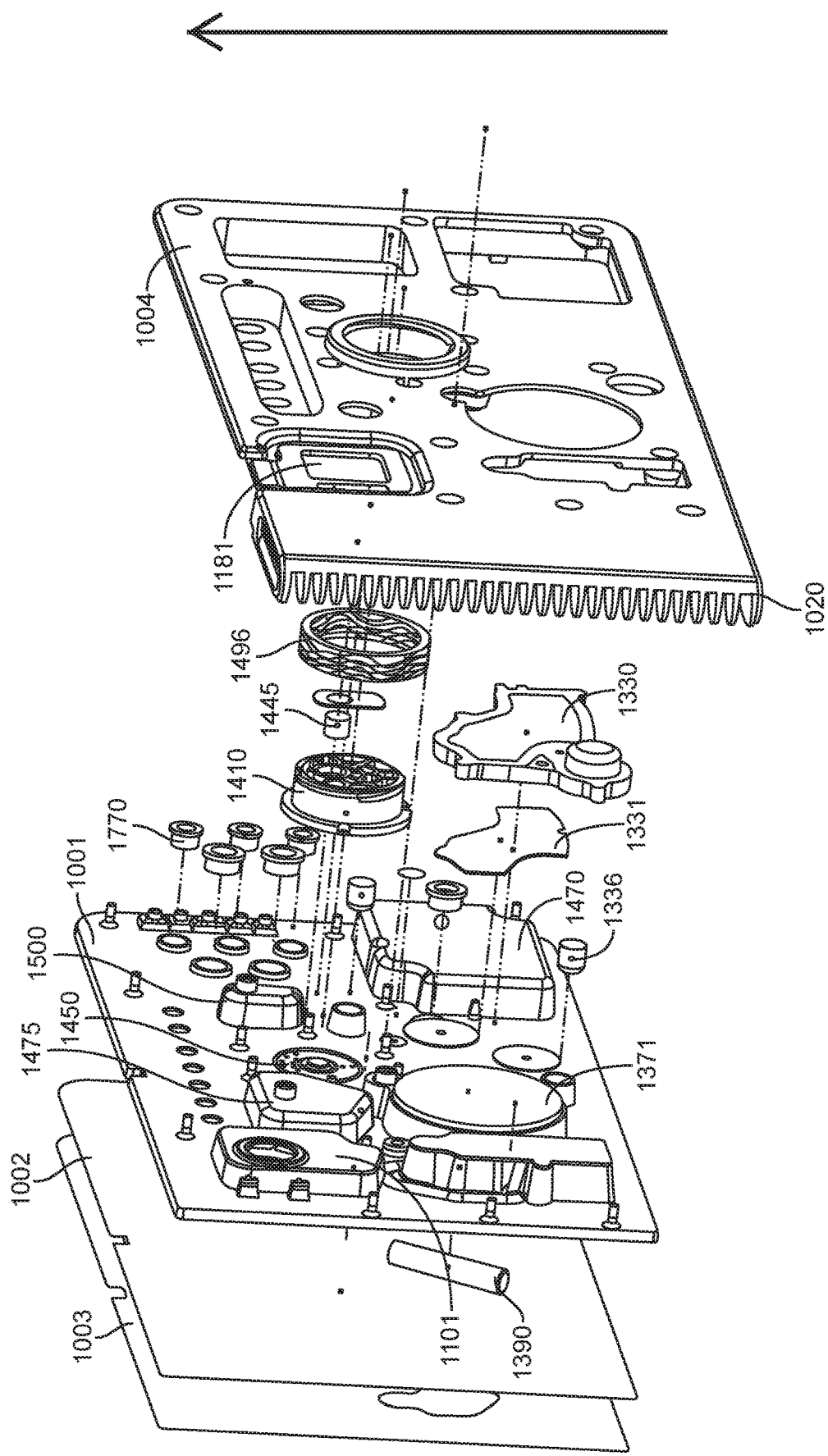

FIG. 89 is an exploded view of a cartridge, according to an exemplified embodiment described herein with regard to FIGS. 69 and 70, comprising a loading module, a lysing module, a purification module, and an amplification module.

Figure 90:
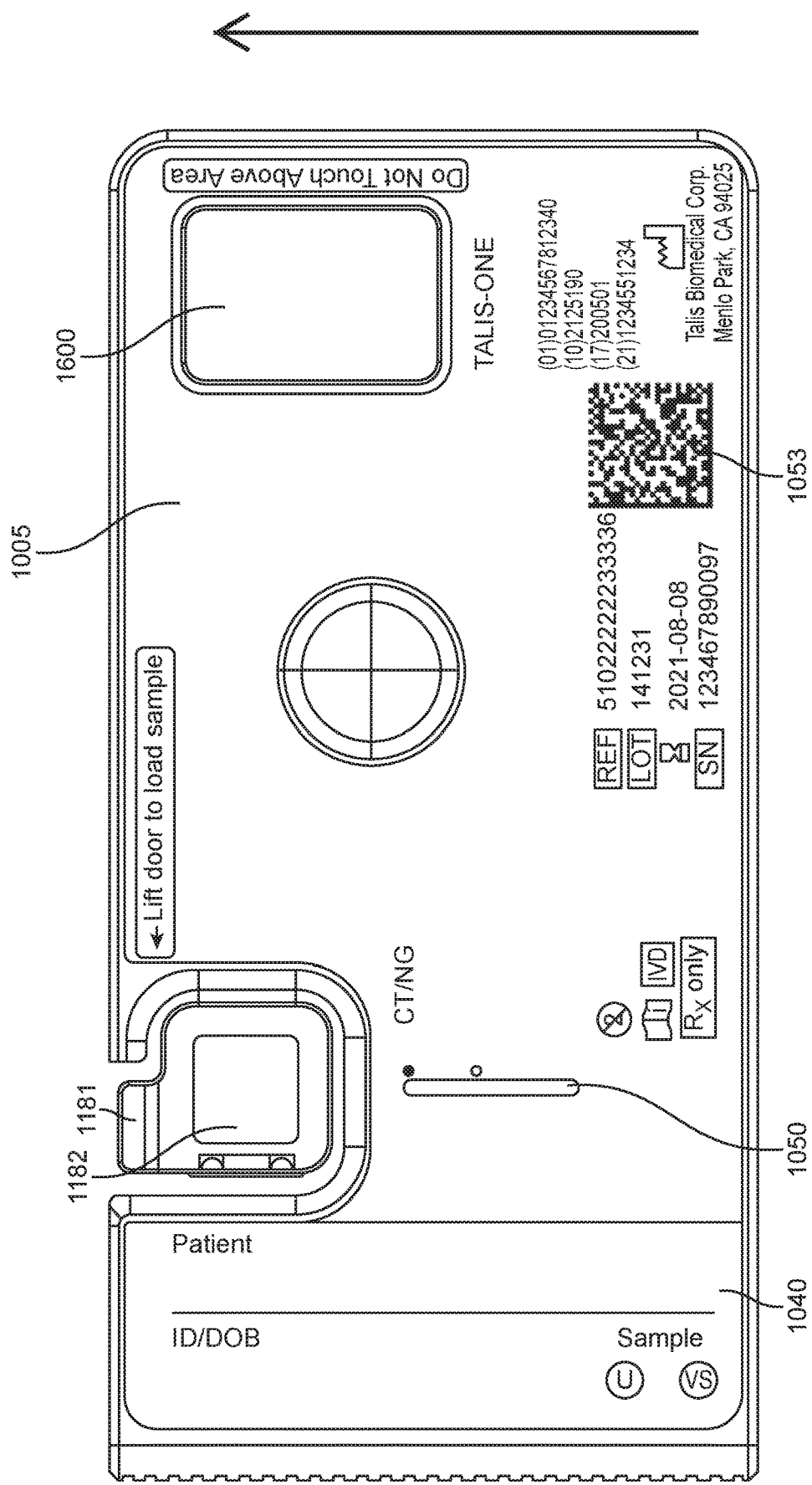

FIG. 90 is an illustration of an exemplary cartridge label for supplying a user and a diagnostic instrument with information associated with a given diagnostic test.

Figure 91:
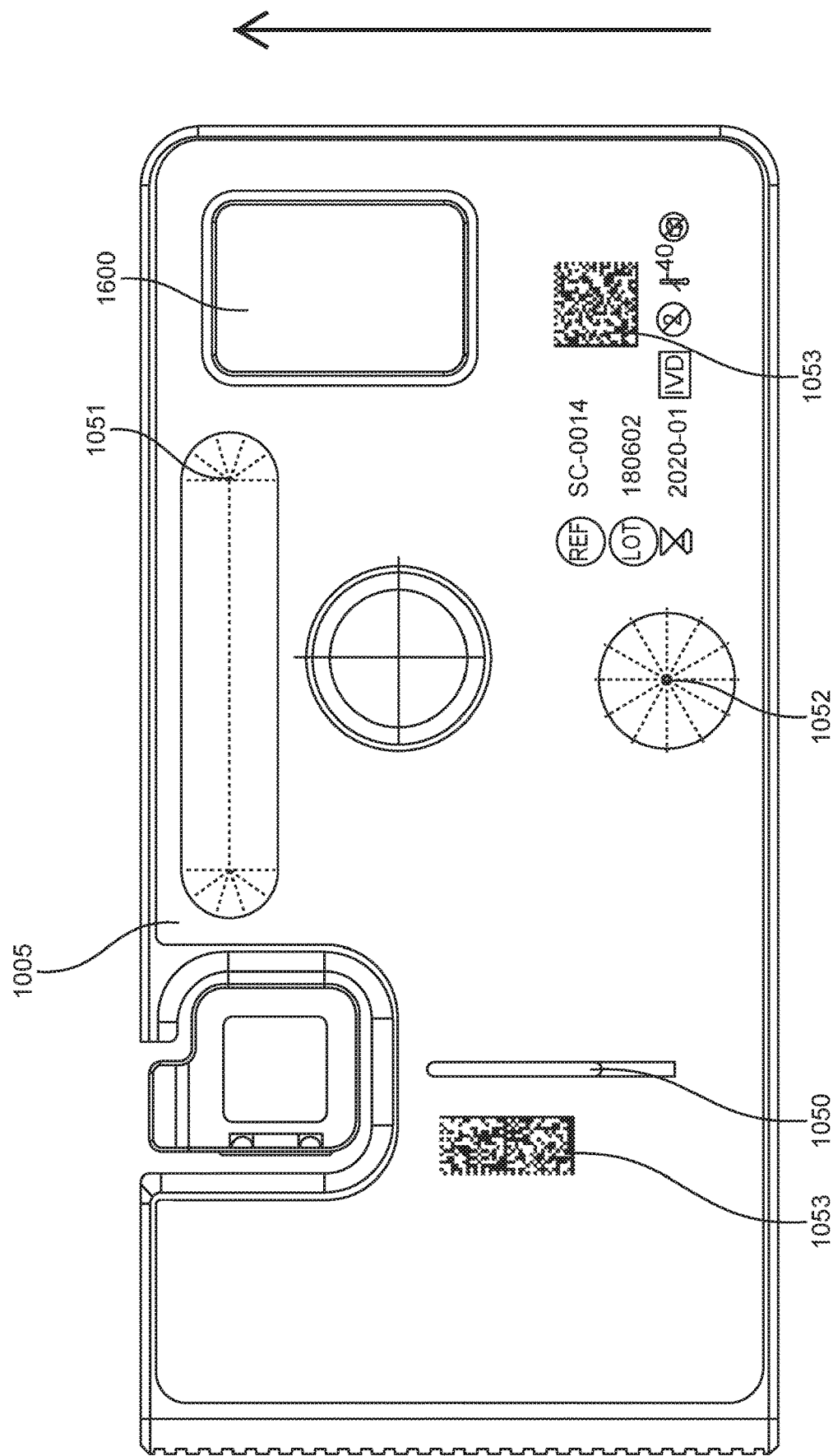

FIG. 91 is an illustration of a cartridge label with one or more perforated areas configured to break when a diagnostic instrument contacts an integrated diagnostic cartridge.

Figure 92:
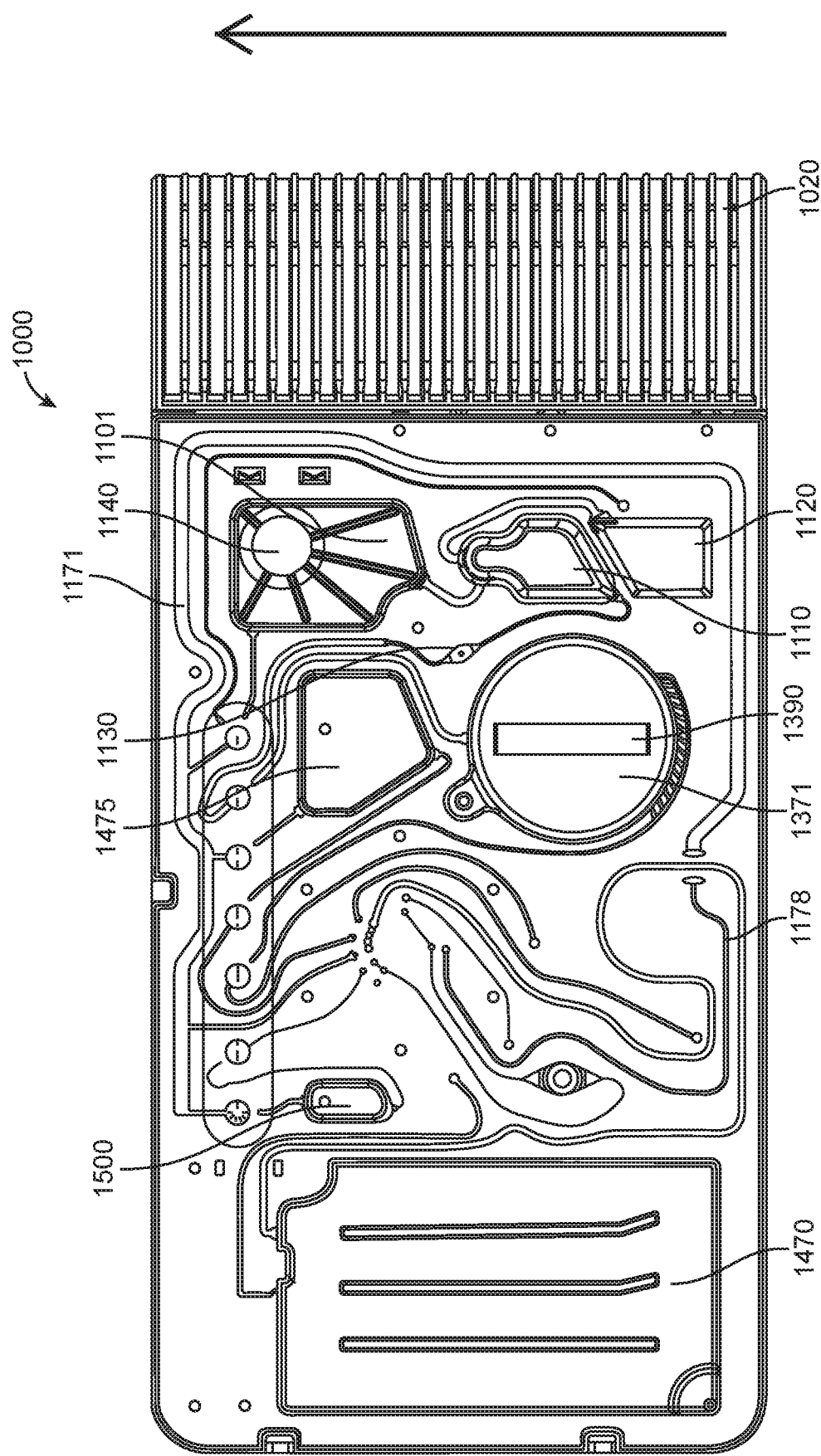

FIG. 92 is an illustration of an alternate cartridge, according to an embodiment, comprising a loading module, a lysing module, and a purification module.

Figure 93:
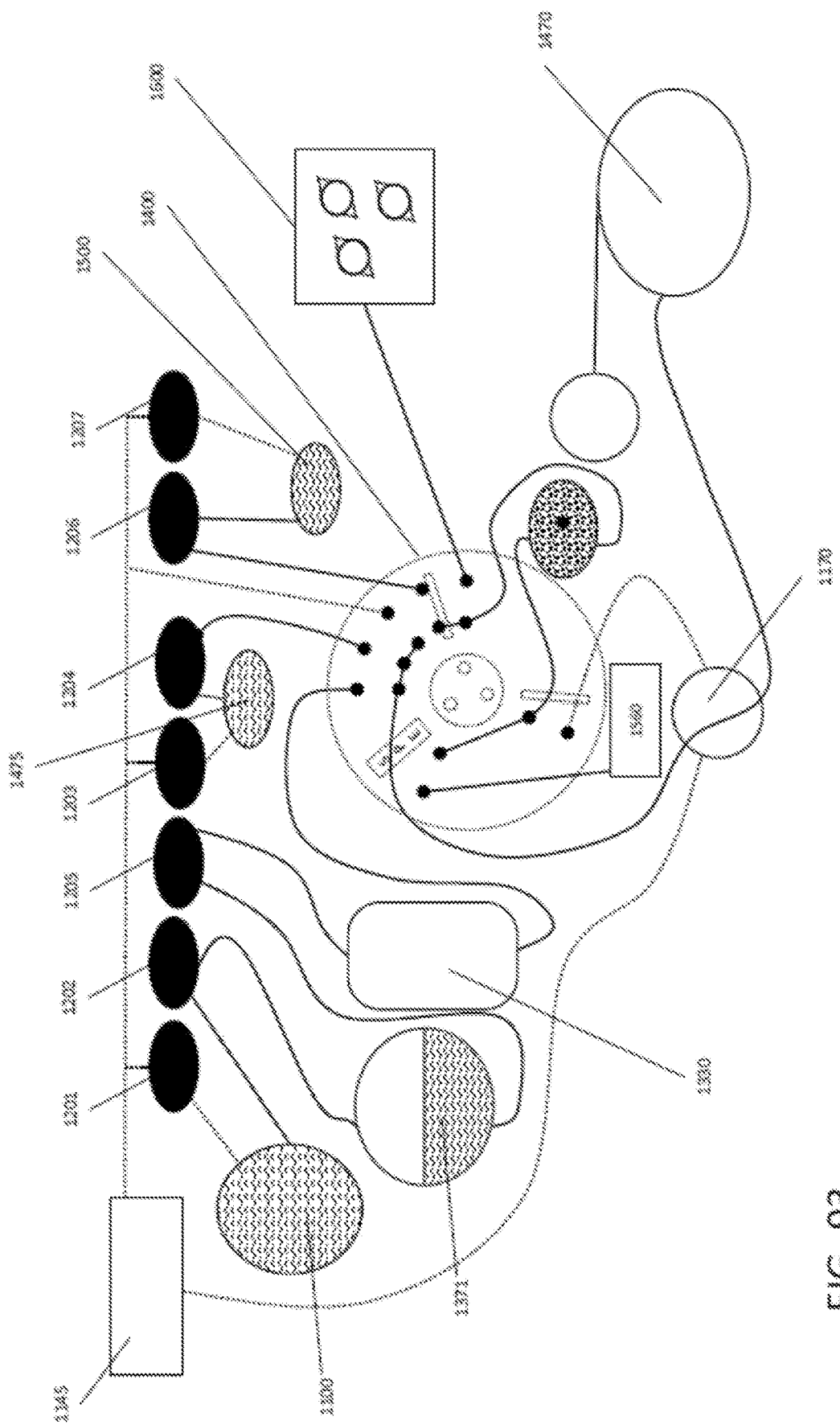

FIG. 93 illustrates the state of an integrated diagnostic cartridge after a biological sample is loaded into the sample port assembly, prior to insertion into a diagnostic instrument and/or prior to actuation of any cartridge features by the diagnostic instrument.

Figure 94:
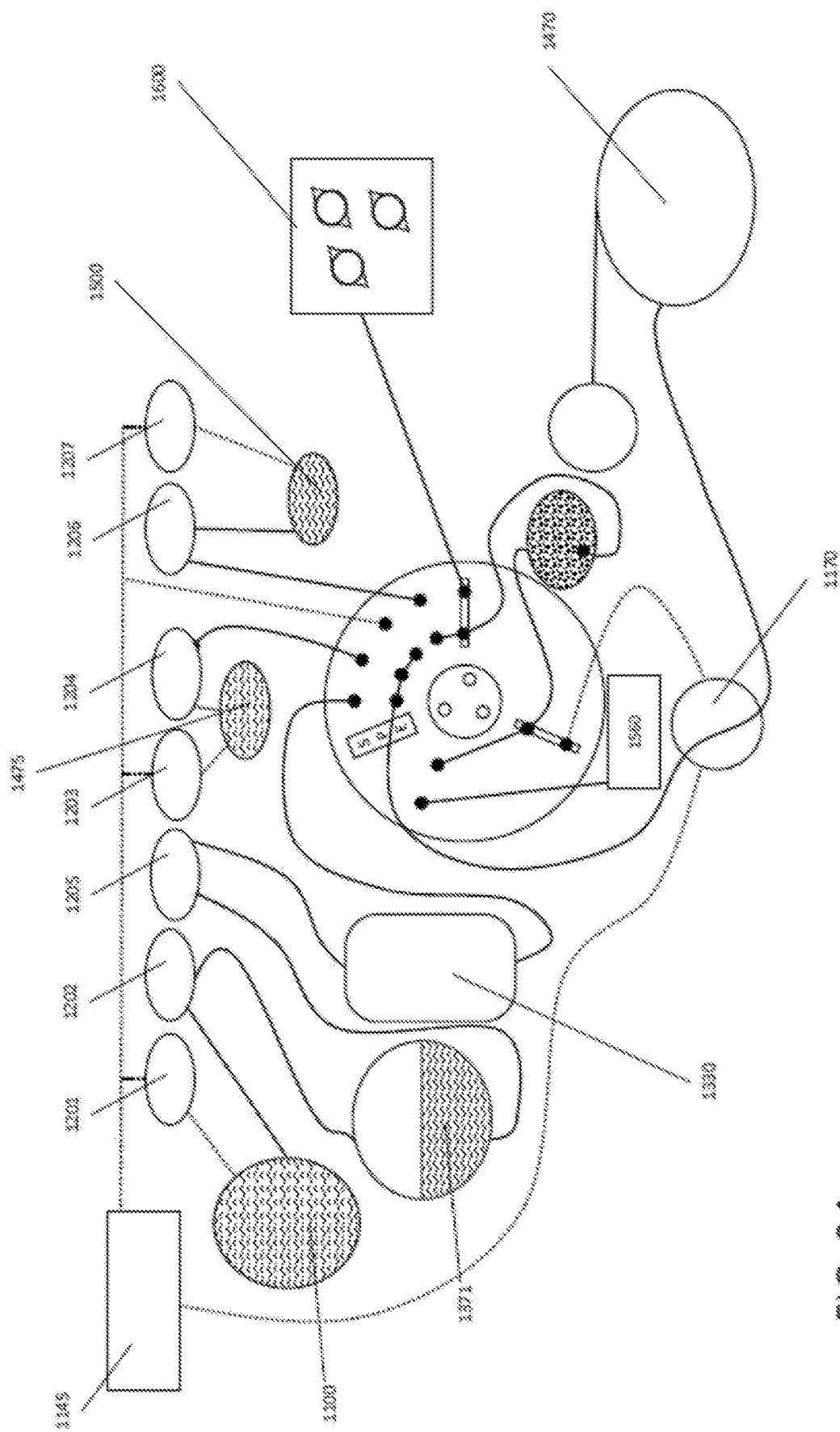

FIG. 94 illustrates the status of the integrated diagnostic cartridge features after cartridge preparation steps are completed and frangible seals are broken. All of the fluids remain in their original positions, as no motive force has yet been applied to the cartridge features.

Figure 95:
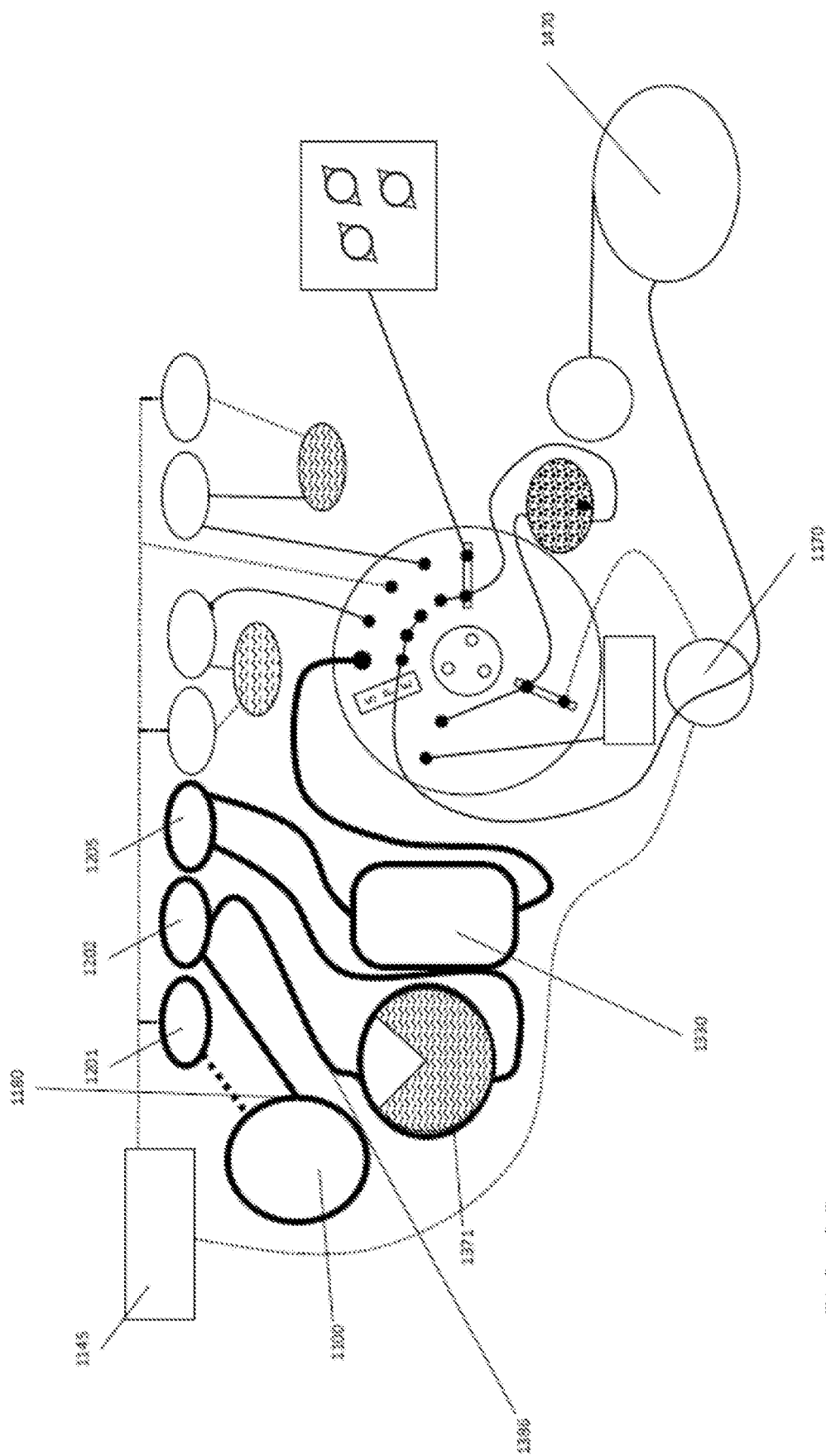

FIG. 95 illustrates the status of the integrated diagnostic cartridge features after the lysis steps are performed.

Figure 96:
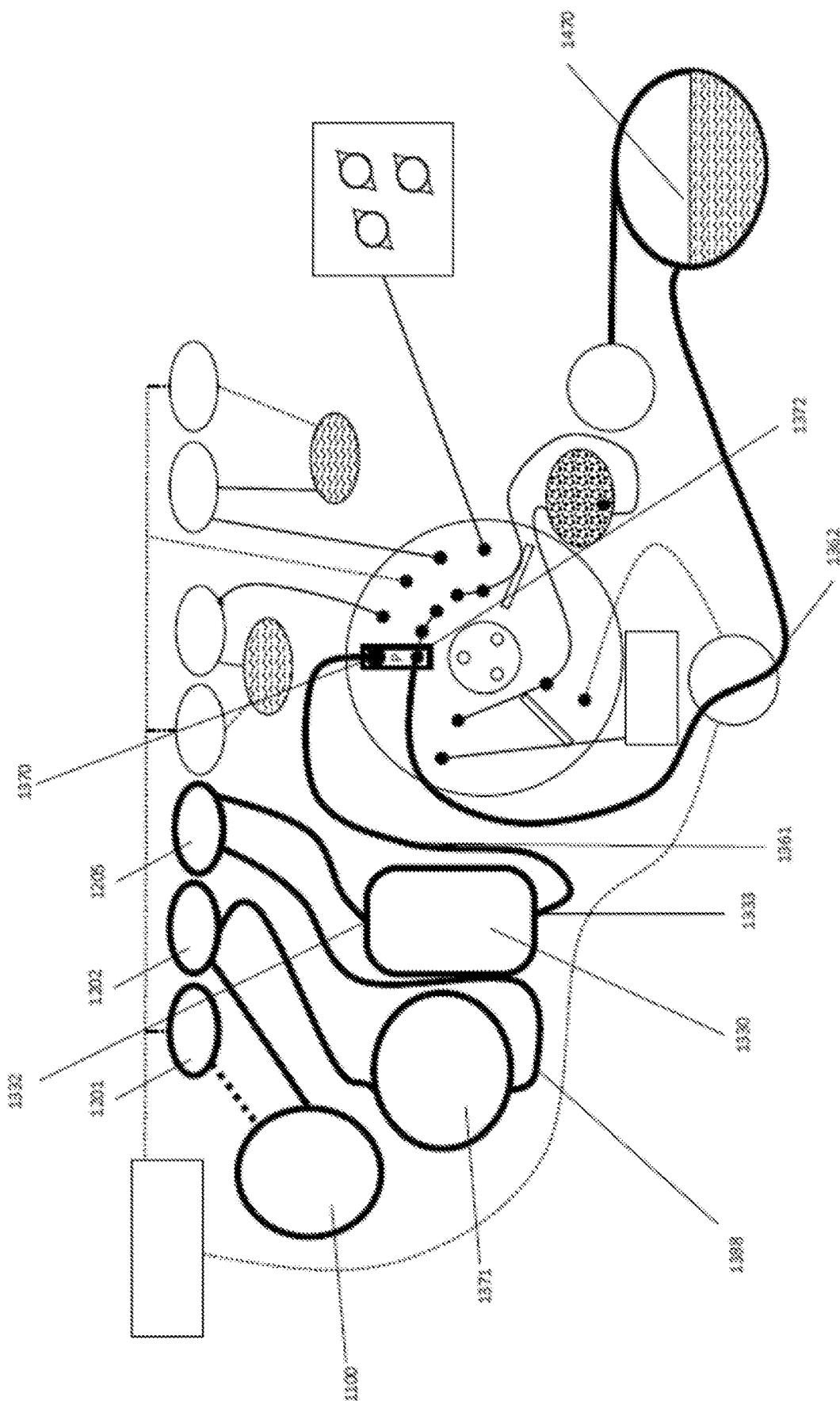

FIG. 96 illustrates the status of the integrated diagnostic cartridge features after the filtration and binding steps—the lysis chamber is empty, and fluid has passed to a waste collection element.

Figure 97:
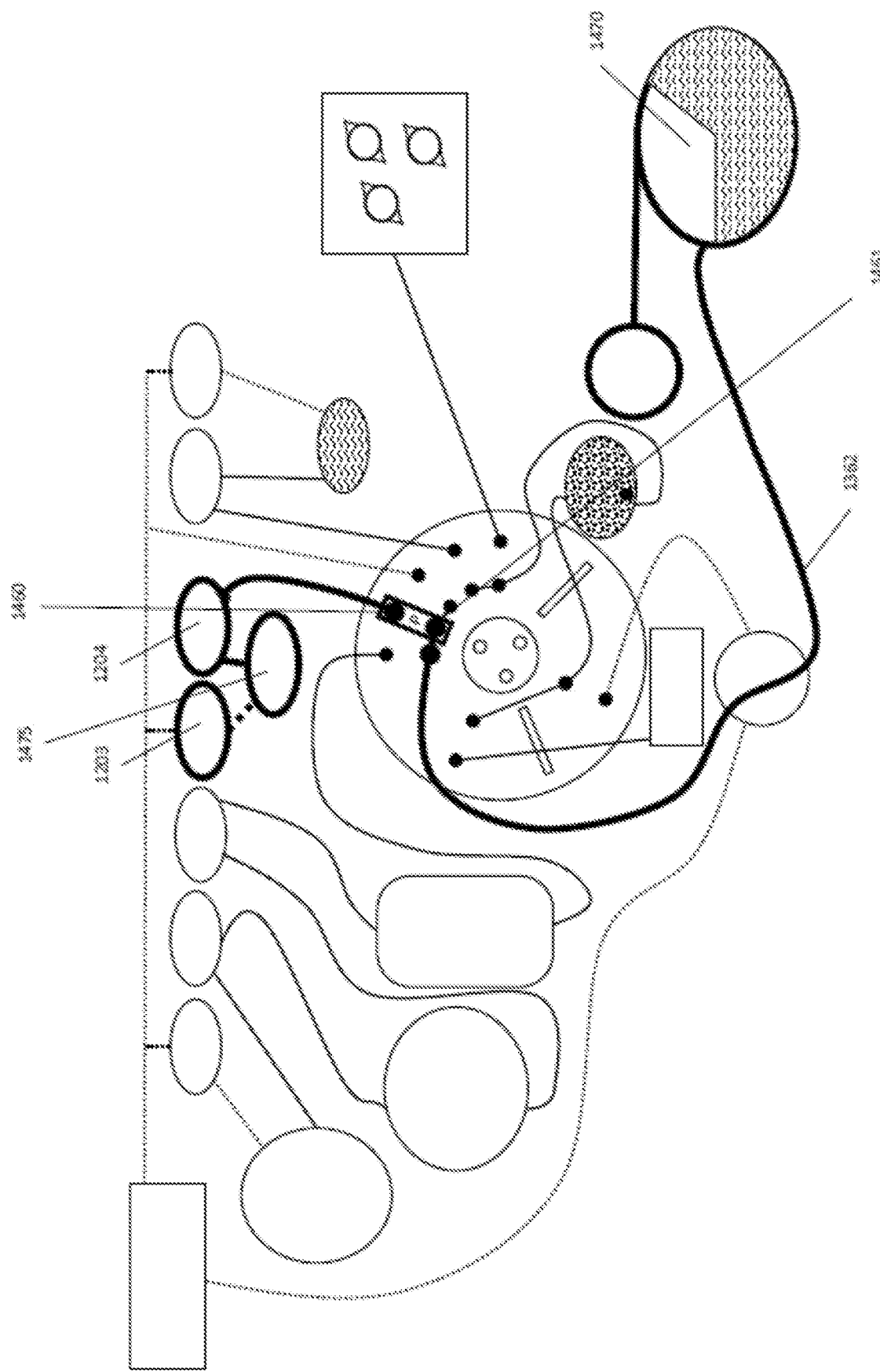

FIG. 97 illustrates the status of the integrated diagnostic cartridge features after completion of the wash step.

Figure 98:
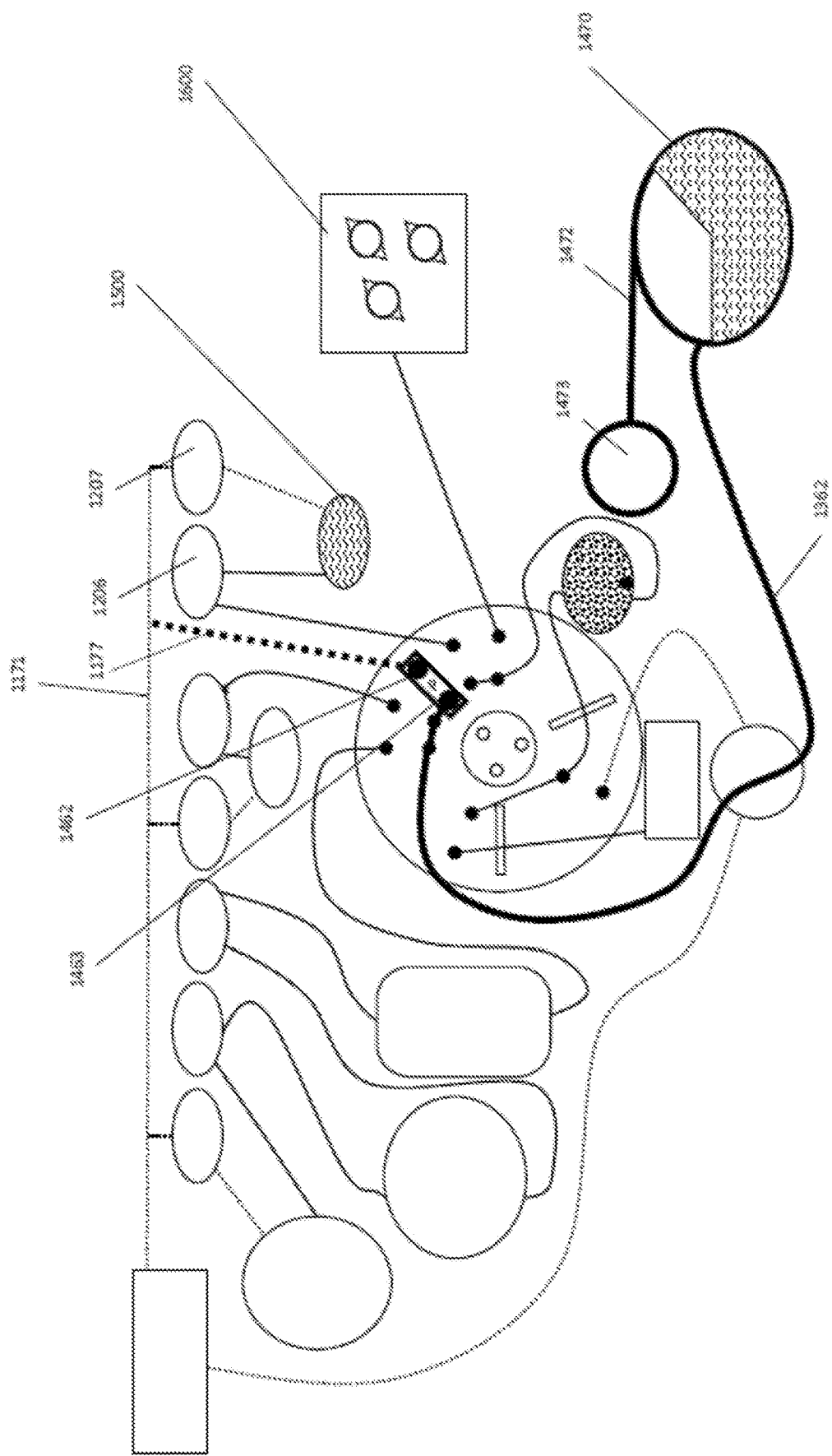

FIG. 98 illustrates the status of the integrated diagnostic cartridge features after completion of the air dry step.

Figure 99:
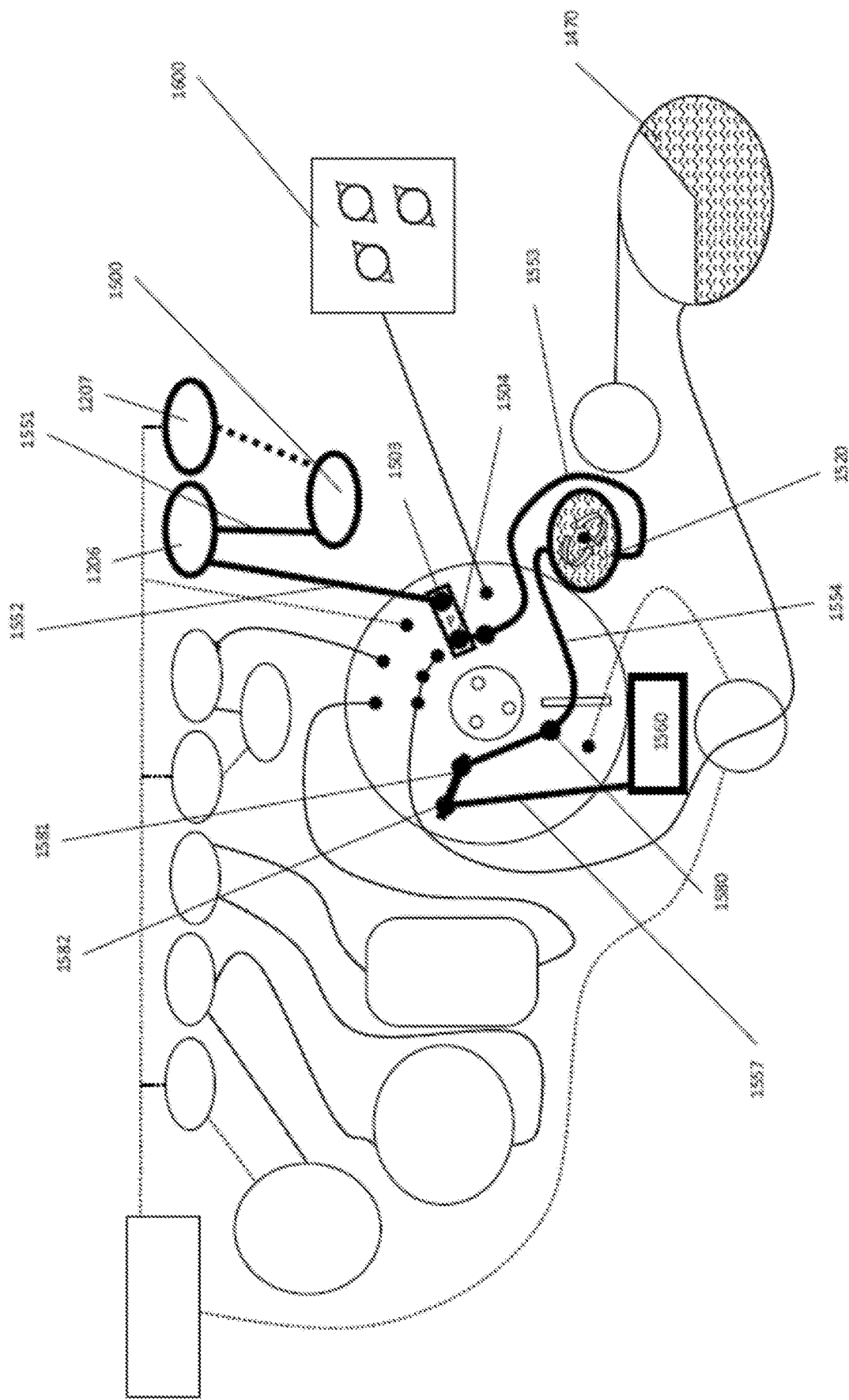

FIG. 99 illustrates the status of the integrated diagnostic cartridge features after the elution and metering step.

Figure 100:
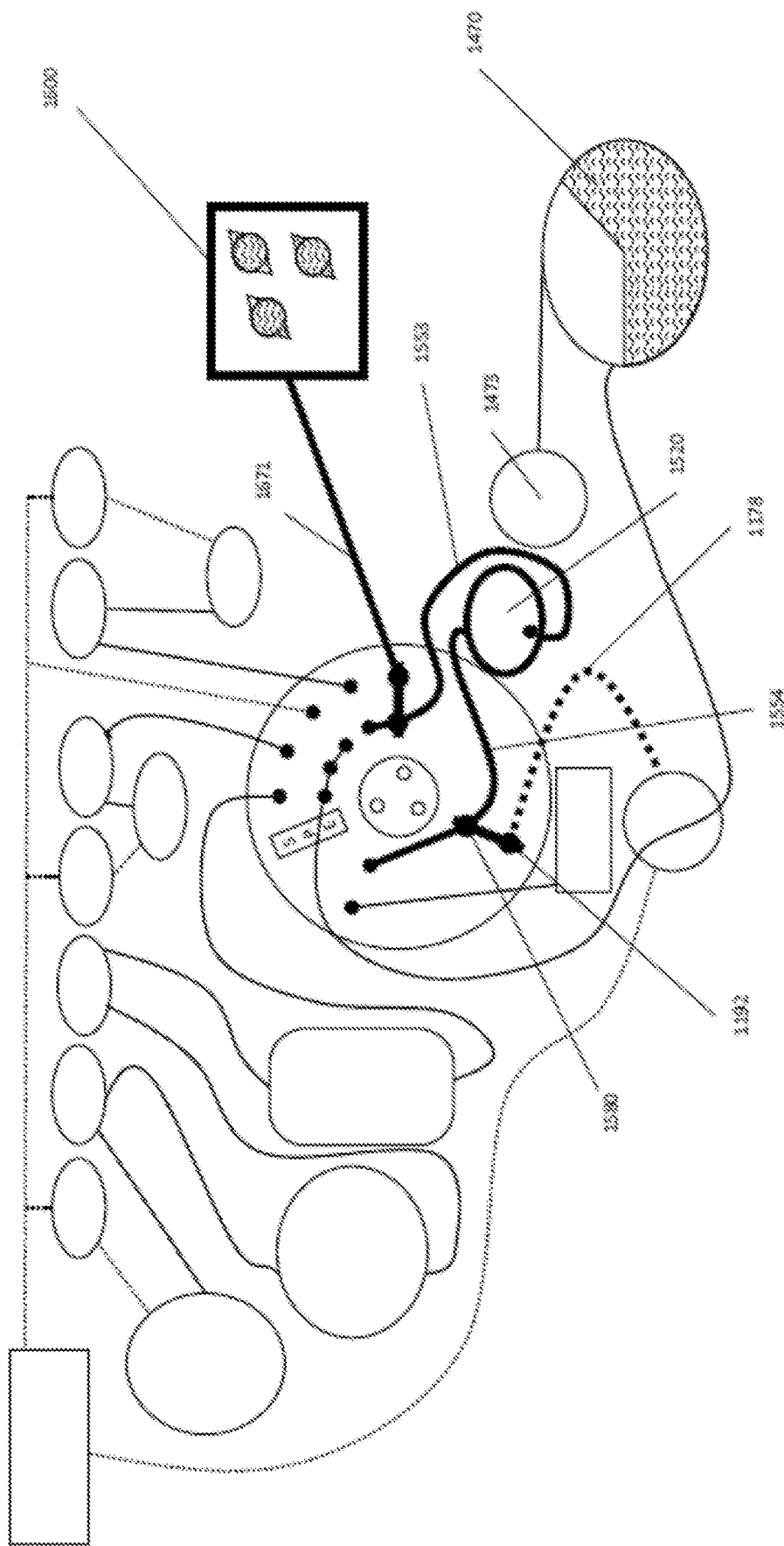

FIG. 100 illustrates the status of the integrated diagnostic cartridge features after loading the assay chambers.

Figure 101:
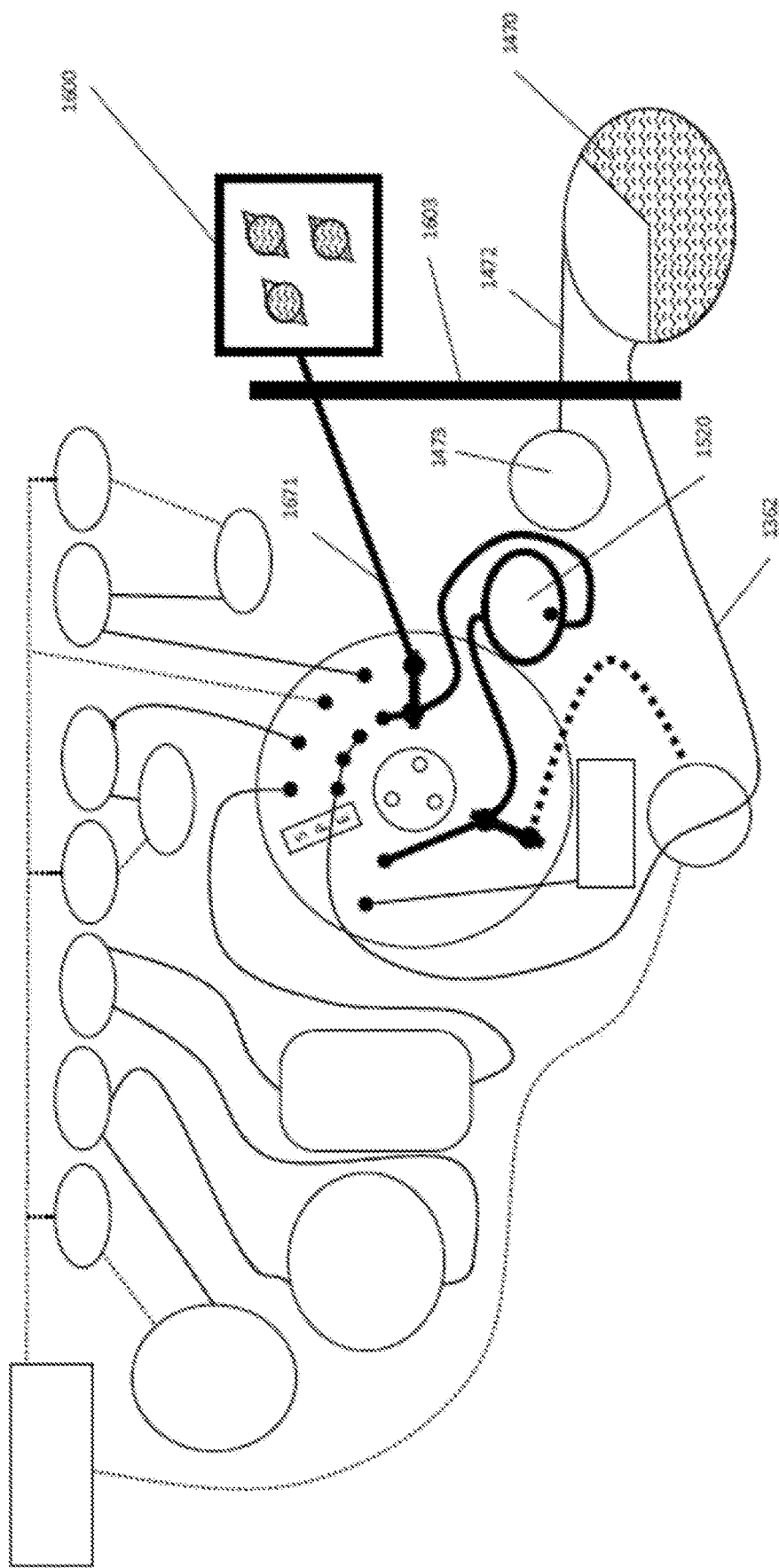

FIG. 101 illustrates the status of the integrated diagnostic cartridge features after heat staking.

Figure 102:
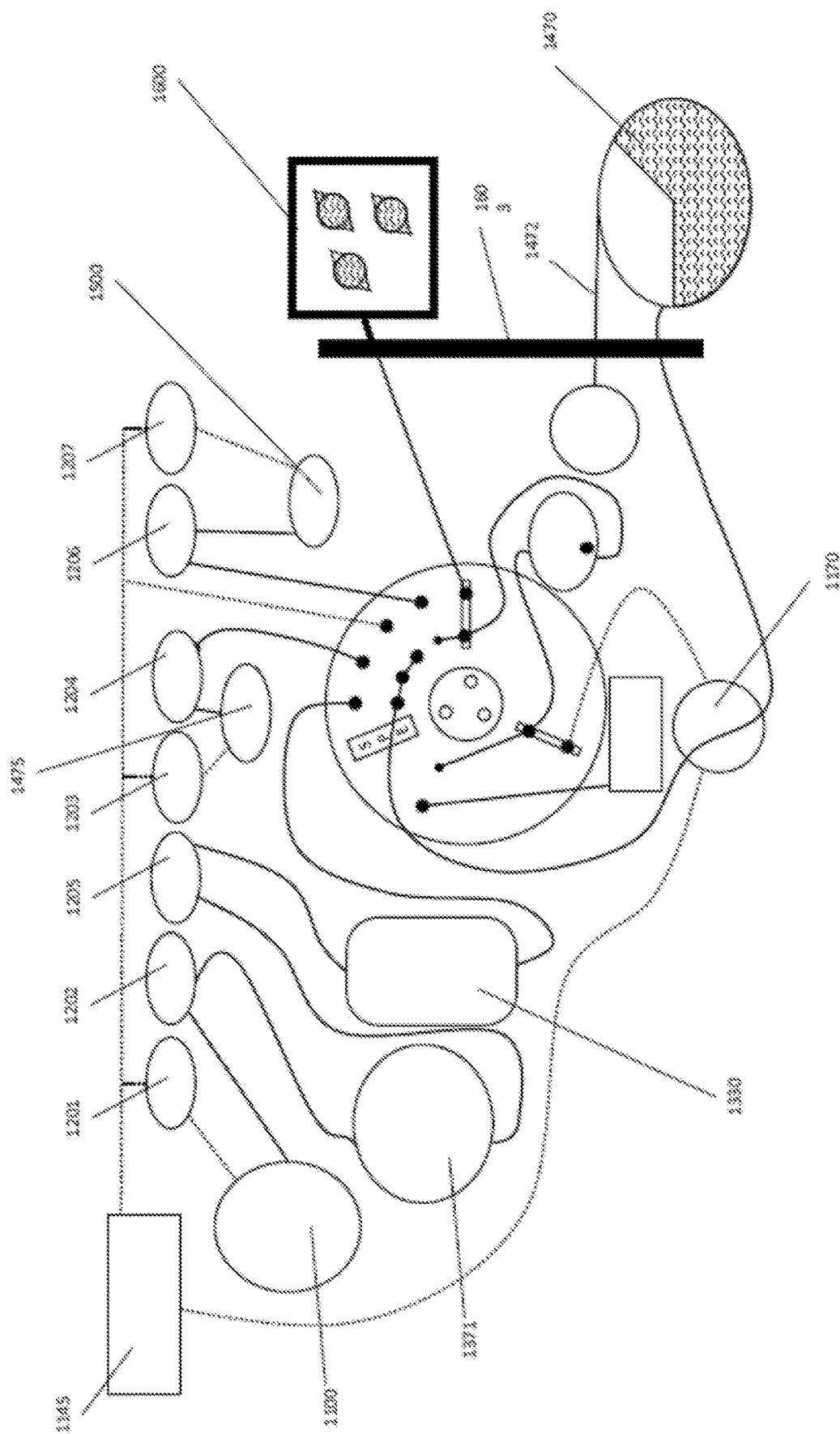
Figure 106A:
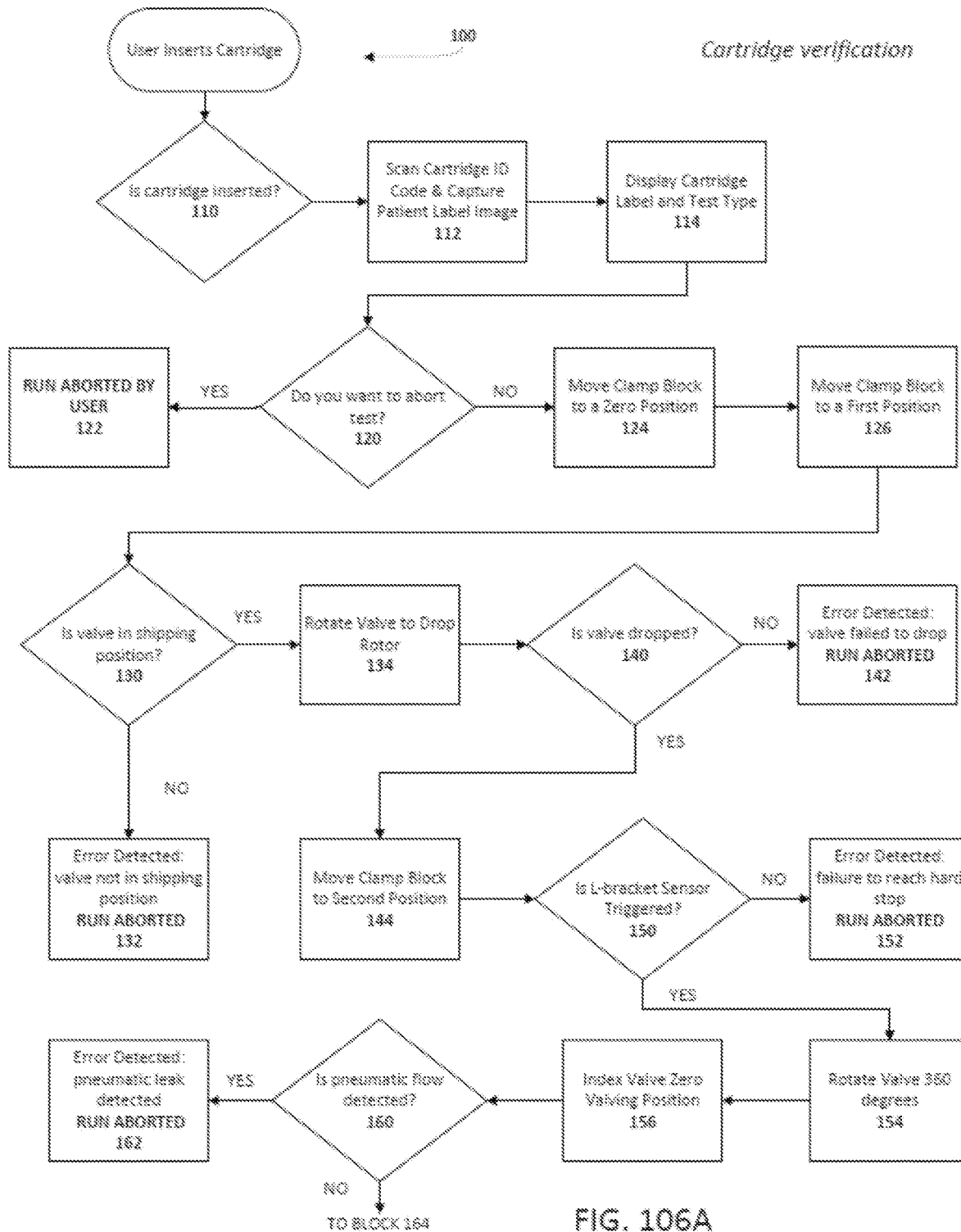
Figure 106B:
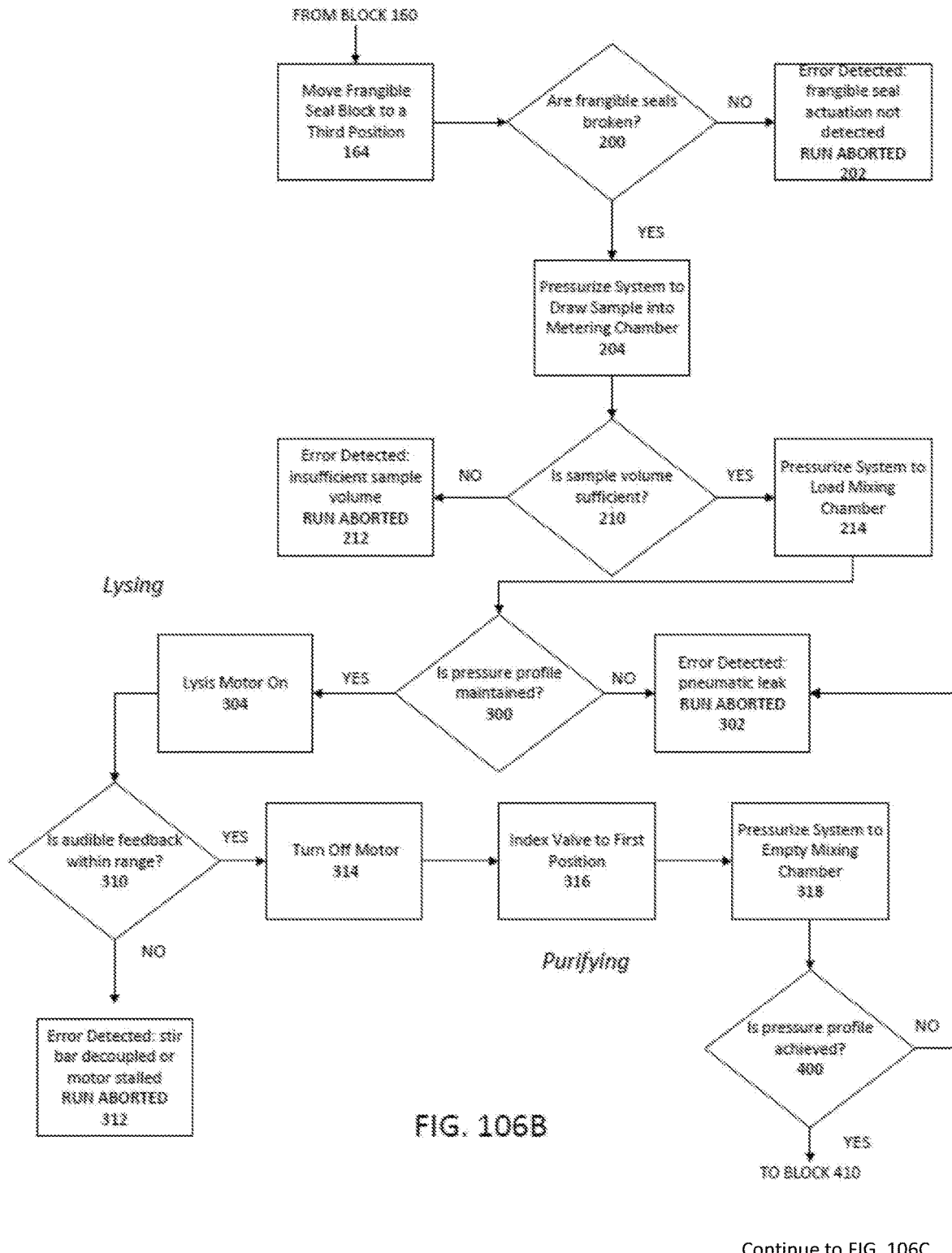
Figure 106C:
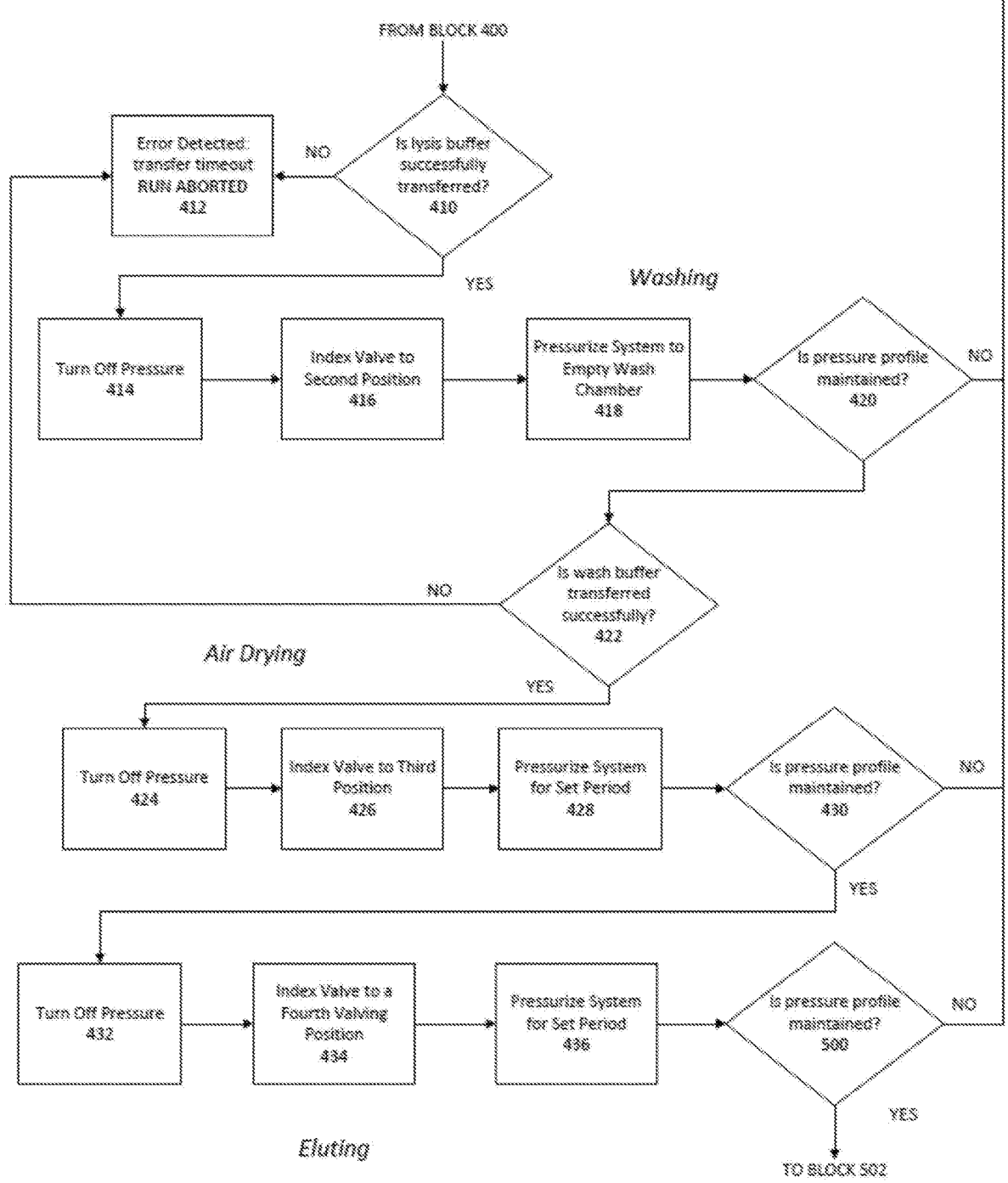
Figure 106D:
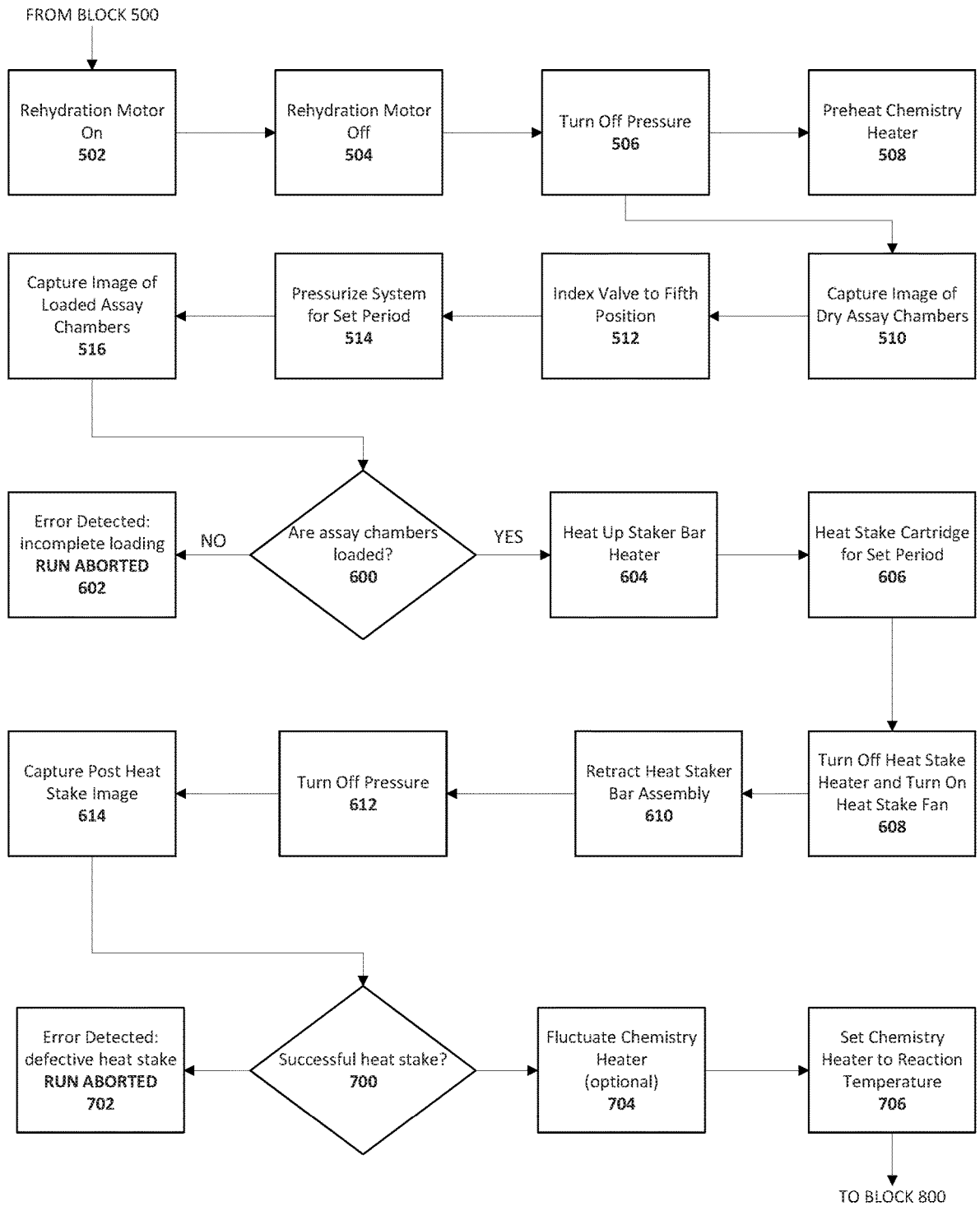
Figure 106E:
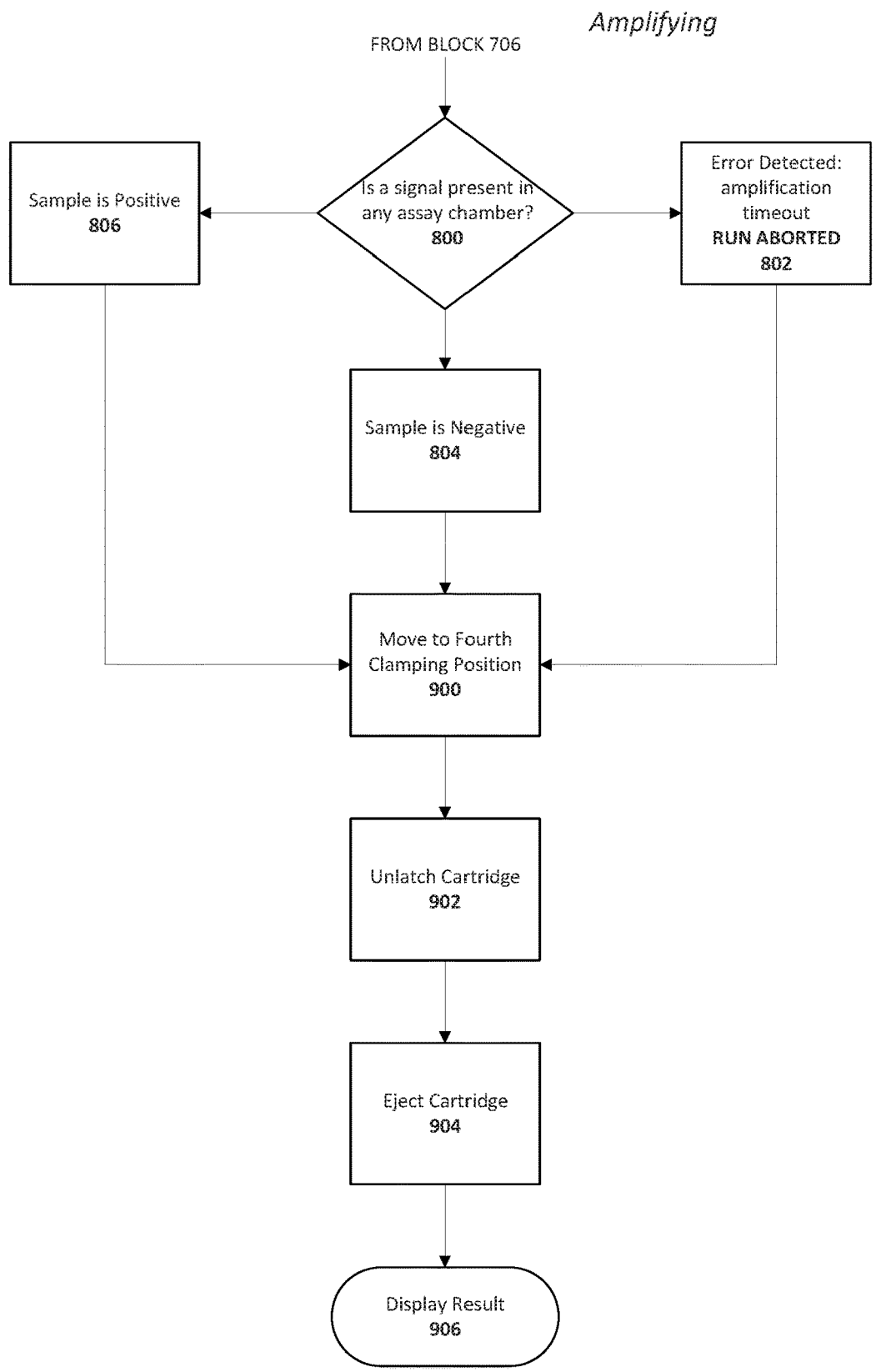

FIG. 102 illustrates the status of the integrated diagnostic cartridge features after release of pressure and during the assay step.

FIG. 103-105 depict a table of reference numbers used herein.

FIG. 106A-106E depict an exemplary sequence of operations executed by a diagnostic instrument to perform a molecular diagnostic test on an integrated diagnostic cartridge, as described in FIGS. 93-102.

Figure 107:
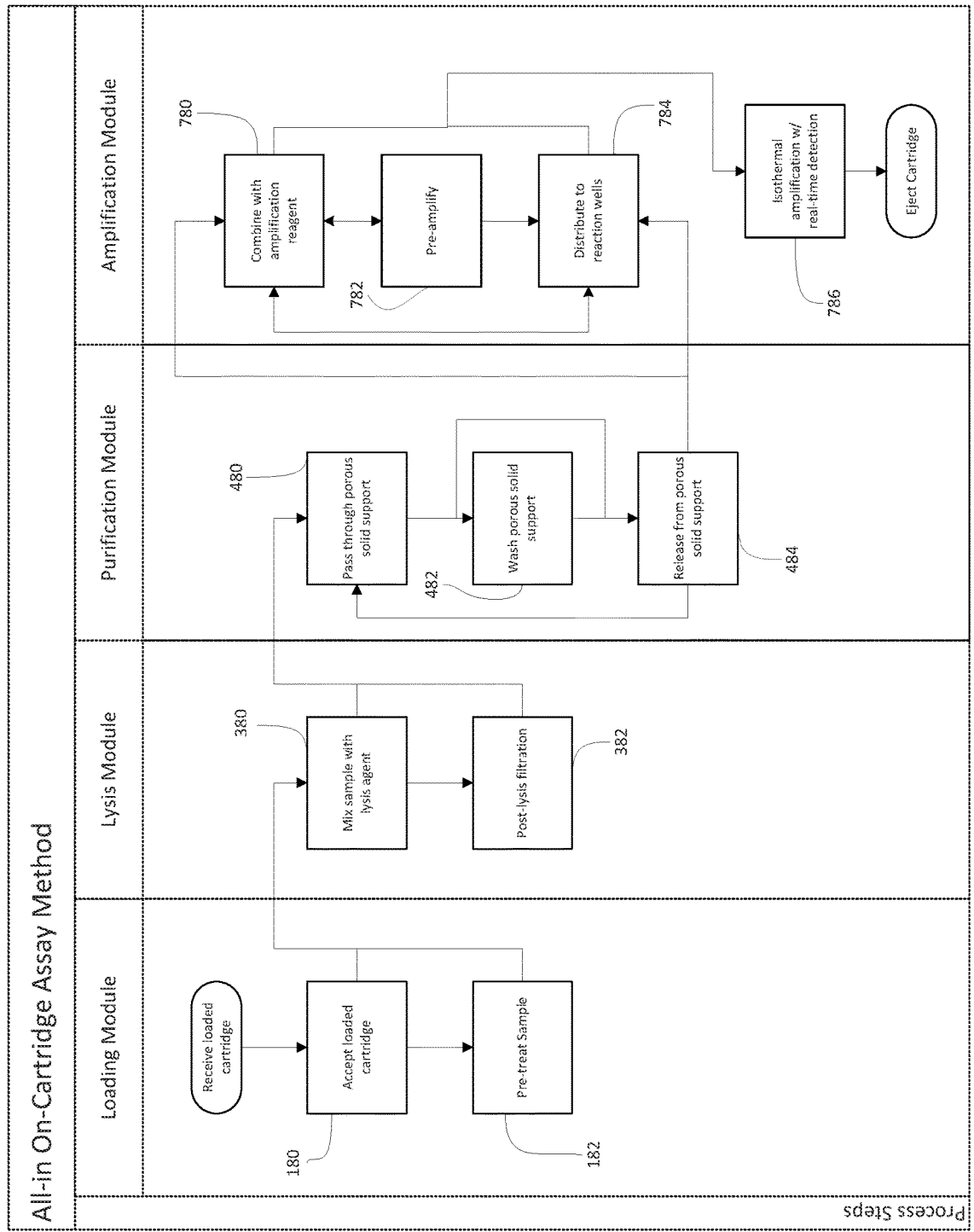

FIG. 107 depicts a workflow diagram of an assay method of testing a sample suspected of containing a target pathogen.

Figure 108:
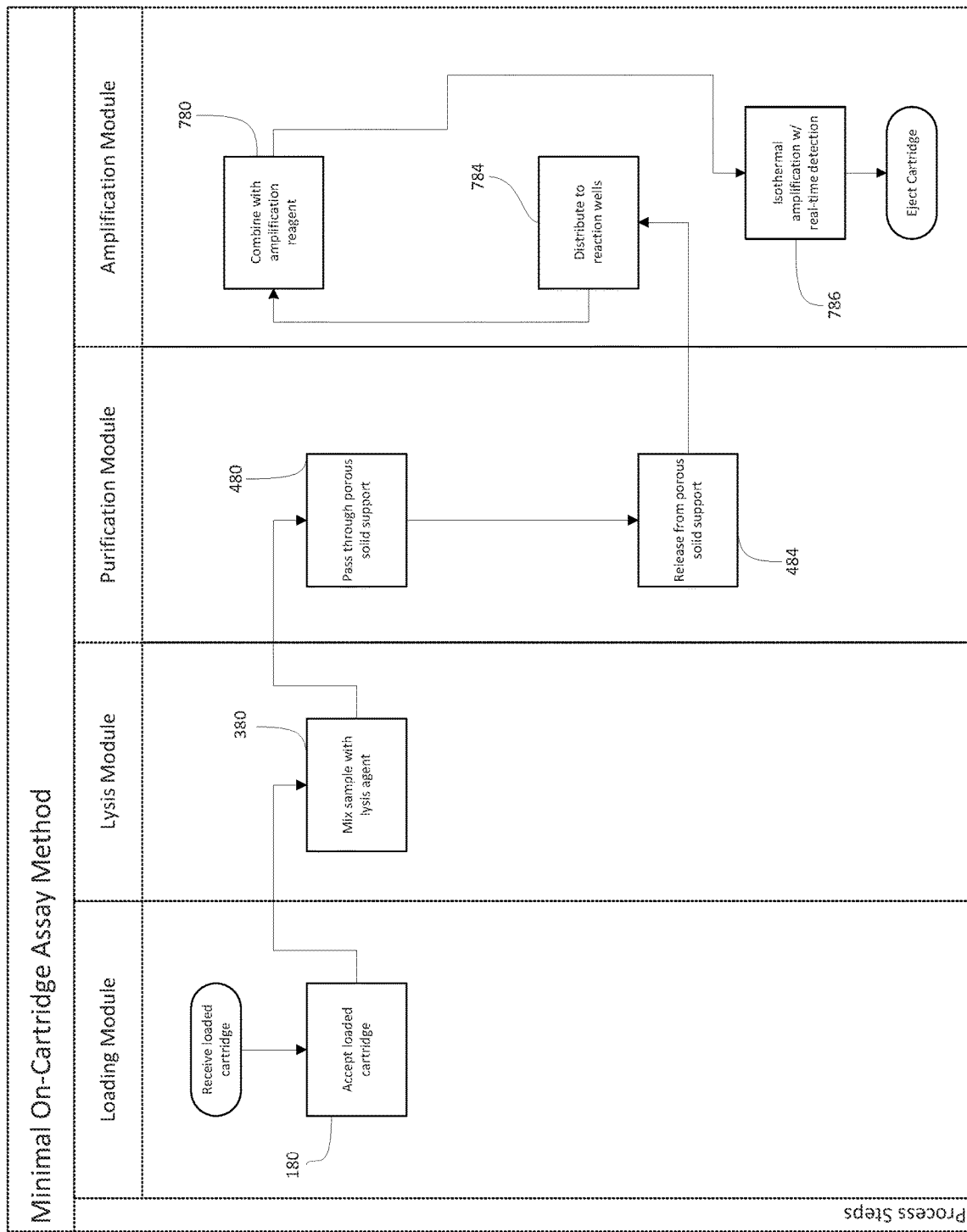

FIG. 108 depicts a workflow diagram of a minimal assay method of testing a sample suspected of containing a target pathogen.

Figure 109:
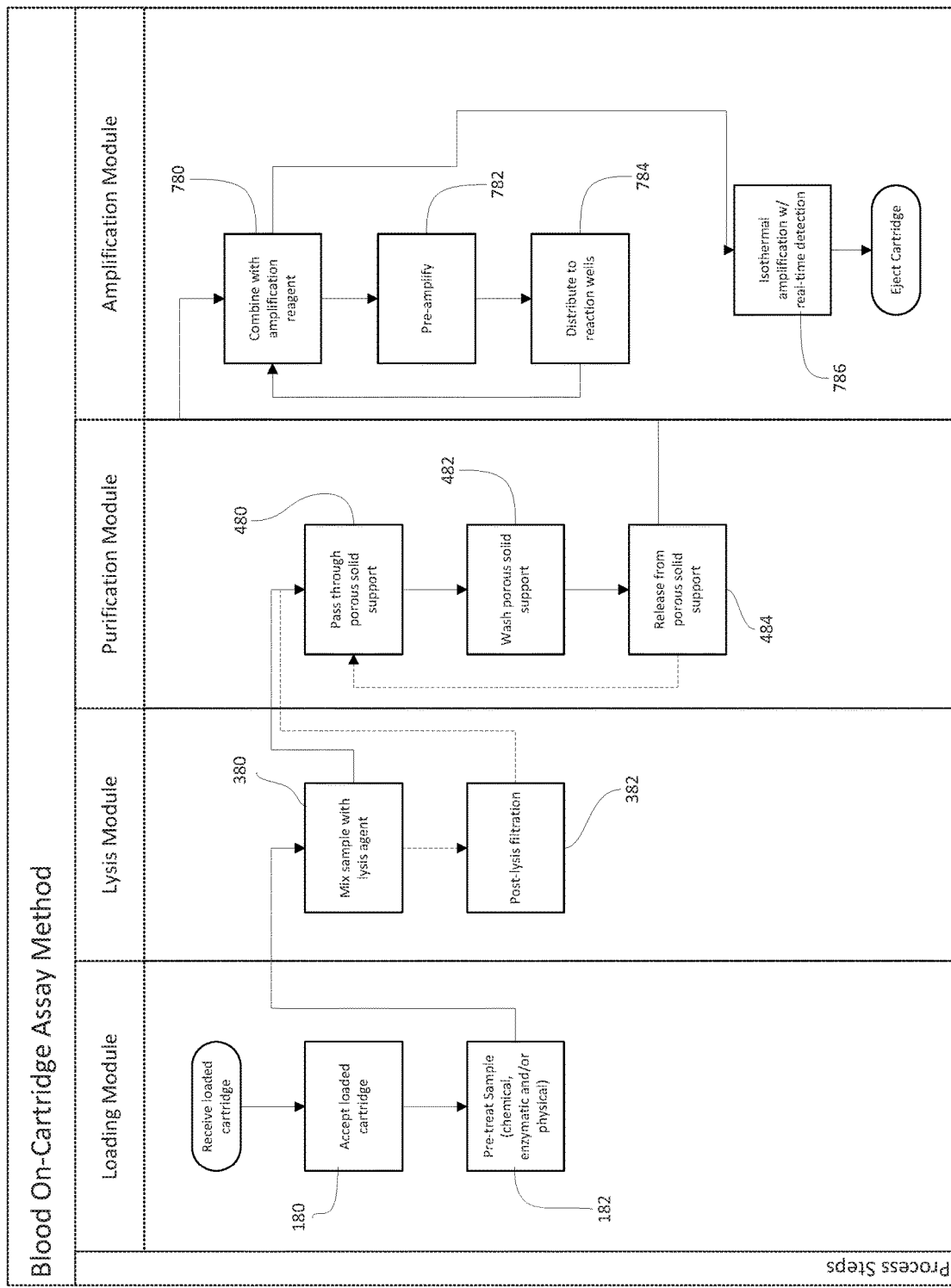

FIG. 109 depicts a workflow diagram of a blood assay method of testing a sample suspected of containing a target pathogen.

Figure 110:
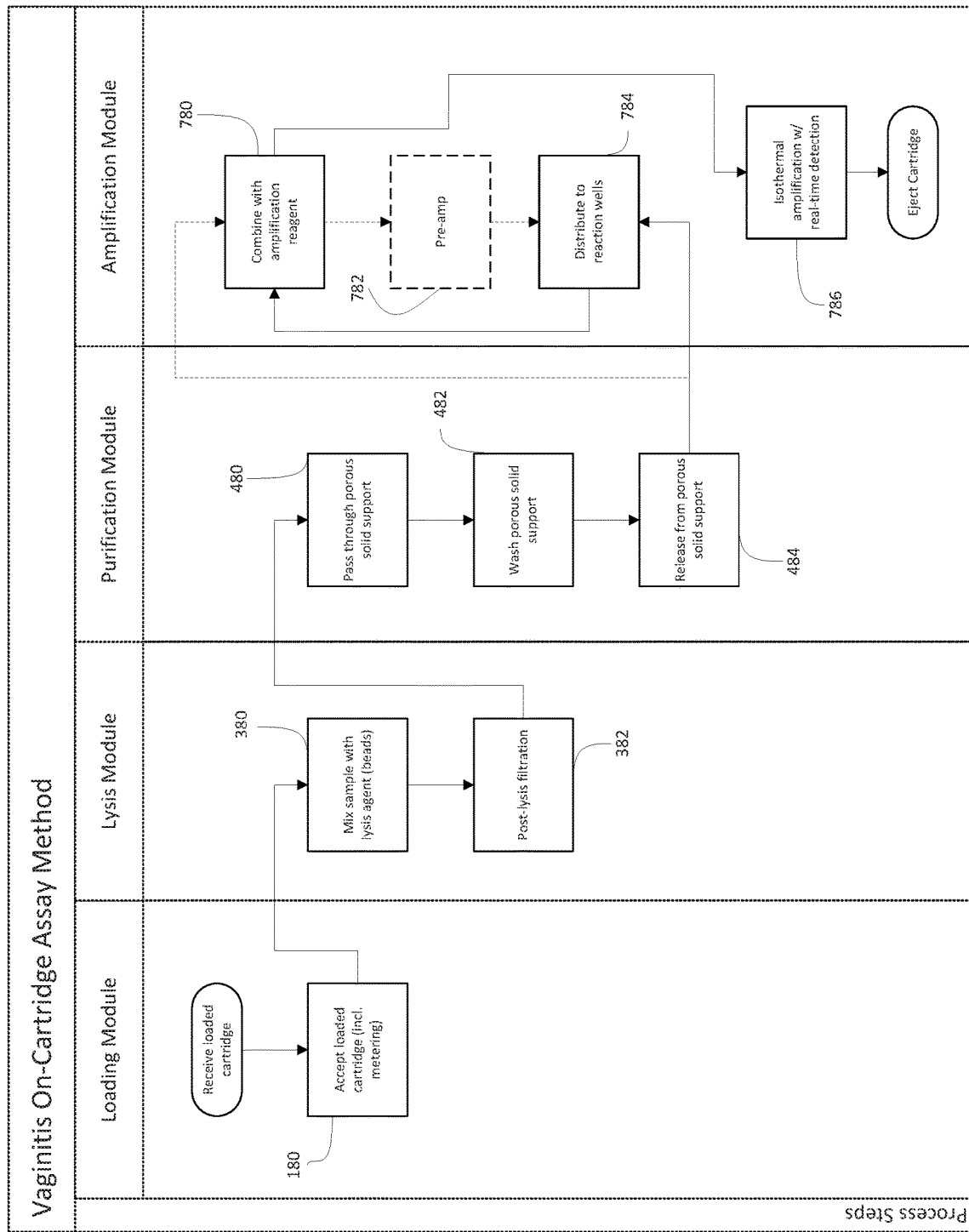

FIG. 110 depicts a workflow diagram of a vaginitis assay method of testing a sample suspected of containing a target pathogen.

Figure 111:
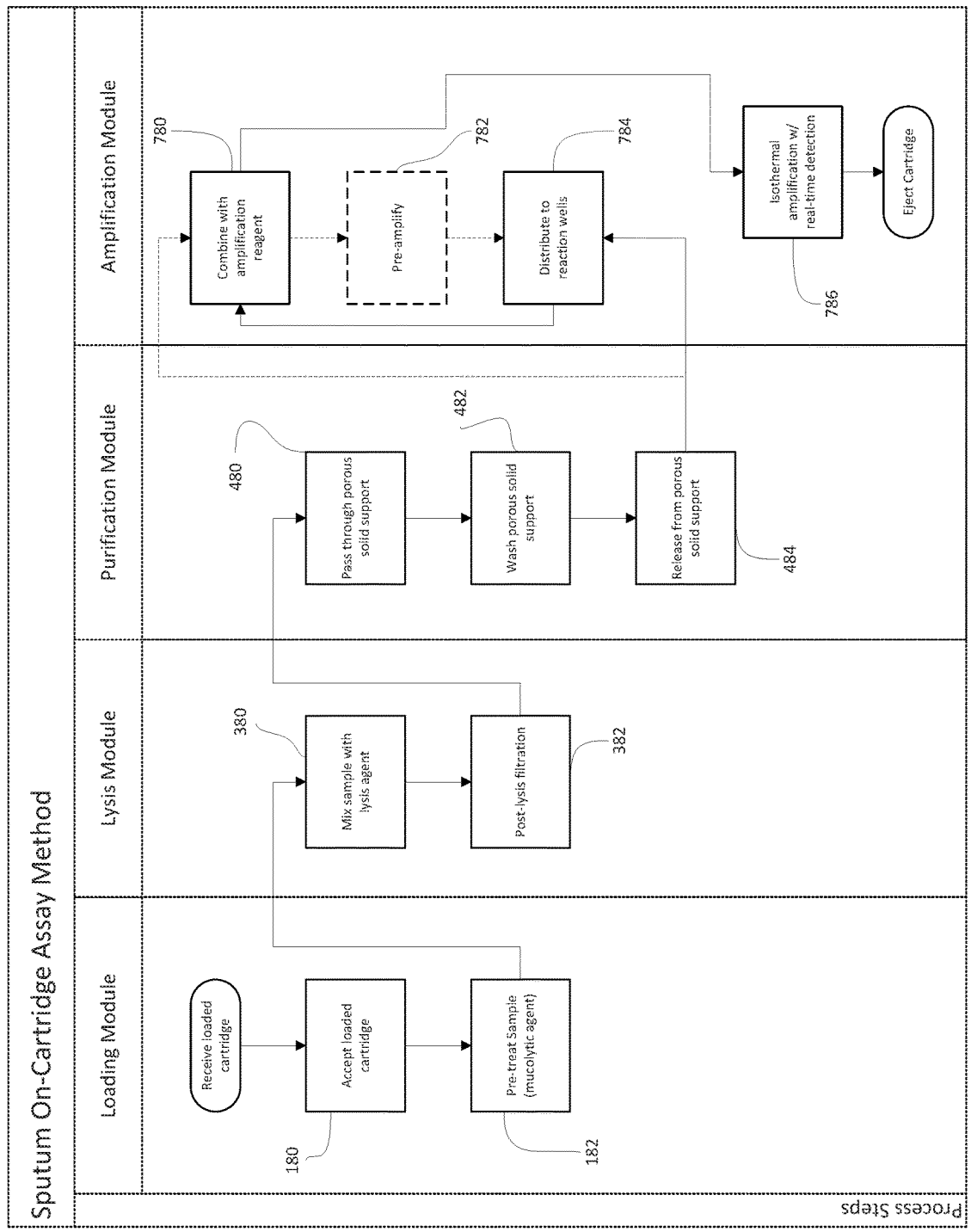

FIG. 111 depicts a workflow diagram of a sputum assay method of testing a sample suspected of containing a target pathogen.

Figure 112:
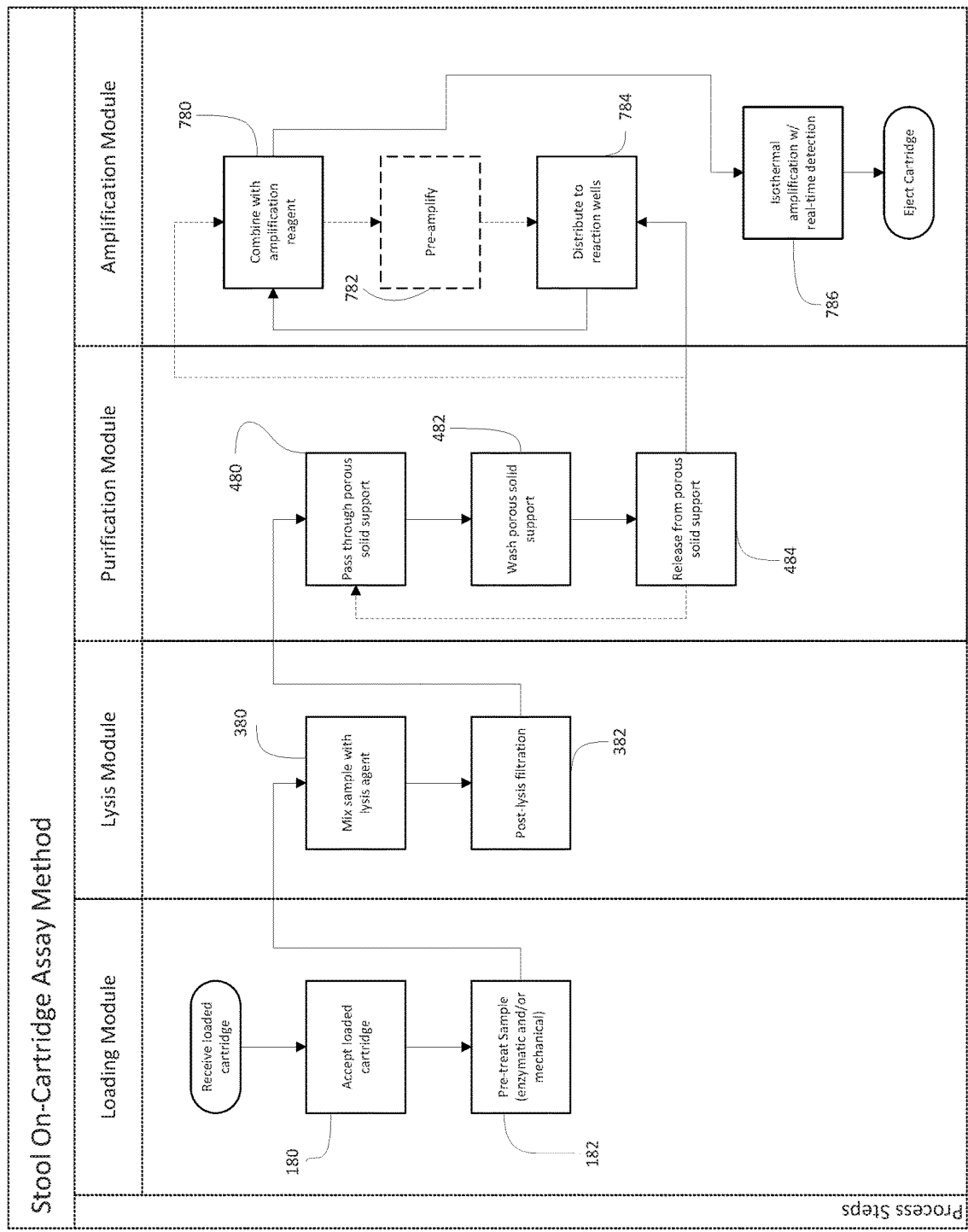

FIG. 112 depicts a workflow diagram of a stool assay method of testing a sample suspected of containing a target pathogen.

Figure 113:
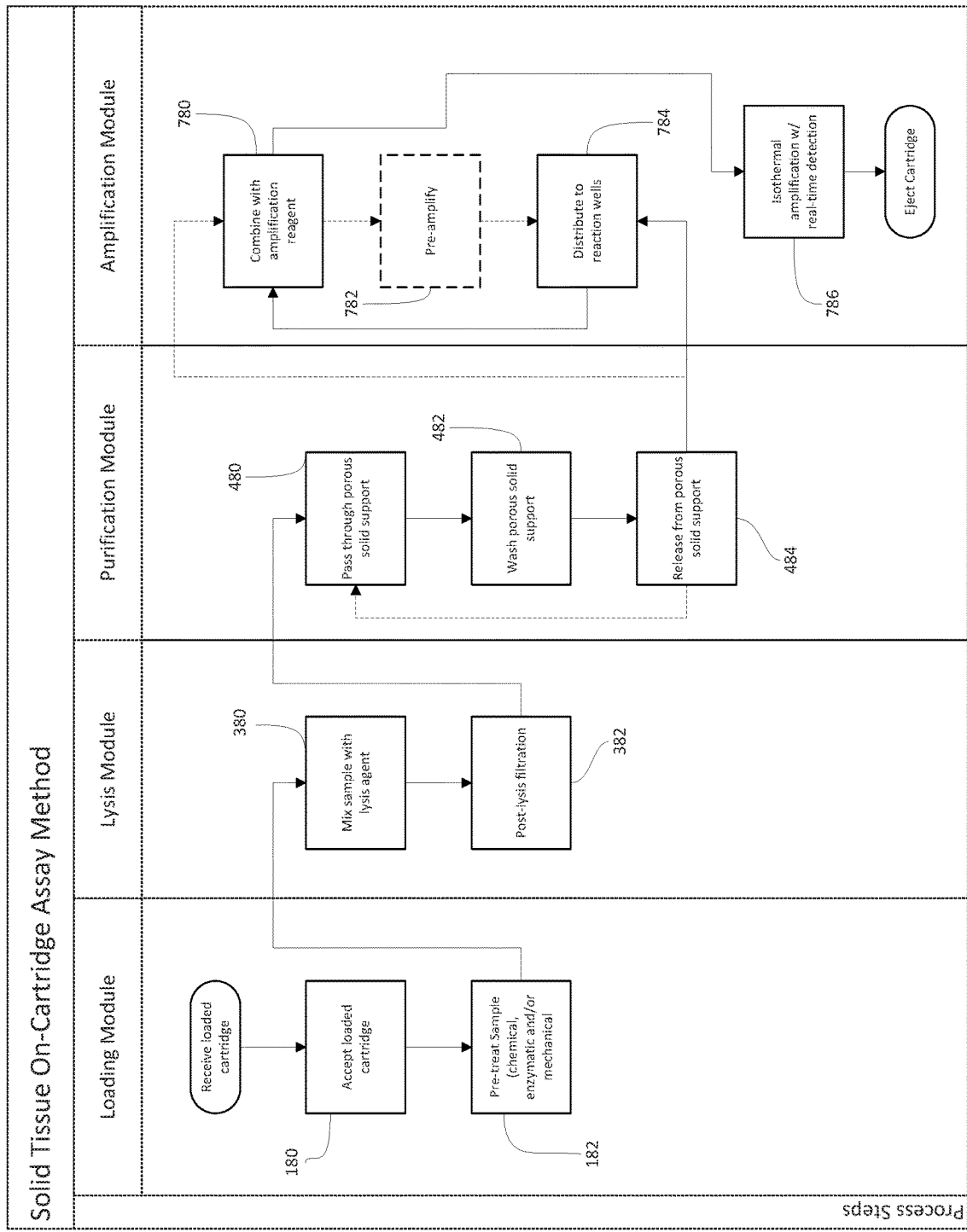

FIG. 113 depicts a workflow diagram of a solid tissue assay method of testing a sample suspected of containing a target pathogen.

VII. DETAILED DESCRIPTION

Figure 1:
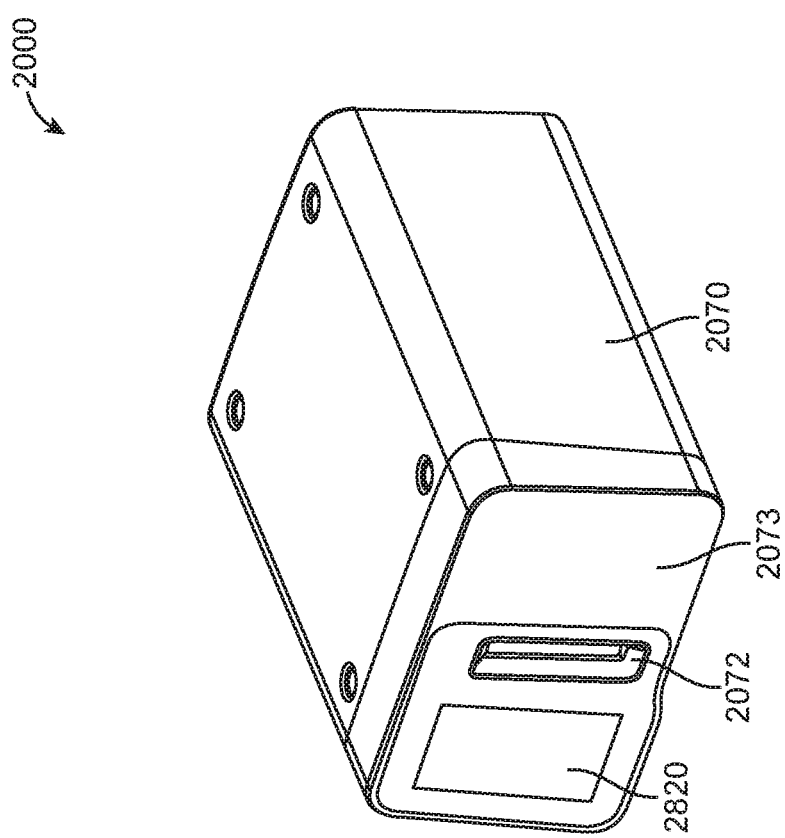
FIG. 1 is an illustration of a diagnostic instrument for conducting a molecular diagnostic test, in accordance to with an embodiment.

Described herein is a diagnostic system for performing rapid molecular diagnostic testing at the point of care. The diagnostic system comprises a diagnostic instrument and an integrated diagnostic cartridge as described in greater detail below. FIGS. 1-5 depict an exemplary workflow of using an integrated diagnostic cartridge in conjunction with a diagnostic instrument to conduct a molecular diagnostic test at the point of care. FIG. 1 illustrates an exemplary instrument configured to be used with this diagnostic system. As seen in FIGS. 2A and 2B, the first step of the workflow is depicted. A user is shown loading an integrated diagnostic cartridge with a sample loader, such as a bulb, syringe or pipette 1060. FIG. 2C illustrates the integrated diagnostic after sample loading is completed and the user seals the cartridge by closing a cap.

FIG. 3 illustrates the step of inserting a diagnostic cartridge 1000 into the front slot 2072 of the front 2073 of instrument 2000. The instrument includes features to ensure that a cartridge is loaded into the instrument only in the preferred orientation. Further description of the loading sequence is detailed below with reference to FIGS. 17A-23B.

Figure 5:
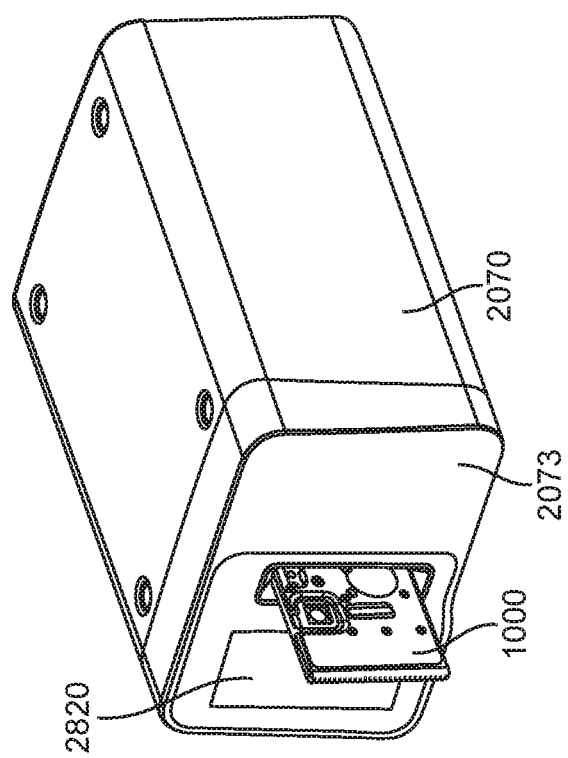
FIG. 5 depicts a diagnostic instrument ejecting an integrated diagnostic cartridge upon completion of a diagnostic test, in accordance with an embodiment.

Once a cartridge is properly loaded and verified by the instrument, the cartridge remains within the instrument slot as shown in FIGS. 4A and 4B. Regarding FIG. 4A, as part of the cartridge verification process, the display 2820 provides information regarding the patient information from the cartridge label and the type of test to be performed by the instrument. Additionally, the display 2820 may be configured to provide touch screen/GUI interactions with the instrument computer operating system. While running the diagnostic test, the instrument display may further provide information regarding the remaining time left for the diagnostic test. Once the automated testing sequence is completed, the cartridge is ejected from the instrument as shown in FIG. 5.

By way of introduction, the diagnostic system will be described according instrument embodiments and cartridge embodiments presented herein. The diagnostic instrument 2000 will be described according to several subsystems and assemblies shown in FIGS. 6-66. The various subsystems and assemblies, as described herein, may operate under the control of a computer system shown in FIGS. 67A-67I. In one aspect, the instrument 2000 is configured to accept an integrated diagnostic cartridge of different configurations. The large number of different cartridge configurations are detailed below with regard to FIGS. 68-92. An exemplary method of using one embodiment of an integrated diagnostic cartridge 1000 is described in FIGS. 93-102. The exemplary method describes how a cartridge can be used to prepare a biological sample to amplify nucleic acid and detect the presence of a suspected pathogen in a diagnostic test. As a result of the modular and highly configurable design of the cartridge, a wide array of sample types may be analyzed by the instrument as described with regard to FIGS. 107-113.

A. Instrument General Overview

FIG. 1 is a front isometric view of a diagnostic instrument 2000 to be used with the diagnostic system described herein. The various embodiments of the instrument 2000 described herein are adapted and configured to accept and process samples using any of a wide array of different testing methodologies and sample types. The instrument 2000 includes a clamping subsystem, a pneumatic subsystem, a thermal subsystem and an optical subsystem. The various relationship between the various subsystems may be appreciated with reference to the exploded isometric views of instrument 2000 provided in FIGS. 6 and 7. The clamping subsystem is described with reference to FIGS. 8-47B. The pneumatic subsystem is described with regard to FIGS. 48 and 49. The thermal subsystem is described with reference to FIGS. 50-57B. Additionally, the optical subsystem is described with regard to FIGS. 58-66.

Returning to FIGS. 6 and 7, in these views, the subsystems are shown outside of the instrument enclosure 2070 with pneumatic subsystem 2130 shown in its position within the instrument enclosure. The major assemblies of the fixed bracket assembly 2010 and the moving bracket assembly 2040 are shown in these views. In FIG. 6, subsystems and assemblies of the diagnostic instrument are shown in a right side exploded view or from a first surface of a fixed support bracket. A reaction imaging assembly 2700 of the optical subsystem is viewed as detached from the fixed bracket assembly 2010 and valve drive assembly 2400 is similarly detached from the moving bracket assembly 2040. Furthermore, a cellular assembly 2800, which provides communication to and from an instrument, and a label imaging assembly 2770 are readily apparent in this view. In FIG. 7, subsystems and assemblies of the diagnostic instrument are shown in a left side exploded view or from a second surface of a fixed support bracket. The fixed bracket assembly 2010 shows multiple components and assemblies supported from the second surface of the fixed support bracket 2013. Additionally, moving bracket assembly 2040 is viewed from a first surface of a clamp block 2042 and holds the remaining assemblies and components configured to interface with an integrated diagnostic cartridge to perform various processing steps.

Throughout the disclosure that follows, the term "vertical" position refers to the relationship of a testing cartridge to a vertical plane and a horizontal plane orientation provided by the design characteristics of a specific instrument embodiment. The vertical plane orientation is one allowing for the use of gravity for fluid movement for processing and handling steps performed during system operations. As such, terms of orientation such as higher and lower, upper and lower are understood in the context of gravitational flows of a generally vertical system orientation. In use, an instrument may be placed on a table or shelf that induces a tilt or incline to the instrument during use. Even though the instrument and cartridge are tilted during use this tilting up to and including +/−30 degrees is considered vertical as used herein. Moreover, tilting may be within the range of +/−15 degrees and also be considered vertical as used herein. Tilting within the above mentioned ranges would retain sufficient desired vertical orientation so as to maintain desired and expected gravity flow and characteristics.

The single use biologic test cartridge is received into and maintained within the instrument enclosure in a single orientation. This orientation is readily identified by the orientation of the slot to the instrument enclosure and along with the vertical and horizontal planes of the instrument. The instrument is adapted and configured to operate with cartridges configured to operate in such an orientation. As such, the meaning of upright is that positioning of the cartridge relative to the components of the instrument while maintaining an orientation of the cartridge so as to operate the cartridge within the designed cartridge orientation principals. In one embodiment, upright refers to an orientation of the cartridge within the instrument to being vertical within the instrument. This is the orientation that is illustrated in the several views of the instrument. In the views of FIGS. 68-72, and 89-92 an arrow indicates the vertical orientation and points towards UP. However, the operation and configurations of the instrument is not so limited. Based on variations in fluid flow characterizations of a specific single use cartridge, the orientation of the cartridge to the components of the instrument may be modified while still enabling the upright fluid flow principals implemented in a specific cartridge design. As a result, in other configurations, upright may include a slightly inclined orientation where the cartridge may be inclined relative to a vertical plane of the instrument while still providing the needed discrete actions of having an up and a down within the cartridge fluid schemes.

B. Clamping Subsystem

The clamping subsystem disposed within the instrument orchestrates the various physical interactions between the instrument 2000 and cartridge 1000 to perform a molecular diagnostic test run on the cartridge. The coordinated operation of the clamping subsystem is under control of the instrument computer controller (see FIGS. 67A-67I). The clamping subsystem is configured to accept and align a cartridge once inserted into the instrument. The clamping process is used to sequentially initiate interface between the instrument and specific cartridge components. Once diagnostic testing of a cartridge sample is completed, the cartridge is ejected from the instrument.

In one embodiment, the clamping subsystem includes a mechanism to break frangible seals within cartridge 1000, thus allowing fluid flow. In another embodiment, a magnetic mixing assembly 2300 is coupled to the clamping subsystem to provide mixing capabilities performed by the cartridge. In one implementation, a valve drive assembly 2400 actuates a rotary valve 1400 on the cartridge to move fluids and includes various sensors to monitor valving positions. In yet another implementation, the clamping subsystem supports an additional magnetic mixing motor to dissolve and rehydrate reagents within a cartridge to perform a diagnostic test.

1. Overview

Figure 8:
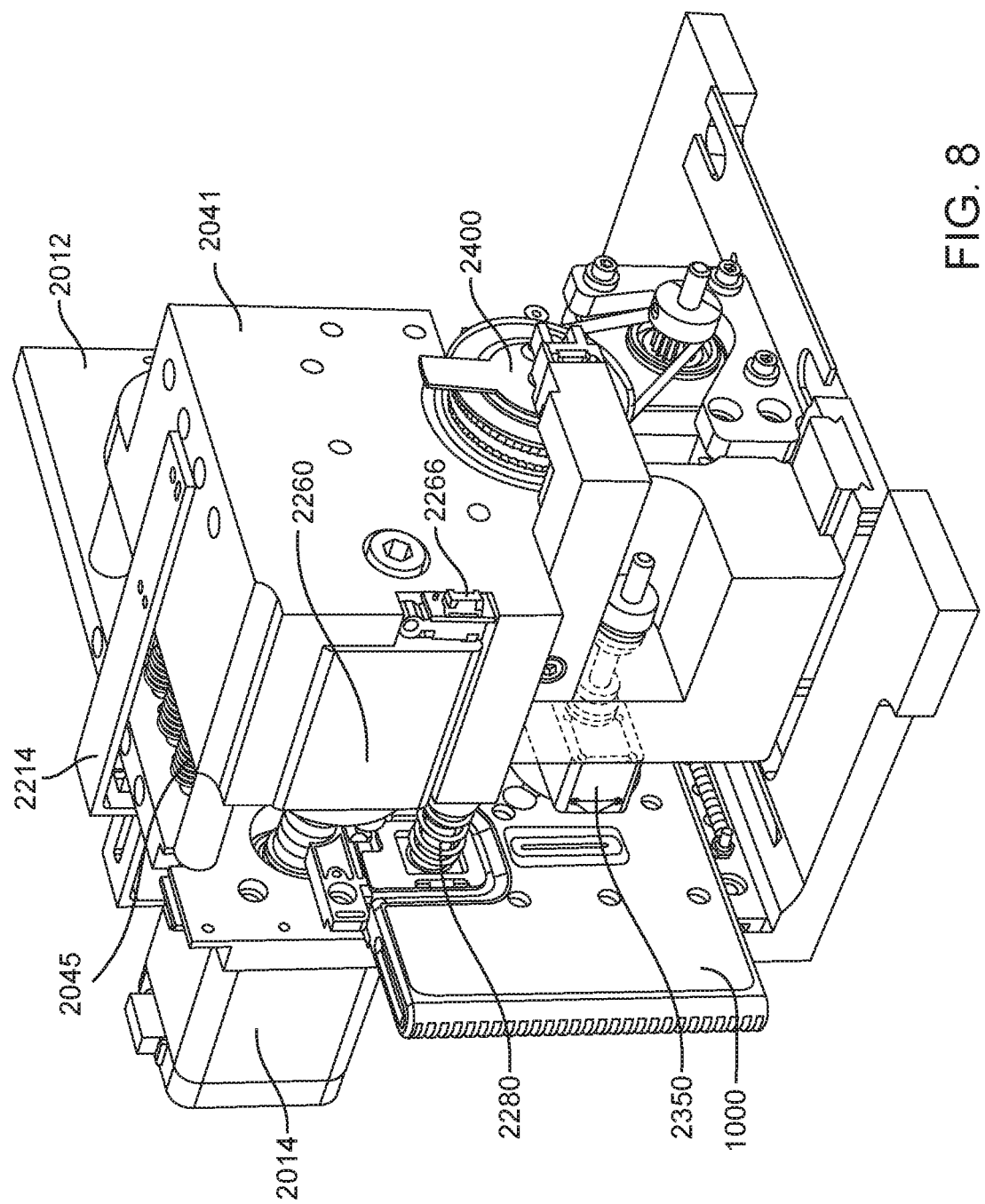
FIG. 8 and FIG. 9 are frontal perspective views of a diagnostic instrument clamping subsystem during clamping of an integrated diagnostic cartridge.
Figure 9:
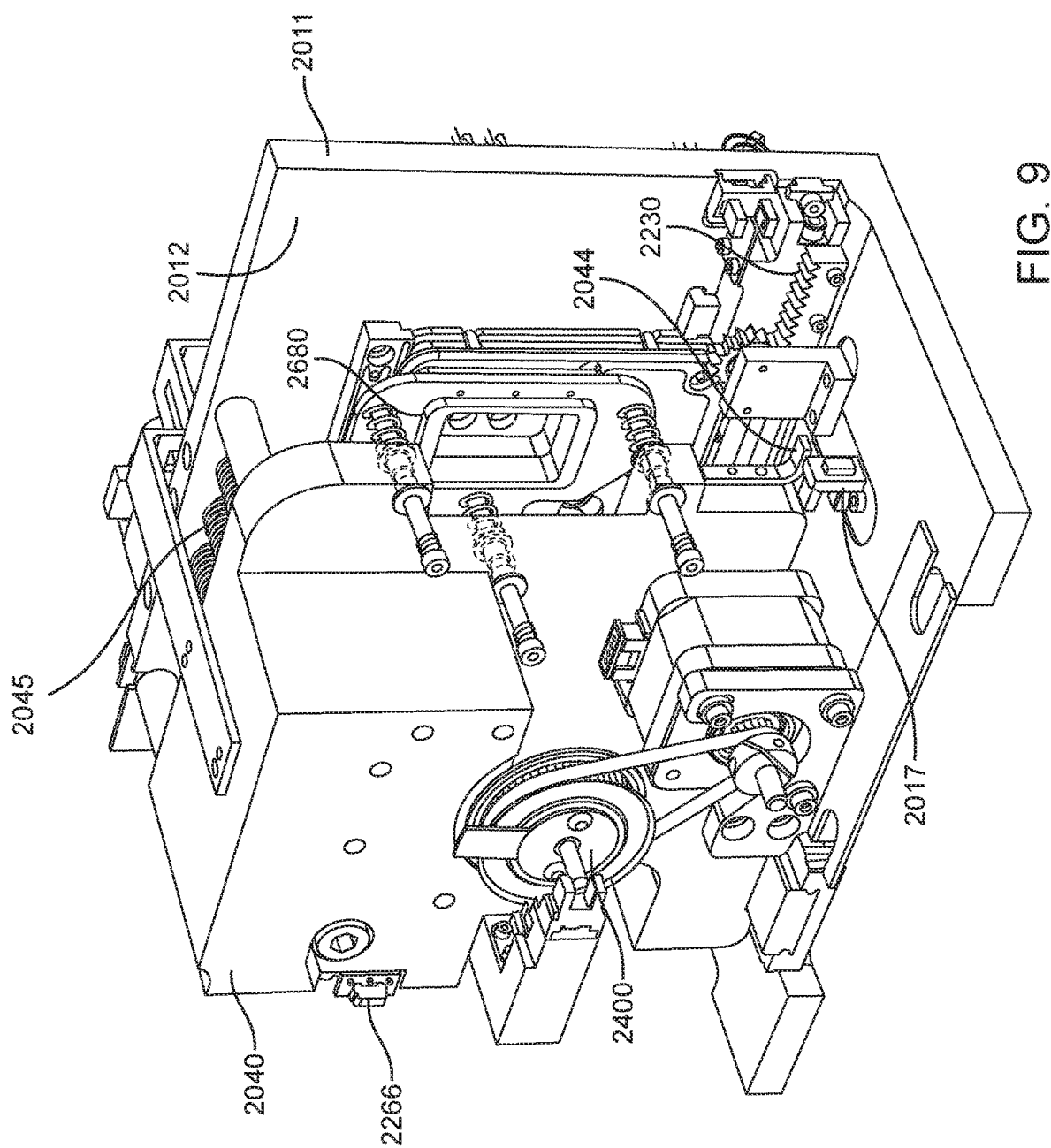

In one aspect of the invention, the clamping subsystem comprises a fixed-bracket assembly 2010 and moving bracket assembly 2040 which provide the foundation from which all other subsystems and assemblies are mounted from. FIGS. 8 and 9 are two frontal views of the clamping subsystem at two angles with cartridge 1000 inserted. Additionally, FIGS. 10 and 11 are two rear views of the clamping subsystem at two angles with cartridge 1000 inserted. Door support assembly 2280 is seen pressing against a sample port assembly 1100 on cartridge 1000. Linear actuator 2014, with lead screw 2016, mates with lead nut 2044 of the frangible seal block within the moving bracket assembly 2040. In FIG. 9 the valve drive assembly 2400 is readily visible. Furthermore, loading assembly 2230 is in a loaded cartridge position while thermal clamp assembly 2680 presses against the distal end of the cartridge. FIGS. 10 and 11 illustrate the clamping subsystem, with cartridge 1000 inserted, from two angles of the second surface of the fixed support bracket 2013. Linear actuator 2014, latch and pin assembly 2210, drive motor 2330 of the driving magnet system 2310, rehydration motor 2510 and thermal subsystem are illustrated in these views.

Figure 12:
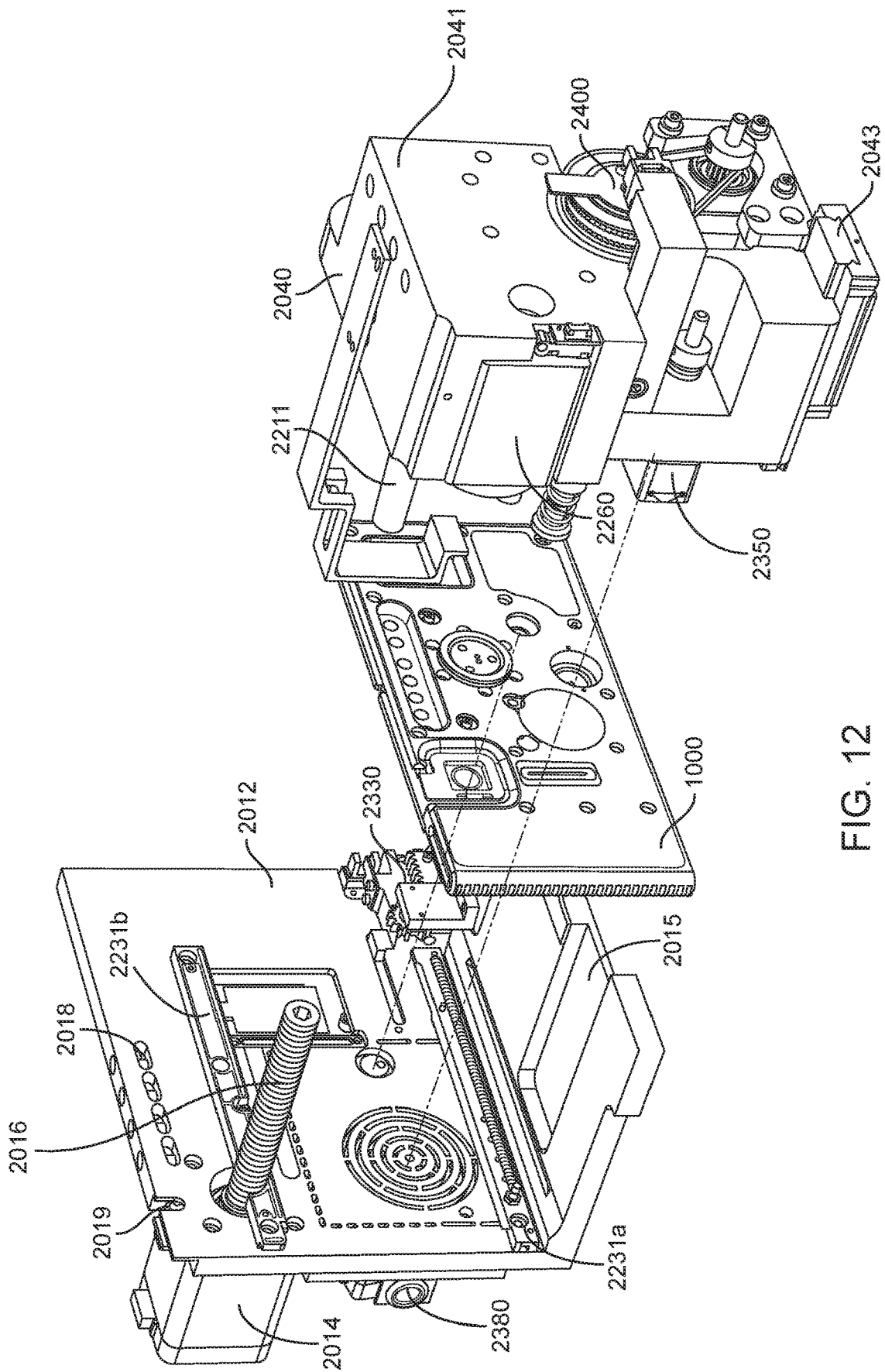
FIG. 12 is a frontal exploded view of a diagnostic instrument clamping subsystem with an integrated diagnostic cartridge disposed between a fixed bracket assembly and a moving bracket assembly.
Figure 13:
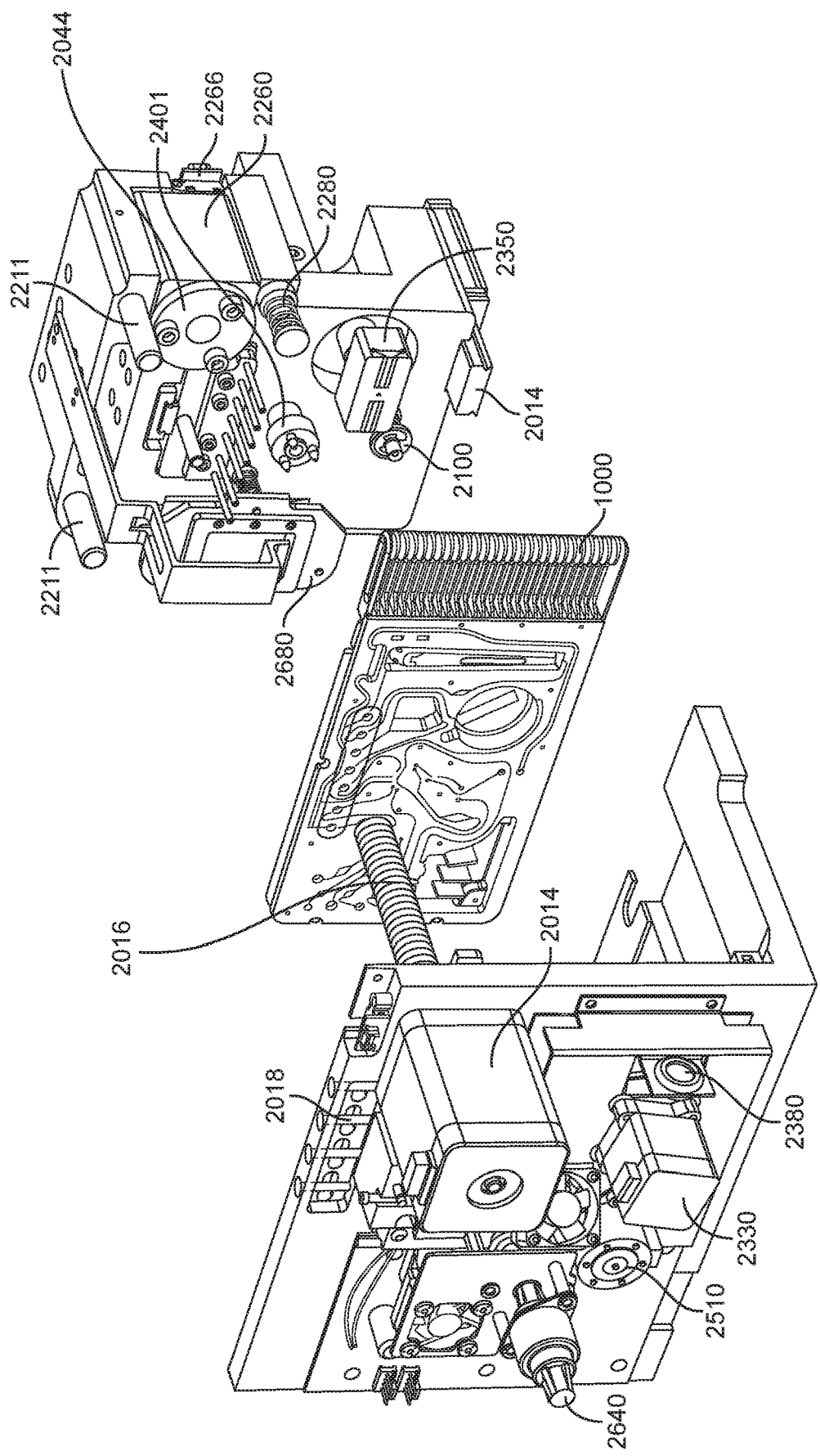
FIG. 13 is a rear exploded view of a diagnostic instrument clamping subsystem with an integrated diagnostic cartridge disposed between a fixed bracket assembly and a moving bracket assembly.

An exploded view of the clamping subsystem with cartridge 1000 is seen from two angles in FIGS. 12 and 13. Notch 2015 on the bottom of the first surface of fixed support bracket 2012 and linear slide 2043 on the moving bracket assembly 2040 define the direction the clamp block can move, such that the moving block assembly is configured to move toward the first surface of the fixed support bracket 2012 in a positive direction and away from the first surface of the fixed bracket support in a negative direction. In one embodiment, the linear actuator 2014 uses lead screw 2016 coupled to lead nut 2044 to move the moving bracket assembly 2040 to clamp and unclamp a cartridge. Lead nut 2044 is bolted to frangible seal block 2260 to drive the moving bracket assembly 2040 along linear slide 2043. Further detail of the assemblies and operation of the fixed bracket assembly 2010 in conjunction with a moving bracket assembly 2040 is described in the following sections.

2. Fixed Bracket Assembly

Fixed bracket assembly 2010 is the stationary component of the clamping subsystem and is composed of the loading assembly 2230, pin and latch assembly 2210, a driving magnet system 2310, and rehydration motor 2510. Various views of the fixed bracket assembly are provided in FIGS. 9, 10, 11, 12 and 13. In one embodiment, the fixed bracket assembly 2010 further supports the thermal subsystem responsible for generating the thermal requirements for executing a molecular diagnostic test and the optical subsystem for imaging separate distinctive areas of a cartridge. The optical subsystem comprises two assemblies: the label imaging assembly and the reaction imaging assembly. The label imaging assembly 2770 is attached to the bottom proximal end of the fixed support bracket, while the reaction imaging assembly 2700 is fixed to the distal end of the fixed support bracket. A frontal view of the fixed support bracket is viewed from a first surface 2012 or cartridge side in FIG. 12. Loading assembly 2230, which accepts and detects a loaded cartridge within the instrument and ejects the cartridge upon completion of a diagnostic test, is attached to the first surface of the fixed support bracket. Notch 2015 on the bottom of the first surface of the fixed support bracket provides the area in which linear slide 2043 within moving bracket assembly 2040 resides. In some embodiments, a sensor 2019 is mounted to the fixed bracket assembly 2010 to detect when the cartridge is successfully clamped between the fixed bracket assembly 2010 and the moving bracket assembly 2040. The sensor 2019 can be viewed in FIGS. 12, 13, and 15A-15E.

A rear view or a view from a second surface 2013 of fixed bracket assembly 2010 is depicted in FIGS. 10, 11 and 13. The fixed bracket assembly 2010 further comprises a linear actuator 2014 attached to a second surface of the fixed support bracket 2013. The linear actuator 2014 uses a lead nut 2016, coupled to lead nut 2044 on the frangible seal block 2260, to pull the moving bracket assembly toward the first surface of the fixed support bracket 2012 during clamping and push the frangible seal block 2260 and clamp block 2041 away from the fixed support bracket during unclamping. Further description of the clamping mechanism between the fixed bracket assembly 2010 and moving bracket assembly 2040 is discussed in greater detail with regard to the clamp block 2041 and frangible seal block 2260. The second surface of the fixed support bracket 2013 additionally serves as the surface responsible for carrying a driving magnet system 2310, rehydration motor 2510, and thermal subsystem of the instrument.

3. Moving Bracket Assembly

A front perspective view of the moving bracket assembly 2040 is viewed in FIG. 14. Exploded views of the moving bracket assembly 2040 from two different angles is viewed in FIGS. 15A and 15B. The moving bracket assembly is the dynamic component of the clamping subsystem and is configured to move linearly toward the fixed support bracket 2011 to clamp and contact the cartridge at numerous locations. The clamp block 2041 supports various systems interfacing with the cartridge and is configured to enable each system to perform respective tasks when running a diagnostic test. In one embodiment, assemblies supported by the clamp block 2041 include a frangible seal block 2260, a door support assembly 2280, a valve drive assembly 2400, a pneumatic interface 2100, a driven magnet system 2350, and a thermal clamp assembly 2680. As described in greater detail in the following sections, it is advantageous to separate the clamp block 2041 and the frangible seal block 2260 to separate the clamping action from the frangible seal actuation. In one implementation, the frangible seal block 2260 is configured to initially move with the moving bracket assembly 2040 and is capable of moving independently of the clamp block 2041. Additionally, the thermal clamp assembly 2680 is configured to move independently from the clamp block 2041. The door support assembly 2280, valve drive assembly 2400, pneumatic interface 2100, and driven magnet system 2350 are fixedly mounted to the clamp block 2041, such that movement of these assemblies entirely depends on the position of the clamp block 2041. The clamp block 2041 further comprises a first surface 2042 from which all cartridge interfacing features extend out of. The first surface of the clamp block 2042 is seen in FIGS. 14 and 15A.

The clamp block sits along linear slide 2043 which corresponds to notch 2015 on the bottom of the first surface of the fixed support bracket 2012 to connect the fixed bracket assembly 2010 to the moving bracket assembly 2040. As described above, the linear actuator 2014 is coupled to lead nut 2044 on the frangible seal block 2260. The linear actuator 2014 rotates lead screw 2016 in a first direction within lead nut 2044 of the frangible seal block 2260 to pull the moving bracket assembly toward the first surface of the fixed bracket assembly 2010 during clamping. Clamping force applied to the cartridge by the moving bracket assembly is not a result of the clamp block contacting the fixed bracket. In one implementation, extension springs 2045, seen in FIGS. 18A and 24, provide the force needed to clamp all assemblies supported by the clamp block to interface with a cartridge. During unclamping the moving bracket assembly is driven away from the fixed support bracket as the lead screw 2016 of the linear actuator 2014 is rotated in a second direction, opposite to the first rotational direction.

The largest displacement the clamp block is configured to move, in the positive direction toward the fixed bracket, is constrained by hard stops 2211 at the top of the clamp block. This configuration separates the clamping action from the frangible seal action, allowing the clamp block to clamp and interface with the cartridge without actuating frangible seals and allowing fluid flow.

The moving bracket assembly includes a door support assembly 2280 comprising a door support 2281 and spring 2282. During clamping, spring 2282 contact pushes door support 2281 against a top of a cap 1181 on a cartridge. Door support 2281 ensures the cap remains closed and sealed during pressurization of cartridge 1000.

4. Frangible Seal Block (Clamp Block)

Frangible seals keep fluids contained within cartridge 1000 and fluidic components isolated when the cartridge is not in use, such as during shipping and storage conditions. Accordingly, the diagnostic instrument includes a puncture mechanism for actuating frangible seals and allowing fluids within the cartridge to flow. The frangible seal block 2260 operates to break the frangible seals of the cartridge and is disposed within clamp block 2041 as a part of the moving bracket assembly 2040. The frangible seal block is a separate component from the clamp block 2041, wherein the frangible seal block and clamp block are coupled by linear slide 2264 to allow the frangible seal block 2260 to move independently from the clamp block 2041 during clamping. FIG. 34 illustrates the frangible seal block 2260 separated from the remaining moving bracket assembly 2040. This configuration disconnects the clamping action from the actuation of frangible seals to enable a cartridge to be clamped but not fluidically active until commanded. Frangible seal block 2260 can be viewed in FIGS. 14, 15A, 15B, 31, 33, 34 and 44. The basic structure of the frangible seal block includes frangible seal pins 2261 and hard stop 2263. Lead nut 2044 is bolted to the front of the frangible seal block and is used to pull the frangible seal block 2260 and moving bracket assembly 2040 toward the fixed bracket assembly 2010 in the positive direction during clamping and drive the frangible seal block 2260 and moving bracket assembly 2040 away from the fixed bracket assembly 2010 in the negative direction during unclamping. The lead nut 2044 is coupled to the lead screw 2016 of linear actuator 2014 mounted on the second surface of the fixed support bracket 2013. The linear actuator 2014 rotates lead screw 2016 in a first rotational direction to pull the frangible seal block in a positive direction towards the fixed bracket assembly 2010. Extension springs 2045 housed within the top of the moving bracket assembly 2040 provide tension to pull the clamp block 2041 against the frangible seal block 2260 to move the frangible seal block and clamp block together along linear slide 2043 during clamping movement in the positive direction. In one implementation, extension springs 2045 are attached to pins 2018 which are fixed to portions of the fixed support bracket 2011 and clamp block 2041.

The moving bracket assembly 2040 is configured such that the frangible seal block 2260 and clamp block 2041 initially move together due to extension springs 2045 until hard stop 2211 on clamp block 2041 contacts the first surface of the fixed support bracket 2012. Hard stop 2211 prevents the clamp block 2041 from being displaced a further distance in the positive direction toward the fixed bracket assembly 2010. However, the separation between the frangible seal block 2260 and the clamp block 2041 enables the frangible seal block to be further displaced in the positive direction along linear slide 2264 toward the fixed support bracket to actuate frangible seals and render the cartridge fluidically active. To actuate frangible seals 1201-1207 on the cartridge, linear actuator 2014 continues to rotate the lead screw 2016 in a first rotational direction after the cartridge is clamped. While the clamp block 2041, remains stationary due to the contact between hard stop 2211 and the first surface of the fixed support bracket 2012, the frangible seal block 2260 is pulled along linear slide 2264, seen in FIG. 31. Frangible seal pins 2261 on the frangible seal block 2260 press against frangible seals 1201-1207 and into pocket 2262, shown in FIG. 32, formed in the first surface of the fixed support bracket 2012 to actuate the seals. Movement of the frangible seal block 2260 is configured to move in the positive direction until hard stop 2263 contacts upper rail 2231a of the loading assembly 2230. Hard stop 2263 prevents the frangible seal pins from over puncturing the frangible seals, which may result in the breaking of the one or more backing films on the cartridge and produce a leak. Additionally, hard stop 2263 prevents damaging the pins.

In one implementation, frangible seal pins 2261 are cylindrical in shape. Other pin shapes are possible included rounded tips or other shapes suited to produce the desired opening in a frangible seal or to have a complementary shape with a preferred seal rupture pattern or design.

One aspect of the invention provides the frangible seal pins 2261 of substantially equivalent length. When frangible seals are of substantially equal length, frangible seal pins on the frangible seal block 2260 will actuate all frangible seals on cartridge 1000 with one linear motion in a positive direction. Furthermore, when the frangible seal block 2260 is moved in a negative direction, all frangible seal pins are retracted from pocket 2262 in the first surface of the fixed support bracket 2012 to release the cartridge during unclamping and ejection. In an alternative embodiment, one or more frangible seal pins 2261 may be of varying lengths, such that different frangible seals on the cartridge may be actuated at different times. In this configuration, the frangible seal block may actuate frangible seals in a sequence to convert one or more frangible seals fluidically active while one or more frangible seals remain fluidically inactive. Sequential actuation of one or more frangible seals depends on the position of the frangible seal block 2260, such that in a first actuation position frangible seal pins 2261 longer in length will actuate frangible seals before frangible seal pins smaller in length. Subsequently, the frangible seal block must be moved in the positive direction to a second actuation position to actuate frangible seals with smaller frangible seal pins to render respective seals fluidically active. As described in the previous sections, the clamp block 2041 remains stationary, clamping the cartridge, due to hard stop 2211 as frangible seal pins are actuated either all at once or in a sequence. This alternative embodiment is illustrated in FIG. 33 with first frangible seal pin 2261a being shown longer than remaining pins 2261b-g.

When a diagnostic test is complete and a cartridge is ready to be unclamped and ejected, linear actuator 2014 rotates the lead screw 2016 in a second rotational direction. Rotating the lead screw 2016 in a second rotational direction initially pushes the frangible seal block in the negative direction along linear slide 2264 away from frangible seals 1201-1207. As an integrated part of the moving bracket assembly 2040, the frangible seal block continues to move in a negative direction along linear slide 2264 until the frangible seal block contacts ledge 2046 of clamp block 2041. The frangible seal block presses against ledge 2046 to subsequently move the entire moving bracket assembly 2040 in the negative direction away from the fixed bracket assembly 2010 to unclamp the cartridge.

5. Clamping Sequence

As described herein, the clamping subsystem can clamp a cartridge 1000 using a sequence of clamping positions to engage different interfaces of the moving bracket assembly 2040 with the cartridge at different times. A representative clamping sequence will be described with reference to FIGS. 16A-16E. As shown in FIG. 16A the moving bracket assembly 2040 described above is in a zero clamping position. Specifically, hard stop 2211 located at the top of the clamp block 2041 does not contact the first surface of the fixed support bracket 2012 and the moving bracket assembly 2040 is spaced apart from the fixed bracket assembly 2010 to allow a cartridge 1000 to be inserted into the instrument 2000. Engagement between each interface, e.g., a frangible seal block 2260, a door support assembly 2280, a valve drive assembly 2400, a pneumatic interface 2100, a driven magnet system 2350, and a thermal clamp assembly 2680, on the moving bracket assembly 2040 and the cartridge has yet to be established.

FIG. 16B shows the moving bracket assembly 2040 after it is moved in the positive direction from the zero clamping position to a first clamping position when linear actuator 2014 rotates lead screw 2016 in a first rotational direction. In the first position, the valve drive assembly 2400, mounted within clamp block 2041, is engaged with rotary valve 1400 on the cartridge. Hard stop 2211 has yet to contact the first surface of the fixed bracket 2012 and sensor 2019 is untriggered. Additionally, the thermal clamp assembly contacts the distal end of the cartridge but is not engaged to seal the reaction area 1600. This position enables the instrument to execute multiple rotary valve verification tests on rotary valve 1400 of the cartridge, described in the sections below, before executing the remainder of the clamping sequence. Rotary valve verification tests ensure a cartridge rotary valve 1400 is in a shipping configuration to ensure an inserted cartridge is unused and can perform a diagnostic test.

FIG. 16C shows the moving bracket assembly 2040 after it is moved in the positive direction from the first clamping position to a second clamping position when linear actuator 2014 rotates lead screw 2016 again in a first rotational direction. In the second position, hard stops 2211 contact the first surface of the fixed support bracket 2012 and sensor 2019, which now hidden from view, is triggered. The door support assembly 2280, pneumatic interface 2100, valve drive assembly 2400, and thermal clamp assembly 2680 are actively engaged with each respective location on the cartridge. In this view, the cartridge is clamped, but not fluidically active. Furthermore, this position is the greatest distance the clamp block 2041 and all assemblies fixedly attached to the clamp block (i.e. door support assembly 2280, valve drive assembly 2400, pneumatic interface 2100, thermal clamp assembly 2680, and driven magnet system 2350) are permitted to move in the direction of the fixed support bracket 2011.

FIG. 16D shows the frangible seal block 2260 after it moved in the positive direction from the second clamping position to a third clamping position. In the third position, the clamp block 2041 remains in the second clamping position and is prevented from moving as hard stops 2211 contact the first surface of the fixed support bracket 2012. All assemblies fixedly to the clamp block 2041 including door support assembly 2280, pneumatic interface 2100, valve drive assembly 2400, and driven magnet system 2350 remain in the second clamping position. Note, while the thermal clamp assembly 2680 is configured to move independently from the clamp block 2041, the thermal clamp assembly also remains in the second clamping position due to being in sealing contact with the distal end of the cartridge. As described herein, frangible seal block 2260 is configured to move independently of the clamp block 2041 along linear slide 2264. The frangible seal block 2260 moves to the third clamping position in the positive direction when linear actuator 2014 rotates lead screw 2016 in a first rotational direction, thus actuating frangible seals on a cartridge. This independent movement is observed by gap 2265 between the frangible seal block 2260 and clamp block 2041. The separation between the clamp block 2041 and frangible seal block 2260 isolates the clamping action of the cartridge from the actuation of frangible seals on the cartridge. In the third clamping position, the cartridge is clamped, fluidically active, and ready to run a diagnostic test in the third position.

FIG. 16E shows the moving bracket assembly 2040 when it is moved in the negative direction away from the fixed bracket assembly 2010 to a fourth clamping position when linear actuator 2014 rotates lead screw 2016 in a second rotational direction. In the fourth position, the moving bracket assembly 2040 is located at a negative distance measured from the zero clamping position to unclamp a cartridge when the diagnostic test is completed. During unclamping, the frangible seal block 2260 is first driven away from the fixed support bracket until the frangible seal block contacts ledge 2046 of the clamp block 2041, thus eliminating gap 2265 seen in FIG. 16D. As the frangible seal block 2260 continues to move in a negative direction, the frangible seal block pushes against ledge 2046 to drive the entire moving bracket assembly 2040 away from the cartridge 1000 and fixed bracket assembly 2010.

6. Loading Assembly (Fixed Support Bracket)

a) Loading

In one aspect, the invention provides a loading assembly 2230 configured to accept a cartridge inserted into instrument 2000 and eject the cartridge upon completion of a diagnostic test. FIGS. 17A-17C, 18A-18B and 19A-19C illustrate various views of the operation of the loading assembly 2230 within instrument 2000. FIGS. 17A-17B illustrate the loading assembly 2230 in a loading position. FIG. 18A-18B illustrate the loading assembly 2230 in a loaded position. FIGS. 19A-19C illustrate a cartridge inserted into the loading assembly 2230 in a loaded position. The loading assembly comprises rails 2231, rack 2232, pinion 2233, pusher carriage 2234, spring 2235 and a load position sensor 2236.

A cartridge inserted into the loading assembly 2230 is viewed in a loading position in FIG. 17A. The cartridge is inserted along upper and lower rails 2231 until the distal end of the cartridge contacts pusher carriage 2234. In a loading position, pusher carriage 2234 is in a forward most position toward the front slot 2072 of the instrument such that load position sensor 2236 is not triggered by flag 2237 located on the pusher carriage. Further description of the load position sensor 2236 and flag 2237 is discussed in reference to the cartridge in a loaded position. An enlarged view of the pusher carriage 2234, rack 2232, and pinion 2233 is viewed in FIG. 17B when a cartridge is in a forward most loading position. FIG. 17C shows an enlarged view of spring 2235 which is fixed between post 2239 and pusher carriage 2234, such that when the cartridge and loading assembly is in a forward most loading position, spring 2235 is in a resting equilibrium position.

FIGS. 18A-18B illustrate the loading assembly 2230 in a loaded position without a cartridge. In the loaded position, pusher carriage 2234 is in a backward most position away from the front slot 2071 of the instrument. As viewed in FIGS. 18B and 19B, load position sensor 2236 is triggered by flag 2237 on the pusher carriage. FIGS. 19A and 19C are perspective views of a cartridge inserted into the loading assembly 2230 while in a loaded position. The cartridge transitions from the loading position, viewed in FIG. 17A, to a loaded position when the cartridge continues to move along rails 2231, with the distal end of the cartridge pushing against the pusher carriage. The cartridge is permitted to move along rails 2231 until pinion 2233 reaches the end of rack 2232 and flag 2237 triggers load position sensor 2236, thus confirming the cartridge is inserted into the instrument. The latch and pin assembly 2210, described in the next section, obstructs the cartridge while in a loaded position to prevent the cartridge from being ejected by spring 2235 prior to the cartridge being clamped by the moving bracket assembly 2040. The cartridge remains in the loaded position for the duration of the diagnostic test until the cartridge is ejected upon completion of the test. A view of the cartridge in a loaded position from the outside of the instrument is seen in FIGS. 4A and 4B.

In one aspect of the invention, the loading assembly 2230 allows an inserted cartridge 1000 to ride along two rails 2231 until the distal end of the cartridge contacts pusher carriage 2234. Interaction between a cartridge and the upper and lower rails is shown in the various views of FIGS. 20-23B. Proper cartridge insertion orientation is ensured through the use of complementary features on both the cartridge and the rails. FIGS. 20 and 21 illustrate an upper rail 2231*a* and lower rail 2231*b*, of the loading assembly 2230, both comprising guide features 2240. A properly aligned cartridge is configured to align with guide features 2240 to maintain proper vertical orientation as described herein. In one embodiment, the width of the rail gap corresponds to the width or edge thickness of the fluidic card. It is to be appreciated that features used to ensure proper cartridge orientation may be used to interfere with one or both of the fluidic card, the cover or any designed gap or spacing formed or partially formed between the fluidic card and cover. In some embodiments, interference features may be included in one or both of a cartridge component or an upper rail or a lower rail to ensure proper cartridge insertion orientation.

A cartridge inserted with proper alignment is shown in a top down view in FIGS. 22A-B and shown in a bottom up view in 23A-B. FIG. 22A illustrates the distal end of the cartridge prior to being inserted into the loading assembly 2230 and prior to interacting with upper guide feature 2240. FIG. 22B shows a cartridge during loading with upper guide feature 2240 in alignment with the cartridge gap or spacing formed or partially formed between the fluidic card and cover. The gap or spacing formed between the fluidic card and cover is configured to interface with the upper guide feature 2240 to direct the cartridge along the upper rail 2231*a*. Additionally notch 1021, used to obstruct the cartridge from being ejected, is further viewed in FIGS. 22A and 22B. In one implementation, an interference feature 1022 is formed within the cartridge cover, as shown in FIGS. 23A and 23B. FIG. 23A illustrates the distal end of the cartridge, in a bottom up view, prior to being inserted into the loading assembly 2230 and prior to lower guide feature 2240 interacting with interference feature 1022. FIG. 23B shows a cartridge during loading with a lower guide feature 2240 in alignment with interference feature 1022. Alignment between the lower guide 2240 and interference feature 1022 prevents a user from inserting the cartridge with an incorrect orientation.

b) Ejection

When the diagnostic test is complete, the cartridge is unclamped by the moving bracket assembly 2240 and unlatched by the latch and pin assembly 2210. The loading assembly 2230 uses spring 2235, as shown in FIG. 17C, along the bottom rail 2231 to provide the force to eject the cartridge upon completion of the diagnostic test. Spring 2235 is fixed between post 2239 and pusher carriage 2234 such that when the cartridge is in a backward most loaded position (i.e. the load position sensor is triggered), spring 2235 is stretched out of equilibrium. During ejection, spring 2235 returns to its resting equilibrium position and pulls the pusher carriage and cartridge back to a forward most position toward the front slot 2072. The cartridge is returned to the loading position, as viewed in FIG. 17A, to eject the cartridge. An ejected cartridge is viewed from the outside of the instrument in FIG. 5.

7. Latch and Pin Assembly (Fixed Support Bracket)

In one embodiment, the instrument of the present invention comprises a latch and pin assembly 2210 to prevent a cartridge from being ejected by spring 2235. The latch and pin assembly 2210 keeps the cartridge stationary in the loaded position while the moving bracket assembly 2240 moves in a positive direction toward the first surface of the fixed support bracket 2011 to clamp the cartridge. Specifically, the latch and pin assembly 2210 is fixed to the second surface of the fixed support bracket 2013 and comprises latch 2212, spring 2213, latch arm 2214, arm slot 2215, and pin 2216. The latch and pin assembly 2210 illustrated in FIG. 24 is discussed in greater detail with regard to FIGS. 25A-28.

FIG. 25A is a perspective frontal view of the latch and pin assembly 2210 with cartridge 1000 fully inserted. In some embodiments, a latch release arm 2214 is attached to the moving bracket assembly 2010 and extends to the second surface of the fixed support bracket 2013 to interact with pin 2216, described in further detail with regards to FIG. 27. Latch 2212 is seen within notch 1021 at the top of the cartridge to prevent the cartridge from being ejected by the loading assembly 2230. It is to be appreciated features used to obstruct the cartridge from being ejected may be formed or partially formed in the fluidic card, such as the one depicted in FIG. 25A, and optionally extent through to the cover. FIGS. 25B and 25C are additionally views illustrating the pin and latch assembly 2210 at two angles with spring 2213 configured to provide a downward force to drop the latch 2212 into notch 1021 when the cartridge is inserted into the loading assembly 2230 of the instrument. In FIGS. 25A-25C, pin 2216 resides within a narrow portion of a slot 2215 formed within the latch release arm 2214.

As described herein, the cartridge travels along upper and lower rails 2231 of the loading assembly 2230 when a user inserts a cartridge with proper alignment and orientation into the instrument. When implemented, the rounded distal end of the cartridge lifts latch 2212 up and spring 2213 drops latch 2212 into notch 2210. When the latch is trapped within the notch, the cartridge is obstructed and remains in a loaded position (i.e. with load position sensor 2236 triggered). FIG. 25D shows the latch and pin assembly 2210 in a side view with cartridge 1000 in a loaded position and latched by the latch and pin assembly. However, the cartridge remains unclamped. Hard stops 2211 of the moving bracket assembly 2040 do not contact the first surface of the fixed support bracket 2012 and hard stop 2263 of the frangible seal block 2260 has yet to contact upper rail 2231 of the loading assembly 2230. Pin 2216 is constrained between the narrow portion of slot 2215 formed within the latch release arm and latch release arm 2214 does not contact the bottom of pin 2216.

FIG. 26A illustrates when a cartridge is in a loaded and latched position. Additionally, the cartridge is clamped and rendered fluidically active as denoted by hard stops 2211 contacting the first surface of the fixed support bracket 2012 and hard stop 2263 contacting upper rail 2231. As shown in FIG. 26B, pin 2216 resides in a widened section of slot 2215 formed within the latch release arm 2214 when a cartridge is clamped by the moving bracket assembly 2040. In some embodiments, latch and pin assembly 2210 uses latch release arm slot 2215 to constrain the movement of pin 2216 within the slot opening. The position of the pin, in relation to slot 2215, is free to gimbal during the clamping of the cartridge due to the widening of the slot opening at the vertical bend of the latch release arm. This feature addresses mild variation tolerances generated from the interaction between cartridge and the various interface features of the moving bracket assembly 2240 when the cartridge is clamped and ensures latch 2212 catches notch 1021 to prevent the cartridge from being ejected.

When the cartridge is ready to be ejected the moving bracket assembly 2240 travels in a negative direction away from the first surface of the fixed support bracket 2012, thus causing the latch release arm, fixedly attached to the moving bracket assembly, to simultaneously move in the negative direction. The unclamping motion of the moving bracket assembly causes tab 2217 on the latch release arm to contact the bottom of pin 2216 and urge latch 2212 upward, shown in FIG. 27. In this configuration, the cartridge is no longer obstructed by the latch 2212 and the cartridge 1000 is free to be ejected by the loading assembly 2230. FIG. 28 illustrates the latch and pin assembly 2210 when the used cartridge is removed from the instrument. Latch 2212 is returned to its resting position and the moving bracket assembly 2040 is separated from the first surface of the fixed support bracket 2012.

8. Valve Drive Assembly (Clamp Block)

As described herein, the moving bracket assembly 2040 comprises a valve drive assembly 2400 to facilitate the delivery and redirection of a sample and any of the necessary reagents through rotary valve 1400 on a cartridge 1000. FIGS. 29 and 30 provide an enlarged view and a perspective view of the details and operation of a valve drive assembly. The valve drive assembly is configured to index the rotary valve 1400 to different valving positions in a sequence of steps for performing a diagnostic test. The valve drive assembly includes a valve drive 2401, a valve drive shaft 2408, a motor 2403, a pulley 2406, and various sensors to detect the valve drive position. As seen in FIG. 29, valve drive 2401 is connected to the valve drive shaft 2408 wherein the end of the valve drive shaft 2408 is coupled to pulley 2406. Motor 2430 supplies the motive force to rotate the valve drive to index the rotary valve to different valving positions. The motor is mechanically coupled to the valve drive using valve drive shaft 2408 and pulley 2406. Specifically, as the motor rotates, belt 2407 translates rotational motion to the pulley thereby causing the valve drive shaft 2408 to rotate the valve drive. In some embodiments, the valve drive assembly may incorporate the use of various sensors to perform multiple verification checks on the rotary valve to ensure an inserted cartridge is suitable to run a diagnostic test (i.e. the cartridge is unused and untampered). In one implementation, the valve drive assembly 2400 uses an interference sensor 2404 to track the linear displacement of the valve drive assembly. In a further implementation, valve drive assembly 2400 includes a homing sensor 2409 to monitor the rotational position of the valve drive 2401.

Valve drive 2401 defines the operational coupling between the valve drive assembly and rotary valve 1400 on a cartridge. In some implementations, the valve drive may further include a plurality, e.g., two, three, four, or more, valve drive pins 4202, shown in FIG. 30, which extend from an outermost peripheral wall or edge of a rotary valve. Valve drive pins 2402 are associated with engagement openings on the rotary valve to interface between the valve drive assembly and rotary valve 1400 when indexing. In various embodiments, the configuration is reversed and the valve drive may include a series of receptacles for receiving projections. In some versions, a rotor portion forms a gear that interlocks with a propulsion element, or a portion thereof and the gear interaction drives the indexing of the rotor. Typically, valve drive pins are arranged concentrically about the rotational axis of the rotary valve. In one embodiment, the valve drive pins may be of cylindrical shape. In a further embodiment, the valve drive pins include a chamfered edge to guide the valve drive pins into engagement openings when the valve drive engages with the rotary valve.

The valve drive assembly 2400 is configured to move linearly in the positive and negative directions, depending on the moving bracket assembly position during clamping and unclamping. In this manner, the valve drive 2401, valve drive shaft 2408, pulley 2406, and belt 2407 are capable of both linear and rotational motion. Interference sensor 2404 tracks the linear position of the valve drive with respect to the cartridge while homing sensor 2405 monitors the rotational position of the valve drive shaft. Both sensors are used to ascertain information about rotary valve 1400 and enable the instrument to perform a series of verification checks to ensure the rotary valve is satisfactory for running the diagnostic test.

Cartridge 1000 is configured for long-term storage and includes a rotary valve 1400 configured for a shipping configuration and an operational configuration when actuated on command. Accordingly, the valve drive assembly is configured to perform a series of verification tests on rotary valve 1400 to verify cartridge 1000 can support a diagnostic test and subsequently actuate the rotary valve into an operational configuration to deliver and direct fluids. In one implementation, the shipping configuration of a rotary valve is determined using interference sensor 2404. When the moving bracket assembly is moved to the first position, the valve drive assembly is the first interface to contact the cartridge. In this position, valve drive pins 2404 are inserted into engagement openings of the rotary valve. The engagement between the valve drive and the rotary valve causes the valve drive shaft to be located at a linear distance away from the cartridge. The interference sensor uses the end of the valve drive shaft to determine the status of the rotary valve. For example, when the valve drive 2401 correctly engages with the rotary valve 1400 the interference sensor 2404 is triggered by the end of the valve drive shaft 2405, thus confirming the rotary valve is in a shipping configuration. Alternatively, the rotary valve 1400 may be defected and not be in a shipping configuration. In such case, the valve drive must move a larger distance in the positive direction to mate valve drive pins 2404, seen in FIG. 30, with the rotary valve. This results in the end of the valve drive shaft being located at a different linear distance from the cartridge. The interference sensor is not triggered by the interference sensor and notifies the instrument that the rotary valve in not in a shipping configuration and is unfit to run a diagnostic test. Upon successful confirmation of rotary valve 1400 in a shipping configuration, the valve drive assembly rotates to transition the rotary valve from a shipping configuration and into an operational configuration, as described hereinwith in greater detail with regard to the cartridge.

In a further embodiment, the valve drive assembly 2400 is configured to conduct a second rotary valve verification check prior to the moving bracket assembly 2010 moving in the positive direction to a second clamping position. The second rotary valve verification check confirms a valve drop into an operational configuration is successful. In a similar manner as the first rotary valve verification check, the valve drive assembly uses the interference sensor 2404 and end of the valve drive shaft 2405 to verify the operational configuration. In one implementation, the valve drive shaft will not trigger the interference sensor, indicating a successful rotary valve drop and proceed onto commanding the moving bracket assembly to a second clamping position. When the interference sensor is triggered, the valve drive assembly 2400 detects a failed valve drop and ejects the cartridge due to an unusable rotary valve. After a successful valve drop into operational configuration, the instrument proceeds to clamp the cartridge to a second clamping position. When all subsequent verification checks are performed and the cartridge is rendered fluidically active, the valve drive assembly may begin the valving sequence to direct the sample and reagents throughout the cartridge to different processing modules. In one embodiment, the valve drive assembly 2400 uses a sensor (i.e. homing sensor 2405) to monitor the valve drive rotational position during rotation.

9. Pneumatic Interface (Clamp Block)

a) General Description

In one embodiment of the present invention, fluids (i.e., a sample, reagents, air) are advanced through the cartridge using a pneumatic source. A pneumatic interface 2100 is included within the moving bracket assembly 2040 and is appreciated with respect to the various views in FIGS. 14, 15A-B, 33, and 35-37C. The pneumatic interface is configured to provide pressurized air from the pneumatic subsystem 2130 to the cartridge to motivate fluids though various locations of a cartridge for different sample processing steps. Shown in FIGS. 14, 15A, and 15B, the pneumatic interface is fixed to the clamp block 2041 such that movement of the pneumatic interface is dictated by the movement of the moving bracket assembly 2040. The pneumatic interface 2100 engages with the cartridge to form a pneumatic seal when the moving bracket assembly is moved in the positive direction to the second clamping position. Plunger 2104 breaks the pneumatic interface perforations on the cartridge label and the plunger surface grips the pneumatic interface cover adaptor. Spring 2102 is urges plunger 2104 into the pneumatic interface cover adaptor by pushing against shim 2105 and housing 2106. FIG. 35 illustrates the pneumatic interface 2100 engaged with the cartridge pneumatic interface.

Referring to FIGS. 36A and 37A, the basic design employs a spring 2102 loaded plunger 2101, with a plunger surface 2104, a shim 2105, and housing 2106. In one implementation, the housing 2106 is fixed to the clamp block and includes plunger 2101 further configured to be moveable within the inner surface of the housing 2108. In one embodiment, housing 2108 has a central opening wherein the central opening has a smaller portion of the central opening and a larger portion of the central opening. Plunger 2101 has a long cylindrical shape and includes a proximal end with a plunger surface 2104, a central portion housed within the smaller portion of the central opening, and a distal end housed within the larger portion of the central opening. Additionally, the plunger further comprises an outer plunger surface 2107. The body of the plunger can be made from any material with appropriate rigidity such as plastics or metals, but is preferentially made from steel. The central portion of the plunger is substantially equivalent in diameter to the proximal end of the plunger, such that the central portion and the proximal end of the plunger are both smaller in diameter than the diameter of the distal end of the plunger. A step-up feature 2109 links the central portion to the distal end of the plunger. The central portion of the plunger is disposed in the smaller portion of the housing central opening. Furthermore, the distal end of the plunger disposed within the larger portion of the housing central opening forms a gap between the outer surface of the plunger 2107 and inner surface of the housing 2108. The space formed between the outer surface of the plunger and inner surface of the housing constrains the movement of the plunger for properly engaging the pneumatic interface 2100 with the pneumatic interface adaptor 1172 on a cartridge. The proximal end of the steel plunger comprises a plunger surface 2104 that is responsible for gripping the pneumatic interface adaptor to form a pneumatic seal. In one embodiment the shape of the plunger surface 2104 is designed with an angled surface, shown in FIG. 37A, to minimize potential pneumatic leaks. In an alternative embodiment shown in FIG. 36A, the plunger surface flat. Engagement with a pneumatic cover interface 1172 on the cartridge is shown in FIGS. 36B, 36C, 37B and 37C and further discussed in greater detail with regard to a gimbaling mechanism described below.

In one embodiment, the pneumatic interface includes a gimbaling mechanism to account for any potential parallelism issues arising during engagement between the moving bracket assembly 2040 and cartridge 1000. FIGS. 36B and 36C depict the gimbaling mechanism of the pneumatic interface with a flat plunger surface seen in FIG. 36A. FIG. 36B illustrates a pneumatic interface with the gimbaling mechanism active when the pneumatic interface engages with the pneumatic interface cover adaptor 1172. Housing 2106 is fixed to the clamp block 2041, such that when plunger 2101 contacts the pneumatic interface cover adaptor, the housing 2106 remains stationary while plunger 2101 is pushed back into the housing central opening to cause spring 2102 to compress between shim 2105 and housing 2106. The position of the plunger within the housing central opening creates a gap between the plunger step-up feature 2109 and the inner surface of the housing 2108. In this configuration, the plunger is permitted to pivot within the housing central opening to ensure a secure pneumatic seal is established when the plunger surface 2104 contacts the pneumatic interface cover adaptor 1172. The degree of pivoting is constrained by the inner surface of housing 2106, where the central portion of the plunger, step up feature, and distal end of the plunger can pivot until any one part of the plunger contacts the inner surface of the housing.

FIG. 36C shows the pneumatic interface with a flat plunger surface 2104 and the gimbaling mechanism locked when the moving bracket assembly 2040 moves to unclamp a cartridge. As the moving bracket assembly 2040 moves in the negative direction away from the pneumatic interface cover adaptor 1172, housing 2106 retracts the plunger 2101 from the pneumatic interface cover adaptor 1172. The larger portion of the central opening contacts the corner of the distal end of the plunger, adjacent to step-up feature 2109, to pull the plunger back as the moving bracket assembly 2040 is moved in the negative direction. The contact between the inner surface of the housing 2108 and the corner of the distal end of the plunger eliminates the gap seen in FIG. 36B when the gimbaling mechanism is active. In this configuration, the plunger is prevented from pivoting while the larger portion of the central opening remains in contact with the corner of the distal end of the plunger. FIG. 37B illustrates the pneumatic interface gimbaling mechanism active when the pneumatic interface 2100 contacts the pneumatic interface cover adaptor 1172 with an angled plunger surface 2104. FIG. 37C illustrates the pneumatic interface with an angled surface when the gimbaling mechanism is locked.

10. Thermal Clamp Assembly (Clamp Block)

The thermal clamp assembly 2680 is a component of the moving bracket assembly 2040 and is connected to the clamp block 2041 (see the various views of FIGS. 38-43). In some embodiments, the thermal clamp assembly is configured to move independently of the clamp block 2041 and is not fixedly attached to clamp block 2040, such that the position of the thermal clamp assembly 2680 does not solely depend on the position of clamp block 2041. The thermal clamp assembly 2680 comprises a clamp plate 2681, a light frame 2686, and a plurality of clamp posts 2682, wherein each clamp post 2682 further comprises a shoulder screw 2684, spring 2683, and bushing 2685. The thermal clamp assembly 2680 is configured to presses against a cartridge 1000 to ensure the cartridge remains flat against the fixed support bracket 2011 during the heat staking process, as described herein, and additionally produces a light seal around the reaction area 1600 of the cartridge during imaging and detection by the reaction imaging assembly 2700. In implementations where the thermal clamp assembly 2680 is configured to move independently of the clamp block, the thermal clamp assembly is connected to the clamp block using a bushing 2685 for each of the plurality of clamp posts 2682, wherein the each bushing is operably coupled to a shoulder screw 2684 thus permitting independent movement of the thermal clamp assembly 2680 along shoulder screws 2684. In one embodiment, each of the plurality of clamp posts, 2682 comprises one or more springs 2683 along shoulder screws 2684 for constraining the maximum movement of the clamp block 2041, with respect to the thermal clamp assembly 2680, in the positive and negative direction during clamping and unclamping. Such configuration allows clamp block 2041 to move in the positive direction toward the fixed bracket assembly until contacted by spring 2683*a* and allows clamp block 2041 to move in the negative direction until contacted by spring 2683*b*. In one implementation, a clamp plate 2681 is fixed to the plurality of clamp posts 2682. Furthermore, as shown by FIG. 38, a light frame 2686 is housed within clamp plate 2681, wherein the light frame 2686 is configured to contact the distal end of the cartridge during the clamping sequence, as described herein below. The light frame 2686 is shaped to correspond to a perimeter about the assay chambers within a specific reaction module configuration of a diagnostic cartridge embodiment.

The thermal clamp assembly 2680 is arranged between the optical block 2710 and cartridge as seen in FIG. 42, wherein the optical block is shown with dashed lines. As illustrated in FIGS. 38-41, the clamp plate 2681 resides in the space between the moving block assembly 2040 and a cartridge in a loaded position defined by loading assembly 2230. In one implementation illustrated in these views, the light frame 2686 is disposed within a pocket 2710 formed within optical block 2710. Additional views of the optical block is further shown in FIGS. 45, 46, 62 and 66. The position of the light frame within the optical block enables the thermal clamp assembly 2680 to form a light seal around reaction area 1600 of a cartridge, viewed in FIG. 45. The light seal around the reaction area, as provided by the light frame 2686, helps ensure the darkest possible background is achieved for a reaction camera 2701 of a reaction imaging assembly 2700 to capture fluorescent images of assay chambers within the reaction area. When a cartridge is in a loaded position, the movement of clamp plate 2681 is constrained between the distal end of the cartridge and optical block 2710, such that the thermal clamp is permitted from moving in the negative direction until clamp block 2041 contacts spring 2685b and light frame 2686 contacts the edge of pocket 2710 within the optical block. By way of example, further description of the movement of the thermal clamp assembly 2680 is depicted in a top down view of the thermal clamp assembly 2680 and optical block 2710 according to the clamping sequence in FIGS. 38-41.

FIG. 38 illustrates the thermal clamp assembly 2680 when the moving bracket assembly 2040 is in the zero clamping position. Cartridge 1000 is in a loaded position given by loading assembly 2230 and latched by the latch and pin assembly 2210. Note light frame 2686 is not in contact with cartridge 1000.

The moving bracket assembly 2040 is moved in the positive direction from the zero clamping position to a first clamping position when linear actuator 2014 rotates lead screw 2016 in a first rotational direction. The clamp block 2041 slides along shoulder screws 2684 and causes light frame 2686 to contact the cartridge. However, a seal between the light frame 2686 and the reaction area 1600 is not established in the first position. As described herein, the first clamping position only establishes an operational coupling between the valve drive assembly 2400 and cartridge rotary valve 1400. FIG. 39 illustrates the thermal clamp assembly 2680 after the moving bracket assembly 2040 is in the first clamping position with light frame 2686 lightly contacting the distal end of the cartridge. In the first clamping position, the movement of the moving bracket assembly 2040 and thermal clamp assembly 2680 causes light frame 2686 to move in the positive direction toward the cartridge and away from pocket 2711 of optical block 2710.

After rotary valve verification checks are performed on the rotary valve in the first clamping position, the moving bracket assembly 2040 is moved in the positive direction to a second clamping position when linear actuator 2014 rotates lead screw 2016 in a first rotational direction. Clamp block 2041 slides along shoulder screws 2684 until the clamp block 2041 compresses spring 2683a to exert a force against the clamp plate 2681. Accordingly, the clamp plate 2681 urges the light frame 2686 into the cartridge and establishes a light seal around the cartridge imaging area 1600. FIG. 40 illustrates the thermal clamp assembly 2680 after the moving bracket assembly 2040 is in the second clamping position to clamp the cartridge. In the second position, the thermal clamp assembly is prevented from moving any further in the positive direction, such that when the frangible seal block 2260 is moved to the third clamping position to actuate frangible seals the position of the thermal clamp assembly 2680 remains unchanged due to light frame 2686 contacting the cartridge and clamp block 2041 contacting spring 2683a. The thermal clamp assembly 2680 will remain in the second clamping position until a diagnostic test run is completed on the cartridge.

The moving bracket assembly 2040 is moved in the negative direction to a fourth clamping position when linear actuator 2014 rotates lead screw 2016 in a second rotational direction to unclamp the cartridge. Clamp block 2041 is driven away from the cartridge by the coupling between the lead screw 2016 and frangible seal block 2260 contacting ledge 2046 of the clamp block, as described herein. This action causes clamp block 2041 to slide along shoulder screws 2684 until the clamp block 2041 contacts spring 2683b. Pocket 2711 formed within optical block 2710 of the reaction imaging assembly 2700 allows the light frame 2686 of the thermal clamp assembly to retract away from the cartridge to establish a clearance between the clamp plate 2681 and cartridge for ejection. FIG. 41 illustrates the thermal clamp assembly 2680 after the moving bracket assembly 2040 is in a fourth clamping position.

11. Magnetic Mixing (Fixed Support Bracket & Clamp Block)

a) Magnetic Mixing Assembly

The clamping subsystem supports two magnetic mixing systems that interface with elements within a cartridge to perform respective functions. The first magnetic mixing system of instrument 2000 is magnetic mixing assembly 2300, illustrated in an exploded view in FIG. 47A and a perspective assembly view in FIG. 47B. The various views illustrate the arrangement, spacing, orientation and operation of the magnetic mixing assembly for use with various vertically oriented diagnostic cartridge and instrument embodiments described herein. Magnetic mixing assembly 2300 provides the means to mix a sample in a lysis chamber using a stir bar alone or in combination with other lysis agents, while minimizing the amount of contact of the stir bar with the walls of the lysis chamber. The driving magnet system 2310 and driven magnet system 2350, as seen in FIGS. 47A, 47B, are arranged to effectuate a magnetic coupling between the one or more driving magnets and the one or more driven magnets. Specifically, each driving magnet and driven magnet are arranged with respect to one another such that an alignment of the driving magnet magnetic axis and an alignment of the driven magnet magnetic axis effectuate a magnetic coupling between the driving magnetic and the driven magnet. Still further, the arrangement and operation of the magnetic mixing assembly is adapted for rotation of a stir bar within the magnetic field produced between the driving and driven magnets. In certain embodiments, to effectuate magnetic coupling between a driving magnet and driven magnet, the driven magnet magnetic axis is parallel to the driving magnet magnetic axis. In further, preferred embodiments, the driven magnet magnetic axis is substantially collinear with the corresponding driving magnet magnetic axis. As used herein, "substantially collinear" encompasses deviations from absolute collinearity of up to 10° and/or 3 mm at a plane bisecting the gap between the driving and driven magnet system.

The magnetic coupling between the driving magnet system and the driven magnet system comprises an attractive magnetic coupling. In such embodiments, the one or more driving magnets and the one or more driven magnets are arranged with respect to one another such that the alignment of the each driving magnet magnetic axis and the alignment of the each driven magnet magnetic axis effectuate an attractive magnetic coupling between the one or more driving magnets and the one or more driven magnets. In general, to effectuate an attractive magnetic coupling between a driving magnet and a driven magnet, the driving magnet magnetic axis and the driven magnet magnetic axis are aligned such that opposing poles of the driving magnet magnetic axis and the driven magnet magnetic axis are located in proximity to one another.

FIG. 47A is an illustration of an exploded view of the magnetic mixing assembly 2300 of instrument 2000, in accordance with an embodiment. A driving magnet system 2310 comprises a first driving magnet 2311 and a second driving magnet 2316 separated by a distance, and a driven magnet system 2350 comprises a first driven magnet 2353 and a second driven magnet 2356 separated by a distance. As shown in both FIGS. 47A, 47B, the drive motor is operably/mechanically coupled to the drive belt 2332, which is operably/mechanically coupled to the driving magnet spindle 2361, which is in turn operably coupled to the driving magnet holder 2325. The driving magnet holder contains a driving magnet system 2310 (in some embodiments, a first driving magnet 2311 and a second driving magnet 2316). The driving magnet holder 2325 is positioned in proximity to a first face of the mixing assembly such that the driving magnet holder is aligned with the lysis chamber 1371. The driven magnet holder 2365 is positioned in proximity to a second face of the mixing assembly that is opposite the first face, such that the driven magnet holder is also aligned within the lysis chamber, and such that the lysis chamber is located between the driving magnet holder and the driven magnet holder 2365. In an embodiment where a magnetic stir bar is provided within the lysis chamber, the operation of the magnetic mixing assembly induces a magnetic field to rotate the stir bar substantially within the vertical plane of the diagnostic cartridge when positioned in the instrument. The driven magnet holder contains a driven magnet system 2350 (in some embodiments, the first driven magnet 2351 and the second driven magnet 2356). Finally, the driven magnet holder is operably coupled to the driven magnet spindle 2361. In certain implementations, a first driving magnet field focuser 2312 can be coupled to the first driving magnet 2311 and/or a first driven magnet field focuser 2352 can be coupled to the first driven magnet 2351.

In certain embodiments, the magnetic mixing assembly can further comprise an acoustic mechanism for detecting magnetic decoupling of the stir bar 1390 from one or more of the driving magnet system 2310 and the driven magnet system 2350. In such embodiments, the acoustic mechanism is configured to detect a change in one or more of an amplitude and a frequency of vibrations produced by the stir bar during rotation of the driving magnet system, the change indicating the magnetic decoupling of the stir bar. In some embodiments, the change comprises a sudden decrease in one or more of the amplitude and the frequency of the vibrations produced by the stir bar. In some embodiments, the acoustic mechanism comprises a microphone 2380 (see FIG. 11).

b) Rehydration

The second magnetic mixing system supported by the clamping subsystem is the mechanism for rehydrating dried reagents contained within a cartridge. In one implementation, motor 2500 contains a magnet to gyrate a magnetic element contained within a reservoir of a cartridge. The motor is mounted to the fixed support bracket and is best seen in the views of FIGS. 10 and 11. In one embodiment, the cartridge reservoir containing a magnetic element holds dried reagents, such that gyration of the magnetic element facilitates rehydration and mixing of dried reagents with fluids.

C. Pneumatic Subsystem

1. Overview

In one embodiment, the instrument includes a pneumatic subsystem that is configured to generate pneumatic pressure to advance fluids to various locations within the cartridge that are responsible for sample preparation, nucleic acid amplification, and detection. FIGS. 48 and 49 illustrate a pneumatic subsystem 2130 in isolation and in position within the instrument enclosure, respectfully. The pneumatic subsystem comprises at least a pump 2131, a pressure regulator 2132, a proportional valve 2133, an accumulator 2135, and a pressure sensor 2134. In some implementations, the pneumatic subsystem includes an output selector valve 2136. The pneumatic pump compresses air to convey fluids through the cartridge, wherein pump 2131 is connected to pressure regulator 2132 to down regulate the pressure to a desired value. An accumulator 2135, in line with a proportional valve 2133, acts as a pressure storage reservoir until pressure is needed on demand.

In one aspect, the pneumatic subsystem includes environmental sensors and additional hardware contained within the instrument to monitor various instrument measurements including internal temperature, atmospheric pressure, and humidity of the instrument. As described herein, the firmware of the pneumatic subsystem allows the instrument to control the time spent varying increasing or decreasing pressure set points and control steady state pressure with varying flow resistances from the cartridge. In some embodiments, the pneumatic subsystem includes a flow sensor to monitor the flow rates of various fluids within the cartridge for sample preparation and amplification. In a preferred embodiment, the pneumatic subsystem contains no flow sensors to monitor flow rates of fluids in the cartridge. In a further preferred embodiment, indirect measurements are used to determine when the pneumatic subsystem completes the act of pushing a fluid or substance through the porous solid support chamber prior to moving on to the next processing step. A feedback control system uses a pressure feedback sensor 2134 and a proportional valve 2133 to push finite amounts of fluid through the porous solid support of the cartridge and indicate when all the fluid has exited the channel. The feedback system, as described herein, replaces a flow sensor by using an actuation signal to indicate when the system is ready for the next fluid sequence.

In one embodiment, the pneumatic subsystem provides pressurized atmospheric air to the cartridge via the pneumatic interface 2100 shown in FIGS. 35, 36A-36C and 37A-37C. The pneumatic interface 2100 punctures a perforated area 1052 on the label of the cartridge to access the cartridge pneumatic interface 1170 located on the cartridge. As described herein, spring 2102 establishes a connection between the cartridge pneumatic interface and pneumatic interface 2100 to deliver the pressurized atmospheric air. In yet another aspect of the invention as described herein, a gimbaling mechanism is used to account for small degrees of misalignment between the cartridge and instrument. FIG. 49 is a perspective view of the clamping subsystem and optical system engaged with a cartridge in a loaded position with the valve drive assembly 2400 removed from the moving block assembly 2040 to demonstrate the connection between the pneumatic subsystem 2130 and the pneumatic interface 2100. In this view, the instrument pneumatic interface 2100 is shown connected to the pneumatic subsystem via tubing 2190. Furthermore, FIG. 49 demonstrates the relationship of the pneumatic subsystem position in reference to the clamping subsystem and the reaction imaging assembly and label imaging assembly of the instrument optical subsystem. In one implementation, the pneumatic subsystem is fixed to the bottom of the instrument, unlike all other subsystems and assemblies which are fixed to either the fixed bracket assembly 2010 or the moving bracket assembly 2040. As a result, the pneumatic subsystem remains stationary during the clamping and unclamping sequence in a similar manner to the fixed bracket assembly.

In one implementation, each pneumatic pressure control component or aspects thereof, such as the pump 2131, pressure regulator 2132, proportional valve 2133, accumulator 2135, output selector valve 2136, and various sensors are mounted in the manifold block 2137. In a further implementation, a control board 2138 contains the proportional valve 2133, pressure sensor 2134, and various environmental sensors, wherein the control board 2138 is mounted within manifold block 2137, as shown in FIG. 48. The manifold block can, in various aspects, be made of one or more rigid materials, such as a polymeric material, like plastic. In some implementations, the manifold block is machined from acrylic. In a further embodiment, the acrylic manifold block is vapor polished. In one aspect, pneumatic routing channels and mounting ports are fabricated in the manifold block for all components of the pneumatic subsystem. Additionally, due to the thermodynamics of the compression of air in the pump, humidity in the air can be condensed. In one embodiment, the instrument manages condensation control with the regulator's manifold entry geometry. Advantageously, the implemented geometry vents moisture/condensation within the instrument enclosure through the use of one or more bleed orifices 2191 so that it does not enter the regulator inlet.

Given the pressurization of the pneumatic subsystem, in one implementation filters are installed on the pump's intake, inlet, and outlet to eliminate the possibility of external particulates from reaching the manifold or cartridge to control the risk of contamination within the instrument. In an exemplified implementation, the pneumatic subsystem is shown in FIG. 48 comprising a pump filter 2160 and outlet filter 2162.

In some embodiments, the pneumatic subsystem optionally comprises several components to minimize noise due to vibration. In one implementation, the assembly uses pump isolation mounts. In another implementation the assembly includes silicone foam damping pads reduce noise of pump components vibrating against manifold. In an alternate implementation, the assembly uses isolation grommets 2194 to reduce the vibration of the pneumatic subsystem against the instrument's enclosure. In a preferred embodiment, the pneumatic subsystem uses pump isolation mounts, silicone foam damping pads, and isolation grommets to provide noise damping.

D. Thermal Subsystem

In one aspect, a cartridge configured to perform sample preparation or both sample preparation and amplification requires the use of one or more heaters supported by the instrument 2000. In one implementation, the thermal subsystem is configured to provide a controlled steady state temperature to areas of the cartridge used to conduct sample preparation and enable controlled heating and cooling of assay chambers to permit isothermal amplification and detection of target nucleic acids during a diagnostic test. In implementations where amplification is performed, avoiding cross-contamination between assay chambers as well as isolating the reaction from the outside environment is imperative to prevent amplicon contamination. Containing amplified nucleic acids ensures false positive results are not obtained on all cartridge runs performed on the instrument thereafter. Accordingly, the thermal subsystem further includes a mechanism for sealing a cartridge to contain amplified nucleic acids. The instrument of the present invention includes a thermal subsystem comprising a cartridge heater assembly 2550, a chemistry heater assembly 2600, and a heat staker assembly 2640 for providing the thermal requirements of sample preparation and amplification when performing a diagnostic test. The various views of the components of the thermal subsystem are provided in FIGS. 50-58. The various components of the thermal subsystem operate under the control of the instrument computer control system as described in FIGS. 67A-67I. The thermal subsystem, as described herein, contains various embodiments used to precisely control the temperature of specific areas of the cartridge to prepare a sample and, if desired, amplify and detect target nucleic acids and prevent amplicon from escaping the cartridge.

1. Overview

A thermal subsystem of the present invention comprises a chemistry heater assembly 2600, a cartridge heater assembly 2550, and a heat staker assembly 2640, wherein the heat staker assembly further comprises a staker bar assembly 2641. All assemblies and components of the thermal subsystem are supported by the fixed bracket assembly 2010. In one implementation, more than one heater e.g., two or more, heaters are used to provide multiple controlled temperatures to different areas of the cartridge responsible for conducting sample preparation and amplification. In one embodiment, the cartridge heater assembly 2550 is configured to maintain an operational temperature within a cartridge heating zone 2552 which include portions of the integrated cartridge containing the wash buffer reservoir 1475, elution buffer reservoir 1500, rehydration chamber 1520, and lysis chamber 1371. In another embodiment, the chemistry heater 2601 is configured to maintain a reaction temperature to the reaction area 1600 of a cartridge to enable the amplification of target nucleic acids within assay chambers. In yet another embodiment, a third heater is used to seal a cartridge according to an embodiment described herein.

2. Chemistry Heater Assembly

In one embodiment, a chemistry heater assembly 2600 is configured to provide a reaction temperature for amplifying nucleic acids contained within a plurality of assay chambers in a cartridge. A cross sectional view of the chemistry heater assembly 2600 is illustrated in FIG. 54 and an exploded view of the chemistry heater assembly 2600 is seen in FIG. 55. In one embodiment, the chemistry heater assembly 2600 comprises a chemistry heater 2601, a flow guide frame 2606, a chemistry heater plate 2602, a chemistry heater fan 2603, a heater plenum 2607, and a fan plenum 2604 with a flow vane 2605. The chemistry heater 2601 can be of any suitable design but is most preferably a resistance heater (e.g. a Kapton heater). In certain aspects of the invention, the chemistry heater assembly further consists a thermistor integrated with the chemistry heater 2601.

In one embodiment, shown in FIGS. 54 and 55, the chemistry heater 2601 is in thermal contact and bonded to a second surface 2622 of chemistry heater plate 2602 using a pressure sensitive adhesive or other adhesive appropriate to the operating temperature range. When assembled, there is a reaction well zone 2620 formed in a first surface of the chemistry heater plate 2621, wherein the first surface of the chemistry heater plate is in thermal contact with the film side of a cartridge. The chemistry heater zone 2620 is viewed from the first surface of the chemistry heater plate 2621 in FIGS. 50 and 51. The cartridge heater plate 2602 is susceptible to thermal effects from the ambient environment. Thus in one embodiment, the chemistry heater assembly addresses the thermal effects on the thermal gradient of the chemistry heater plate by bonding chemistry heater plate 2602 to a flow guide frame 2606. In a further embodiment, the flow guide frame 2606 is flush with the second surface of the fixed support bracket 2013. In another implementation the chemistry heater plate 2602 is bonded to the flow guide frame 2606 to ensure proper thermal contact is maintained between the first surface of the chemistry heater plate 2621 and the film side of the cartridge regardless of mechanical tolerances.

In some implementations, a chemistry heater fan 2603 is fluidically coupled to a fan plenum 2604 with flow vane 2605 and a heater plenum 2607 to direct cooled air through a cutout disposed within the flow guide frame 2606 and directly over chemistry heater 2601. As shown in FIG. 54, arrows demonstrate the flow path of air from the chemistry heater fan 2603 and through the opening formed within the flow guide frame 2606 and heater plenum 2607. This configuration is advantageous when optionally thermally fluctuating the chemistry heater between two or more temperatures rapidly prior to setting the chemistry heater to a reaction temperature. As described according to an embodiment herein, thermally fluctuating the chemistry heater generates convection of the fluids within the assay chambers. Specifically, the convection generated within a plurality of assay chambers facilitates mixing of a sample with dried reagents within the assay chambers prior to beginning amplification. Chemistry heater fan 2603, fan plenum 2604, flow vane 2605, and heater plenum 2607 are fluidically coupled to facilitate a faster cooling ramp rate of the chemistry heater 2601 to a low temperature during the sequence of thermal fluctuations. In one implementation, the chemistry heater fan 2603 may be turned off after the sequence of thermally fluctuations and remains off for the remainder of the diagnostic test while the chemistry heater is set to the reaction temperature.

In various aspects, a flow guide frame 2606 is composed, e.g., entirely composed, of one or more polymeric materials (e.g., materials having one or more polymers including, for example, plastic). A flow guide frame 2606 can be composed of any of the elastic materials provided herein. Materials of interest for the flow guide frame include, but are not limited to, polymeric materials, e.g., plastics. In a preferred embodiment, the flow guide frame is polyether ether ketone (PEEK).

Thermal boundary conditions affect the temperature gradient of the chemistry heater plate 2601 in contact with the film side of a cartridge and can result in undesired temperature variation across assay chambers. Uniformity among assay chambers is critical to amplifying nucleic acids for accurate detection. According to various embodiments, the chemistry heater assembly 2600 includes a chemistry heater plate 2602 comprising a machine pocket geometry for thermal gradient reduction.

Returning to FIGS. 50 and 51, the chemistry heater plate 2601 is viewed from a first surface 2621. In one embodiment, the reaction well zone includes a machined pocket geometry 2623 comprising grooves 2624. The machined pocket geometry 2623 is a series of grooves arranged in a pattern to decrease heat flux through the center of the reaction well zone 2620 to compensate for edge heat loss due to the environment. The configuration, as described herein, provides precise isothermal control of the reaction well zone 2620 of the chemistry heater plate 2602 to supply a uniform temperature to the plurality of assay chambers conducing amplification.

The term "grooves," is used herein, refer to any hole, cutout, orifice, aperture, gap, or space machined into the chemistry heater plate 2602 to reduce heat flux variation between the chemistry heater 2601 and chemistry heater plate 2602 to supply a consistent temperature to the reaction well zone for amplification. In some embodiments, grooves extend entirely through the chemistry heater plate from a first surface of the chemistry heater plate 2621 to a second surface 2622. In other implementations, grooves extend partially at a depth measured from the first surface of the chemistry heater plate. Examples of geometries for cutouts include, but are not limited to, circles, rectangles, rounded rectangles, ovals, ellipses, or any combinations thereof.

3. Cartridge Heater Assembly

In one embodiment, a cartridge heater assembly 2550 provides controlled heating of sample preparation areas of the cartridge, i.e., a cartridge heater zone. FIG. 50 provides a perspective view of cartridge heater zone 2552 from the first surface of the fixed support bracket 2012, wherein the first surface of the fixed support bracket is in contact with the film side of the cartridge. In one embodiment, the cartridge heater zone 2552 is in thermal contact with a wash buffer reservoir 1475, elution buffer reservoir 1500, rehydration chamber 1520, and lysis chamber 1371 housed within an integrated diagnostic cartridge to provide a controlled steady state temperature to areas of the cartridge performing sample preparation. In one aspect, the cartridge heater assembly comprises a cartridge heater 2551 and insulator 2553. FIG. 52 illustrates the cartridge heater assembly and FIG. 53 illustrates the cartridge heater assembly in an exploded view. The cartridge heater 2551 can be of any suitable design but is most preferably a resistance heater (e.g. a Kapton heater). In one embodiment, the cartridge heater 2551 is in thermal contact and bonded to a second surface of the fixed support bracket 2013 with a pressure sensitive adhesive. The thermal contact between cartridge heater 2551 and the second surface of the fixed support bracket forms the cartridge heater zone 2552 in the first surface of the fixed support bracket 2012 viewed in FIG. 50. In another embodiment, an insulator 2553 is in thermal contact with the cartridge heater 2551 to prevent thermal energy from escaping into the ambient environment.

Thermal boundary conditions affect the uniformity of heat transfer between the cartridge heater assembly zone 2552 and areas of the cartridge housing the wash buffer reservoir 1475, elution buffer reservoir 1500, rehydration chamber 1520, and lysis chamber 1371. In one implementation, as shown by FIG. 50, the cartridge heater assembly 2550 further comprises a series of cutouts 2554 around the perimeter of cartridge heater zone 2552 for thermal gradient reduction to control heat loss.

The term "cutouts," as used herein, refer to any hole, groove, orifice, aperture, gap, or space machined into the fixed support bracket 2011 to reduce heat flux variation between the cartridge heater 2551 and the cartridge heater zone 2552 to provide a consistent temperature to areas of the cartridge responsible for sample preparation. In some implementations, cutouts may extend through from the first surface of the fixed support bracket 2012 to the second surface of the fixed support bracket 2013. In other implementations, the cutouts may partially extend a depth measured from the first surface of the fixed support bracket 2012. Examples of geometries for cutouts include, but are not limited to, circles, rectangles, rounded rectangles, ovals, ellipses, or any combinations thereof.

In a further embodiment, the cartridge heater zone may comprise a plurality of perforations 2377. In embodiments of the magnetic mixing assembly of the instrument, the driving magnet system 2310 and driven magnet system 2350 rotate in a circular pattern. As such, eddy currents are induced in the fixed support bracket 2012 radially from a center of the circular pattern. To limit the induction of eddy currents in the fixed support bracket, the plurality of perforations can be arranged in a concentric pattern around the center of the circular pattern of the magnetic mixing assembly 2300, as described herein. This concentric arrangement of the plurality of perforations causes the eddy currents induced in the fixed support bracket to follow a convoluted path along their radial induction pathways. This convoluted pathway limits the formation of the eddy currents in the fixed support bracket.

4. Heat Staker Assembly

The high sensitivity of nucleic acid amplification methods, in particular isothermal amplification methods, pose the threat of amplicon contamination. A cartridge unable to successfully contain amplified nucleic acids will contaminate the instrument and lead to subsequent false positive results on all cartridges run thereafter. The instrument's thermal subsystem provides a heat staker assembly 2640 as appreciated with reference to the various views of FIGS. 51, 52, 55, 56, 57A, 57B and 58. The operation of the heat staker assembly forms a heat stake across a number of individual fluid channels on the integrated diagnostic cartridge to seal off the channels one from another and prevent sample contamination. Advantageously, the heat stake is performed under sufficient pressure across the main loading channel leading to the assay chambers to prevent amplified nucleic acids from escaping the cartridge and mitigate the risk of amplicon contamination. In addition, the heat staker assembly is configured to heat stake the channel leading to and exiting from the waste collection element to stop fluids from exiting the waste chamber when the cartridge is removed from the instrument. In a preferred embodiment, the integrated diagnostic cartridge has a portion of the fluid channels arranged with planar portions intended to support this integrated heat stake operation. Still further, the fluid pathways of the integrated diagnostic cartridge are arranged so that they are adjacent in a spacing which permits the use of a single linear heat stake element.

The term "heat stake," as used herein, refers to the process of melting and rapidly cooling a portion of the cartridge to form a seal and prevent fluids from leaving the cartridge. In implementations where the cartridge comprises one or more polymeric films, the heat staker assembly 2640 provides the means to melt and fuse the stack of polymeric films attached to the fluidics side of the cartridge, wherein melting the one or more films into the cartridge forms a barrier across selected fluid channels to retain liquids within. The term "heat stake" may also refer to the seal or barrier formed as a result of the heat staking process. According to an embodiment described herein, the one or more thermoplastic films may be placed on the fluidic card or used as part of the cartridge as part of a heat stake compatible design. In one specific embodiment, there are two thermoplastic films used each having a different melting temperature wherein the first film has a substantially similar melting temperature as the cartridge and the second film has a higher melting temperature than the first film such that only the second film will melt during a heat stake operation to form the barrier. The two thermoplastic film approach described herein has the added benefit of protecting other components or the integrity of the fluidic card or cartridge during heat staking.

FIG. 56 depicts a heat staker assembly 2640 comprising a linear actuation motor 2642, a spring 2643, a staker bar assembly 2641, heat staker fan 2644, and an inductive linear sensor 2645. In one embodiment, a spring 2643 provides the force needed to perform heat staking. As used herein, the linear actuation motor is configured to move the heat staker bar assembly 2641 to make contact with the film side of a cartridge. The linear actuator motor does not, however, provide the force or depth control necessary for heat staking. The linear actuation motor 2642 releases spring 2643, which supplies the force necessary to heat stake, to push the staker bar assembly 2641 into the film side of the cartridge. In one implementation, an inductive linear sensor 2645 enables the measurement of linear displacement heat staker assembly 2640 and provides a means for heat staking error detection.

FIGS. 57A and 57B provide perspective and cross section views of the staker bar assembly 2641. As shown in FIGS. 57A and 57B the staker bar assembly 2461 comprises a heater 2661, a staker blade 2660, and a depth stop 2662. The heater can be of any suitable design but is most preferably a resistance heater (e.g. a wire heater) and is in thermal contact with the staker blade 2660. In one implementation, the staker blade 2660 has a draft angle to form the heat stake when the blade contacts the polymeric films of the cartridge without tearing. In a further implementation, the draft angle of the staker blade is surrounded by a depth stop 2662 to control the depth of the heat stake to a desired displacement range. Linear actuation motor 2642 moves the staker bar assembly 2641 to the cartridge and then releases spring 2643 to apply the force needed to press the heated staker blade 2660 into the film side of the cartridge. The staker blade is permitted to melt into the cartridge until depth stop 2662 contacts the cartridge, thus preventing the staker blade from traveling further.

In various aspects, a depth stop is composed, e.g., entirely composed, of one or more polymeric materials (e.g., materials having one or more polymers including, for example, plastic). The polymeric depth stop can be composed of any of the elastic materials provided herein. Materials of interest include, but are not limited to, polymeric materials, e.g., plastics. In a preferred embodiment, the depth stop is polyether ether ketone (PEEK) suited to the operational temperature range of the heat stake assembly.

According to the subject embodiments, the staker blade can be composed of a variety of materials and can be composed of the same or different materials. Materials that the staker blade described herein can be composed of include, but are not limited to, metals, such as aluminum. In a preferred embodiment the staker blade is aluminum.

E. Optical Subsystem

Instrument 2000 includes an optical subsystem comprising two assemblies which separately interact with cartridge 1000. FIGS. 58, 59, 60 and 61 provide various views of a label imaging assembly 2770. The label imaging subsystem illuminates and captures an image of the cartridge label area. The label imaging assembly may further be configured to illuminate and capture a series of images of the loading module to aid in monitoring and verification that an adequate sample is loaded into the cartridge prior to running a diagnostic test. The reaction imaging assembly 2700 is illustrated in the various views of FIGS. 62-66. In implementations where one or more assay chambers are configured to produce a fluorescent signal indicative of the presence of a target pathogen, the reaction imaging assembly 2700 provides excitation wavelength illumination to the cartridge reaction area 1600 and captures images of fluorescence resulting from the amplification of target nucleic acids. Both optical assemblies are supported by the fixed support bracket and remain stationary during the clamping and unclamping of a cartridge.

1. Label Imaging Assembly

Label imaging assembly 2770 is configured to illuminate and capture images of the patient label and loading module. As shown in FIGS. 58 and 59, the label imaging assembly is mounted to the antenna ground plate 2810 and comprises a camera 2771, LED 2772, aperture 2773 and diffuser 2774. The label imaging assembly 2770 will include at least one, but preferably more than one (e.g., two or three), LEDs 2772 for illuminating the patient label area 1040 and the loading module while minimizing shadows cast in the patient label area. The aperture 2773 defines an opening to transmit and reshape illumination by LEDs to reduce off axis light and stray light from affecting the patient label image quality. Once illumination from the LEDs passes through each respective aperture 2773, light travels through diffuser 2774 which generates a more uniform illumination intensity on the patient label and loading module. In one implementation, seen in FIGS. 60 and 61, the LEDs may be arranged in an oblique configuration to illuminate the patient label. This arrangement can be advantageous for increasing the contrast of images and improving the overall image quality of the cartridge.

In a preferred implementation, the label imaging assembly 2770 is further configured to image the sample port assembly 1100 to verify adequate sample is loaded into a cartridge prior to running a diagnostic test. Given the low concentrations of target pathogens in some samples, it is advantageous to determine a sufficient sample volume is present in the loading module. In a preferred implementation, the label imaging assembly is configured to capture an image of the sample port assembly 1100 and detect a mechanism (e.g., a ball disposed within the loading module) to determine the sample volume. Alternatively, the label imaging assembly may detect the meniscus of the sample fluid. Furthermore, the label imaging assembly may be configured to read the sample volume through a sample window 1050 provided by a cut out in the cartridge label.

2. Reaction Imaging Assembly

In some implementations of the present invention, a visual signal, e.g., fluorescent signal, is used to indicate the presence of nucleic acids of a target pathogen within a sample. A wide variety of fluorophores are known in the art and one of ordinary skill would be able to select an appropriate fluorophore for a given assay performance. The instrument 2000 includes a reaction imaging assembly 2100 to provide excitation wavelengths to excite a fluorophore and various features to filter and capture emitted wavelengths to determine the presence or absence of target nucleic acids. The arrangement and operation of the reaction imaging assembly are shown in FIGS. 62-66.

In a preferred implementation, the reaction imaging assembly 2700 shown in FIG. 62 is designed with an epifluorescence arrangement, such that illumination and emitted wavelengths travel through the same objective lens. Unlike oblique illumination, the epifluorescence arrangement illuminates uniformly within the plug structures, described herein with regard to a cartridge amplification module, of the assay chambers to minimize or prevent shadows. Shadows casted on assay chambers hinder the likelihood of detecting a positive sample for an infectious disease. In one implementation, the reaction imaging assembly 2700 comprises a camera 2701, dichroic beam splitter 2702, excitation lens cell 2730, emission lens cell 2750, objective lens 2706, and a fold mirror 2704. All components of the reaction imaging assembly are either contained within or fixedly attached to an optical block 2710 or a beam splitter block 2707. In one embodiment, the optical block and beam splitter block are joined to form the reaction imaging assembly. A pocket 2711 is an opening within the optical block 2710 configured to permit the transmission of excitation wavelengths from the excitation lens cell to the cartridge imaging plane 2760 and emission wavelengths from the plurality of assay chambers to the reaction camera. The reaction imaging assembly is fixed to the first side of the fixed support bracket 2012 and therefore remains stationary during the clamping and unclamping of a cartridge. Reaction camera 2701 captures images of the assay chambers within a cartridge reaction area 1600 for an instrument image processing to determine result of the diagnostic test. Dichroic beam splitter 2702 separates excitation light from emitted light by reflecting shorter wavelengths of light from the excitation lens cell 2703 and passing longer wavelengths emitted from the fluorophore. A fold mirror 2704 directs excitation wavelengths to the reaction well image plane 2760 and redirects emitted wavelengths from the reaction well image plane to the reaction camera 2701.

In one embodiment, an excitation lens cell generates excitation wavelengths for a fluorophore to absorb and is comprised of at least one or more excitation LED 2731, a plano-convex lens 2733, an aspheric lens 2734, an aperture 2732, and a bandpass filter 2735. The excitation lens cell is shown in FIGS. 63 and 64 as section views. In one embodiment, the at least one or more excitation LED 2731 illuminates the plurality of assay chambers. The optical path of the excitation light travels through aspheric lens 2734 to correct for spherical aberration, an optical effect commonly observed with plano-convex lenses, where incident light rays focus at different points resulting in a blurry image. Aspheric lens 2734 focuses incident light from the excitation LED 2731 to a small point, thus improving the image quality. In one implementation, an aperture is used to reshape excitation illumination. Focused excitation light is transmitted through the aspheric lens 2734 and enters aperture 2732 such that, aperture 2732 alters the illumination shape from the excitation LED to minimize off axis light and stray light from hindering fluorescent imaging. In one embodiment, one or more bandpass filters may be used within the excitation lens cell to selectively transmit light of specific wavelengths. Excitation light passes through bandpass filter 2735 to filter wavelengths outside the fluorophore excitation bandwidth and transmit wavelengths within the excitation bandwidth. Furthermore, the excitation bandpass filter substantially prevents light in the fluorophore emission band from entering the reaction well imaging plane due to the epifluorescence arrangement. Filtered excitation light travels through a plano-convex lens 2733 to diffuse the light prior to reaching dichroic beam splitter 2702. Filtered excitation light strikes the dichroic beam splitter 2702 and reflects shorter excitation wavelengths to the objective lens 2706 while longer wavelengths are transmitted through the dichroic beam splitter 2702. In one implementation, transmitted longer wavelengths from the dichroic beam splitter are directed to a light trap 2703. When implementing a light trap, the light trap prevents excitation light from entering the camera by reflecting the light off multiple angled surfaces substantially away from the camera. Excitation wavelengths reflected by the dichroic beam splitter 2702 are transmitted through the objected lens 2706 where fold mirror 2704 redirects the light to the image plane 2760 of the reaction well area 1600 of the cartridge.

The excitation LED peak wavelength and intensity can vary with temperature, thus requiring precise thermal control of the LED temperature. The excitation lens cell further includes various elements to ensure the excitation cell 2730 functions properly. As shown in FIG. 64, a temperature sensor 2738 provides temperature feedback control while photodiode 2739 monitors the LED output to ensure the LED is on. A thermal isolation spacer 2737 isolates the excitation system from short ambient thermal transients and heat sink 2736 provides cooling.

In another embodiment, the reaction imaging assembly 2700 includes emission lens cell 2750, shown in FIG. 65, comprising an image lens 2751, long pass filter 2752, and objection lens 2706. The fluorophore absorbs excitation light from the excitation lens cell 2730 and almost instantaneously emits emission wavelengths to fold mirror 2704. The bent emitted light travels through objective lens 2706 where the longer emitted wavelengths are subsequently transmitted through the dichroic beam splitter 2702. In one implementation, the emission lens cell 2750 comprises one or more longpass filters to transmit emitted wavelengths from the fluorophore. A longpass filter 2752 ensures light in the emission band enters the reaction camera 2701 and substantially eliminates interfering wavelengths, outside of the emission band, from the excitation LED.

FIGS. 45, 46 and 66 illustrate the relationship between the label imaging assembly 2700 and the reaction imaging assembly 2700 of the instrument optical subsystem. Regarding FIG. 66, the label imaging assembly is shown fixed to the antenna ground plate 2810 at the proximal end of the instrument near front slot 2072, while the reaction imaging assembly is fixed to the distal end of the instrument in close proximity to the loading assembly 2230. In such a configuration, the label imaging assembly 2770 is advantageously separated from the reaction imaging assembly 2700. In this way, the label imaging system 2770 may be used initially to detect an insufficient sample volume error and eject a cartridge prior to executing sample preparation steps for an assay to be imaged by the reaction imaging assembly 2700.

With regard to FIGS. 45 and 46, a cartridge 1000 is shown with respect to the label imaging assembly 2770 and reaction imaging assembly 2700 in a loading and loaded position, as described herein. FIG. 45 depicts the cartridge in a forward most loading position within the loading assembly 2230. Patient label area 1040 is not within the field of view of the label imaging assembly 2770, as observed in FIGS. 59, 60, and 61. Furthermore, in the forward most loading position the reaction area 1600 of a cartridge containing a plurality of assay chambers 1621 is adjacent to the reaction imaging assembly 2700 and outside of pocket 2711 within optical block 2710. Note, the loading position of the loading assembly 2230 in FIG. 45 reiterates the loading position shown in FIGS. 17A and 17B. The cartridge is shown in a loaded position in FIG. 46. Patient label area 1040 is now hidden by the label imaging assembly 2770 and is within the field of view as shown in FIGS. 59, 60, and 61. Furthermore, the reaction area of the cartridge 1600 is disposed within pocket 2711 of the optical block and is hidden from view. The loaded position of the loading assembly 2230 similarly reflects the loaded position in FIGS. 18A, 18B, 19A, 19B, and 19C. Additional details of the positioning of the cartridge and the movement of the thermal clamp assembly 2680 with respect to the reaction imaging system 2700 may be appreciated with reference to FIGS. 38-42. The position of the reaction imaging assembly relative to other components of the instrument, (e.g., the moving bracket assembly 2040) may be appreciated with reference to the various views provided in FIGS. 43 and 44.

F. Exemplary Computer System

FIGS. 67A-67I represent various schematic views of a representative computer control system for use with a diagnostic instrument described herein. Generally, the instrument computer control system includes instructions in computer readable code used to coordinate the synchronous performance of the one or more of the operations described herein related to receiving, handling, processing and analyzing a suspected sample in a cartridge. Additional details of the various steps performed related to receiving, handling, processing and analyzing a suspected sample in a cartridge are provided with regard to FIGS. 93-102 and 106A-113. The computer system may comprise an exemplary client or server computer system. Computer system includes a number of communication channels or busses for communicating control signals, sensor information, or other information from a component or system within the instrument to a processor. These various communication pathways are indicated by the lines connecting each of the various components, systems and subsystems. The host processor 2900 is used for processing information and generating signals according to one or a number of programmed control sequences. Processor 2900 may be any suitable computer controller, processor with co-processor, microprocessor or suitable combination thereof.

Additionally or optionally, the instrument computer control system may include one or more of a random access memory (RAM), or other dynamic storage device (referred to as main memory) coupled to bus for storing information and instructions to be executed by processor. Main memory also may be used for storing temporary variables or other intermediate information during execution of instructions by processor.

Instrument computer system also includes a read only memory (ROM) and/or other static storage device coupled to bus for storing static information and instructions for processor, and a data storage device, such as a magnetic disk or optical disk and its corresponding disk drive. Data storage device is coupled to bus for storing information and instructions.

With reference to FIG. 67A, the host processor 2900 is in communication with a communications module 2905 which includes a cellular antenna 2800 located in the front panel 2073 of the instrument 2000 along with associated firmware and software. Additionally, the host processor 2900 is in communication with a USB and Ethernet port 2903 as well as any other external communication port. There is access provided to data storage including encrypted data 2901 along with calibration, firmware upgrade and test results data. There is also provided appropriate storage for de-identified patient results data. The host processor 2900 is also in communication with a display or graphical user interface 2902 such as the one on the instrument front panel 2073. The host processor 2900 is also in communication with various instrument application software 2904. This software and firmware corresponds, by way of example, to particular testing routines to be implemented by the diagnostic instrument 2000 based on the type of sample/integrated diagnostic cartridge 1000 that is loaded into and detected by the instrument 2000. Additionally, the instrument software and firmware 2904 includes computer readable instructions for an instrument operating system along with the various appropriate computer drivers for instrument components. The host processor 2900 is also configured to access and execute the camera operation and imaging firmware 2915 responsible for executing the specific imaging routines performed by the label imaging camera 2771 and the reaction chemistry or assay chamber camera 2701.

FIG. 67A also illustrates the communication busses to each of the different computer subsystems utilized in the instrument. Each one includes appropriate software, firmware and communication components adapted and configured to the functional and operational requirements of that specific instrument subsystem. As such, each instrument subsystem is provided appropriate communication channels for transmission and receipt of computer readable instructions from the one or more processors, co-processors or suitable microprocessor(s). Additionally, a number of specifically configured subsystem of the instrument control system are configured to deliver, receive or monitor signals from one or more actuators, components, switches or sensors as will now be described.

Advantageously, the instrument computer system may include a host processor and a co-processor 2900 in coordinated operation. In one configuration, the host processor 2900 includes instrument operating system and device drivers, specific instrument application software and firmware 2915 for operation of the label camera 2771 and reaction well camera 2701. A second processor may be configured as a slave processor to handle other commands such as the operation of various motors and actuator in the diagnostic instrument 2000. Additionally, the co-processor would be responsible for prioritization and execution of various control signals throughout the various instrument subsystems. The instrument computer system memory or computer readable storage may include stored or accessible computer records of various test methods, scripts, parameters, completed records storage, instrument calibration readings and results based on specific operations performed by the instrument 2000 for a specific cartridge diagnostic test or sample type.

In general, the instrument computer system includes the following functional subsystems adapted and configured to correspond to the steps performed in a wide variety of functions corresponding to a desired preprogrammed testing sequence. As shown in FIG. 67A, the functional subsystems are optical cartridge label subsystem 2910, the optical reaction well subsystem 2990, the thermal subsystem 2970, the lysing drive subsystem 2950, the loading cartridge subsystem 2920, the cartridge seal rupturing subsystem 2930, the pneumatic-interface subsystem 2960, the valve drive subsystem 2940 and the rehydration mixing subsystem 2980. In one aspect, these functional groups may be functionally grouped more generally into an optical subsystem, a thermal subsystem and a clamping subsystem. One or more of these functional groups may be assigned to the co-processor.

The optical subsystem includes an optical cartridge label subsystem 2910 (FIG. 67B) and an optical reaction well subsystem 2990 (FIG. 67C).

As shown in FIG. 67B, the optical cartridge label subsystem 2910 includes software, firmware and communication components adapted and configured to for use with a cartridge label imaging camera 2771, a label illumination LED 2792 and a sample illumination LED 2775. Under control of instructions from the one or more processors 2900, the optical cartridge label subsystem 2910 interacts with the patient label area 1040 and sample port assembly 1100 of a cartridge 1000 undergoing processing within the instrument 2000.

As shown in FIG. 67C, the optical reaction well or assay imaging subsystem 2990 includes software, firmware and communication components 2980 adapted and configured for use with a reaction camera 2701. Additionally, the optical reaction well subsystem 2990 controls a bright field LED 2753, an excitation LED heater 2741, an excitation LED 2791, an LED excitation intensity sensor 2740, an assay well reaction camera 2701, and an LED excitation temperature sensor 2738. Under control of instructions from the one or more processors 2900, optical reaction well subsystem 2990 interacts with the assay chamber 1621 in the reaction area 1600 of a cartridge 1000 undergoing processing within the instrument 2000.

As shown in FIG. 67D, the thermal subsystem 2970 includes software, firmware and communication components 2960 adapted and configured to for use with an heat stake cooling fan 2644, a chemistry heater 2601, chemistry heater sensor 2608, heat staker heater 2661, cartridge heater temperature sensor 2555, heat staker motor 2642, cartridge heater 2551, heat stake temperature sensor 2646, staker linear displacement sensor 2645, and chemistry heater cooling fan 2603. Under control of instructions from the one or more processors 2900, the thermal subsystem 2970 interacts with the central cartridge portion, assay wells and heat stake zone portions of a cartridge undergoing processing within the instrument.

As shown in FIG. 67E, the lysing drive subsystem 2950 includes software, firmware and communication components adapted and configured for use with a lysing drive motor 2330 and an audible sensor/microphone 2380. Under control of instructions from the one or more processors 2900, the lysing drive subsystem 2950 interacts with the stir bar or other lysing agents within the lysis-lysis chamber 1371 of the cartridge while being monitored for magnetic uncoupling via the audible sensor 2380.

As shown in FIG. 67F, the loading cartridge subsystem 2920 includes software, firmware and communication components adapted and configured for coordinated operation of a linear actuator 2014, hardstop clamping sensor 2019, cartridge door support assembly 2280, homing clamping sensor 2017, cartridge loading sensor 2236, and frangible seal switch 2266. Under control of instructions from the one or more processors 2900, the loading cartridge subsystem 2920 provides coordinated interactions with cartridge to ensure proper loading, positioning and clamping of the cartridge with respect to the instrument interior.

As shown in FIG. 67G, the pneumatic subsystem 2960 includes software, pneumatic control firmware and communication components adapted and configured to for use with a pneumatic pump 2131, proportional valve 2133, output selector valve 2136, altitude sensor 2140, pressure regulator 2132, and a humidity sensor 2142. Under control of instructions from the one or more processors 2900, the pneumatic subsystem 2960 interacts with a pneumatic interface 2100 on the cartridge to deliver pneumatic drive signals to the cartridge undergoing processing within the instrument.

As shown in FIG. 67H, the valve drive subsystem 2940 includes software, firmware and communication components adapted and configured to for use with a valve drive motor 2403, an interference sensor 2404 and a valve drive homing sensor 2409. Under control of instructions from the one or more processors 2900, the valve drive subsystem 2940 interacts with the rotary valve on the cartridge to index the rotary valve for alignment of a desired flow channel on the cartridge undergoing processing within the instrument.

As shown in FIG. 67I, the rehydration mixing subsystem 2980 includes software, firmware and communication components adapted and configured for use with a rehydration motor 2510 and rehydration motor rotation sensor 2530. Under control of instructions from the one or more processors 2900, the rehydration motor 2510 interacts with a stir ball or other component within the master mixing rehydration chamber of the cartridge while being monitored for rotation using the motor rotation sensor 2530.

Additional alternative computing environments and modifications to both user experience and user interaction are possible and within the scope of the various embodiments described herein, The instrument computer control system may further be coupled to a display device, such as a liquid crystal display (LCD) including touch screen or other functionality by direct connection or wirelessly. The display is also coupled to bus for displaying information to an instrument user. An alphanumeric input device, including alphanumeric and other keys, may also be provided via the touch display or coupled to bus for communicating information and command selections to processor. An additional user input device is cursor control, such as a mouse, trackball, trackpad, stylus, or cursor direction keys, voice or touch controllers coupled to bus for communicating direction information and command selections to processor, and/or for controlling cursor movement on display.

Another device that may be coupled to bus is hard copy device, which may be used for marking information on a medium such as paper, film, or similar types of media. Additionally, the computer system may include wired and wireless communication capabilities depending on configuration. Remote communications using the communications module described above with the instrument computer system may be utilized for transferring information, calibration, service, maintenance or other system or patient information collected or produced by the instrument computer system.

Note that any or all of the components of system and associated hardware may be used in the present invention. However, it can be appreciated that other configurations of the instrument computer system may include some or all of the devices. Certain variations of system may include peripherals or components not illustrated in these various exemplary figures. Additional such components may be included and configured to receive different types of user input, such as audible input, or a touch sensor such as a touch screen.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions. The label imaging camera firmware or the optical cartridge label subsystem may be adapted and configured to recognize machine readable markings as part of a cartridge verification protocol as well as to aid in the identification of a particular sample type and/or diagnostic testing routine to be performed with that sample/cartridge.

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

The digital processing device(s) described herein may include one or more general-purpose processing devices such as a microprocessor or central processing unit, a controller, or the like. Alternatively, the digital processing device may include one or more special-purpose processing devices such as a digital signal processor (DSP), an application specific integrated circuit (ASIC), a field programmable gate array (FPGA), or the like. In an alternative embodiment, for example, the digital processing device may be a network processor having multiple processors including a core unit and multiple micro engines. Additionally, the digital processing device may include any combination of general-purpose processing device(s) and special-purpose processing device(s).

G. Integrated Diagnostic Cartridge

The embodiments described herein relate to a disposable single use device (a "cartridge") used for molecular diagnostic testing. The cartridge can contain a plurality of modules for performing a variety of functions in order to effect the diagnostic test including, but not limited to, a loading module, a lysis module, a purification module, and an amplification module. The loading module is configured to receive a sample, minimize the spilling of the sample, and prepare the sample for lysis. The lysis module is configured to disrupt cells walls and cell membranes in order to release inter-cellular materials such as nucleic acids (DNA, RNA), protein or organelles from a cell, and, in some cases, clear debris from the lysate. The purification module is configured to isolate and/or enrich nucleic acid from a lysed sample. The amplification module is configured to generate and detect a signal from target amplicon, indicative of the presence of target pathogen in the sample.

FIG. 68 is a top down view of an exemplary integrated diagnostic cartridge 1000. In this illustrative embodiment, the integrated cartridge 1000 includes a loading module, a lysis module, a purification module and an amplification module. In this embodiment, the loading module is on one end of the cartridge adjacent to the patient label area 1040 while the amplification module containing reaction area 1600 is on the other end of the cartridge. Further to the compact and modular design aspects of the various cartridge embodiments, the lysis module and the purification module are arranged to occupy the portion of the cartridge existing between the loading module and the amplification module. As such, the frangible seal area 1200, the rotary valve 1400, the rehydration chamber 1520, the cartridge pneumatic interface 1170 and the lysis chamber 1371 are shown in an advantageous arrangement not only as to the loading module and the amplification module but also to take advantage of vertical orientation within the instrument for sample processing.

The instrument is configured to recognize and interact with the cartridge in order to perform the diagnostic assay. Accordingly, the cartridge comprises a number of interfaces to the instrument. FIG. 68 illustrates exemplified instrument interfaces on the cartridge. In some cases, the interfaces are physical interactions. For example, the door support assembly 2280 presses upon the fill port cap 1181, the valve drive assembly 2400 inserts into engagement openings in the rotary valve 1400, and the instrument pneumatic interface 2100 presses against the cartridge pneumatic interface 1170. In other cases, the interaction is magnetic. For example, the magnetic mixing assembly 2300 acts upon the contents of the lysis chamber 1371 and a magnet associated with the rehydration motor 2510 acts upon a magnetic ball 1524 with the rehydration chamber 1520. In other cases, the interface is visual. For example, a camera 2771 within the label imaging assembly 2770 can capture an image of the patient label area 1040 or the reaction camera 2701 of the reaction imaging assembly 2700 can capture and image of the reaction area 1600 of the cartridge. Since the instrument is configured to act upon a variety of cartridges, each designed to perform a different diagnostic assay, these interface points are held constant in each of the different cartridge embodiments.

In certain implementations, the cartridge is comprised of a fluidics card, which comprises most of the functional structures of the cartridge, and a cover 1004, which protects the active areas of the cartridge. FIG. 69 illustrates a cartridge from the feature side 1007 of the fluidics card 1001. The cover is substantially removed to permit visualization of the fluidics features hidden behind the cover. Similarly, FIG. 70 illustrates the cartridge from the fluidics side 1006, which provides the fluidic network for transporting a sample and various substances to different modules of a cartridge. Typically the fluidics side comprises a plurality of fluidic channels, ducts, and pathways formed within the surface of the cartridge. In many embodiments, the channels, ducts and pathways are enclosed with a film applied against the fluidics side of the cartridge. In a preferred implementation, the channels, ducts and pathways are microfluidic features having a smallest dimension of 750 μm or less. In other implementations, the smallest dimension can be 600 μm or less, 500 μm or less, 400 μm or less, 200 μm or less, or 100 μm or less. In another aspect, the fluidics side 1006 can include multiple vias, e.g. openings, passages or ports configured for passing fluids therethrough from one side of the fluidics card to the other, e.g. from the fluidics side 1006 to a structure on the features side 1007. In another aspect, the fluidics side 1006 can include multiple vias, e.g. openings configured for passing fluids therethrough from one side of the fluidics card to the other, e.g. from the fluidics side 1006 to a structure on the features side 1007. A via can have any of the dimensions, such as the cross-sectional diameter of any of the channels provided herein. In another embodiment, the feature side 1007 of a fluidics card 1001 defines the various structures to enable the loading, lysing, purifying, and amplification of a sample.

In some implementations, one or more fluidic channels may specifically be pneumatic channels, wherein only pressurized air or gas is permitted to flow. The diameter of the pneumatic channels may be of similar dimensions of fluidic channels as described herein. Such pneumatic channels may be configured for venting and rerouting air or gas within the cartridge when a sample is loaded.

The terms "fluidic communication" as used herein, refers to any duct, channel, tube, pipe, or pathway through which a substance, such as a liquid, gas, or solid may pass substantially unrestricted when the pathway is open. When the pathway is closed, the substance is substantially restricted from passing through.

It is noted that, as used herein, the term "input" refers to vias or channels of a cartridge where active pressurization is applied to motivate a liquid (i.e. a sample or reagent) or a gas (i.e. air) residing within a channel. As used herein, the term "output" refers to the leading front of said motivated liquid or gas which is displaced as a result of active pressurization and which terminates at a via or channel for venting. In one aspect, the input and/or output may comprise one or more filter plugs for filtering a fluid. In one embodiment, a filter plug is configured to capture pollutants and particles from pressurized air. In another embodiment, a filter plug is configured to be hydrophobic to vent gasses while retaining liquids.

As described above, fluids are motivated throughout the fluidic network of a cartridge using pressurized air. Thus, the cartridge is configured to receive pressurized air through one or more pneumatic vias. In the cartridge exemplified in FIG. 69, main pneumatic via 1193 is present on the feature side of the cartridge. Each pneumatic via is in fluidic communication with a pneumatic channel, such that pneumatic channels enable the motive force to transport a sample and liquids through various modules within the cartridge.

Given the pressurization of the device, as will become apparent in the sections to follow, in some embodiments, the cartridge, optionally, includes a liquid trap configured to capture liquids to prevent contamination of various structures of the cartridge. The liquid trap, preferably, is formed by a widening or depression in a pneumatic channel, wherein liquid droplets fall to bottom of the depression thereby captured outside the main pneumatic flow within the cartridge. Alternatively, the liquid trap can be a physical structure, such as a sintered vent plug placed within the pneumatic channel.

In some embodiments, the cartridge cover can further include a cartridge label to supply the user and instrument with information associated with a given diagnostic test. FIG. 90 illustrates an exemplary cartridge label 1005. In some embodiments, the cartridge label includes a cut out to provide visual access to a sample window 1050 formed within a metering chamber 1110, enabling the user and/or a system, such as instrument 2000 as described herein, to view and detect the sample volume loaded into the device. Additionally, one cut out within the cartridge label may be configured to exclude the reaction area 1600 enabling the amplification and detection of target nucleic acids from optically transparent plugs, as described herein. A portion of the cartridge label, i.e., the patient label area 1040, in some embodiments, is configured to be written on to enable a user to provide patient information relating to the diagnostic test. Such information can include, for example, the name of the patient, the date of birth of a patient, and the sample type gathered from the patient. In some embodiments, the cartridge label may include computer readable information. In some embodiments, the cartridge label provides a computer readable visual code 1053 to store computer readable information. Such information can include, for example, the type of test the cartridge is configured to run and general manufacturing information, e.g., a lot number, expiration date, and/or recalls associated with the cartridge. In some implementations, the computer readable information is configured to be encrypted. The computer readable information may be configured to be read by a system or instrument, such as instrument 2000, as described herein. In a further implementation, illustrated in FIG. 91, the cartridge label 1005 can include one or more perforated areas within said cartridge label configured to be broken when contacted. In one implementation, a perforated area 1051 exists around the frangible seal area. In another implementation, a perforated area 1052 is located around the cartridge pneumatic interface to enable a pneumatic interface, for example like pneumatic interface 2100 of instrument 2000 to break the perforated area to make contact with the device.

1. Loading Module

In one embodiment, a cartridge of the present invention comprises a loading module configured to, e.g., accept a sample, prevent the sample from spilling liquids outside the cartridge, and optionally prepare the sample for lysis. The loading module defines a sample volume used to perform a diagnostic test. In some implementations, the loading module includes a metering chamber and an overflow chamber to produce a metered sample volume. The loading module may further comprise a mechanism for detecting a sufficient sample volume is present in the device. A window may be included to allow a user or an instrument to detect the mechanism indicative of a sufficient sample volume. In another implementation, the loaded sample is drawn into the cartridge using a converging channel.

In some embodiments the loading module comprises a sample port assembly 1100 disposed within the cartridge. Optionally, the sample port assembly 1100 is configured to produce a metered sample of predetermined volume. Specifically, as discussed in greater detail below regarding FIG. 71, the sample port assembly comprises an entry port 1140, a fill chamber 1101, a metering chamber 1110, metering channel 1113, an overflow chamber 1120, overflow channel 1122, vent 1165, and gas conduit 1150. The entry port 1140 of the assembly defines an opening of the fill chamber to receive a sample, wherein the fill chamber 1101 is in fluidic communication with metering chamber 1110. A sample loader, such as a bulb, syringe or pipette 1060, can be useful for loading a sample into the cartridge.

The fill chamber has dimensions including a volume, said volume being between 100 µl and 15 ml, between 200 µl and 7.5 ml, between 0.5 ml and 5 ml, between 0.5 ml and 3 ml, between 5 ml and 10 ml, between 1 ml and 3 ml, between 0.5 and 1.5 ml. While the fill chamber illustrated in the FIGS. 69-71 is configured to hold up to 2.4 ml of fluid, cartridges of the invention may accommodate larger sample volume by increasing the depth of the fill chamber. Increasing the depth of the fill chamber results in an overall thickness increase of the cartridge as a function of the depth of the fill chamber. Advantageously, increasing the thickness of the cartridge can allow for increased volume of chambers holding liquid reagents and the waste chamber as discussed in greater detail below. Thicker cartridges can be accommodated by the instrument simply by changing the clamping position of the moving bracket assembly 2040 as described herein.

When implemented, the metering chamber 1110 is in fluidic communication with the fill chamber 1101 via a metering channel 1113. In some embodiments, the metering chamber includes a mechanism for detecting a sample volume present within the metering chamber, e.g., a buoyant ball 1114. The ball may be detected through a sample window 1050 by a user or instrument 2000 for indicating an adequate sample volume is in the metering chamber 1110 prior to executing a diagnostic test. Alternatively, the meniscus of the fluid sample can be detected through the sample window by a user or instrument. Referring to FIG. 68, the label imaging system 2770, that captures an image of the patient label area, can also capture an image of the meniscus or buoyant ball 1114 through the sample window 1050. The metering chamber has dimensions including a volume, which can range from 0.1 to 10 ml, from 0.5 to 5 ml, from or 1 to 3 ml.

When implementing a metering chamber, the cartridge typically further comprises an overflow chamber 1120 configured to capture excess sample that was loaded into the fill chamber 1101 and cannot be accommodated by fully filled metering chamber. The overflow chamber is in fluidic communication with the metering chamber 1110 through an overflow channel 1122, such that excess sample flows though the overflow channel and is retained in the overflow chamber. Taking advantage of the vertical orientation of the cartridge with the instrument, the sample flows from the fill chamber 1101 through the metering channel 1113 into the top of the metering chamber 1110. Once the metering chamber 1110 is filled, any excess fluid remaining in the fill chamber passes from the metering channel 1113 to the overflow channel 1122 and then to the overflow chamber 1120 without substantially entering the metering chamber. This geometry can be advantageous for instances in which the metering chamber comprises a chemical or enzymatic agent to pretreat the sample prior to passing the sample on to the lysis module. After metering, the meter fluid within the metering channel can be withdrawn from the metering chamber though a channel at the bottom of the metering chamber. In a preferred embodiment, the lower bound of the metering chamber is angled toward the exit such that gravity will assist in emptying the chamber.

The sample port assembly 1100 further comprises a structure for separating the sample from the outside environment, e.g. a cap 1181 configured to be opened to permit addition of a sample and then resealed prior to the sample being loaded to the device. Given the pressurization inherent to the devices described herein, the closure, i.e. the cap, preferably is air tight. The configuration, as described herein, creates an airlock within the loading module to prevent sample within fill chamber 1001 from passing to the metering chamber 1110 until actuated by pressurization. Such an airlock further prevents liquid from entering the metering chamber when the device is tilted vertically.

In some embodiments, the loading module is configured to be emptied using pneumatic force. Specifically, a sample is transferred from the fill chamber 1001 to the metering chamber 1114 when pneumatic line 1171 to the fill chamber is pressurized. In one implementation, the port is pressurized using constant pressure. In another implementation the port is pressurized using a series of applied pressure pulses each followed by a period of zero applied pressure. In the instance where an excess sample volume is present, excess sample enters overflow channel 1121 and is retained in the overflow chamber 1120.

In an alternative embodiment shown in FIG. 72, the loading module may comprise an entry port in fluidic communication with a reservoir containing a converging channel and one or more diverging channels. Such a configuration enables a loaded sample to be drawn to the distal end of the converging channel, wherein the sample exits the converging channel and fills the one or more diverging channels. Further description of a sample port configured to wick a sample can be found in U.S. patent application titled "Vented Converging Capillary Sample Port and Reservoir," filed 13 Sep. 2018, and assigned application Ser. No. 16/130,927, which is incorporated by reference herein.

2. Lysis Module

The cartridge further comprises a lysis module configured to disrupt cell walls and/or cells membrane to release inter-cellular materials such as nucleic acids (DNA, RNA), protein or organelles from a cell. In a one implementation, the lysis module comprises a lysis chamber 1371 and a stir bar 1390. In one aspect, the lysis module may further include a filter assembly to rid the sample of cell debris after lysis to minimize the potential for clogging downstream features in the cartridge.

In a preferred implementation, the lysis module comprises a mixing assembly for combining the sample with one or more lysis agents. In one embodiment, illustrated in FIG. 70, the cartridge includes a mixing assembly comprising a lysis chamber 1371 and a stir bar 1390. The lysis chamber 1371 is configured to receive the sample from a sample transfer channel 1386 through inlet 1373 that is preferably located at or near the top of the lysis chamber 1371. In some implementations, the cartridge comprises a chemical lysis reagent prior to loading the sample. When the chemical lysis reagent is a liquid, the reagent preferably is sealed into the lysis chamber prior to use of the cartridge. In one such embodiment, the channel leading to the lysis chamber 1386 and the channel for draining the lysis chamber 1388 are both closed with a frangible seal prior to use. When the cartridge is inserted into the instrument and readied for use, the frangible seals are broken, thus permitting pressurized air to transfer the sample into the lysis chamber for lysis. The magnetic mixing assembly, as described herein with regard to instrument 2000, is activated to rotate the stir bar 1390 and thereby mix the sample with the one or more lysis reagents.

When used with the balanced magnet mixing assembly 2300 described above, the stir bar 1390 need not be a permanent magnet. In a preferred implementation, the stir bar is a composed of a ferromagnetic material, which is not magnetized in the absence of an external magnetic field. In some embodiments, the ferromagnetic material of the stir bar is ferritic stainless steel or duplex stainless steel. In additional embodiments, a relative magnetic permeability of the stir bar can be between 500-1,000,000. The stir bar can comprise any shape and/or volume. For example, the shape of the stir bar can be selected from a group consisting of cylindrical, spherical, and triangular-prism-shaped. Further description of stir bar, lysis chamber and balanced magnetic mixing assembly can be found in US patent publication 2019/0160443 A1, titled "Magnetic Mixing Apparatus," which is incorporated by reference herein.

In embodiments where one of the one or more lysis reagents is a chemical agent, the ferromagnetic material is preferably coated with an inert material to protect the stir bar from corrosion and to deter release of iron, a suspected inhibitor of amplification, from being released into the lysate. One of ordinary skill in the art would be able to select an appropriate impermeable material that would not interfere with magnetic flux through the stir bar. Example materials include, but are not limited to PTFE, parylene C, parylene D, functionalized perfluoropolyethers (PFPEs), FEP, Xylan Fluoropolymer, epoxy, and urethane. Similarly, the impermeable material can be applied to the stir bar by any method known in the art, such as by tumble coating. In one implementation, the ferromagnetic material of the stir bar is passivated prior to coating. In a preferred implementation, the stir bar is tumble-coated with a layer of parylene C between 20 µm and 200 µm thick.

By placing a ferromagnetic stir bar within the lysis chamber 1371 located in a gap between a driving magnet system 2310 and a driven magnet system 2350 of instrument 2000, a magnetic dipole can be induced across and within the stir bar. This dipole of the stir bar effectuates a magnetic coupling between the stir bar 1390, the one or more driving magnets of the driving magnet system 2310, and the one or more driven magnets of the driven magnet system 2350. Specifically, the introduction of the stir bar 1390 into the magnetic field causes the stir bar to be attracted to the one or more driving magnets and the one or more driven magnets. In preferred embodiments in which a magnetic strength of the corresponding driving magnet equals a magnetic strength of the driven magnet, and the driving magnet magnetic axis is substantially collinear with the driven magnet magnetic axis, attraction of the stir bar to the driving magnet and driven magnet causes the stir bar to be located roughly equidistant from driving magnet and driven magnet. In an even further preferred embodiment in which a center of the lysis chamber 1371 is located an equal distance from the driving magnet system and the driven magnet system, as a result of the attractive forces between the stir bar and the one or more driving magnets and the stir bar and the one or more driven magnets, the stir bar can be centered within the lysis chamber thereby minimizing the amount of contact between the stir bar and the bounding surface.

In some embodiments, the lysis chamber 1371 further comprises beads. In such embodiments, mixing the fluid sample with the beads promotes lysis of the one or more cells. Preferably, the sample and beads, plus optionally one or more additional lysis reagents, are stirred at least 500 rpm, at least 1000 rpm, at least 2000 rpm or at least 3000 rpm for at least 15 seconds 30 seconds, 60 seconds or 2 minutes to generate a lysed sample, or lysate. Following mixing of the fluid sample with the beads, the lysate is removed from the lysis chamber. In a preferred embodiment, the beads are separated from the fluid sample in conjunction with the sample being removed from the lysis chamber. To separate the beads from the fluid sample, in some embodiments, bead filter channels 1387 are appended to the lysis chamber. The bead filter channels are located along an edge of the lysis chamber and are configured to retain the beads in the lysis chamber while allowing the fluid sample to exit. Preferably the bead filter channels are located at the bottom of the lysis chamber to take advantage of gravitation forces to move the lysate from the lysis chamber without generating bubbles or foam in the lysate. In a preferred implementation, a cross sectional area of each bead filter channel comprises a first dimension such that the beads are too large to enter the bead filter channels, and a second dimension such that the beads are unable to block fluid flow. In this way use of the bead filter channels enables fluid to be drawn from the lysis chamber without beads.

In some implementations, the lysis module further comprises a process control. A process control establishes a factor of confidence in a test result when executing a diagnostic test. Controls are treated and tested in parallel with target pathogen and are used to generate a predetermined expected result. When the expected result is reported, one or more aspects of the diagnostic test are confirmed to be working as intended, enabling the user of to verify the diagnostic test as valid. However, when the predetermined result is not obtained, one or more aspects of the test does not meet the expected performance and would invalidate the test results obtained from a cartridge. In one embodiment, a cartridge can include a process control chamber 1130 comprising an inlet 1131, an outlet 1132, and a control plug 1133 for doping a sample with a process control. In one aspect, sample within the metering chamber is flowed through the process control chamber to dope a sample with a process control. In a further embodiment, the process control is a positive control. Prior to mixing the sample with at least one lysis agent, a process control can be added to the sample. In such an implementation, one of the assay chambers will comprise a primer set specific to a nucleic acid sequence found in the process control. The process control chamber is exemplified in FIGS. 69-71.

Preferably, the process control can function as a positive control for lysis, purification and amplification within the cartridges described herein. One exemplified process control is a bacterial spore, such as a spore of a *Bacillus* species. Bacterial spores typically are more difficult to lyse than any other target cell and can therefore serve as a universal control for cell lysis. Suitable spores can be comprised of any species of *Bacillus*, including, e.g., *Bacillus globgii, Bacillus atrophaeus, Bacillus subtilis*, and *Bacillus stearothermophilus*. Alternatively, a process control can be added to the lysed sample prior to passing the lysed sample through the porous solid support. Such a process control would act as a positive control for purification and amplification, but not lysis.

In some implementations, the cartridge further comprises one or more filter assemblies 1330 to remove undesired cellular material and debris from a sample by passing the sample through filter assembly 1330. In one implementation, the lysis module comprises a filter assembly located before the lysis chamber to filter a sample before lysing. In another embodiment, the lysis module comprises a filter assembly placed after the lysis chamber to filter a lysed sample. Specifically, the lysis module can comprise one or more filter assemblies located downstream of the lysis chamber.

FIGS. 73 and 74 illustrate a filter assembly according to an embodiment described herein. FIGS. 74 and 75 provides section views through the cartridge depicting a filter assembly 1330 comprising a filter 1331, an inlet via 1332, an outlet via 1333, flow directors 1334, a filter plug 1336, and a pneumatic interface cover adaptor 1172. Filter 1331 can be configured to capture one substance, e.g., larger cells, more effectively, e.g., substantially more effectively, than another substance, e.g., a liquid, such as a sample suspected on contained a target pathogen, when the substances are exposed to the filter and at least one of them is moved substantially therethrough. For example, a filter 1331 can enable the solid components, such as, e.g., cells, debris or contaminant, to be separated from the liquid components of the solution. Alternatively, a filter can enable larger solid components, such as, e.g., proteinaceous aggregates, aggregated cell debris, or larger cell, to be separated from smaller components, e.g. virus, bacterial cells or nucleic acid, from a solution. In aspects of this embodiment, a filter useful for separating components contained in a solution can be, e.g., a size-exclusion filter, a plasma filter, an ion-exclusion filter, a magnetic filter, or an affinity filter. In other aspects of this embodiment, a filter useful for separating components contained in a solution can have a pore size of, e.g., 0.1 µm, 0.2 µm, 0.5 µm, 1.0 µm, 2.0 µm, 5.0 µm, 10.0 µm, 20.0 µm, 30 µm, 40 µm, 50 µm, 60 µm, 70 µm, 80 µm, 90 µm, 100 µm, or more. In yet other aspects of this embodiment, a filter useful for separating components contained in a solution can have a pore size of, e.g., at least 0.2 µm, at least 0.5 µm, at least 1.0 µm, at least 2.0 µm, at least 5.0 µm, at least 10.0 µm, at least 20.0 µm, at least 30.0 µm, at least 40.0 µm, at least 50.0 µm, at least 60.0 µm, at least 70.0 µm, at least 80.0 µm, at least 90.0 µm, or at least 100.0 µm. In still other aspects of this embodiment, a filter useful for separating components contained in a solution can have a pore size of, e.g., at most 0.1 µm, at most 0.2 µm, at most 0.5 µm, at most 1.0 µm, at most 2.0 µm, at most 5.0 µm, at most 10.0 µm, at most 20.0 µm, at most 30.0 µm, at most 40.0 µm, at most 50.0 µm, at most 60.0 µm, at most 70.0 µm, at most 80.0 µm, at most 90.0 µm, or at most 100.0 µm. In other aspects of this embodiment, a filter useful for separating components contained in a solution can have a pore size between, e.g., about 0.2 µm to about 0.5 µm, about 0.2 µm to about 1.0 µm, about 0.2 µm to about 2.0 µm, about 0.2 µm to about 5.0 µm, about 0.2 µm to about 10.0 µm, about 0.2 µm to about 20.0 µm, about 0.2 µm to about 30.0 µm, about 0.2 µm to about 40.0 µm, about 0.2 µm to about 50.0 µm, about 0.5 µm to about 1.0 µm, about 0.5 µm to about 2.0 µm, about 0.5 µm to about 5.0 µm, about 0.5 µm to about 10.0 µm, about 0.5 µm to about 20.0 µm, about 0.5 µm to about 30.0 µm, about 0.5 µm to about 40.0 µm, about 0.5 µm to about 50.0 µm, about 1.0 µm to about 2.0 µm, about 1.0 µm to about 5.0 µm, about 1.0 µm to about 10.0 µm, about 1.0 µm to about 20.0 µm, about 1.0 µm to about 30.0 µm, about 1.0 µm to about 40.0 µm, about 1.0 µm to about 50.0 µm, about 2.0 µm to about 5.0 µm, about 2.0 µm to about 10.0 µm, about 2.0 µm to about 20.0 µm, about 2.0 µm to about 30.0 µm, about 2.0 µm to about 40.0 µm, about 2.0 µm to about 50.0 µm, about 5.0 µm to about 10.0 µm, about 5.0 µm to about 20.0 µm, about 5.0 µm to about 30.0 µm, about 5.0 µm to about 40.0 µm, about 5.0 µm to about 50.0 µm, about 10.0 µm to about 20.0 µm, about 10.0 µm to about 30.0 µm, about 10.0 µm to about 40.0 µm, about 10.0 µm to about 50.0 µm, about 10.0 µm to about 60.0 µm, about 10.0 µm to about 70.0 µm, about 20.0 µm to about 30.0 µm, about 20.0 µm to about 40.0 µm, about 20.0 µm to about 50.0 µm, about 20.0 µm to about 60.0 µm, about 20.0 µm to about 70.0 µm, about 20.0 µm to about 80.0 µm, about 20.0 µm to about 90.0 µm, about 20.0 µm to about 100.0 µm, about 30.0 µm to about 40.0 µm, about 30.0 µm to about 50.0 µm, about 30.0 µm to about 60.0 µm, about 30.0 µm to about 70.0 µm, about 30.0 µm to about 80.0 µm, about 30.0 µm to about 90.0 µm, about 30.0 µm to about 100.0 µm, about 40.0 µm to about 50.0 µm, about 40.0 µm to about 60.0 µm, about 40.0 µm to about 70.0 µm, about 40.0 µm to about 80.0 µm, about 40.0 µm to about 90.0 µm, about 40.0 µm to about 100.0 µm, about 50.0 µm to about 60.0 µm, about 50.0 µm to about 70.0 µm, about 50.0 µm to about 80.0 µm, about 50.0 µm to about 90.0 µm, or about 50.0 µm to about 100.0 µm.

In certain implementations, the filter can be a depth filter. Depth filters consist of a matrix of randomly oriented, bonded fibers that capture particulates within the depth of the filter, as opposed to on the surface. The fibers in the depth filter can be comprised of glass, cotton or any of a variety of polymers. Exemplified depth filter materials may include, type GF/F, GF/C and GMF150 (glass fiber, Whatman), Metrigard® (glass fiber, Pall-Gelman), APIS (glass fiber, Millipore), as well as a variety of cellulose, polyester, polypropylene or other fiber or particulate filters, so long as the filter media can retain a sufficient contaminant to allow further processing of the sample.

In alternate implementations, the size-exclusion filter can be a membrane filter, or mesh filter. Membrane filters typically performs separations by retaining particles larger than its pore size on the upstream surface of the filter. Particles with a diameter below the rated pore size may either pass through the membrane or be captured by other mechanisms within the membrane structure. Membrane filters can support smaller pore sizes, including small enough to exclude bacterial cells. Membrane filters can be used to concentrate solutions, e.g. bacterial cell suspensions, by filtering a first larger volume through the membrane filter, thereby holding the bacterial cells to the upstream surface of the membrane filter (or suspended in residual fluid retained on the upstream side of the filter). The bacterial cells can then be resuspended in a second small volume of fluid by either passing the suspension fluid in the reverse direction to float the bacterial cells off the membrane surface or by washing the suspension fluid across the upstream surface of the filter to wash the bacterial cells off the filter. Exemplified membranes may include, polyethersulfone (PES) membranes (e.g., Supor® 200, Supor® 450, Supor® MachV (Pall-Gelman, Port Washington, N.Y.), Millipore Express PLUS® (Millipore)). Other possible filter materials may include, HT Tuffryn® (polysulfone), GN Metricel® (mixed cellulose ester), Nylaflo® (Nylon), FP Verticel (PVDF), all from Pall-Gelman (Port Washington, N.Y.), and Nuclepore (polycarbonate) from Whatman (Kent, UK).

As illustrated in FIG. 74 and FIG. 75, the filter 1331 can be fixedly, e.g., laser welded, attached to a feature side 1007 of a fluidics card 1001, such that a deformation space 1335 is formed between the filter 1331 and the pneumatic interface cover adaptor 1172. The filter can be enclosed by a frame. In certain implementations, such as illustrated in FIGS. 69 and 75, the frame holding the filter can be comprised into another structure, such as the pneumatic interface cover adaptor. In some implementations, filter frame, e.g. the pneumatic interface cover adaptor 1172, includes a plurality of flow directors 1334 integrally formed within the body for directing a filtered liquid passed therethrough to the outlet via 1333 onwards to the purification module.

FIG. 74. is a sectional view of the filter assembly. In various embodiments, an inlet via 1332 provides the opening for a fluid, e.g. a sample or lysate, to enter the filter assembly 1330. In configurations wherein the filter is fixedly attached to the feature side of a fluidics card 1007, a sample enters the filter assembly through inlet via 1332. The fluid pressure generated, resulting from the sample entering the filter assembly 1330, causes filter 1331 to expand. Expansion of the filter is accommodated by deformation space 1335, such that the filter is permitted to expand until contacted by flow directors 1334. Substances, e.g., a sample, such as a lysed sample, is transmitted through the filter while other substances, e.g., particles, such as larger cells or cell debris, is prevented from passing therethrough to produce a filtered sample. The filtered sample is collected in the spaces formed between the flow directors, thereby directing the filtered sample to the outlet via 1333. As shown in FIG. 73, filter 1331 includes a cutout around outlet via 1333 to permit the filtered sample to enter the outlet via.

In some aspects, the pneumatic interface cover adaptor can be a structure which receives pressurized air from the instrument pneumatic interface 2100. In various embodiments, the pneumatic interface cover adaptor is configured to hold a filter plug 1336 for filtering the pressurized air input. As illustrated in FIG. 75, pressurized air enters input via 1195 of the cartridge pneumatic interface 1170 and is filtered by filter plug 1336 before exiting the main pneumatic via 1193 and pneumatic via 1194, such that main pneumatic via 1193 is fluidically coupled to the main pneumatic line 1171 and pneumatic via 1194 is fluidically coupled to pneumatic line 1178.

3. Purification Module

The cartridges of the invention further comprise a purification module for capturing nucleic acids from a lysed sample. In one aspect the purification module is configured to purify a lysed sample using a rotary valve, wherein the rotary valve comprises a porous solid support. The porous solid support captures nucleic acid while allowing the remainder of the sample and liquid waste to be directed to a waste collection element. In such an embodiment, the device additionally includes reagent reservoirs to store on-board reagents necessary for sample purification.

In one aspect, the purification module comprises one or more rotary valves comprising an integrated flow channel containing a porous solid support for filtering, binding and/or purifying analytes within a fluid stream. In one implementation, the rotary valve comprises a stator 1450 comprising a stator face and a plurality of passages 1454, each passage comprising a port 1453 at the stator face; a rotor 1410 operably connected to the stator and comprising a rotational axis, a rotor valving face, and a flow channel having an inlet 1441 and an outlet 1442 at the rotor valving face, wherein the flow channel comprises a porous solid support 1445; and a retention element 1490 biasing the stator and the rotor together at a rotor-stator interface to form a fluid tight seal.

The cross section view of FIG. 76 illustrates an orientation of the rotor and the stator that establishes a fluid pathway from a stator fluid passage 1454*a* via the stator port 1453*a*, the solid support chamber 1446 containing the porous solid support 1445, and finally port 1453*b*, exiting through a second stator fluid passage 1454*b*. As a result, a flow channel 1440 within the rotor body 1411 provides fluid communication with the porous solid support 1445 within the solid support chamber 1446. The flow channel 1440 is accessed whenever the gasket inlet 1484 and outlet 1485 are aligned with two stator ports 1453 which in this embodiment occurs when the gasket inlet 1484 and outlet 1485 are aligned to stator ports 1453*a* and 1453*b*.

The fluid flow pathway through the solid support chamber 1446 is also visible in FIG. 76. An exemplary flow path begins at the stator 1450 at the first port 1453*a*. There is next a pathway through the gasket 1480 via the gasket inlet 1484. Next, the fluid enters the rotor body 1411 via inlet 1441 and thence through the first fluid conduit 1443. The outlet of the first conduit 1443 leads to a fluid pathway defined by the spacing between the rotor upper surface and the bottom surface of the cap cover 1430. The upper surface of the rotor body in this region is shaped to include a short channel to provide a portion of desired flow path between the first fluid conduit 1443 and the solid support chamber 1446. The partial flow path is completed when the cap cover 1430 is secured to the rotor top surface. Next, the fluid enters into the solid support chamber 1446 containing the porous solid support 1445. Fluid then passes to the bottom of solid support chamber 1446 to the second conduit 1444 and then to rotor outlet 1442. From rotor outlet 1442 the fluid exits the rotor and passes through the gasket 1480 via outlet 1485 and to the stator opening 1453*b* and through fluid passage 1454*b*.

The rotary valve for use in the cartridges of the invention are described in greater detail in U.S. patent application titled "Rotary Valve," filed 15 Feb. 2018, and assigned application Ser. No. 15/898,064, and in international patent application, also titled "Rotary Valve," filed 15 Feb. 2019 and assigned application no. PCT/US2019/018351, each of which is incorporated by reference herein.

As an integral part of the rotor, a flow channel is configured for rotational motion, rotating with the other portions of the rotor with respect to other valve aspects, such as a stator. In a preferred implementation, the flow channel is not concentric with the rotational axis of the rotor. As illustrated in FIG. 76, a flow channel can include one or more inlets 1441 and one or more outlets 1442 and provide fluidic communication between the inlet and the outlet. In a preferred implementation, each flow channel will comprise a single inlet and a single outlet. The inlet and outlet typically, but not necessarily, will adopt the same form as a cross-section of the flow channel immediately adjacent to that inlet or outlet. The inlet and/or outlet can be circular, rectangular or any other appropriate shape consistent with forming fluid-tight fluidic connections within the valve interface.

The rotor can be configured to hold one or more porous solid supports. As shown in FIG. 77, each support chamber 1446*a*-1446*d* may vary in shape, size, dimension, volume or by the content of the solid support contained in a specific support chamber 1446.

Optionally, the flow channel also includes a flow channel spacer 1449 for spacing a porous solid support from a surface, e.g., a bottom surface, of a porous solid support chamber 1446. In various embodiments, a flow channel spacer can be crescent shaped and extend in an arcuate manner along its length. The flow channel spacer can facilitate fluid flow through the outlet by preventing the porous solid support, e.g., beads or fibers, from physically blocking the exit from the solid support chamber. Illustrious flow channel spacer variations include: (a) a flow channel spacer may be segmented rather than a continuous structure; (b) a flow channel spacer may include more than one structure along a surface of the solid support chamber such as a sidewall or bottom; (c) a flow channel spacer may be spaced apart from the chamber exit or terminate at the edge of the exit; and (d) a flow channel spacer may be raised above a chamber interior surface such as a bottom or a sidewall, recessed into a chamber interior surface such as a bottom or a sidewall.

Porous solid supports can be configured to capture and thereby concentrate analyte, e.g., concentrate analyte from a first concentration to a second concentration, from a sample flowed therethrough by an amount of analyte concentration, such as 1000× or more in any of the time amounts described herein, such as in 30 min or less, such as 1 hour or less. In various embodiments, a porous solid support is bounded, such as bounded at an upstream face and/or a downstream face by a frit.

In some aspects, a porous solid support can be a selective membrane or a selective matrix. As used herein, the terms "selective membrane" or "selective matrix" as referred to herein is a membrane or matrix which retains one substance, e.g., an analyte, more effectively, e.g., substantially more effectively, than another substance, e.g., a liquid, such as portions of a sample other than the analyte and/or water and/or buffer, when the substances are exposed to the porous solid support and at least one of them is moved at least partially therethrough. For example, a porous solid support, such as a selective matrix, having a biological sample flowed therethrough can retain an analyte, e.g., nucleic acids, while the remainder of the sample passes through the porous solid support.

Examples of porous solid supports include, but are not limited to: alumina, silica, celite, ceramics, metal oxides, porous glass, controlled pore glass, carbohydrate polymers, polysaccharides, agarose, Sepharose™, Sephadex™, dextran, cellulose, starch, chitin, zeolites, synthetic polymers, polyvinyl ether, polyethylene, polypropylene, polystyrene, nylons, polyacrylates, polymethacrylates, polyacrylamides, polymaleic anhydride, membranes, hollow fibers and fibers, or any combinations thereof. The choice of matrix material is based on such considerations as the chemical nature of the affinity ligand pair, how readily the matrix can be adapted for the desired specific binding.

In some embodiments, a porous solid support is a polymeric solid support and includes a polymer selected from polyvinylether, polyvinylalcohol, polymethacrylate, polyacrylate, polystyrene, polyacrylamide, polymethacrylamide, polycarbonate, or any combinations thereof. In one embodiment, the solid support is a glass-fiber based solid support and includes glass fibers that optionally can be funcationalized. In some embodiments, the solid support is a gel and/or matrix. In some embodiments, the solid support is in bead, particle or nanoparticle form.

A myriad of functional groups can be employed with the subject embodiments to facilitate attachment of a sample analyte or ligand to a porous solid support. Non-limiting examples of such functional groups which can be on the porous solid support include: amine, thiol, furan, maleimide, epoxy, aldehyde, alkene, alkyne, azide, azlactone, carboxyl, activated esters, triazine, and sulfonyl chloride. In one embodiment, an amine group is used as a functional group. A porous solid support can also be modified and/or activated to include one or more of the functional groups provided that facilitate immobilization of a suitable ligand or ligands to the support.

In some embodiments, a porous solid support has a surface which includes a reactive chemical group that is capable of reacting with a surface modifying agent which attaches a surface moiety, such as a surface moiety of an analyte or ligand of a sample, to the solid support. A surface modifying agent can be applied to attach the surface moiety to the solid support. Any surface modifying agent that can attach the desired surface moiety to the solid support may be used in the practice of the present invention. A discussion of the reaction a surface modifying agent with a solid support is provided in: "An Introduction to Modern Liquid Chromatography," L. R. Snyder and Kirkland, J. J., Chapter 7, John Wiley and Sons, New York, N.Y. (1979), the entire disclosure of which is incorporated herein by reference for all purposes. The reaction of a surface modifying agent with a porous solid support is described in "Porous Silica," K. K. Unger, page 108, Elsevier Scientific Publishing Co., New York, N.Y. (1979), the entire disclosure of which is incorporated herein by reference for all purposes. A description of the reaction of a surface modifying agent with a variety of solid support materials is provided in "Chemistry and Technology of Silicones," W. Noll, Academic Press, New York, N.Y. (1968), the entire disclosure of which is incorporated herein by reference for all purposes.

In one implementation of a rotary valve described herein, the rotary valve includes a threaded rotor and a threaded retention ring for maintaining a gap between the gasket and at least one of the rotor and stator, thereby preventing the gasket from sealing against at least one of the rotor and stator, wherein when threaded rotor is rotated, the gasket seals the rotor and stator together in a fluid tight manner.

As best seen in FIGS. 78 and 79, a retention ring 1491 includes a threaded portion 1492. In the illustrated embodiment, the threaded portion 1492 includes threads. A rotor includes an outer wall having a threaded portion 1411. In the illustrated embodiment, the threaded portion includes grooves 1411 that correspond to the threads 1492 of the retention ring. In the shipping configuration shown in FIGS. 78 and 79, a biasing element 1496 maintains engagement between threads 1492 and grooves 1411 aiding in maintaining the desired gap between the rotor sealing surface (gasket 1480) and the stator valving face 1452. As best seen in FIG. 79, the top of rotor cap 1430 is substantially flush with an upper surface of retention ring 1491 maintaining a low-profile rotary valve design factor. Rotation of the rotor relative to the retention ring 1491 moves the rotor towards the stator and into the operational configuration shown in FIGS. 80 and 81. The transition out of the storage configuration is clear in this view, as the rotor cap is recessed below the top surface of the retention ring 1491 and the gasket 1480 provides a fluidic seal between the rotor and the stator. Also visible in FIG. 81 it is that the rotor is detached from the threaded portion 1492 of the retention ring 1491. Movement of the threaded rotor into this position ensures that the rotor is free to be indexed relative to the stator as described herein.

In consideration of FIGS. 79-81, there is provided a rotary valve comprising a rotor 1410 having a rotational axis, a rotor valving face, an outer face opposite the rotor valving face. Additionally, there is a stator 1450 having a stator valving face positioned opposite the rotor valving face. The rotary valve also includes a retention element 1490 biasing the rotor and stator towards one another comprising a retention ring 1491 and a biasing element 1496. The rotary valve is maintained in a shipping configuration while a threaded portion of the retention ring is engaged with a threaded portion of the rotor. In one configuration, a relative motion between the rotor and the stator produces a fluid tight arrangement between the rotor valving surface and the stator valving surface or the relative motion between the rotor and the stator is rotation of the rotor so as to move the rotor along the threaded portion of the retention ring until released to seal against the stator. As such, a rotary valve having a threaded rotor used for engagement in a shipping configuration may be configured to transition to provide a fluid tight seal within the rotary valve with a rotation of less than one revolution, half a revolution, a quarter of a revolution or one-eighth of a revolution of the threaded rotor. Still further, it is to be appreciated that while the threaded components of a threaded rotor rotary valve are engaged a gasket disposed between the rotor valving face and the stator valving face does not form a fluid tight seal with the stator valving surface.

In one aspect of the invention, the purification module stores on-board liquid reagents in reagent reservoirs for easy delivery of reagents used herein to prepare a sample suspected of containing a target pathogen. Such reagent reservoirs can be of any structure formed in the fluidics card 1001 configured to contain liquid therein, such that the fluidics card forms a first bounding surface. In one embodiment reagent reservoirs may comprise a second bounding surface provided by one or more sealing films fixedly attached, e.g. welded, to the fluidics side 1006 of the fluidics card (see, e.g. FIG. 89, discussed in greater detail below). In one implementation, reagent reservoirs are sealed by frangible seals to define a receptacle for long-term storage of the liquid reagents contained therein. Reagent reservoirs are rendered fluidically active when actuated to break the frangible seal allowing fluid to be emptied from the reagent reservoir and redirected throughout the cartridge. In one implementation, reagent reservoirs are in direct fluidic communication with main pneumatic line 1171 to deliver pressurized air to a reagent reservoir inlet to empty the contents of the reagent reservoir. The reagent reservoir additionally includes a reagent reservoir outlet to transfer the contents of the reagent reservoir from its holding receptacle to appropriate sample processing locations on the cartridge.

In one implementation, the device comprises one or more frangible seals configured to seal the device and allow on board liquids to be stored therein. In some implementations, breaking the one or more frangible seals renders the device fluidically active to allow liquid substances contained therein, e.g., lysis buffer or wash buffer, to be directed through the fluidic network of channels. A variety of configurations of frangible seals for closing microfluidic channels are well known in the art, any of which can be used in conjunction with the cartridges disclosed herein. For example, a description of frangible seals can be found in U.S. Pat. Nos. 10,183,293, 10,173,215, 9,309,879, 9,108, 192, U.S. Patent Application publication 2017/0157611, and published European Patent Application 3406340 A1, all of which are incorporated by reference herein.

In one implementation, a reagent reservoir is configured to store a wash buffer to form a wash buffer reservoir 1475 (see, e.g. FIG. 70). Wash buffer removes unbound or loosely bound contaminants from a porous solid support while target analyte, e.g. nucleic acids, remain bound to the porous solid support. In one embodiment, the wash buffer reservoir is in direct fluidic communication with the main pneumatic line 1171 such that pressurized air can be sent to the wash buffer reservoir through a wash reservoir inlet 1476 to empty the wash buffer reservoir. The wash buffer exits the wash buffer reservoir through wash outlet 1477 and is transferred to the porous solid support chamber within the rotary valve, thus washing the porous solid support of contaminants. Wash buffer exits the porous solid support chamber, and the wash buffer containing cell debris is then conveyed to the waste collection element 1470.

In another one implementation, a reagent reservoir is configured to store an elution buffer to form an elution buffer reservoir 1500 (see, e.g. FIG. 70). Elution buffer enables the release of target nucleic acids bound to a porous solid support in a sample to form a purified sample. The elution buffer reservoir further includes an elution reservoir inlet 1501 from which pressurized air can enter the elution buffer reservoir to empty the contents. The inlet of the elution buffer reservoir can be in direct fluidic communication with main pneumatic line 1171 to deliver the pressurized air. The elution buffer is emptied from the elution buffer reservoir through an elution reservoir outlet 1502 and flowed over the porous solid support in the rotary valve to release target nucleic acid to produce an eluate, or eluted nucleic acid. In another embodiment, the eluate may subsequently be directed to a rehydration chamber, described in further detail below.

a) Waste Collection Element

The waste collection element 1470 is configured for receiving and storing liquid waste in a secure manner. In some embodiments, the waste collection element 1470 comprises a waste inlet 1471, a vent channel 1472, vent 1473, at least one waste outlet 1474, and outlet filter plug 1478. Accordingly, liquid waste is directed to the waste collection element from channel 1362 through a waste inlet 1472. The waste collection element will include at least one, but preferably more than one, waste outlets in fluidic communication with a vent channel 1472. Multiple waste outlets coupled to the vent channel allow continuous venting in the instance that one or more waste outlets become clogged or obstructed by fluid. In one embodiment, the vent channel terminates at a vent 1473. The vent 1473, optionally, can include an outlet filter plug 1478 configured to capture aerosolized liquid particles that may travel through the waste collection element given the pressurization applied to the device.

In one aspect of the invention, the cartridge uses the force of gravity for retaining fluids within the waste collection element during a diagnostic test run. Active pressurization applied to the cartridge motivates fluids, e.g., the sample, reagents, and air, through the fluidic network of the cartridge. Specifically, liquid waste is directed through channels and enters the to the waste collection element through channel 1362. The vertical orientation of the cartridge within the instrument 2000 allows the waste collection element to be configured as a liquid trap until all incoming and outgoing channels in fluidic communication with the waste collection element are sealed, i.e., heat staked, according to an embodiment described herein. Sealing the channels to and from the waste collection element forms a closed system to prevent liquid waste contained therein to escape the waste collection element regardless of the cartridge orientation.

As mentioned above, sealing the channels leading to and exiting from the waste collection element to retain fluids therein, regardless of cartridge orientation, can be achieved by selectively heat staking a portion of the device. In one embodiment, the cartridge prevents liquid waste from exiting the waste collection element to mitigate contamination control by heat staking channel 1362 leading to the waste collection element and vent channel 1472 in a process described herein. Heat staking the channel 1362 and channel 1472 seals all access channels leading to the waste collection element. In some embodiments, a portion of the cartridge may be configured to include a raised platform 1605 to facilitate heat staking. Further description of the raised platform in context to sealing the cartridge by heat staking is discussed in the sections to follow. In another implementation, the waste collection element can contain a bibulous pad for absorbing liquid waste captured by the waste collection element.

4. Amplification Module

In an additional embodiment, a device comprises an amplification module configured to supply amplification reagents required to perform an assay, amplify nucleic acid from a purified sample and detect a signal indicative of the presence of a target pathogen. The amplification module has a reaction area comprising a plurality of assay chambers of defined volume, each configured to receive nucleic acids, where the said nucleic acids are amplified to yield a greater copy number of the nucleic acid sequence for detection. One or more nucleic acid targets can be read on a chamber-by-chamber basis to permit multiplex amplification and detection. The large number of amplicons generated in nucleic acid amplification poses a threat for contamination to laboratory work surfaces. In some implementations, the amplification module includes a mechanism for amplicon containment.

In various aspects, the amplification module includes one or more rehydration chambers for rehydrating dried reagents with a substance, e.g., a liquid, such as a purified sample. As illustrated in FIG. 70, the cartridge can comprise a rehydration chamber 1520 that accepts nucleic acid solution eluted from the porous solid support of the rotary valve. Referring to FIG. 82, one exemplified rehydration chamber comprises a double tapered chamber which in turn comprises tapered inlet 1521, a tapered outlet 1522, two curved boundaries 1525, and a reagent plug 1523. In certain implementations, a first bounding surface is formed by the fluidics card 1001, and a second bounding surface is formed by a plug. The plug comprises a body and a cap. The body of the plug protrudes into the fluidics card 1001 of the rehydration chamber 1520 to form the second bounding surface of the rehydration chamber. In further embodiments, one or more films form a third bounding surface of the rehydration chamber such that the first bounding surface, the second bounding surface, and the third bounding surface together enclose the rehydration chamber volume. In some embodiments, the plug cap comprises an internal cavity 1774 configured to hold one or more dried amplification reagents for use in an assay to take place in the assay chambers, described in greater detail in the following section. Additionally, a magnetic mixing element may be located in the rehydration chamber to facilitate actuation of an assay in the assay chamber. In one implementation, the magnetic mixing element is a magnetic ball 1524.

In various embodiments, the amplification module of the cartridge comprises one or more assay chambers 1621 configured to detect a signal indicative of target amplicon generated from the nucleic acid. Referring to FIG. 70, the assay chambers are located within the reaction area 1600 and are visible to the reaction camera 2701 of the reaction imaging assembly 2700.

In one implementation, the assay chambers 1621 comprise a double tapered chamber which in turn comprises tapered inlet 1641, a tapered outlet 1642, two curved boundaries, and a reagent plug 1770. In certain embodiments, the assay chamber comprises a first bounding surface formed in a monolithic substrate (i.e., fluidics card 1001), and a second bounding surface formed by a plug. The plug comprises a body and a reagent surface. The body of the plug protrudes into the monolithic substrate of the assay chamber at a depth such that the assay chamber volume can be readily changed by altering the depth at which the body of the plug protrudes into the monolithic substrate of the assay chamber. In particular, the reagent surface of the plug forms the second bounding surface of the assay chamber. In further embodiments, a film may form a third bounding surface of the assay chamber such that the first bounding surface, the second bounding surface, and the third bounding surface together enclose the assay chamber volume. In some embodiments, the plug reagent surface comprises an internal cavity 1774 configured to hold one or more dried reagents for use in an assay for a diagnostic test to take place in the assay chamber.

With regard to FIGS. 83A and 83B, in some embodiments, the plug further comprises a flange 1773 that can be welded and/or adhered to a surface of the assay chamber to stabilize the position of the plug body within the opening of the fluidic card of the assay chamber. The plug body further includes a central opening 1777 with a side wall 1778 and a bottom surface 1776. The plug protrudes into the monolithic substrate at a depth such that the component of the plug that is visible on the exterior of the assay chamber is the surfaces of the central opening of the plug. In embodiments in which the plug cap includes a flange, the flange is also visible on the exterior of the assay chamber as shown in FIGS. 83A and 83B. FIG. 83A is a cross section view of an assay chamber taken through the tapered inlet 1622 and the tapered outlet 1632 which shows the plug flange 1753 supported by a raised annulus 1797 integrally formed within a fluidics card 1001. FIG. 83B is a cross section view of an assay chamber taken through the midpoint of the assay chamber showing the flange supporting the plug and the double tapered sidewalls towards the inlet.

In some embodiments, such as embodiments in which the assay chamber is used to contain an assay, the plug is transparent such that the assay within the assay chamber is optically detectable from outside of the assay chamber. FIG. 84 shows a signal indicative of the presence of target nucleic acids from a target pathogen viewed through a transparent plug as described herein. In a preferred embodiment, the signal visible through the transparent plug is a fluorescent signal. Alternatively, the signal visible through the transparent plug is a colorimetric (i.e. color change) signal.

The one or more dried reagents, used in combination with a plurality of assay chambers, enables multiplexing to test a sample for the presence of more than one target nucleic acid. The cartridge exemplified herein can achieve multiplexing through several methods. First, the cartridge can comprise a plurality of assay chambers, with each chamber comprising primers and probes specific to a different target pathogen or process control. Additionally, a single assay chamber can comprise multiple primer/probe sets, each set specific to a different target pathogen or process control. The probe for each different target can be differentiated by the signal generated by the probe. For example a single assay chamber can contain a first primer/probe set in which the probe comprises a Texas Red fluorophore and a second primer/probe set in which the probe comprises a fluorescein (green) fluorophore. A wide variety of fluorophores are known in the art, as well as the mechanisms and filters one can use to differentiate signals from multiple fluorophores in the same assay chamber. In one implementation, the plurality of assay chambers can detect the presence of up to 3 target nucleic acids. In one implementation, the plurality of assay chambers can detect the presence of up to 5 target nucleic acids. Similarly stated, in some embodiments, the assay chambers can produce a visible signal, wherein the visible signal is associated with the presence of the target amplicon and/or target pathogen.

In some implementations, it may be desirable to fill the assay chambers simultaneously regardless of the assay chamber fluid volume. In such implementations, one or more air chambers 1631 are included in a cartridge to balance a ratio of the volume of the assay chamber to the volume of the air chamber to fill simultaneously (FIG. 70). For example, air chambers may be described in U.S. Pat. No. 10,046,322, titled "Reaction Well for Assay Device" and assigned application no. PCT/US19/23764, all of which are incorporated herein by reference. The invention contemplates cartridges having assay chambers that differ in volume, see for example, the assay chambers 1621 illustrated in FIG. 70. In such embodiments, each assay chamber will be associated with its own air chamber. In order to achieve concurrent filling of each assay chambers that differ in volume, the ratio of the assay chamber volume to its associated air spring volume will be approximately the same for each assay chamber/air spring pair on the cartridge.

In an alternative embodiment, the above described features, characteristics and functionality of the various the reagent plug 1523, plug cap or plug 1770 embodiments may be provided by an plug that similarly forms part of an associated assay chamber without extending into the diagnostic cartridge as in FIGS. 82, 83A, 83B, 84, 88 and 89. In contrast, these alternative reagent plugs embodiments may be positioned in a planar or raised aspect to the assay chamber or other associated component. In one variation the plug functionality is provided by a capsule design that is raised above surface of the diagnostic cartridge. Additionally or optionally, the capsule style plug may be mounted to the surface of diagnostic cartridge with appropriately shaped raised or recessed support elements to aid in readily mounting the capsule plug in position. The capsule plug mounts may provide appropriately sized and shaped raised or recessed mounting features similar to the plug cap flange 1773. Appropriate capsule plug flanges or mounting features may be incorporated which ensure placement of the capsule relative to the assay chamber or other chamber while ensuring appropriate fluidic communication relative to inlets, outlets or other conduits associated with the chamber.

As a result, in general, in one embodiment, an integrated diagnostic cartridge includes a loading module, a lysis module, a purification module, and a reaction module. The reaction module includes a reagent storage component including a capsule capable of holding a liquid or solid sample. In one embodiment the capsule includes an opening, a closed end and a wall extending from the closed end to the opening. The capsule is oval-shaped and the wall is rounded, and the closed end and wall define an interior volume having a substantially smooth surface.

In still another alterative capsule style plug embodiment, there is an integrated diagnostic cartridge includes a loading module, a lysis module, a purification module, and a reaction module. The reaction module includes a capsule capable of holding a liquid or a solid sample. The capsule includes an inner surface extending from the bottom of said capsule to an oval-shaped opening at the top of the capsule, wherein said inner surface is substantially smooth and includes a concave shape extending from the bottom of the capsule, and a planar layer affixed around the oval-shaped opening of said capsule and oriented in the same plane as the oval-shaped opening of said capsule. The planar layer includes a top surface and a bottom surface. The top surface is aligned with the inner surface of said capsule at said oval-shaped opening to provide a continuous surface.

This and other capsule style plug embodiments may include one or more of the following features. The capsule can be capable of holding a volume from approximately 50 μL to approximately 200 μL. Still other embodiments provide for an oval-shaped opening contained within an area of 9 mm×9 mm. Still further, the capsule can include a dried reagent as described elsewhere in this specification. Additional details of these and additional embodiments are provided in Published International Patent Application WO 2018/111728 entitled "Capsule Containment of Dried Reagents" having International Application Number PCT/US2017/065444 filed on Dec. 8, 2017, incorporated herein by reference. In particular, the details of the embodiment of the capsule plug configuration illustrated and described with regard to FIG. 6 as well as the contents of paragraphs [0149-0152] are incorporated herein specifically.

The cartridge of the invention can be configured to be heat sealed in order to maintain sample within each assay chamber. In one implementation, the configuration of the main loading channel 1671 may consist of a u-bend 1607 (FIG. 85). By sealing off a connection between a main channel 1671 and any loading channels 1672, the loading channel, assay chamber 1621 and air chambers 1631 form a completely closed system from which matter cannot travel in or out, and for which, internal pressure within the assay chamber, loading channel, and air chamber remains constant, unless the environment is substantially changed, e.g. by heating the cartridge. One acceptable method of sealing the loading channels 1672 is heat staking with a heated element such that the loading channels are sealed off from the main channel. In one implementation of the method, the heated element is heat staker assembly 2640 of instrument 2000. Note that the supply pressure of the fluid sample is maintained during the heat staking process.

In some embodiments, as described herein, a first film is adhered to the fluidics side 1006 of a fluidics card 1001, such that the first film forms one wall of the main channel and loading channels. In one implementation the first film has a similar melting point as the substrate of the device. In further embodiments, a second film is adhered to the first film. In such embodiments, the second film has a higher melting point than the first film and the surface of the device such that when heat is applied to the device via the heat staker assembly 2640 to heat stake the loading channel, the first film and the surface of the device melt prior to the second film. This higher melting point of the second film prevents the pressurized sample from escaping from the loading channels, thus emptying assay chambers, as the first film and the surface of the device re melted. The result of this heat staking process is a melted first film, which forms a heat stake 1603 seen in FIGS. 101 and 102.

In some embodiments, the fluidics card 1001 can further include a raised platform 1605 within each of the loading channels 1672 such that, the raised feature is positioned between an inlet to the assay chamber and the main channel. The heat staked region can be formed using a portion of the raised platform, as depicted in FIGS. 85, 86, and 87. In various implementations, the raised platform may further extend throughout a fluidics card 1001 to include one or more channels from different modules. For example, the raised platform may extend to include channel 1362 leading to the waste collection element and vent channel 1472 exiting the waste collection element as seen in FIG. 88. In such a configuration, the heat staker assembly 2640 contacts the main channel 1671, each of the plurality of loading channels 1672, u-bend 1607, channel 1362, and vent channel 1472 to selectively melt these areas of the cartridge to form closed systems.

5. Example Cartridge a) 4 Module Cartridge—Sample Prep+Amp

FIG. 89 is an exploded view of the exemplary cartridge illustrated in FIGS. 69 and 70, configured for a disposable, single use diagnostic test. The cartridge, according to the exemplified embodiment, comprises a loading module, a lysing module, a purification module, and an amplification module. Cartridge 1000 comprises a fluidics card 1001, wherein the fluidics card further comprises a fluidic side 1006 and a feature side 1007, a first film 1002, a second film 1003, and a cartridge cover 1004. The loading module, lysing module, purification module, and amplification module are integrally formed, e.g., molded, within the fluidics card 1001 to provide the structures necessary to perform each sample processing step for a diagnostic test. In some embodiments, the cartridge is between 150 and 200 mm long, 75 mm to 100 mm wide and 10 to 30 mm tall. The cartridge can be 175 to 200 mm long, 80 to 90 mm wide and 10 to 20 mm tall. In a particularly preferred embodiment, as illustrated in FIG. 70, the cartridge is approximately 180 mm long, about 90 mm and about 12 mm tall.

The loading module is configured to accept and seal a sample. As described herein, the loading module is configured to define a metered sample and comprises an entry port 1140, a fill chamber 1101, a metering chamber 1110 and an overflow chamber 1120. Such a configuration defines the volume of the sample and can accommodate for excess sample loaded into the fill chamber by directing the excess sample to the overflow chamber.

The lysis module is configured to lyse a metered sample generated by the loading module. The lysing module produces a lysed sample upon mixing a sample in the lysis chamber 1371 with one or more lysis reagents and subsequently produces a filtered lysate after flowing the lysed sample through a filter assembly 1330. The lysis chamber 1371 formed within the fluidics card 1001 is configured to hold a stir bar 1390 to mix the metered sample with a substance contained therein, e.g., lysis buffer, to disrupt the cell wall and/or outer membrane of cells. Lysing a sample releases the contents of cells including various organelles, proteins, and nucleic acids. As exemplified, the lysing module includes a filter assembly 1330 through which the lysed sample flows. The filter assembly is fluidically downstream from the lysis chamber 1371 to filter a lysed sample. An inlet via 1332 allows the lysed sample to enter the filter assembly where filter 1331 is configured to filter the lysed sample of cellular debris and other contaminants. Flow directors 1334 direct a filtered sample to the outlet, wherein outlet via 1333 enables the filtered sample to exit the filter assembly and be directed to amplification module.

In cartridges described herein, the purification module is configured to purify a filtered sample to capture nucleic acids associated with a suspected target pathogen. As exemplified, the purification module includes a rotary valve 1400 comprising a porous solid support 1445. In such a configuration, the porous solid support 1445 allows a filtered lysate to flow through the porous solid support 1445 to capture nucleic acids while passing proteins, lipids and other cell debris. The purification module includes a waste collection element 1470 to which liquid waste from the filtering module and purification module is conveyed. In this embodiment, the waste collection element 1470 comprises an output filter plug 1478 configured to capture aerosolized liquid particles, thus avoiding contamination of the instrument or laboratory environment. Furthermore, the waste collection element 1470 is configured to be sealed off to not cause any other areas of the cartridge or the inside of instrument 2000 to be contaminated by previously used substances, e.g., liquids, such as the sample or wash buffer. Another feature of the purification module, reagent reservoirs, are formed within the fluidics card 1001 to for on-board storage of liquid substances, including a wash buffer and an elution buffer. Prior to operation of the cartridge, the reagent reservoirs are sealed by frangible seals to form closed systems to prevent the cartridge from being fluidically activated until actuated at the time of the diagnostic test.

In the exemplified cartridge, the amplification module provides a plurality of assay chambers 1621 such that the amplification module can perform an isothermal nucleic acid amplification on the sample deposited into the loading module. In this embodiment, each of the assay chambers is a double tapered chamber which comprises tapered inlet 1641, a tapered outlet 1642, two curved boundaries, and a reagent plug 1770. In some embodiments, the plug cap comprises an internal cavity 1774 configured to hold one or more dried reagents for use in an assay for a diagnostic test to take place in the assay chamber. In such embodiments, the one or more dried reagents are configured to produce a visual signal, e.g., fluorescent signal, to indicate the presence of nucleic acids from a target pathogen within the sample. The reagent plugs are configured to be transparent such that the assay within the assay chamber 1621 is optically detectable from outside of the assay chamber.

As exemplified, the cartridge includes a rehydration chamber 1520 and a portion of the cartridge is configured to be heat staked, as described above. The rehydration chamber comprises tapered inlet 1521, a tapered outlet 1522, two curved boundaries, and a reagent plug 1770. The reagent plug of the rehydration chamber comprises an internal cavity 1774 configured to hold one or more dried reagents. A portion of the cartridge includes a raised platform feature 1605 to heat stake a cartridge to maintain the sample level in the plurality of assay chambers therein without active pressurization. As described herein, heat staking seals the assay chambers 1621 and the waste collection element 1470 from the remainder of the features of the cartridge and from the outside environment. Specifically, a portion of the main channel 1671, loading channels 1672, channel leading to the waste collection element 1362, and the vent channel 1472 exiting the waste collection element are configured to include a raised platform feature 1605 to melt the two films attached to the fluidics side of a fluidics card to retain liquids therein.

b) 3 Module Cartridge—Sample Prep

An alternate configuration of the cartridge is depicted in FIG. 92 In this alternative configuration, the device comprises a loading module, a lysing module, and a purification module configured to receive a sample, lyse cells in the sample, and subsequently purify nucleic acids from the sample. This cartridge configuration is intended to be used as a sample preparation device and is not configured to perform a nucleic acid amplification test, not to report an assay result. This sample preparation-inly configuration can be processed using an assay instrument as described herein, or on an abbreviated sample-preparation instrument that lacks the chemistry heater assembly and the reaction imaging assembly.

In such sample preparation embodiments, the loading module is configured to accept and seal a sample. As described herein, the loading module is configured to define a metered sample and comprises an entry port 1140, a fill chamber 1101, a metering chamber 1110 and an overflow chamber 1120. Such a configuration defines the volume of the sample and can accommodate for excess sample loaded into the fill chamber by directing the excess sample to the overflow chamber 1120.

The lysis module, in some embodiments, is configured to lyse a metered sample generated by the loading module. The lysing module produces a lysed sample upon mixing a sample with one or more lysis reagents in the lysis chamber 1371 with a stir bar 1390 as described above. In the sample preparation cartridge, the lysing module may further include a filter assembly 1330 to produce a filtered lysate after flowing the lysed sample through a filter assembly.

The purification module of the sample preparation cartridge, similar to a standard assay cartridge, is configured to purify a filtered lysate to enrich nucleic acids. For example, the purification module includes a rotary valve 1400 comprising a porous solid support 1445. The porous solid support 1445 allows a filtered lysate to flow through the porous solid support 1445 to capture nucleic acids while passing proteins, lipids and other cell debris therethrough. The purification module includes a waste collection element 1470 to which liquid waste from the purification module is conveyed. Another aspect of the purification module, reagent reservoirs, are formed within the fluidics card to for on-board storage of liquid substances, such as a wash buffer and an elution buffer. The sample preparation cartridge will include one or more frangible seals to seal reagent reservoirs, allowing the cartridge to be fluidically inactive, until actuated by a system, such as instrument 2000 described herein.

This embodiment of the device, as described herein, further comprises a retrieval port for retrieving a purified sample from the device. In some implementations, the retrieval port comprises a cap, similar to the cap 1181 configured to cover entry port 1140 of the loading module. Preferably the cap of the retrieval port is configured to be opened to permit retrieval of a purified sample and then resealed prior to disposal of the device. Alternatively, the sample can be retrieved via a puncturable septa or large one-way valve. In some implementations, the retrieval port is enclosed with a film that is cut, punctured or otherwise ruptured to permit access to the purified nucleic acid. The sample preparation system can include a sample loader, such as a bulb or syringe, useful for retrieving a purified sample from the device.

Since the sample preparation cartridge does not require any structures related to the amplification module, a sample preparation cartridge having the same dimensions as a test cartridge and designed to be run on an assay instrument can process larger volumes than the corresponding test cartridge. As illustrated in FIG. 92, the waste collection element can be expanded to accept larger volumes of sample, lysis reagent, and/or wash buffer. As described above, the capacity of the sample preparation cartridge can be further augmented by increasing the thickness of the cartridge.

H. Methods of Use—Cartridge

The cartridge, and any of the cartridges described herein, can be configured for use in a decentralized testing facility. In a further embodiment, the device can be a CLIA-waived device and/or operate in accordance with methods that are CLIA-waived. FIGS. 93 to 102 depict one exemplary method that can be used to prepare a biological sample to amplify nucleic acid and detect the presence of a suspected pathogen in a diagnostic test using one embodiment of a cartridge 1000, as described herein. The features of the cartridge used to perform the method for a diagnostic test is depicted in FIG. 93. The relative size of the features and the routing between features is for illustration of the method and are not to scale. Each step is summarized in the Table 1 below. Various processing steps and alternative embodiments are discussed in greater detail below.

TABLE 1

Cartridge Test Method Steps

| Step | FIG. | Method |
|---|---|---|
| 0 | 93 | Load Sample |
| 1 | 94 | Cartridge Preparation |
| 2 | 95 | Lyse and Mix Sample |
| 3 | 96 | Filter and Bind Lysed Sample |
| 4 | 97 | Wash Bound Sample |
| 5 | 98 | Air Dry |
| 6 | 99 | Elute and Meter Purified Sample |
| 7 | 100 | Load Reaction Chambers |
| 8 | 101 | Heat Stake |
| 9 | 102 | Assay |

FIG. 93 illustrates the state of a cartridge after a biological sample is loaded into the sample port assembly 1100, prior to insertion into an instrument and/or prior to actuation of any cartridge features by the instrument. Frangible seal 1201 is configured to maintain the sample within the sample port assembly. Frangible seals 1202 and 1205 are configured to maintain a lysis agent solution within the lysis chamber 1371. Frangible seals 1203 and 1204 are configured to maintain wash buffer within the wash buffer reservoir 1475. Frangible seals 1206 and 1207 are configured to maintain elution buffer within the elution buffer reservoir 1500. Prior to insertion into and actuation by the instrument, all of the frangible seals 1201-1207 remain intact. The rotary valve 1400 is positioned such that the rotor and stator are not in contact (indicated by dashed outline of the rotary valve feature in FIG. 93). In FIGS. 93-102, channels that conduct only air (pneumatic pressure) are indicated by dashed lines. Channels that conduct fluids are indicated by solid lines. When the fluid channels are active, i.e. subject to a motive force, such as pneumatic pressure, the solid lines 'bolded' (indicated with thicker solid lines as compared to inactive channels). Liquid within features of the cartridge is indicated by waved patterning within the relevant feature. Dried reagents are depicted with speckled patterning.

The cartridge is inserted into instrument where cartridge verification tests are performed to ensure the cartridge is suitable for use and certain cartridge preparation steps are performed. The rotary valve 1400 is moved into operational configuration and the cartridge is clamped by the clamping subsystem. The frangible seals 1201-1207 are ruptured with pins in the instrument. After rupture, the fluidic channels are no longer physically blocked and fluids within the cartridge are free to flow when exposed to a motive force. Rotary valve 1400 is rotated 360 degrees and indexed to a zero valving position to begin the series of sample processing steps. FIG. 94 illustrates the status of the cartridge features after these cartridge preparation steps are completed. All of the fluids remain in their original positions, as no motive force has yet been applied to the cartridge features.

Next, sample is transferred from the sample port assembly to the lysis chamber 1371 to effect lysis of any cells, including any suspected pathogen, contained in the sample. Pneumatic pressure is applied to the main pneumatic via 1193, permitting air to flow through the liquid trap 1145 positioned in the main pneumatic line 1171 and to the frangible seals. Rotary valve 1400 remains in the zero valving position to dead-end fill the lysis chamber 1371 under pressure. The instrument pressurizes the cartridge to transport sample through exit port 1180, frangible seal 1202, sample transfer channel 1386 and into the lysis chamber 1371. Pressure is applied to the cartridge while magnetic mixing assembly 2300 mixes the sample with lysis buffer by effectuating a magnetic coupling between the driving magnet system 2310, driven magnet system 2350, and stir bar 1390 contained in the lysis chamber 1371 to produce a lysed sample. The pressure applied to the cartridge is turned off after the sample is mixed for a set period. Due to the vertical orientation of the cartridge, the liquid lysate settles to the bottom of the lysis chamber and does not back flow toward the sample loading assembly when the lysis chamber is no longer under pressure. FIG. 95 illustrates the status of the cartridge features after the lysis steps are performed.

After the lysis step, the rotary valve 1400 is indexed to a first valving position, thereby fluidically connecting the empty sample loading assembly 1100, lysis chamber 1371, filter assembly 1330, via 1370 in fluidic communication with the solid support chamber of the rotary valve, and the waste collection element 1470. This alignment of features permits filtering of the lysed sample and binding of target analyte, e.g. nucleic acid, to a porous solid support located in the rotary valve. Pressure applied at the main pneumatic via provides a motive force. The lysed sample exits the lysis chamber 1371 through exit channel 1388 passing through frangible seal 1205. Lysed sample advances to filter inlet via 1332 and flows through filter 1330 to produce a filtered sample. The filtered sample exits filter outlet via 1333 and into channel 1361 before entering the solid support chamber of the rotor using via 1370. The filter assembly captures and removes undesired cellular material and debris that may clog the porous solid support to generate a filtered sample. As the filtered sample passes through the porous solid support contained within the solid support chamber, target analyte, e.g. nucleic acid, is bound to the porous solid support. The remainder of the filtered sample, e.g., proteins, lipids, or carbohydrates, exits via 1372 and flows through channel 1362 to waste collection element 1470. Optionally, pressure applied to the cartridge is turned off when the pneumatic subsystem detects pushing the filtered sample over the porous solid support is complete. FIG. 96 illustrates the status of the cartridge features after the filtration and binding steps—the lysis chamber 1371 is empty, and fluid has passed to the waste collection element 1470.

In order to remove unbound or loosely bound contaminants from a porous solid support while continuing to bind the target analyte, e.g. nucleic acids, a wash buffer is passed through the porous solid support to remove the contaminants. In an exemplary embodiment, the porous solid support is a silica resin and the wash buffer is an aqueous alcohol solution. The rotary valve 1400 is indexed to a second valving position to flow wash buffer from the wash buffer reservoir over the matrix. Pneumatic pressure is applied to the main pneumatic via 1193. Wash buffer contained in wash buffer reservoir 1475 is pressurized to pass through frangible seal 1204, wash inlet via 1460, and porous solid support thereby removing undesired contaminants while target analyte remains bound. Wash buffer carrying contaminants travels through the wash outlet via 1461 and channel 1362 where it is directed to waste collection element 1470. FIG. 97 illustrates the status of cartridge features after completion of the wash step.

In implementations using a wash buffer containing volatile components, such as alcohol, the excess wash buffer occupying the dead volume of the column advantageously is removed prior to releasing bound analyte by air drying the porous solid support. To execute such a step, the rotary valve 1400 is indexed to a third valving position permitting pressurized air to flow over the porous solid support through main pneumatic line 1171. Pneumatic pressure is applied to the main pneumatic via 1193, passes through the pneumatic line 1177 to air inlet via 1462 on the rotor thereby drying the porous solid support removing residual volatile components of the wash buffer from the porous solid support. Air exits the solid support chamber through air outlet via 1463 and channel 1362 where it is directed to waste collection element 1470 and ultimately to a vent 1473. Due to the vertical orientation of the waste collection element, having the inlet and outlet along the upper boundaries of the element, passing air through the waste collection element does not disturb fluid waste already stored in the waste collection element. Further to avoid accidental release of fluidic contaminants from the cartridge, the vent 1473, optionally includes an outlet filter plug which is configured to capture aerosolized liquid particles that may travel through the waste collection element. FIG. 98 illustrates the status of cartridge features after completion of the air dry step.

The bound analyte, e.g. nucleic acid, is then released from the porous solid support. To effect release, the rotary valve 1400 is indexed to a fourth valving position thereby fluidically connecting the elution buffer reservoir 1500 to the porous solid support and then to the rehydration chamber 1520. Elution buffer exits the elution buffer reservoir 1500 through channel 1551, frangible seal 1206, channel 1552, elution inlet via 1503 and then over the porous solid support to release target analyte, thereby generating a purified analyte solution, e.g. an enriched nucleic acid solution. The purified analyte solution exits eluate outlet via 1504 and is directed to the rehydration chamber 1520 using channel 1553. The fourth valving position fills the rehydration chamber while simultaneously metering the purified sample to a produce a desired volume. The purified sample fills beyond the rehydration chamber and into channel 1554, where the purified sample passes two vias, 1580 and 1581, before flowing through metering via 1582 to fill metering channel 1557 up against a metering vent 1560. Metering, while optional, is advantageous to avoid generating an overly dilute solution when the dried reagents are rehydrated. While pressure remains on, magnetic element in the instrument rotates causing a magnetic ball with the rehydration chamber to gyrate, thereby assisting dissolution and homogenization of dried down reagents with the purified analyte solution. Completion of this step generates an analyte/reagent solution. The pressure applied to the cartridge can be after the metering step is competed. FIG. 99 illustrates the status of cartridge features after the elution and metering step.

The analyte/reagent solution is now ready to be passed to the assay chambers. The rotary valve 1400 is indexed to a fifth valving position to load the assay chambers within the cartridge reaction area 1600. Pneumatic pressure is applied to pneumatic via 1194, thereby pressuring pneumatic line 1178 and vias 1192 and 1580. The pressurized air subsequently travels through channel 1554 to push the analyte/reagent solution through channel 1553 to main channel 1671 and then loading channels 1672 (not shown), where the analyte/reagent solution is split and distributed to a plurality of assay chambers in the reaction area 1600. The cartridge remains pressurized after all assay chambers are successful loaded. FIG. 100 illustrates the status of cartridge features after loading the reaction chambers.

While it is possible to perform an assay maintaining the analyte/reagent solution in the assay chambers with pneumatic pressure, it is preferable to physically isolate each of the assay chambers from the others to avoid cross-contamination as well as to isolate the reaction from the outside environment. Such isolation is particularly advantageous when performing nucleic acid amplification reactions, as amplicon contamination is a well understood risk of such methods. To isolate the assay chambers, rotary valve 1400 remains in the fifth valving position during the heat stake process and pneumatic pressure continues to be applied to the pneumatic via 1194. The instrument heat stakes the cartridge under pressure by melting a selected area of the cartridge across the assay chambers, loading channels, as well as, channel 1362 leading to the waste collection element 1470, and venting channel 1472 exiting from the waste collection element to produce heat stake 1603. The heat stake is illustrated in FIG. 101 with a very heavy straight line across the channels. Heat stake 1603 seals each of the effected channels and functions to contain amplified nucleic acids and minimize the threat of contamination when performing a diagnostic test. FIG. 101 illustrates the status of cartridge features after heat staking.

Finally, the cartridge is ready to perform a diagnostic test. Since the analyte/reagent solution is safely contained within the reaction chambers, pneumatic pressure is no longer required in the cartridge. Pneumatic pressure is released from pneumatic via 1194. The rotary valve remains indexed to the fifth valving position. FIG. 102 illustrates the status of cartridge features after release of pressure and during the assay step. The cartridge 1000 can be configured to produce the visibly detectable signal within about 30 minutes, more preferably within about 25 minutes, and most preferably within 20 minutes or less, from when the sample is received by the loading module. Since the reacted analytes and waste are contained by the heat stake, the cartridge can be disposed without any further processing by the instrument or user.

I. Methods of Use—Instrument

FIGS. 106A-106E illustrate a detailed process flow chart of a method 100 running a diagnostic test executed the instruments, as described herein. The method begins at 110 after insertion of a cartridge into the instrument to conduct a diagnostic test. Latch and pin assembly 2210 drops latch 2212 into notch 1021 at the top of the cartridge to prevent the cartridge from being ejected by the loading assembly 2230. The instrument verifies that a cartridge is inserted at 110 using an load position sensor 2236 located within the loading assembly 2230. The cartridge is verified to be in a loaded position within the instrument when flag 2237 is detected by the load position sensor. At step 112 instrument 2000 scans a cartridge ID code indicating the type of test to be run on the cartridge. The label imaging system 2770 illuminates and captures an image of the patient label area during this step. At 114 the instrument displays the image of the patient label and the type of diagnostic test about to be run on a graphical user interface (GUI). At step 120, the user is given the option to abort the test run, e.g. if the wrong cartridge was loaded. The instrument aborts a diagnostic test when the user elects to abort the test at 122. In one implementation, the GUI requires user input to proceed in running the diagnostic test diagnostic test. In an alternative implementation, the method proceeds in the absence of user input within a set period of time, e.g. 10 seconds.

When the method proceeds, the instrument begins the clamping sequence to perform a series of verification checks to confirm the inserted cartridge is unused and suitable to run a diagnostic test. Instrument 2000 first establishes a zero clamping position to set the reference point from which all other clamping positions are measured from. The moving bracket assembly 2040 moves in a negative direction until tab 2047 triggers sensor 2017 fixed to the bottom of the fixed support bracket 2011. When sensor 2017 is triggered, the moving bracket assembly subsequently moves a calibrated distance in the positive or negative direction to define the zero clamping position at 124. The instrument turns the linear actuator 2014 on to rotate the lead screw 2016 in a first rotational direction, such that rotating the lead screw pulls the moving bracket assembly 2040 toward the fixed bracket assembly 2010 in a positive linear direction to a first clamping position, shown by 126. In the first clamping position, the valve drive assembly 2400 contacts the rotary valve on a cartridge and light frame 2686 of the thermal clamp assembly 2680 contacts the reaction area 1600. A first rotary valve verification test on the rotary valve 1400 is performed in the first clamping position. At step 130, the first verification test checks that the rotary valve is in the shipping configuration. As described herein, rotary valves with prematurely dropped rotors pose the risk of leaking due to gasket deformation from compressing a gasket for long periods of time prior to immediate use. In this embodiment, the rotary valve 1400 is configured for a shipping configuration to prevent the gasket from sealing against the stator until the time of operation. The valve drive assembly 2400 checks the shipping configuration of the rotary valve 1400 by using an interference sensor 2404 and the end of the valve drive shaft 2405. The valve drive shaft will not trigger the interference sensor, indicating the rotary valve is in shipping configuration, when valve drive pins 2402 mate correctly with engagement openings 1417 on the rotary valve. In this instance where the valve is confirmed to be in shipping configuration, the instrument proceeds with the next step of the method 134 to drop the rotor. An error is detected when the end of the valve drive shaft 2405 triggers the interference sensor at 132. Triggering the interference sensor is indicative of the rotary valve not in a shipping configuration. Conditions that trigger an error include valve drive pins not fully inserted into engagement openings or failure to be inserted at all. This condition renders the cartridge unusable. The instrument aborts the test at step 132, displaying a shipping configuration error to the GUI and unclamping the cartridge for ejection.

After the rotary valve is confirmed to be in the shipping configuration the valve drive assembly rotates to drop the rotor at 134 to transition the valve from a shipping configuration to an operational configuration. Rotating the rotary valve drops the rotor, as described herein, off the threaded retention ring to seal the gasket between the rotor and stator. At step 140 the instrument executes a second rotary valve verification test to determine the valve drop state. The valve drive assembly 2400 checks the state of the rotary valve using the interference sensor to confirm a successful rotor drop. The valve drive shaft will not trigger the interference sensor, indicating a successful rotary valve drop and proceeds onto step 144 to move the moving bracket assembly 2040 to a second clamping position. When the interference sensor is triggered, indicating an unsuccessful valve drop, the instrument aborts the test at step 142, displaying a failed valve drop error at the GUI and unclamping the cartridge for ejection.

The moving bracket assembly 2040 moves in the positive direction to the second clamping position 142 at which hard stops 2211 contact the first surface of the fixed bracket assembly 2010. At step 150, the instrument confirms sensor 2019 is triggered by the hard stops 2211. The second clamping position is the largest displacement in the positive direction the clamp block 2041 moves in this exemplified method. In the second clamping position, the door support assembly 2280 presses against cap 1181, pneumatic interface 2100 forms a pneumatic seal with the pneumatic interface cover adaptor 1172, thermal clamp assembly 2680 is engaged and light frame 2686 forms a seal around the reaction area 1600, and the valve drive 2401 remains engaged with rotary valve 1400. An error is detected when sensor 2019 is not triggered by hard stops 2211 contacting the first surface of the fixed support bracket at 152. Failing to trigger the hard stop sensor indicates the moving bracket assembly 2040 unsuccessfully clamped the cartridge. The instrument aborts the test at step 152, displaying a failed hard stop error at the GUI and unclamping the cartridge for ejection. Completion of all rotary valve verification tests and successful clamping of the cartridge, as indicated by sensor 2019, signals instrument may begin the fluidic sequence portion of the method.

At steps 154 and 156, the valve drive assembly 2400 of the instrument rotates the valve 360 degrees (step 154) and then indexes the valve to a zero valving position (step 156) using homing sensor 2409. The rotary valve is configured to seal off all inlet vias and outlet vias in the fluidics card in zero valving position, such that no fluidic communication is permitted. This configuration allows the instrument to perform a pneumatic leak test, step 160. The instrument pressurizes the cartridge and ensures no pneumatic flow is detected. An error is detected if the pneumatic subsystem detects any pneumatic flow, thus indicating a pneumatic leak is present within the cartridge. Such a pneumatic leak renders the cartridge unreliable and/or unusable. The instrument aborts the test at step 162, displaying a pneumatic leak error at the GUI and unclamping the cartridge for ejection. If no pneumatic leaks are detected, the instrument has completed the cartridge verification tests, indicating that the cartridge is competent to perform the diagnostic assay.

At step 164 of the method (see FIG. 106B), the frangible seal block 2260 moves in a positive direction to a third clamping position to break all frangible seals on the cartridge with frangible seal pins. The frangible seal block is permitted to move in the positive direction until hard stop 2263 contacts upper rail 2231 of the loading assembly 2230. In the third clamping position, the clamp block 2041 and all assemblies (i.e. door support assembly 2280, pneumatic interface 2100, valve drive 2400, and thermal clamp 2680) remain stationary in the second clamping position due to hard stops 2211 contacting the first surface of the fixed support bracket 2012. As described herein, the frangible seal block 2260 and the clamp block 2041 are separate components mechanically coupled by linear slide 2264. This configuration separates the clamping action from the actuation of frangible seals enabling the instrument to perform rotary valve verification tests prior to rendering the cartridge fluidically active. When the frangible seal block 2260 is moved in the positive direction to a third clamping position at 164, all frangible seals are punctured. In an alternative embodiment, frangible seal pins can be varying in length to allow frangible seals to be punctured in a sequence when the frangible seal block is moved to different positions in the positive direction. At step 200 the instrument confirms frangible seals are broken using sensor 2266. An error is detected if sensor 2266 on the frangible seal block is not triggered. This condition renders the cartridge unusable due to frangible sealing failing to be actuated, indicating that one or more flow paths within the cartridge are obstructed by an unruptured seal. The instrument aborts the test at step 202, displaying a frangible seal actuation error at the GUI and unclamping the cartridge for ejection. Upon successful completion of steps 164 and 202, frangible seals are fluidically active and the cartridge is ready to begin sample preparation of a sample suspected of containing a target pathogen at step 204.

To begin sample preparation, the pneumatic subsystem pressurizes the cartridge using alternating periods of applied pressure and zero pressure to draw the sample from the fill chamber 1101 and into the metering chamber 1110 at 204. Camera 2271 of the label imaging assembly 2770 illuminates the sample window 1050 and confirms adequate sample volume is loaded into the cartridge at step 210. The instrument detects the presence of a ball 1114 present in the metering chamber 1110 to determine whether adequate sample volume is present. An error is detected when the instrument fails to identify the presence of the ball at a location indicating a sufficient sample volume is present in the metering chamber. The instrument aborts the test at step 212, displaying an insufficient sample volume error at the GUI and unclamping the cartridge for ejection.

If sufficient sample volume is present, the instrument proceeds with pressurizing the cartridge to empty the loading module 214, forcing the sample into the lysis chamber 1371, which already contains a lysis buffer comprising at least one chemical lysis agent. The instrument pressurizes the cartridge for a set period to transfer the sample from the metering chamber into the lysis chamber at 214. The lysis chamber is filled by pneumatic pressure against a dead-end provided by the zero valving position of the rotary valve, which remains stationary when performing the lysing step. This configuration enables the instrument to perform a pressure maintenance check for a constant pressure profile reading seen at step 300. An error is detected when the cartridge fails to maintain a constant pressure profile. Inability to maintain a constant pressure profile indicates a pneumatic leak may be present within the cartridge, rending the cartridge unreliable or inoperable. The instrument aborts the test at step 302, displaying a pneumatic leak error to the GUI and unclamping the cartridge for ejection. Confirmation of maintenance of a constant pressure profile for the set period signals the instrument may move onto the mixing step. The instrument continues to maintain pressure in the cartridge while drive motor 2330 of the magnetic mixing assembly 2300 turns on for a set period at 304. Magnetic coupling is effectuated between the driving magnet system 2310, driven magnet system 2350, and stir bar 1390 of the lysis chamber, such that when drive motor 2330 rotates, the driven magnet system 2350 and stir bar 1390 also rotate. Rotation of the stir bar mixes the contents of the lysis chamber and lyses the sample to produce a lysed sample.

Simultaneously during the set period of mixing, a microphone 2380 monitors the audible feedback of the lysis chamber and drive motor at step 310. An error can be detected when the audible signal is not within a preset range. Conditions that cause the audible feedback to not be within the preset range include decoupling of the stir bar from the magnetic mixing assembly or stalling of the drive motor. If the audible signal falls outside the preset range, the instrument aborts the test at step 312, displaying an audible feedback error to the GUI and unclamping the cartridge for ejection. The drive motor is subsequently turned off at 314, given the audible feedback of the magnetic mixing assembly remains in range for the entire duration of the set period.

After completion of a successful lysis operation, the valve drive assembly 2400 indexes the rotary valve to a first valving position at 316 and the instrument pressurizes the cartridge to empty the lysis chamber at 318. The lysed sample containing nucleic acids and other cell debris flow over a porous solid support contained within the solid support chamber of the rotary valve according to an embodiment described herein. The porous solid support captures nucleic acids while permitting cell debris and lysis buffer to be directed to a waste collection element 1470. The instrument performs a pressure verification check at 400 to confirm the pressure profile is achieved in the allotted amount of time. An error is detected when the pressure profile is not achieved in the allotted time, indicating a pneumatic leak may be present within the cartridge. The instrument aborts the test at step 302, displaying a pneumatic leak error to the GUI and unclamping the cartridge for ejection.

The instrument continues to monitor the pressure profile while the lysed sample is transferred from the lysis chamber 1371 to the porous solid support chamber 1446 of the rotary valve 1400. In one aspect of the present invention, pneumatic subsystem 2130 lacks a flow sensor and instead uses a feedback control loop based on an actuation signal sent to the proportional valve to determine when the lysed sample transfer to the porous solid support chamber is complete. At step 410 (FIG. 106C), the instrument detects that lysis buffer transfer is complete using the feedback control look of the pneumatic subsystem. A transfer time out error is identified when the instrument fails to detect a successful transfer of the lysed sample within a preset time period. The instrument aborts the test at step 412, displaying a timeout error to the GUI and unclamping the cartridge for ejection. Upon successful detection of the lysed sample transfer, the applied pressure is turned off at step 414 and the instrument is ready to perform a washing step.

To align the wash buffer reservoir with the porous solid support chamber, the valve drive assembly 2400 indexes the rotary valve to a second valving position at 416 and the instrument pressurizes the cartridge to empty the wash buffer reservoir 1475 at 418. Wash buffer flows out of the wash buffer reservoir and passes through the porous solid support 1445 contained within the solid support chamber 1446 of the rotary valve 1400 to remove unbound cell debris or other contaminants remaining in the porous solid support. The wash buffer is directed to the waste collection element 1470 leaving predominantly nucleic acids bound to the porous solid support 1445. In a manner similar to step 400, the instrument performs a pressure verification check at 420 to confirm the pressure profile is achieved in the allotted amount of time like the test performed during the lysed sample transfer. An error is detected when the expected pressure profile is not achieved in the preset allotted time, potentially indicating a pneumatic leak within the cartridge. The instrument aborts the test at step 302, displaying a pneumatic leak error to the GUI and unclamping the cartridge for ejection. The instrument continues to monitor the pressure profile while the wash buffer is transferred from the wash buffer reservoir 1475 to the porous solid support chamber 1446 of the rotary valve 1400. The feedback control loop of the pneumatic subsystem described above monitors the actuation signal sent to the proportional valve to determine when wash buffer transfer to the porous solid support chamber is complete at 422. An error is detected when the instrument fails to detect a successful transfer of wash buffer in the allotted time. The instrument aborts the test at step 412, displaying a timeout error to the GUI and unclamping the cartridge for ejection. Upon successful detection of the wash buffer transfer, the applied pressure is turned off at 424 and the instrument is ready to perform an air drying step.

To air dry the porous solid support, the valve drive assembly 2400 indexes the rotary valve to a third valving position at 426 and the instrument pressurizes the cartridge at 428 to perform an air drying step. Pressurized air is blown through the porous solid support contained within the solid support chamber 1446 of the rotary valve and directed to the waste collection element 1470 for a set period. Performing the air drying pushes residual fluids and evaporates lingering volatile compounds that may be present in the solid support chamber after the washing step. One of ordinary skill in the art would recognize the advantages of minimizing the residual presence of lysis buffer and/or wash buffer in a final assay. During the air drying step, the instrument again performs a pressure verification check at 430 to confirm the pressure profile is achieved in the allotted amount of time. An error is detected when the pressure profile is not achieved in the allotted time, indicating a pneumatic leak may be present within the cartridge. The instrument aborts the test at step 302, displaying a pneumatic leak error to the GUI and unclamping the cartridge for ejection. Upon successful completion of the air drying process, the pressure is turned off at step 432 and the instrument is ready to perform an elution step.

To align the elution buffer reservoir with the porous solid support chamber, the valve drive assembly 2400 indexes the rotary valve to a fourth valving position at 434 and the instrument pressurizes the cartridge to empty the elution buffer reservoir 1475 as seen by step 436. Eluent flows out of the elution buffer reservoir 1475, passing through the porous solid support 1445 contained within the solid support chamber of the rotary valve to release nucleic acids bound to the porous solid support thereby generating an enriched nucleic acid solution. The enriched nucleic acid is directed to the rehydration chamber 1520 to rehydrate dried reagents deposited within the chamber. The cartridge remains pressurized while the instrument performs another pressure verification check at 500 to confirm the pressure profile is maintained for the preset period. An error is detected when the cartridge fails to maintain a constant pressure profile. Inability to maintain a constant pressure profile indicates a pneumatic leak may be present within the cartridge. The instrument aborts the test at step 302, displaying a pneumatic leak error to the GUI and unclamping the cartridge for ejection.

The instrument continues to pressurize the cartridge to fill the rehydration chamber 1520 with purified sample and proceeds to push the purified sample to the metering channel 1557 producing a metered purified sample volume. While pressure remains applied, rehydration motor 2510 is turned on at step 502 for a set period to gyrate the magnetic mixing element (i.e., a ball 1524) within the rehydration chamber to dissolve and mix dried reagents with the metered purified sample (see FIG. 106D). At step 504 of the method, rehydration motor is turned off. Pressure is turned off at 506 and the chemistry heater 2601 of the chemistry heater assembly 2600 is simultaneously turned on at 508 to preheat the chemistry heater to a loading temperature for filling the assay chambers 1621.

While preheating the chemistry heater 2601, the reaction imaging assembly 2700 captures an image of the dry assay chambers at step 510. Subsequently, the valve drive assembly 2400 indexes the rotary valve to a fifth valving position at 512 to align the rehydration chamber 1520 with the dry assay chambers. The instrument pressurizes the cartridge at 514 to pass the solution from the rehydration chamber into the assay chambers, thereby loading the assay chambers. In one implementation, the pneumatic subsystem 2130 pressurizes the cartridge using a stepwise ramping function to load the assay chambers. In an alternative implementation of the method, the assay chambers are loaded using a constant pressure profile. Pressure remains applied while the reaction imaging assembly captures an image of the loaded assay chambers at step 516. The instrument uses the image to verify the assay chambers successfully loaded 600. An error is detected when the instrument identifies incomplete loading of the assay chambers. The instrument aborts the test at step 602, displaying an incomplete loading error to the GUI and unclamping the cartridge for ejection.

After confirmation of loaded assay chambers, the heater 2661 of the heat staker assembly 2640 is activated to bring the staker bar assembly 2641 up to a preset staking temperature at step 604. The instrument uses motor 2642 to move the staker bar assembly 2641 toward the cartridge until the staker blade 2660 contacts the cartridge. The motor releases a spring 2643, which applies the force required to press the staker bar assembly into the film side of the cartridge to heat stake the cartridge at 606, as described herein. The hot staker blade 2660 melts selected areas of the cartridge, e.g. across u-bend 1607, loading channels 1672, channel 1362 leading to the waste collection element, and venting channel 1472 exiting from the waste collection element 1470. Heat staking these specific channels prevent liquids from escaping the cartridge thereby mitigating the risk for release of amplicon or potentially contaminated biological waste into the outside environment. The heat staker assembly 2640 heat stakes the cartridge for a set period 606 and then turns off the heater 2661 of the heat staker assembly. Fan 2644 turns on at 608 and the heat staker blade 2660 is actively cooled by the fan until the instrument detects the staker bar is cooled to the desired temperature. At step 610, motor 2642 retracts the heat staker assembly 2640 from the cartridge and the pneumatic pressure applied to the cartridge is turned off at 612.

At step 614, the reaction imaging assembly captures an image of the assay chambers 1621 after heat staking and release of pneumatic pressure. The image verifying assay chambers remain loaded with the sample mixture at 700 is used to confirm a successful sealing by the heat stake 1603. Failure of the assay chambers to remain loaded indicate a cartridge leak due to an unsuccessful heat stake. The instrument aborts the test at step 702, displaying a failed heat stake error to the GUI and unclamping the cartridge for ejection. Confirmation of a successful heat stake allows the instrument to proceed onto an amplification step.

At this step in the method, the chemistry heater 2601 of the chemistry heater assembly 2600 has come up to the loading temperature and is ready to facilitate an amplification of nucleic acids within the assay chambers. In an alternative embodiment, the chemistry heater 2601 may be fluctuated between a high and low temperature one or more times prior to being set to a reaction temperature shown by step 704. The chemistry heater is warmed until the chemistry heater reaches the high temperature. Thereafter, the chemistry heater is turned off and actively cooled by fan 2603 until the assay chambers 1621 cool to the low temperature to complete one cycle. The assay chambers optionally may be fluctuated one or more times before being set to the reaction temperature.

The chemistry heater 2601 is then set to the reaction temperature for the duration of the test at 706. At a predetermined frequency, the reaction imaging assembly 2700 captures images of the assay chambers 1621 during amplification allowing the instrument to process the images of the assay chambers. In one implementation, the instrument turns on the excitation LED 2731 of the excitation lens cell 2730 and reaction camera 2701 captures an image of the assay chambers every 20 seconds of the amplification. In an alternative embodiment, the instrument turns on the excitation LED 2731 and reaction camera 2701 captures an image of the assay chambers every 15 seconds of the amplification. The instrument processes the sequence of images captured by the reaction imaging assembly 2700 to determine the presence of a signal, such as a fluorescent signal, indicative of the presence of target nucleic acids in each of the plurality of assay chambers, as shown by step 800. In embodiments where the device is configured to perform a multiplex assay, the instrument may detect a positive or negative signal for each of the plurality of assay chambers. In certain embodiments, e.g. cartridges containing a process control expected to generate a positive signal in at least one assay chamber, the instrument may produce a timeout error, as shown by 802, when the expected signal is not determined within the allotted time. The instrument aborts the test at step 802, displaying an error to the GUI and unclamping the cartridge for ejection at 900.

Upon completion of the amplification steps, either by detecting a positive signal in each well or after an allotted time for amplification elapses, the unclamping and ejection sequence begins at with linear actuator 2014 on the fixed bracket assembly 2010 rotating the lead screw 2016 in a second rotational direction to first push the frangible seal block 2260 away from the cartridge. The lead screw continues to rotate in the second rotational direction as the frangible seal block 2260 contacts ledge 2046 of the clamp block 2041 and pushes entire moving bracket assembly 2040 in a negative direction away from the cartridge to a fourth clamping position at 900. As the moving bracket assembly moves in the negative direction, latch release arm 2214 contacts the end of pin 2216 to lift latch 2212 out of notch 1021 on top of the cartridge at 902. The loading assembly 2100 ejects the cartridge at 904 using spring 2235 to pull the pusher carriage 2234 and the cartridge to a forward most loading position towards the slot 2072 of the instrument to eject the cartridge. Steps 900 through 904 are executed each time an error is detected that leads to aborting the method and ejecting a cartridge. When the method is successfully completed, the last step of the method displays the result of the diagnostic result to the GUI, shown by step 906.

VIII. METHODS OF USE—BIOLOGY

One aspect of the invention provides methods of testing a sample suspected of containing a target pathogen, comprising (a) accepting a cartridge having a loading chamber containing the sample suspected of containing the target pathogen, (b) advancing the sample to a lysis chamber having at least one lysis reagent therein, (c) mixing the sample with the at least one lysis agent to generate a lysed sample; (d) passing the lysed sample through a porous solid support to capture a nucleic acid on the porous solid support, (e) releasing the captured nucleic acid from the porous solid support to generate an enriched nucleic acid, (f) distributing the enriched nucleic acid to two or more assay chambers and combining the enriched nucleic acid with one or more amplification reagents, (g) isolating each one of the two or more assay chambers from each one of all the other two or more assay chambers, and (h) performing an isothermal amplification reaction within each one of the two or more assay chambers while simultaneously detecting amplification product, wherein presence of an amplification product is an indication of a presence, an absence or a quantity of the target pathogen in the sample suspected of containing the target pathogen. The method is implemented on a modular assay system comprising a loading module, lysis module, purification module and amplification module.

A. Loading module

In some cases, the cartridge comprises a sample entry port, a sample input well, or a fill chamber. Given the pressurization inherent to the devices described herein, the entry port preferably is air tight when sealed by a cap. In certain implementations, the cap is configured to be opened to permit addition of a sample and then resealed prior to the sample being loaded to the device. Alternatively, the sample can be loaded via a puncturable septa or large one-way valve. The diagnostic system can include a sample loader, such as a bulb or syringe, useful for loading a sample into the device. The cartridge can be packaged with a sample collection device, such as a syringe, bulb, swab, scraper, biopsy punch, or other tool for a user to collect a sample.

Samples can be obtained from a subject (e.g., human subject), a food sample (e.g., including an organism), or an environmental sample (e.g., including one or more organisms). (e.g., microbiological cultures). A sample may include a specimen of synthetic origin (e.g., microbiological cultures). Samples may be obtained from a patient or person and includes blood, feces, urine, saliva or other bodily fluid. Exemplary, non-limiting samples include blood, plasma, serum, sputum, urine, fecal matter (e.g., stool sample), swab (e.g. of skin, wound, mucosal membrane, cervix, vagina, urethra, throat or nasal cavity), sweat, cerebrospinal fluid, amniotic fluid, interstitial fluid, tear fluid, bone marrow, tissue sample (e.g., a skin sample or a biopsy sample), a buccal mouthwash sample, an aerosol (e.g., produced by coughing), a water sample, a plant sample, or a food sample. The sample can include any useful target or analyte to be detected, filtered, concentrated, and/or processed.

Analysis can indicate the presence, absence, or quantity of an analyte of interest. For example, nucleic acid amplification can provide qualitative or quantitative information about a sample, such as the presence, absence, or abundance of a cell, cell type, pathogen (e.g., bacteria, virus), toxin, pollutant, infectious agent, gene, gene expression product, methylation product, genetic mutation, or biomarker (e.g., nucleic acid, protein, or small molecule).

Analysis can indicate the presence, absence, or quantity of an analyte of interest. For example, nucleic acid amplification can provide qualitative or quantitative information about a sample, such as the presence, absence, or abundance of a cell, cell type, pathogen (e.g., bacteria, virus), toxin, pollutant, infectious agent, gene, gene expression product, methylation product, genetic mutation, or biomarker (e.g., nucleic acid, protein, or small molecule). Analytical targets of interest can include indicators of diseases or illnesses such as genetic diseases, respiratory diseases, cardiovascular diseases, cancers, neurological diseases, autoimmune diseases, pulmonary diseases, reproductive diseases, fetal diseases, Alzheimer's disease, bovine spongiform encephalopathy (Mad Cow disease), *chlamydia*, cholera, cryptosporidiosis, dengue, giardia, gonorrhea, human immunodeficiency virus (HIV), hepatitis (e.g., A, B, or C), herpes (e.g., oral or genital), human papilloma virus (HPV), influenza, Japanese encephalitis, malaria, measles, meningitis, methicillin-resistant *Staphylococcus aureus* (MRSA), Middle East Respiratory Syndrome (MERS), onchocerciasis, pneumonia, rotavirus, schistosomiasis, *shigella*, strep throat, syphilis, tuberculosis, *trichomonas*, typhoid, and yellow fever. Analytical targets can include biomarkers indicative of traumatic brain injury, kidney disease, cardiovascular disease, cardiovascular events (e.g., heart attack, stroke), or susceptibility of certain infectious agents (such as bacteria or viruses) to certain therapeutic agents. Analytical targets can include genetic markers, such as polymorphisms (e.g., single nucleotide polymorphisms (SNPs), copy number variations), gene expression products, specific proteins or modifications (e.g. glycosylation or other post-translational processing) of proteins. In preferred implementations, the analyte of interest is a nucleic acid useful in the identification of microbes including viruses, bacteria, unicellular fungi and parasites.

In many implementations, it is desirable to subject the sample to one or more treatments before attempting to lyse the target pathogen. In some implementations, the treatment occurs prior to passing the sample to the lysis chamber. In other implementations, the treatment occurs after passing the sample to the lysis chamber, but prior to mixing the sample with at least one lysis reagent.

The diagnostic system comprising a device and instrument described herein can be used to detect target pathogens from any biological sample. Solid samples or semi-solid, such as tissue samples, require chemical, enzymatic, physical and/or mechanical treatment to release the pathogen into a fluid sample suitable to flow through the test cartridge. Similarly, other biological sample types may preferably be subjected to a chemical, enzymatic, physical or mechanical pre-treatment prior to mixing with one or more lysis agents. Such pre-treatment can be performed within a cartridge or prior to loading the sample into the cartridge. Chemical pretreatments include, e.g. n-acetylcysteine to break up mucus in sputum samples or lysis of animal cells with saponin to release intracellular pathogen or debulk the sample. Dithiothreitol is also commonly used to break up mucus as well as disintegrate solid tissue samples. In another implementation, the sample can be enzymatically pre-treated, e.g. with an elastase, collagenase or proteinase K to preferentially degrade connective tissues in a solid tissue sample. In yet another implementation, the sample can be treated with a nuclease, e.g. a DNase or RNase, to remove extracellular nucleic acid from the sample prior to lysis. Such nucleases can be deactivated by subsequent addition of a nuclease inhibitor or by denaturation with a chaotropic lysis agent. Finally, certain samples can be disrupted with bead beating prior to addition of a chemical lysis agent.

In some implementations, an undesired contaminant can be physically separated from the target pathogen(s), e.g. by filtration. Filtration enables the separation of one component or fraction of a sample from another component or fraction. For example, a filter can enable the solid components, such as, e.g., cells, debris or contaminant, to be separated from the liquid components of the solution. Alternatively, a filter can enable larger solid components, such as, e.g., proteinaceous aggregates, aggregated cell debris, or larger cell, to be separated from smaller components, e.g. virus, bacterial cells or nucleic acid, from a solution. In aspects of this embodiment, a filter useful for separating components contained in a solution can be, e.g., a size-exclusion filter, a plasma filter, an ion-exclusion filter, a magnetic filter, or an affinity filter. In other aspects of this embodiment, a filter useful for separating components contained in a solution can have a pore size of, e.g., 0.1 µm, 0.2 µm, 0.5 µm, 1.0 µm, 2.0 µm, 5.0 µm, 10.0 µm, 20.0 µm, 30 µm, 40 µm, 50 µm, 60 µm, 70 µm, 80 µm, 90 µm, 100 µm, or more. In yet other aspects of this embodiment, a filter useful for separating components contained in a solution can have a pore size of, e.g., at least 0.2 µm, at least 0.5 µm, at least 1.0 µm, at least 2.0 µm, at least 5.0 µm, at least 10.0 µm, at least 20.0 µm, at least 30.0 µm, at least 40.0 µm, at least 50.0 µm, at least 60.0 µm, at least 70.0 µm, at least 80.0 µm, at least 90.0 µm, or at least 100.0 µm. In still other aspects of this embodiment, a filter useful for separating components contained in a solution can have a pore size of, e.g., at most 0.1 µm, at most 0.2 µm, at most 0.5 µm, at most 1.0 µm, at most 2.0 µm, at most 5.0 µm, at most 10.0 µm, at most 20.0 µm, at most 30.0 µm, at most 40.0 µm, at most 50.0 µm, at most 60.0 µm, at most 70.0 µm, at most 80.0 µm, at most 90.0 µm, or at most 100.0 µm. In other aspects of this embodiment, a filter useful for separating components contained in a solution can have a pore size between, e.g., about 0.2 µm to about 0.5 µm, about 0.2 µm to about 1.0 µm, about 0.2 µm to about 2.0 µm, about 0.2 µm to about 5.0 µm, about 0.2 µm to about 10.0 µm, about 0.2 µm to about 20.0 µm, about 0.2 µm to about 30.0 µm, about 0.2 µm to about 40.0 µm, about 0.2 µm to about 50.0 µm, about 0.5 µm to about 1.0 µm, about 0.5 µm to about 2.0 µm, about 0.5 µm to about 5.0 µm, about 0.5 µm to about 10.0 µm, about 0.5 µm to about 20.0 µm, about 0.5 µm to about 30.0 µm, about 0.5 µm to about 40.0 µm, about 0.5 µm to about 50.0 µm, about 1.0 µm to about 2.0 µm, about 1.0 µm to about 5.0 µm, about 1.0 µm to about 10.0 µm, about 1.0 µm to about 20.0 µm, about 1.0 µm to about 30.0 µm, about 1.0 µm to about 40.0 µm, about 1.0 µm to about 50.0 µm, about 2.0 µm to about 5.0 µm, about 2.0 µm to about 10.0 µm, about 2.0 µm to about 20.0 µm, about 2.0 µm to about 30.0 µm, about 2.0 µm to about 40.0 µm, about 2.0 µm to about 50.0 µm, about 5.0 µm to about 10.0 µm, about 5.0 µm to about 20.0 µm, about 5.0 µm to about 30.0 µm, about 5.0 µm to about 40.0 µm, about 5.0 µm to about 50.0 µm, about 10.0 µm to about 20.0 µm, about 10.0 µm to about 30.0 µm, about 10.0 µm to about 40.0 µm, about 10.0 µm to about 50.0 µm, about 10.0 µm to about 60.0 µm, about 10.0 µm to about 70.0 µm, about 20.0 µm to about 30.0 µm, about 20.0 µm to about 40.0 µm, about 20.0 µm to about 50.0 µm, about 20.0 µm to about 60.0 µm, about 20.0 µm to about 70.0 µm, about 20.0 µm to about 80.0 µm, about 20.0 µm to about 90.0 µm, about 20.0 µm to about 100.0 µm, about 30.0 µm to about 40.0 µm, about 30.0 µm to about 50.0 µm, about 30.0 µm to about 60.0 µm, about 30.0 µm to about 70.0 µm, about 30.0 µm to about 80.0 µm, about 30.0 µm to about 90.0 µm, about 30.0 µm to about 100.0 µm, about 40.0 µm to about 50.0 µm, about 40.0 µm to about 60.0 µm, about 40.0 µm to about 70.0 µm, about 40.0 µm to about 80.0 µm, about 40.0 µm to about 90.0 µm, about 40.0 µm to about 100.0 µm, about 50.0 µm to about 60.0 µm, about 50.0 µm to about 70.0 µm, about 50.0 µm to about 80.0 µm, about 50.0 µm to about 90.0 µm, or about 50.0 µm to about 100.0 µm.

In certain implementations, the size-exclusion filter can be a depth filter. Depth filters consist of a matrix of randomly oriented, bonded fibers that capture particulates within the depth of the filter, as opposed to on the surface. The fibers in the depth filter can be comprised of glass, cotton or any of a variety of polymers. Exemplified depth filter materials may include, type GF/F, GF/C and GMF150 (glass fiber, Whatman), Metrigard® (glass fiber, Pall-Gelman), APIS (glass fiber, Millipore), as well as a variety of cellulose, polyester, polypropylene or other fiber or particulate filters, so long as the filter media can retain a sufficient contaminant to allow further processing of the sample.

In alternate implementations, the size-exclusion filter can be a membrane filter, or mesh filter. Membrane filters typically performs separations by retaining particles larger than its pore size on the upstream surface of the filter. Particles with a diameter below the rated pore size may either pass through the membrane or be captured by other mechanisms within the membrane structure. Membrane filters can support smaller pore sizes, including small enough to exclude bacterial cells. Membrane filters can be used to concentrate solutions, e.g. bacterial cell suspensions, by filtering a first larger volume through the membrane filter, thereby holding the bacterial cells to the upstream surface of the membrane filter (or suspended in residual fluid retained on the upstream side of the filter). The bacterial cells can then be resuspended in a second small volume of fluid by either passing the suspension fluid in the reverse direction to float the bacterial cells off the membrane surface or by washing the suspension fluid across the upstream surface of the filter to wash the bacterial cells off the filter. Exemplified membranes may include, polyethersulfone (PES) membranes (e.g., Supor® 200, Supor® 450, Supor® MachV (Pall-Gelman, Port Washington, N.Y.), Millipore Express PLUS® (Millipore)). Other possible filter materials may include, HT Tuffryn® (polysulfone), GN Metricel® (mixed cellulose ester), Nylaflo® (Nylon), FP Verticel (PVDF), all from Pall-Gelman (Port Washington, N.Y.), and Nuclepore (polycarbonate) from Whatman (Kent, UK).

In some embodiments, an undesired contaminant can be removed from a sample by exposing the sample to a capture agent, such as a capture antibody, is immobilized on a solid substrate. The solid substrate can be contacted with the sample such that contaminant in the sample can bind to the immobilized antibody. In some embodiment, a capture antibody can be used that has binding affinity for red blood cells. The antibody may be a monoclonal antibody or a polyclonal antibody. Suitable solid substrates to which a capture antibody can be bound include, without limitation, membranes such as nylon or nitrocellulose membranes, and beads or particles (e.g., agarose, cellulose, glass, polystyrene, polyacrylamide, magnetic, or magnetizable beads or particles). In an alternate implementation, the capture agent can be any protein having specific and high affinity for binding to an undesired contaminant.

B. Lysis Module

Cell lysis refers to a process in which the outer boundary or cell membrane is broken down or destroyed in order to release inter-cellular materials such as nucleic acids (DNA, RNA), protein or organelles from a cell. Lysis resulting in release of nucleic acids can be achieved by chemical, enzymatic, physical and/or mechanical interventions.

In one implementation, the lysis agent is a chemical lysis agent. Chemical lysis methods disrupt the cell membrane, e.g., by changing pH or by addition of detergents and/or chaotropic agents to solubilize membrane proteins and thereby rupture the cell membrane to release its contents. These chemical lysis solutions can include one or more chemical lysis agents such as anionic detergents, cationic detergents, non-ionic detergents or chaotropic agents. Non limiting examples of non-ionic detergents include 3-[(3-cholamidopropyl) dimethylammonio]-1-propanesulfonate (CHAPS), Triton X, NP-40, Tween, and 3-[(3-cholamidopropyl)dimethylammonio]-2-hydroxy-1-propane-sulfonate (CHAPSO), a zwitterionic detergent. Suitable chaotropic agents include, but are not limited to, urea, guanidine (e.g. guanidinium isothiocyanate or guanidinium hydrochloride), ethylenediaminetetraacetic acid (EDTA) and lithium perchlorate. In a preferred implementation, the suspected pathogen is a virus or a gram-negative bacteria and the chemical lysis reagent is a chaotropic agent.

The lysis agent can be an enzyme, or enzymatic lysis agent. Enzymatic cell lysis advantageous can allow for selective lysis of certain types of cells. For example, the enzymatic lysis agent can selectively cleave peptidoglycans found only in bacterial cell walls. Exemplified enzymatic lysis agents include achromopeptidase, lysostaphin, lysozyme, mutanolysin. Alternatively, a lyticase or chitinase, specific to yeast cells, can be used as the enzymatic lysis agent. In some cases enzymes with broad specificity and no specific target cell type, such as proteinase K, can be used as the lysis agent. Any of the enzymatic enzymes can be used in combination with mechanical or chemical lysis agents to promote faster and/or more complete lysis.

For use in the cartridges described here, bead beating is a preferred mechanical lysis mechanism, in which cells are disrupted by agitating, e.g. mixing, tiny beads made of glass, steel or ceramic with the cell suspension at high speeds. Bead beating is capably of lysing a variety of cells, including yeast and gran-positive bacteria. A preferred lysis method combines both mechanical and non-mechanical (e.g. chemical) methods, for example bead beating in a solution containing guanidine and/or Triton X-100. In some implementations, the mechanical lysis agent is ceramic beads, glass beads or steel beads, and mixing comprises rotating a stir bar at at least 500 rpm, at least 1000 rpm, at least 2000 rpm or at least 3000 rpm for at least 30 seconds, at least one minute, or at least two minutes. Bead beating is a preferred method for use in disrupting cells with significantly structured cell walls. Accordingly, in some implementations utilizing a mechanical lysis agent comprised of ceramic, glass or steel beads, the suspected pathogen is a gram-negative bacterium, a fungus such as a yeast, or a plant cell.

In samples having high organic loads, such as stool samples, blood samples, sputum samples or swab samples collected from mucus membranes, significant debris may be present in the lysed sample. In such cases, it is advantageous to filter the lysed sample prior to passing it through the porous solid support. In a preferred implementation, the lysed sample is passed through a size-exclusion filter, wherein nucleic acid passes through the filter. In a more preferred implementation, the lysed sample is passed through a depth filter. Preferably such post-lysis filters have a pore size of 20 μm or less, more preferably 10 μm or less.

C. Purification Module

After lysis, the lysed sample is passed through a first porous solid support thereby capturing nucleic acid. In some implementations, the porous solid support may preferentially bind DNA more than RNA or RNA more than DNA or certain lengths of nucleic acid (e.g. fragmented genomic DNA more than complete genomic DNA). However, a porous solid support for capturing nucleic acid in the devices described herein, preferably, binds nucleic acid regardless of the sequences present in the nucleic acids. When the lysed sample is passed through porous solid support having affinity for nucleic acids, the nucleic acids are captured by the porous solid support while proteins, lipids, polysaccharides, and other cell debris that can inhibit nucleic acid amplification pass through the column and to the waste chamber. In some implementations, after capturing the nucleic acid, a wash solution is passed through the porous solid support to further remove contaminants. Captured nucleic acid is then released from the porous solid support with an elution buffer to generate an enriched nucleic acid.

In a preferred implementation, the porous solid support is a silica resin, e.g. silica fibers. Salt is important to binding nucleic acid to silica resins. In implementations where a chemical lysis agent, such as guanidinium isothiocyanate, is used, the lysis agent can provide the necessary salt. In other implementations, it is advantageous to supplement the lysed sample with a chaotropic salt. The addition of alcohol, such as ethanol or isopropanol, can further enhance and influence the binding of nucleic acids to the silica resin. In a preferred implementation, the silica resin column is washed with a dilute salt and/or alcohol solution. If a dilute salt solution is used, preferably a send wash buffer containing alcohol but no salt is also passed over the silica resin. Prior to elution, preferably excess alcohol is removed, e.g., by drying with forced air. Finally, enriched nucleic acid is released from the silica resin with water or buffered (e.g. 10 mM Tris) water. Higher molecular weight DNA can be preferably released from the resin with 10 mM Tris at pH 8-9. RNA can be preferentially released from the silica resin with water.

In some implementations, it may be desirable to remove additional contaminants from the enriched nucleic acid by passing is through a second solid support. In such implementations, prior to distributing the enriched nucleic acid to the assay chambers, the method further comprises passing the enriched nucleic acid through a second porous solid support. The second porous solid support can be the same as the first solid support. In cases in which the first and second solid support are comprised of the same material, the enriched nucleic acid is mixed with a matrix binding agent prior to passing through the second solid support. For example, when the first and second solid support are a silica resin, the matrix binding agent can be a salt and/or alcohol solution as described above. In an alternate implementation, the second solid support is different than the first solid support. In some such implementations, the second solid support has an affinity for nucleic acid and the method further comprises releasing the captured nucleic acid from the second solid support to generate a twice enriched nucleic acid. In other implementations, the second solid support does not have an affinity for the nucleic acid, but rather captures one or more contaminants, thereby removing the contaminant from the enriched nucleic acid.

In an alternate embodiment, it may be desirable to remove contaminant from the lysed sample prior to passing it through the first porous solid support. In such cases, the method further comprises passing the lysed sample through a second solid support, wherein the second solid support does not bind nucleic acid, but rather has affinity for one or more contaminants, thereby removing the one or more contaminants from the lysed sample.

In order to implement a method using more than one solid support on the devices described herein, the rotor can comprise a plurality of flow channels, each flow channel comprising an inlet 1441, an outlet 1442, and a porous solid support 1445. In certain implementation, the rotor comprises a main body and a cap 1430 operably connected to the main body, and wherein one wall of the flow channel is defined by the cap. The rotor comprises an outer face 1413 opposite the rotor valving face, wherein the outer face can comprise an opening for engaging a spline. The multiple flow channels can have the same or different dimensions. Similarly, the multiple flow channels can contain the same or different porous solid supports. Accordingly, nucleic acid may be purified from a particularly contaminated same by binding the nucleic acid to a first column, washing the bound nucleic acid and eluting a partially purified nucleic acid solution. The partially purified nucleic acid can be mixed with a binding buffer and passed through a second solid support, binding the nucleic acid to the second support, while allowing contaminants to pass. The bound nucleic acid is washed and then eluted to generate a double-purified nucleic acid solution. Alternatively the second solid support can be specific for a contaminant, allowing nucleic acid to pass, but retaining the undesired contaminant, thereby generating a more purified nucleic acid solution.

D. Amplification Module

The amplification module comprises a plurality of assay chambers of defined volume, each configured to receive a purified nucleic acid. The amplification module includes a heater such that the amplification module can perform an isothermal or thermocycling amplification reaction on the target nucleic acid. The amplification module further is configured to detect a signal indicative of target amplicon generated from the nucleic acid. In one implementation, the distributing step is performed prior to combining the enriched nucleic acid with an amplification reagent. Alternatively, the enriched nucleic acid is combined with one or more amplification reagents before the distributing step. The amplification reagent can be any reagent that is necessary or beneficial for nucleic acid synthesis, including, but not limited to, a DNA polymerase, a reverse transcriptase, a helicase, nucleotide triphosphates (NTPs), a magnesium salt, a potassium salt, an ammonium salt, a buffer, or combinations thereof. In many implementations the one or more amplification reagents comprise a primer or primer set. The primer set can be specific to a first nucleic acid sequence present in one of the one or more target pathogens. In some implementations, a first reaction well contains a first primer set specific to a first nucleic acid sequence and a second reaction well contains a second primer set specific to a second nucleic acid sequence. The first nucleic acid sequence can be present in one or more of the target pathogen or present in a process control.

In addition to the primary amplification assay, the method can comprise the step of pre-amplifying the enriched nucleic acid. Such preamplification is particularly useful when a very limited amount of target nucleic acid is in the sample, either due to few pathogen cells and/or to low copy of the target nucleic acid within the pathogen cells. Using a cartridge with a large number of wells, i.e. highly multiplexed, also benefits from pre-amplification. For such implementation, the isothermal amplification is initiated prior to distributing the enriched nucleic acid to the two or more assay chambers. Optionally, after the distributing step, but prior to performing the isothermal amplification reaction, the method further comprises combining the enriched nucleic acid with a primer set specific to one of the one or more target pathogens.

E. Alternate Workflows

The instruments and cartridges described herein can be adapted to analyze a variety of biological samples, including cerebrospinal fluid (CSF), urine, throat or nasal swabs, blood, genital swabs (e.g. vaginal, cervical or urethral swabs), sputum, stool or solid tissue sample. In each case the method of testing a sample suspected of containing a target pathogen, comprising the following basic steps (a) accepting a cartridge having a loading chamber containing the sample suspected of containing the target pathogen 180, (b) advancing the sample to a lysis chamber having at least one lysis reagent therein, (c) mixing the sample with the at least one lysis agent to generate a lysed sample 380; (d) passing the lysed sample through a porous solid support to capture a nucleic acid on the porous solid support 480, (e) releasing the captured nucleic acid from the porous solid support to generate an enriched nucleic acid 484, (f) distributing the enriched nucleic acid to two or more assay chambers 784 and combining the enriched nucleic acid with one or more amplification reagents 780, (g) isolating each one of the two or more assay chambers from each one of all the other two or more assay chambers and (h) performing an isothermal amplification reaction within each one of the two or more assay chambers while simultaneously detecting amplification product 786, wherein presence of an amplification product is an indication of a presence, an absence or a quantity of the target pathogen in the sample suspected of containing the target pathogen. For certain sample types, between steps (a) and (c), the method further comprises pretreating the sample 182. The pretreatment can be a chemical, physical, mechanical or enzymatic pretreatment as described above. For some sample types, subsequent to step (c) but prior to step (d), the method further comprises filtering the lysed sample 382, preferably by passing the lysed sample through a size-exclusion filter. In many cases, after step (d) and prior to step (e), the method further comprises washing the porous solid support 482. Some samples will contain a high level of contaminants, in such case it may be advantageous to repeats steps (d) and (e) on passing the lysed sample and then enriched nucleic acid through a first and second porous solid support.

Some sample types, e.g. blood, is expected to contain the target pathogen at very low concentrations. Some cartridges will comprise a large number of assay chambers. In cases where the concentration of pathogen is very low and the number of assay chambers is high, can lead to false negative determinations due to partitioning. For example, when an enriched nucleic acid that contains five copies of nucleic acid associated with the suspected pathogen is assayed in a cartridge having eight wells, at least three assay chambers will not receive a copy of the nucleic acid associated with the suspected pathogen. If the primer set associated with the target pathogen is in one of those three wells, the cartridge will falsely report that no pathogen is present. This result can be avoided by pre-amplifying certain nucleic acid targets prior to distributing the enriched nucleic acid to the plurality of reaction well 782.

For simple, clear patient samples, such as cerebrospinal fluid, urine or cell suspensions extracted from throat or nasal swabs (FIG. 108), the method comprises (a) accepting a cartridge having a loading chamber containing the sample suspected of containing the target pathogen 180, (b) advancing the sample to a lysis chamber having at least one lysis reagent therein, (c) mixing the sample with the at least one lysis agent to generate a lysed sample 380; (d) passing the lysed sample through a porous solid support to capture a nucleic acid on the porous solid support 480, (e) releasing the captured nucleic acid from the porous solid support to generate an enriched nucleic acid 484, (f) distributing the enriched nucleic acid to two or more assay chambers 784 and combining the enriched nucleic acid with one or more amplification reagents 780, (g) isolating each one of the two or more assay chambers from each one of all the other two or more assay chambers and (h) performing an isothermal amplification reaction within each one of the two or more assay chambers while simultaneously detecting amplification product 786, wherein presence of an amplification product is an indication of a presence, an absence or a quantity of the target pathogen in the sample suspected of containing the target pathogen. Typically, the lysis agent is a chemical agent such as a detergent, a chaotropic agent or a combination thereof. If the target pathogen is resistant to chemical lysis, e.g. a yeast or gram positive bacterium, the one or more lysis agent further comprises a mechanical lysis agent such as beading beating.

Exemplified pathogens that may be suspected in CSF include, but are not limited to, *Brucella, Haemophilus influenzae, Bacillus anthracis, Listeria, Streptococcus pneumoniae, Leptospira, Borrelia burgdorferi* (Lyme's disease), *Mycobacterium tuberculosis, Cryptococcus*, and *Candida*. Exemplified pathogens that may be suspected in urine include, but are not limited to, *Escherichia coli, Klebsiella, Enterobacter, Serratia, Pseudomonas* sp. (e.g., *Pseudomonas aeruginosa*), *Enterococcus* sp. (e.g., *Enterococcus faecalis* or *Enterococcus faecium*), *Leptospira, Chlamydia* sp. (e.g. *Chlamydia trachomatis*), *Mycoplasma* sp. (e.g. *Mycoplasma genitalium*), and *Trichomonas vaginalis*. Exemplified pathogens that may be suspected in a throat or nasal swab include, but are not limited to, *Haemophilus influenzae, Bordetella pertussis, Corynebacterium diphtheriae, Streptococcus* sp. (e.g. Group A or Group B strep), *Mycoplasma* sp. (e.g. *Mycoplasma pneumoniae*), *Candida* sp. (e.g. *Candida albicans*), Influenza, and coronavirus (e.g. MERS or SARS).

Sputum is the thick mucus or phlegm that is expectorated from the lower respiratory tract (bronchi and lungs) and is important for the investigation of certain respiratory diseases, e.g. tuberculosis. Other exemplified pathogens that may be detected in sputum include, but are not limited to, *Klebsiella* sp., *Enterobacter* sp., *Serratia* sp., *Legionella* sp., *Bordetella pertussis, Yersinia* sp. (e.g. *Yersinia pestis*), *Pseudomonas* sp. (e.g., *Pseudomonas aeruginosa*), *Streptococcus pneumoniae, Mycoplasma* sp. (e.g. *Mycoplasma pneumoniae*), *Blastomyces dermatitidis*, and *Mycobacterium* sp., (e.g. *Mycobacterium tuberculosis*).

Given the high viscosity of sputa in some patients, e.g. from patients with advanced cystic fibrosis, sputa must first be liquefied mechanically by bead beating or chemically with mucolytic agents such as n-acetylcysteine (Mucomyst; Bristol) or dithiothreitol (Sputolysin). Referring to FIG. 111, the invention provides methods of identifying one or more suspected pathogens in a sputum sample, the method comprising the steps of: (a) accepting a cartridge having a loading chamber containing the sample suspected of containing the target pathogen 180, (b) pretreating the sputum sample with a mucolytic agent 182, (c) advancing the sample to a lysis chamber having at least one lysis reagent therein, (d) mixing the sample with the at least one lysis agent to generate a lysed sample 380; (e) filtering the lysed sample 382, preferably by passing the lysed sample through a size-exclusion filter, (f) passing the lysed sample through a porous solid support to capture a nucleic acid on the porous solid support 480, (g) passing a wash solution through the porous solid support 482, (h) releasing the captured nucleic acid from the porous solid support to generate an enriched nucleic acid 484, (i) distributing the enriched nucleic acid to two or more assay chambers 784 and combining the enriched nucleic acid with one or more amplification reagents 780, (j) isolating each one of the two or more assay chambers from each one of all the other two or more assay chambers and (k) performing an isothermal amplification reaction within each one of the two or more assay chambers while simultaneously detecting amplification product 786, wherein presence of an amplification product is an indication of a presence, an absence or a quantity of the target pathogen in the sputum sample suspected of containing the target pathogen. Optionally, the enriched nucleic acid is pre-amplified 782 prior to distributing the nucleic acid to the two or more assay chambers.

Referring to FIG. 110, the invention provides methods of identifying one or more suspected pathogens in a sample extracted from a genital swab (e.g. vaginal, cervical or urethral swab), the method comprising the steps of: (a) accepting a cartridge having a loading chamber containing the sample suspected of containing the target pathogen 180, (b) advancing the sample to a lysis chamber having at least one lysis reagent therein, (c) mixing the sample with the at least one lysis agent to generate a lysed sample 380; (d) filtering the lysed sample 382, preferably by passing the lysed sample through a size-exclusion filter, (e) passing the lysed sample through a porous solid support to capture a nucleic acid on the porous solid support 480, (f) passing a wash solution through the porous solid support 482, (g) releasing the captured nucleic acid from the porous solid support to generate an enriched nucleic acid 484, (h) distributing the enriched nucleic acid to two or more assay chambers 784 and combining the enriched nucleic acid with one or more amplification reagents 780, (i) isolating each one of the two or more assay chambers from each one of all the other two or more assay chambers and (j) performing an isothermal amplification reaction within each one of the two or more assay chambers while simultaneously detecting amplification product 786, wherein presence of an amplification product is an indication of a presence, an absence or a quantity of the target pathogen in the sample suspected of containing the target pathogen. Optionally, the enriched nucleic acid is pre-amplified prior to step (h). Exemplified pathogens that may be suspected in a urogenital swab include, but are not limited to, *Chlamydia* sp. (e.g. *Chlamydia trachomatis*), *Mycoplasma* sp. (e.g. *Mycoplasma genitalium*), *Candida* sp. (e.g. *Candida albicans*), human papilloma virus (HPV), *Trichomonas vaginalis, Gardnerella vaginalis, Lactobacillus* sp., *Bacteroides* sp., *Prevotella* sp, *Mobiluncus* sp., and *Peptostreptococcus* sp., *Atopobium vaginae*, and *Sneathia* (*Leptotrichia*).

Blood samples can be particularly difficult for nucleic acid amplification testing, as heme (a component of hemoglobin in red blood cells) is a well-known inhibitor of nucleic acid amplification. According, blood samples will require additional processing prior to the amplification steps. Referring to FIG. 109, the invention provides methods of identifying one or more suspected pathogens in a blood sample, the method comprising the steps of: (a) accepting a cartridge having a loading chamber containing the sample suspected of containing the target pathogen 180, (b) subjecting the blood sample to one or more chemical, enzymatic or physical pretreatments 182, (c) advancing the sample to a lysis chamber having at least one lysis reagent therein, (d) mixing the sample with the at least one lysis agent to generate a lysed sample 380; (e) filtering the lysed sample 382, preferably by passing the lysed sample through a size-exclusion filter, (f) passing the lysed sample through a porous solid support to capture a nucleic acid on the porous solid support 480, (g) passing a wash solution through the porous solid support 482, (h) releasing the captured nucleic acid from the porous solid support to generate an enriched nucleic acid 484, (i) pre-amplifying the enriched nucleic acid 782, (j) distributing the enriched nucleic acid to two or more assay chambers and combining the enriched nucleic acid with one or more amplification reagents 784, (k) isolating each one of the two or more assay chambers from each one of all the other two or more assay chambers and (l) performing an isothermal amplification reaction within each one of the two or more assay chambers while simultaneously detecting amplification product 786, wherein presence of an amplification product is an indication of a presence, an absence or a quantity of the target pathogen in the blood sample suspected of containing the target pathogen. Optionally steps (f), (g) and (h) are repeated with a first and second porous solid support. Exemplified pathogens that may be suspected in a blood sample include, but are not limited to, *Brucella, Campylobacter* sp., *Escherichia coli, Haemophilus influenzae, Klebsiella, Enterobacter, Serratia, Yersinia* (e.g. *Yersinia pestis*), *Pseudomonas* (e.g., *Pseudomonas aeruginosa*), *Salmonella* sp. (e.g. *Salmonella typhimurium* or *Salmonella typhi*), *Francisella tularensis, Bacillus anthracis, Listeria, Staphylococcus aureus* (e.g. MRSA or MSSA), *Streptococcus* sp. (e.g. Group A or Group B strep), *Treponema pallidum* (syphilis), *Leptospira, Borrelia burgdorferi* (Lyme's disease), *Coccidioides immitis* (Valley fever), coronavirus (e.g. MERS or SARS), hepatitis, and human immunodeficiency virus (HIV).

As with blood samples, fecal samples (e.g. stool samples) contain a high concentration of contaminants, such as organic matter and high commensal bacterial load, and may require additional processing prior to the amplification steps. Referring to FIG. 112, the invention provides methods of identifying one or more suspected pathogens in a fecal sample, the method comprising the steps of: (a) accepting a cartridge having a loading chamber containing the sample suspected of containing the target pathogen 180, (b) subjecting the fecal sample to one or more enzymatic or mechanical pretreatments 182, (c) advancing the sample to a lysis chamber having at least one lysis reagent therein, (d) mixing the sample with the at least one lysis agent to generate a lysed sample 380; (e) filtering the lysed sample 382, preferably by passing the lysed sample through one or more size-exclusion filters, (f) passing the lysed sample through a porous solid support to capture a nucleic acid on the porous solid support 480, (g) passing a wash solution through the porous solid support 482, (h) releasing the captured nucleic acid from the porous solid support to generate an enriched nucleic acid 484, (i) distributing the enriched nucleic acid to two or more assay chambers and combining the enriched nucleic acid with one or more amplification reagents 780, (j) isolating each one of the two or more assay chambers from each one of all the other two or more assay chambers and (l) performing an isothermal amplification reaction within each one of the two or more assay chambers while simultaneously detecting amplification product 786, wherein presence of an amplification product is an indication of a presence, an absence or a quantity of the target pathogen in the fecal sample suspected of containing the target pathogen. Typically, the mechanical pretreatment is required to homogenize and liquify the fecal sample. Such homogenization can be achieved within the cartridges described herein by stirring the fecal sample with ceramic, glass or steel beads in the lysis chamber prior to exposing the fecal sample to the lysis agent. The enzymatic pretreatment of step (b) can be incubating the fecal sample with a protease and/or nuclease. Optionally steps (f), (g) and (h) are repeated with a first and second porous solid support. Optionally, prior to step (i), the method further comprises pre-amplifying the enriched nucleic acid 782. Exemplified pathogens that may be suspected in a fecal sample include, but are not limited to, *Campylobacter* sp. (e.g., *Campylobacter jejuni*), *Vibrio* sp. (e.g. *Vibrio cholerae*), *Salmonella* sp. (e.g. *Salmonella typhimurium* or *Salmonella typhi*), *Shigella*, and *Bacillus anthracis*.

Finally, the cartridges and instruments described herein can be used to detect suspected pathogen in solid tissue samples. Such tissue samples require additional processing to separate the cells of the tissue sample. Referring to FIG. 113, the invention provides methods of identifying one or more suspected pathogens in a tissue sample, the method comprising the steps of: (a) accepting a cartridge having a loading chamber containing the tissue sample suspected of containing the target pathogen 180, (b) subjecting the tissue sample to one or more enzymatic, chemical or mechanical pretreatments 182, (c) advancing the sample to a lysis chamber having at least one lysis reagent therein, (d) mixing the sample with the at least one lysis agent to generate a lysed sample 380; (e) filtering the lysed sample 382, preferably by passing the lysed sample through one or more size-exclusion filters, (f) passing the lysed sample through a porous solid support to capture a nucleic acid on the porous solid support 480, (g) passing a wash solution through the porous solid support 482, (h) releasing the captured nucleic acid from the porous solid support to generate an enriched nucleic acid 484, (i) distributing the enriched nucleic acid to two or more assay chambers and combining the enriched nucleic acid with one or more amplification reagents 780, (j) isolating each one of the two or more assay chambers from each one of all the other two or more assay chambers and (l) performing an isothermal amplification reaction within each one of the two or more assay chambers while simultaneously detecting amplification product 786, wherein presence of an amplification product is an indication of a presence, an absence or a quantity of the target pathogen in the tissue sample suspected of containing the target pathogen. Typically, the mechanical pretreatment is required to disintegrate and liquify the tissue sample. Such homogenization can be achieved within the cartridges described herein by stirring the tissue sample with ceramic, glass or steel beads in the lysis chamber prior to exposing the tissue sample to the lysis agent. The enzymatic pretreatment of step (b) can comprise incubating the tissue sample with an elastase, collagenase or proteinase K. The chemical pretreatment of step (b) can comprise incubating the tissue sample with dithiothreitol (DTT). Optionally steps (f), (g) and (h) are repeated with a first and second porous solid support. Optionally, prior to step (i), the method further comprises pre-amplifying the enriched nucleic acid 782. Exemplified pathogens that may be suspected in a solid tissue sample include, but are not limited to, *Bacillus anthracis* (e.g. from skin scraping), *Corynebacterium diphtheriae*, and *Aspergillus* (lung).

IX. EXAMPLES

To demonstrate functionality of the diagnostic system of the invention for the qualitative detection of *Chlamydia trachomatis* (CT) and *Neisseria gonorrhoeae* (NG), the instrument described herein was paired with an integrated diagnostic cartridge populated with CT- and NG-specific RTLAMP reagents. The CT-specific reagents are described in detail in U.S. Pat. No. 10,450,616 B1, incorporated herein by reference. The NG-specific reagents are described in detail in U.S. patent application Ser. No. 16/523,609, filed 26 Jul. 2019, said application incorporated herein by reference.

Fresh urine samples from healthy non-infected donors were co-spiked with live CT and NG and used as samples loaded into the cartridge loading assembly. Specifically, frozen, single use aliquots of titered bacterial stocks, either grown in-house (NG) or purchased from ATCC (CT), underwent a 30 second thaw at 37□C followed by serial dilution at room temperature in Mueller Hinton cation-adjusted growth medium. Bacteria were diluted 1:10 into pools of negative urine to achieve a final concentration of 1 IFU/mL of CT and 1 CFU/mL of NG.

Urine samples were mixed by short vortex, 1 mL of sample removed and loaded onto the integrated diagnostic cartridge via the fill chamber using a pipette. To initiate the method (time, T=0), cartridges were inserted into the instrument. Using pneumatic pressure, the instrument advanced the urine sample to the lysis chamber, which held a chemical lysis buffer including, inter alia, guanidinium isothiocyanate and isopropanol. The urine sample and lysis buffer were mixed in the lysis chamber at 1300 rpm for 30 seconds to generate a lysed sample.

The valve drive assembly of the instrument rotated the rotary valve to fluidically connect the sample exit channel of the lysis chamber, the porous solid support chamber of the rotor, contained therein a silica fiber matrix, and the waste collection element. The instrument then pressurized the lysis chamber to forcibly pass the lysed sample through the silica fiber matrix (i.e. the porous solid support), capturing nucleic acid on the matrix and passing cell debris, urine and other contaminants to the waste collection element. The matrix was washed to further rid the matrix of contaminants, and then eluted with buffered water to release nucleic acid from the matrix to generate an enriched nucleic acid. The enriched nucleic acid was used without dilution to rehydrate a dried amplification reagent solution in a rehydration chamber with agitation from a mixing ball for 20 seconds. The nucleic acid/amplification reagent solution was then distributed to five assay chambers, such that the assay chambers are fully loaded at T=6:12 (mm:ss).

The instrument captured an image of the filled assay chambers and heat staked across the loading channels leading to the assay chambers while under pressure. Pneumatic pressure to the assay chambers was subsequently released and the reaction imaging assembly of the instrument captured another image of the assay chambers to confirm that the contents of the assay chambers do not leak out of the reaction area. At T=9:53, the instrument initiated the amplification reaction and images were collected for an additional 18 minutes. For these test runs, image acquisition time was extended to collect additional amplification information. Total run time, including image processing was approximately 27 minutes. In this initial test, 12 cartridges were run, presenting 10 contrived (CT+/NG+) samples and 2 clean urines. In addition to CT- and NG-specific reagents, one assay well in the cartridge contained primers and probes specific for human beta actin, which is present in human urine, as a positive control. The CT and NG were detected, as expected, in each of the contrived samples. The human beta actin was detected in both contrived and clean urine samples. Amplification results are summarized in Table

TABLE 1

Sample-to-Answer Test Results

| Target | Time to positive ($T_p$) |
|---|---|
| 1 CFU NG | 7.44 ± 0.33 |
| 1 IFU CT | 10.59 ± 0.45 |
| b-actin | 6.32 ± 0.41 |

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A method of testing a sample suspected of containing one or more target pathogens, comprising:
   accepting a cartridge having a sample port assembly containing the sample suspected of containing the one or more target pathogens;
   advancing the sample suspected of containing the one or more target pathogens to a lysis chamber within the cartridge having at least one lysis reagent therein;
   mixing the sample with the at least one lysis agent to generate a lysed sample;
   passing the lysed sample through a first porous solid support within the cartridge to capture a nucleic acid on the porous solid support;
   releasing the captured nucleic acid from the first porous solid support to generate an enriched nucleic acid;
   introducing the enriched nucleic acid into a rehydration chamber within the cartridge containing one or more dried reagents;
   after introducing the enriched nucleic acid into a metering channel, mixing the contents of the rehydration chamber to produce an analyte/reagent solution;
   distributing the analyte/reagent solution to two or more assay chambers within the cartridge;
   combining the analyte/reagent solution with one or more amplification reagents after performing the distributing step;
   sealing each one of the two or more assay chambers within the cartridge containing analyte/reagent solution from each one of all the other two or more assay chambers within the cartridge containing analyte/reagent solution and a waste chamber; and
   performing an isothermal amplification reaction within each one of the two or more assay chambers in the cartridge while simultaneously detecting amplification product, wherein presence of an amplification product is an indication of a presence, an absence or a quantity of the one or more target pathogens in the sample suspected of containing the one or more target pathogens.

2. The method of testing a sample according to claim 1, wherein in mixing the sample with the at least one lysis agent, the lysis agent is a mechanical agent.

3. The method of testing a sample according to claim 2, wherein the mechanical agent is ceramic beads, glass beads or steel beads, and the mixing the sample step comprises rotating a stir bar within the lysis chamber at at least 1000 rpm.

4. The method of testing a sample according to claim 3, wherein mixing the sample comprises rotating the stir bar or the ceramic, glass or steel beads along with a chemical lysis agent.

5. The method of testing according to claim 1, wherein the at least one lysis agent is a chemical lysis agent.

6. The method of testing a sample according to claim 5, wherein the one or more target pathogens is a virus or a gram-negative bacterium and the lysis reagent is a chaotropic agent.

7. The method of testing a sample according to claim 1, wherein prior to passing the lysed sample through the porous solid support, the method further comprises passing the lysed sample through a size-exclusion filter, wherein nucleic acid passes through the filter.

8. The method of testing a sample according to claim 1, wherein reagents comprises a primer set specific to one of the one or more target pathogens.

9. The method of testing a sample according to claim 1, wherein a first assay chamber contains a primer set specific to a first nucleic acid sequence.

10. The method of testing a sample according to claim 9, wherein the first nucleic acid sequence is present in one of the one or more target pathogens.

11. The method of testing a sample according to claim 9, wherein prior to mixing the sample with at least one lysis agent, a process control is added to the sample and the first nucleic acid sequence is present in the process control.

12. The method of testing a sample according to claim 9, wherein prior to passing lysed sample through the porous solid support, a process control is added to the lysed sample and the first nucleic acid sequence is present in the process control.

13. The method of testing a sample according to claim 9, wherein a second assay chamber contains a primer set specific to a second nucleic acid sequence, wherein the second nucleic acid sequence is present in one of the one or more target pathogens.

14. The method of testing a sample according to claim 1, wherein the performing an isothermal amplification reaction step is completed in less than 15 minutes.

15. The method of testing a sample according to claim 1, further comprising: providing a result containing a determination made during the performing step relating to the presence, the absence or the quantity of the one or more target pathogens in the sample suspected of containing the one or more target pathogens.

16. The method of testing a sample according to claim 1, wherein the method further comprises, prior to advancing the sample to a lysis chamber, pretreating the sample with a chemical reaction.

17. The method of testing a sample according to claim 16, wherein the sample is sputum and the chemical reaction is incubation with a mucolytic agent.

18. The method of testing a sample according to claim 1, wherein the method further comprises, prior to advancing the sample to a lysis chamber, pretreating the sample with an enzymatic reaction.

19. The method of testing a sample according to claim 18, wherein the enzymatic reaction is incubation of the sample with a nuclease, a protease, an amylase, a glycosylase, or a lipase.

20. The method of testing a sample according to claim 1, wherein the method further comprises, prior to advancing the sample to a lysis chamber, pretreating the sample with a physical treatment.

21. The method of testing a sample according to claim 20, wherein the physical treatment comprises passing the sample through a size-exclusion filter in a first direction.

22. The method of testing a sample according to claim 20, wherein the physical treatment comprises exposing the sample to a capture agent immobilized on a solid substrate.

23. The method of testing a sample according to claim 22, further comprising, after exposure, separating the solid substrate from the sample.

24. The method of testing a sample according to claim 22, wherein the capture agent is an antibody with affinity for red blood cells.

25. The method of testing a sample according to claim 1, wherein the sample is sputum and the method further comprises, prior to mixing the sample with the at least one lysis reagent, bead beating the sputum to liquify the sample.

26. The method of testing a sample according to claim 25, wherein the bead beating comprises mixing the sputum with ceramic, glass, or steel beads.

27. The method of testing a sample according to claim 1, wherein prior to introducing the enriched nucleic acid into the rehydration chamber and distributing the analyte/reagent solution to two or more assay chambers, the method further comprises passing the enriched nucleic acid through a second porous solid support.

* * * * *